US012577245B2

(12) United States Patent
Li et al.

(10) Patent No.: US 12,577,245 B2
(45) Date of Patent: Mar. 17, 2026

(54) SULFONYL BENZAMIDE DERIVATIVES AS Bcl-2 INHIBITORS

(71) Applicants: ASCENTAGE PHARMA (SUZHOU) CO., LTD., Suzhou (CN); ASCENTAGE PHARMA GROUP CORP LIMITED, Central (CN)

(72) Inventors: Dongbo Li, Suzhou (CN); Jianyong Chen, Suzhou (CN); Fang Liu, Suzhou (CN); Hao Chen, Suzhou (CN); Xianchan Zha, Suzhou (CN)

(73) Assignees: Ascentage Pharma (Suzhou) Co., Ltd. (CN); Ascentage Pharma Group Corp Limited (CN)

( * ) Notice: Subject to any disclaimer, the term of this patent is extended or adjusted under 35 U.S.C. 154(b) by 414 days.

(21) Appl. No.: 18/263,249

(22) PCT Filed: Jan. 30, 2022

(86) PCT No.: PCT/CN2022/075239
§ 371 (c)(1),
(2) Date: Jul. 27, 2023

(87) PCT Pub. No.: WO2022/161496
PCT Pub. Date: Aug. 4, 2022

(65) Prior Publication Data
US 2024/0166644 A1 May 23, 2024

(30) Foreign Application Priority Data
Feb. 1, 2021 (WO) ................ PCT/CN2021/074709

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................... C07D 471/04
USPC .................................................... 514/210.16
See application file for complete search history.

(56) References Cited

U.S. PATENT DOCUMENTS

2015/0329541 A1* 11/2015 Bruncko ................ A61P 35/02
544/362

FOREIGN PATENT DOCUMENTS

| | | | |
|---|---|---|---|
| CN | 1906183 | A | 1/2007 |
| CN | 102307872 | A | 1/2012 |
| CN | 102947283 | A | 2/2013 |
| CN | 105026394 | A | 11/2015 |
| CN | 108658983 | A | 10/2018 |
| CN | 110177788 | A | 8/2019 |
| CN | 113444078 | A | 9/2021 |
| WO | WO2019185025 | A1 | 10/2019 |
| WO | WO2020088442 | A1 | 5/2020 |
| WO | WO2020238785 | A1 | 12/2020 |

OTHER PUBLICATIONS

May 5, 2022 International Search Report for PCT/CN2022/075239, 17 pages.

* cited by examiner

*Primary Examiner* — Niloofar Rahmani
(74) *Attorney, Agent, or Firm* — Honigman LLP; Lucy Yang; Li Gao

(57) ABSTRACT

The present disclosure provides compounds having Formula I: and the pharmaceutically acceptable salts and solvates thereof, wherein variables are as defined as set forth in the specification. The present disclosure also provides compounds of Formula I for use to treat a disease, disorder, or condition responsive to Bcl-2 protein inhibition, particularly Bcl-2 WT and/or Bcl-2 G101V.

(I)

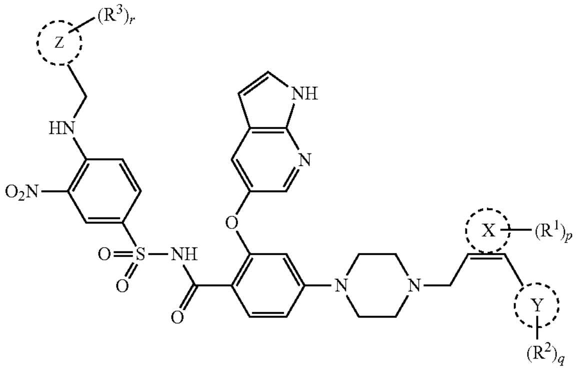

21 Claims, No Drawings

SULFONYL BENZAMIDE DERIVATIVES AS Bcl-2 INHIBITORS

CROSS-REFERENCE TO RELATED APPLICATIONS

This application is a 35 U.S.C. § 371 United States National Phase Application of, and claims priority to, PCT Application No. PCT/CN2022/075239, filed Jan. 30, 2022, which claims priority to PCT Application No. PCT/CN2021/074709, filed Feb. 1, 2021. The entire contents of the aforementioned applications are incorporated herein by reference.

FIELD OF THE INVENTION

The present disclosure provides Bcl-2 protein inhibitors and therapeutic methods of treating diseases, disorders, or conditions wherein inhibition of Bcl-2 proteins provides a benefit.

BACKGROUND

Apoptosis, the process of programmed cell death, is an essential biological process for tissue homeostasis. In mammals, it has been shown to regulate early embryonic development. Later in life, cell death is a default mechanism by which potentially dangerous cells, e.g., cells carrying cancerous defects, are removed. Several apoptotic pathways are known. One of the major apoptotic pathways involves the Bcl-2 family of proteins which are key regulators of the mitochondrial (also called "intrinsic") pathway of apoptosis. See Danial and Korsmeyer, *Cell* 116:205-219 (2004). The structural homology domains BH1, BH2, BH3 and BH4 are characteristic of Bcl-2 family proteins. The Bcl-2 family of proteins can be further classified into three subfamilies depending on how many of the homology domains each protein contains and on its biological activity, i.e., whether it has pro- or anti-apoptotic function.

The first subgroup of Bcl-2 proteins contains proteins having all four homology domains, i.e., BH1, BH2, BH3 and BH4. Their general effect is anti-apoptotic, that is, to preserve a cell from starting a cell death process. Proteins such as Bcl-2, Bcl-w, Bcl-xL, Mcl-1, and Bfl-1/A1 are members of this first subgroup. Proteins belonging to the second subgroup of Bcl-2 proteins contain the three homology domains BH1, BH2, and BH3, and have a pro-apoptotic effect. The two main representative proteins of this second subgroup are Bax and Bak. The third subgroup of Bcl-2 proteins is composed of proteins containing only the BH3 domain and members of this subgroup are usually referred to as "BH3-only proteins." Their biological effect on the cell is pro-apoptotic. Bim, Bid, Bad, Bik, Noxa, Hrk, Bmf, and Puma are examples of this third subfamily of proteins. The exact mechanism by which the Bcl-2 family proteins regulate cell death is not entirely known. In one hypothesis of regulation of cell death by Bcl-2 family proteins, the BH3-only proteins are further categorized as either "activator," e.g., Bim and Bid, or "sensitizer," e.g., Bad, Bik, Noxa, Hrk, Bmf, and Puma, proteins depending on their regulatory function.

One of the keys to tissue homeostasis is achieving a balance in the interactions among the three subgroups of Bcl-2 proteins in cells. Studies have elucidated the mechanisms by which pro-apoptotic and anti-apoptotic subgroups of Bcl-2 family proteins interact to allow a cell to undergo programmed cell death. After receiving intra- or extracellular signals in cells, post-translational or transcriptional activation of BH3-only proteins occurs. The BH3-only proteins are the primary inducers of an apoptotic cascade that includes, as one step, the activation of the pro-apoptotic proteins Bax and Bak on the mitochondrial membrane in cells. Upon activation of Bax and/or Bak that are either already anchored to the mitochondrial membrane or migrate to this membrane, Bax and/or Bak oligomerize to result in mitochondrial outer membrane permeabilization (MOMP), the release of cytochrome C, and downstream activation of effector caspases, to ultimately result in cell apoptosis. Some researchers hypothesize that certain BH3-only proteins, e.g., Puma, Bim, Bid, are "activators" in that these proteins directly engage pro-apoptotic proteins Bax and Bak to initiate MOMP, while other BH3-only proteins, e.g., Bad, Bik and Noxa, are "sensitizers" and induce Bax and Bak oligomerization indirectly by binding anti-apoptotic proteins, e.g., Bcl-2, Bcl-xL, Bcl-w, Mcl-1, and displacing and "freeing-up" the "activator" BH3-only proteins, which subsequently bind to and activate pro-apoptotic proteins, e.g., Bax, Bak, to induce cell death. Other research suggests that anti-apoptotic proteins engage and seqeuester Bax and Bak directly and all BH3-only proteins regulates this interaction by binding to anti-apoptotic proteins, e.g., Bcl-2, Bcl-xL, Bcl-w, Mcl-1, which results in the release Bax and Bak. See Adams and Cory, *Oncogene* 26:1324-1337 (2007) and Willis et al., *Science* 315:856-859 (2007). Although the exact interactions through which the anti- and pro-apoptotic Bcl-2 family proteins regulate apoptosis remain under investigation, there is a large body of scientific evidence to show that compounds which inhibit the binding of BH3-only proteins to anti-apoptotic Bcl-2 family proteins promote apoptosis in cells.

Dysregulated apoptotic pathways have been implicated in the pathology of many significant diseases such as neurodegenerative conditions (up-regulated apoptosis), such as for example, Alzheimer's disease; and proliferative diseases (down-regulated apoptosis) such as for example, cancer, autoimmune diseases and pro-thrombotic conditions.

Down-regulated apoptosis (and more particularly the Bcl-2 family of proteins) may be involved in the onset of cancerous malignancy. Research has shown, for example, the anti-apoptotic proteins, Bcl-2 and Bcl-xL, are over-expressed in many cancer cell types. See Zhang, *Nature Reviews Drug Discovery* 1:101 (2002); Kirkin et al., *Biochimica* et *Biophysica Acta* 1644:229-249 (2004); and Amundson et al., *Cancer Research* 60:6101-6110 (2000). The effect of this deregulation is the survival of altered cells which would otherwise have undergone apoptosis in normal conditions. The repetition of these defects associated with unregulated proliferation is thought to be the starting point of cancerous evolution. Additionally, research has shown that BH3-only proteins can act as tumor suppressors when expressed in diseased animals.

These findings have made possible new strategies in drug discovery for targeting cancer. If a small molecule that could mimic the effect of BH3-only proteins were able to enter the cell and overcome the anti-apoptotic protein over-expression, then it could be possible to reset the apoptotic process. This strategy can have the advantage that it can alleviate the problem of drug resistance which is usually a consequence of apoptotic deregulation (abnormal survival). Therapeutic strategies for targeting Bcl-2 and Bcl-$X_L$ in cancer to restore cancer cell sensitivity and overcome resistance of cancer cells to apoptosis have been reviewed. See Adams et al., *Science* 281:1322 (1998) and Reed, *Adv. Pharmacol.* 41:501 (1997); Reed et al., *J. Cell. Biochem.* 60:23 (1996).

Platelets also contain the necessary apoptotic machinery, e.g., Bax, Bak, Bcl-xL, Bcl-2, cytochrome c, caspase-9, caspase-3 and APAF-1, to execute programmed cell death through the intrinsic apoptotic pathway. Although circulating platelet production is a normal physiological process, a number of diseases are caused or exacerbated by excess of, or undesired activation of, platelets. This suggests that therapeutic agents capable of inhibiting anti-apoptotic proteins in platelets and reducing the number of platelets in mammals may be useful in treating pro-thrombotic conditions and diseases that are characterized by an excess of, or undesired activation of, platelets.

Small molecule BH3-only protein mimetics such as ABT-737 and ABT-263 bind strongly to a subset of anti-apoptotic Bcl-2 proteins including Bcl-2, Bcl-w and Bcl-xL, and weakly to Mcl-1 and A1. These small molecules were tested in animal studies and demonstrated cytotoxic activity in certain xenograft models as single agents, as well as enhanced the effects of a number of chemotherapeutic agents on other xenograft models when used in combination. See Tse, C. et al., *Cancer Res* 68: 3421-3428 (2008) and van Delft, M. F. et al., *Cancer Cell* 10:389-399 (2006). These in vivo studies suggest the potential utility of inhibitors of anti-apoptotic Bcl-2 family proteins for the treatment of diseases that involve a dysregulated apoptotic pathway. ABT-199 (Venetoclax) is a potent Bcl-2 inhibitor that has been approved by the U.S. Food and Drug Administration for the treatment of chronic lymphocytic leukemia. See Cang et al., *Journal of Hematology & Oncology* 8:129 (2015) and Souers et al., *Nature Medicine* 19:202-208 (2013).

The natural expression levels of anti-apoptotic Bcl-2 family proteins members vary in different cell types. For example, in young platelets, Bcl-xL protein is highly expressed and plays an important role in regulating cell death (life span) of platelets. Also, in certain cancer cell types, the cancer cell's survival is attributed to the dysregulation of the apoptotic pathway caused by the over-expression of one or more anti-apoptotic Bcl-2 protein family members. In view of the important role for Bcl-2 family of proteins in regulating apoptosis in both cancerous and normal, i.e., non-cancerous, cells, and the recognized inter-cell type variability of Bcl-2 family protein expression, it is advantageous to have a small molecule inhibitor that selectively targets and preferably binds to one type or a subset of anti-apoptotic Bcl-2 protein(s), for example, to an anti-apoptotic Bcl-2 family member that overexpressed in a certain cancer type. Such a selective compound also may confer certain advantages in the clinical setting, by providing, for example, the flexibility to select a dosing regimen, a reduced on-target toxic effect in normal cells, among others, e.g., lymphopenia has been observed in Bcl-2 deficient mice. See Nakayama, K. et al. *PNAS* 91:3700-3704 (1994).

Mutation of drug-binding sites is a common mechanism by which malignant cells evade therapies. Venetoclax was approved in 2016 and there is a limited understanding of potential resistance mechanisms. To predict potential resistance mutants, a mouse model was used to induce Venetoclax tolerance in cancer cells. See, e.g., Fresquet, V. et al., *Blood* 123, 4111-4119 (2014). This study identified that a mutation of phenylalanine 104 (human numbering) to either leucine (F104L) or cysteine (F104C), located within Bel-2's BH3-binding groove, rendered the lymphoma cell line resistant to Venetoclax. Subsequent work confirmed that these mutations can also confer resistance in models of human leukemia and lymphoma, but have not yet been observed in patients. See, Tahir, S. K. et al., *BMC Cancer* 17, 399 (2017).

Recently a novel Bcl-2 mutation was described exclusively in patients undergoing treatment with Venetoclax.

See, Blombery, P. et al., *Cancer Discov.* 9, 342-353 (2018). This mutant, G101V, was found in chronic lymphocytic leukemia (CLL) patients from the clinical trials who had initially responded to treatment but developed CLL-type clinical progression after 19-42 months. The presence of the mutation in patient samples was predictive of clinical progression. The Bcl-2 G101V mutation reduces the affinity for the drug to Bcl-2 by approximately 180-fold. On the other hand, Bcl-2 G101V maintains affinity for the BH3 motif of pro-apoptotic proteins, such as BAX and BIM, and thus can still function to suppress apoptosis. By selectively reducing affinity to Venetoclax, the BCL-2 G101V mutation provides resistance to the therapy.

There is an ongoing need, therefore, for small molecules that selectively inhibit the activity of one type or a subset of Bcl-2 proteins, including wild type and mutant variants, for the treatment of hyperproliferative diseases such as cancer.

SUMMARY OF THE INVENTION

In one aspect, the present disclosure provides compounds represented by any one of the Formulae below, and the pharmaceutically acceptable salts and solvates, e.g., hydrates, thereof, collectively referred to herein as "Compounds of the Disclosure."

One embodiment of the present disclosure includes a compound having Formula I:

(I)

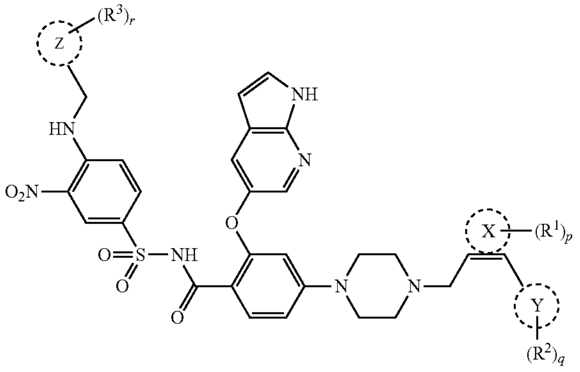

or a pharmaceutically acceptable salt or solvate thereof, wherein:

Ring X is a 5- or 6-membered ring, containing one or more additional degrees of unsaturation;

each $R^1$ independently is selected from the group consisting of $C_{1-6}$ alkyl, $C_{2-6}$ alkenyl, $C_{2-6}$ alkynyl, $C_{1-6}$ haloalkyl, and halogen;

p is 0, 1, or 2;

Ring Y is a 5- to 9-membered mono- or fused-ring system, including at least one S, and optionally containing one or more additional heteroatom selected from the group consisting of O, N, or S, and containing one or more degrees of unsaturation;

each $R^2$ independently is selected from the group consisting of $(CH_2)_t$—$R_4$, CONH—$R_4$, NHC(O)—$R_4$, $NHR_4$, and (C≡C)—$R_4$;

each $R^4$ independently is $C_{1-6}$ alkyl, $C_{2-6}$ alkenyl, $C_{2-6}$ alkynyl, $C_{1-6}$ haloalkyl, $C_{3-10}$ cycloalkyl, aryl, $C_{3-10}$ heterocyclyl, heteroaryl;

each $R^4$ may be substituted with one or more of the group consisting of $C_{1-6}$ alkyl, $C_{2-6}$ alkenyl, $C_{2-6}$ alkynyl, $C_{1-6}$ haloalkyl, halogen, $C_{3-6}$ cycloalkyl, $C_{3-6}$ heterocyclyl, $OSO_2CH_3$, $NH_2$, $NHC_{1-6}$ alkyl, N($C_{1-6}$ alkyl), $C_{1-6}$ alkoxy, OH, $C_{1-6}$ alkyl-OH, $C_{2-6}$ alkyl(OH)($C_{3-6}$ cycloalkyl), $C_{1-6}$ haloalkyl-OH, $C_{3-6}$ cycloalkyl-OH, $C_{1-6}$ alkyl-COOH, $C_{1-6}$ alkyl-O—$C_{1-6}$ alkyl, CN, $C_{1-6}$ alkyl-CN, $C_{1-6}$ alkyl-NHC(O)—$C_{1-6}$ alkyl, and $C_{1-6}$ alkyl-C(O)NH—$C_{1-6}$ alkyl;

q is 1 or 2;

each t is 0, 1, 2, 3, 4, 5, or 6;

Ring Z is a saturated 6-membered ring, optionally containing one or more O;

each $R^3$ is selected from the group consisting of one or more of $C_{1-6}$ alkyl, $C_{1-6}$ alkoxy, and OH; and r is 0, 1, or 2.

One embodiment of the present disclosure includes wherein Ring X is a 6-membered cyclohexenyl ring and the compound is of Formula Ix:

(Ix)

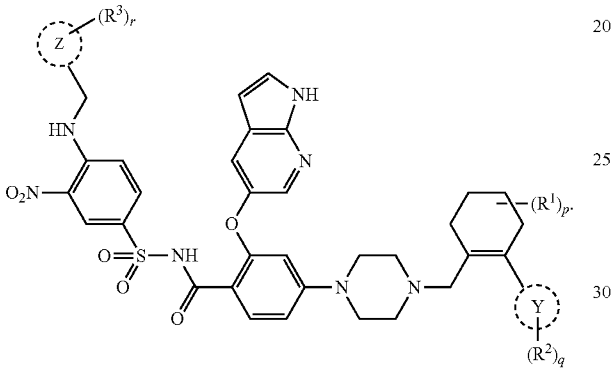

One embodiment of the present disclosure includes wherein p is 2 and each $R^1$ is substituted from the same atom. One embodiment of the present disclosure includes wherein each $R^1$ is $C_{1-6}$ alkyl. One embodiment of the present disclosure includes each $R^1$ is methyl. One embodiment of the present disclosure includes wherein each methyl is substituted para from the depicted point of attachment from the piperazine-methylene and the compound of formula Ixi:

(Ixi)

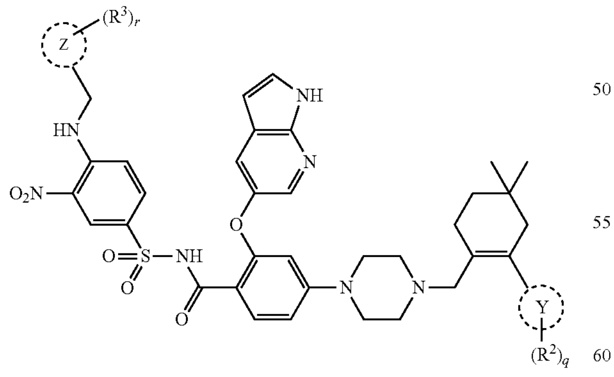

One embodiment of the present disclosure includes wherein Ring Y is a thiophene. One embodiment of the present disclosure includes wherein the S atom is located in an alpha position to Ring X and the compound is of Formula Iy:

(Iy)

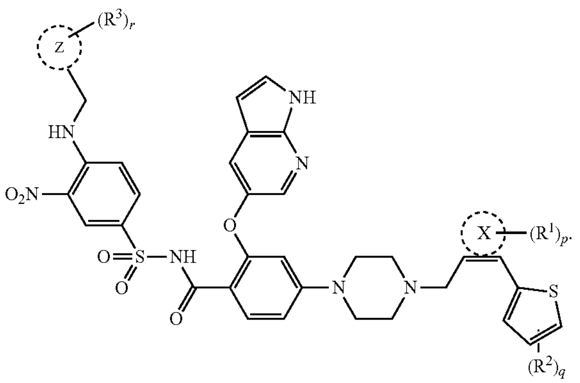

One embodiment of the present disclosure includes wherein q is 1. One embodiment of the present disclosure includes wherein each $R^2$ independently is $(CH_2)_t$—$R_4$. One embodiment of the present disclosure includes wherein t is 0 and $R^4$ is directed substituted from the depicted thiophene. One embodiment of the present disclosure includes wherein q is 1 and $R^4$ is substituted beta to the depicted S in the depicted thiophene ring and the compound is of Formula Iyi:

(Iyi)

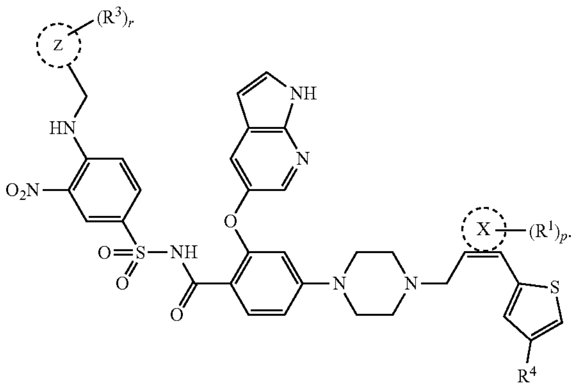

One embodiment of the present disclosure includes wherein $R^4$ is aryl. One embodiment of the present disclosure includes wherein $R^4$ is phenyl. One embodiment of the present disclosure includes wherein $R^4$ is substituted with one or more of the group consisting of $C_{1-6}$ alkyl, $C_{1-6}$ haloalkyl, halogen, OH, $C_{1-6}$ alkyl-OH, and $C_{1-6}$ haloalkyl-OH. One embodiment of the present disclosure includes wherein $R^4$ is substituted with one or more of the group consisting of halogen, $C_{1-6}$ alkyl-OH, and $C_{1-6}$ haloalkyl-OH. One embodiment of the present disclosure includes wherein Ring Z is selected from a substituted cyclohexyl and a 1,4-dioxane. One embodiment of the present disclosure includes wherein the cyclohexyl is substituted with each of a methyl and an OH group, from the same atom, and located para to the point of attachment from the depicted amine:

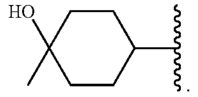 [SMILES: *C1CCC(C)(O)CC1]

One embodiment of the present disclosure includes having the depicted stereochemistry:

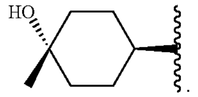

One embodiment of the present disclosure includes having the depicted stereochemistry:

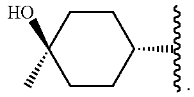

One embodiment of the present disclosure includes a compound, or a pharmaceutically acceptable salt thereof, selected from the group consisting of:

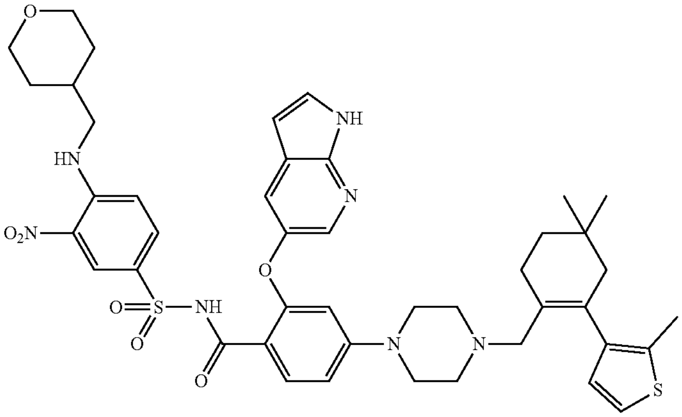

Molecular Weight: 854.05

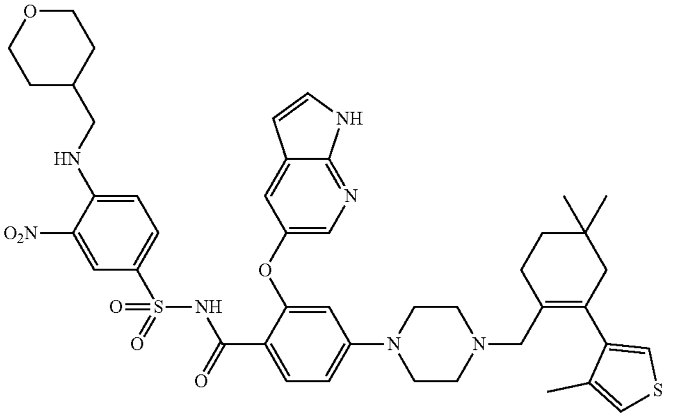

Molecular Weight: 854.05

-continued
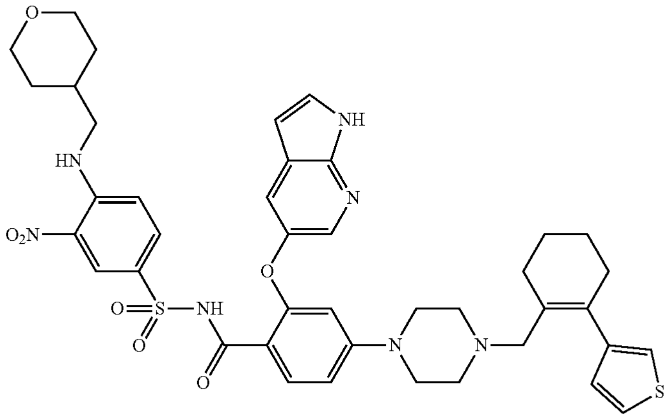
Molecular Weight: 811.97
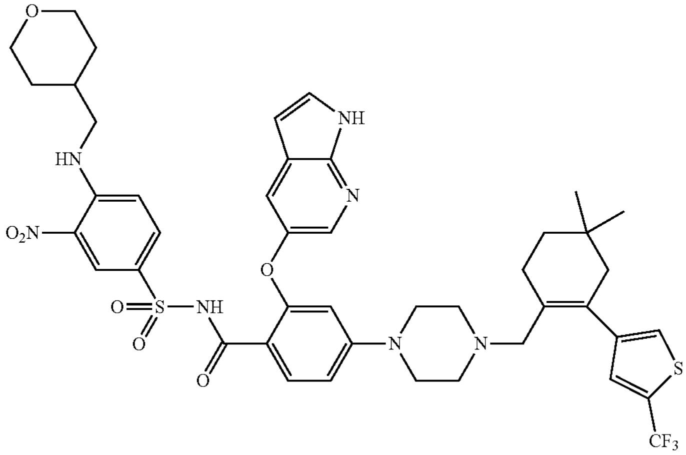
Molecular Weight: 908.02
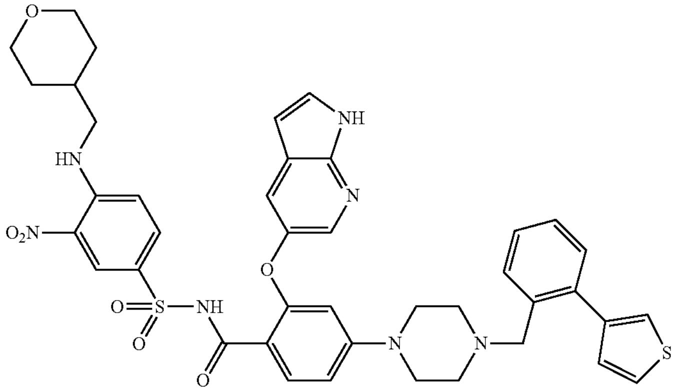
Molecular Weight: 807.94

-continued
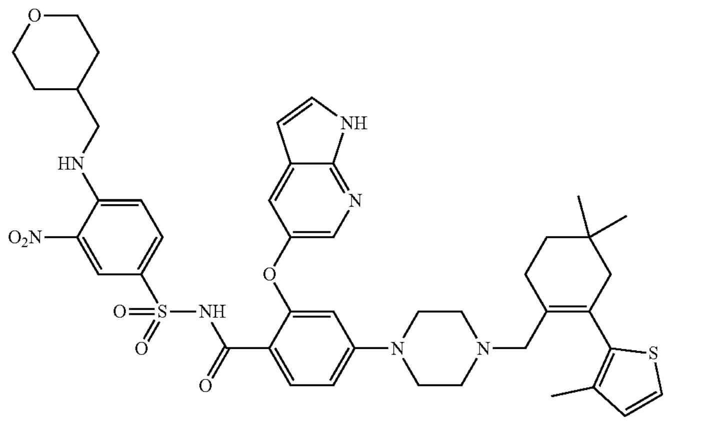
Molecular Weight: 854.05•TFA
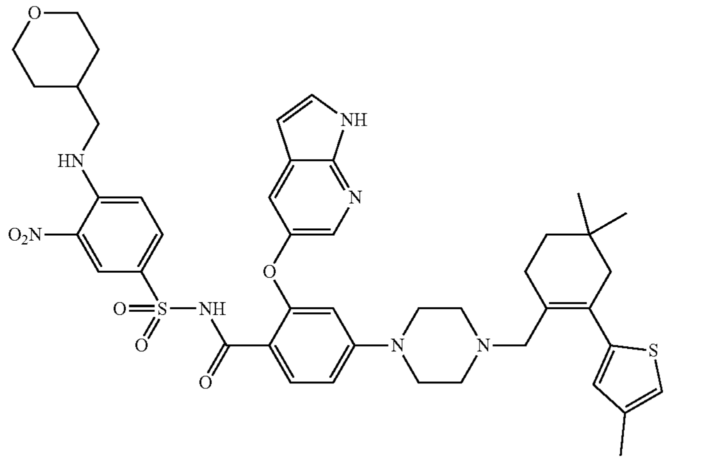
Molecular Weight: 854.05•TFA
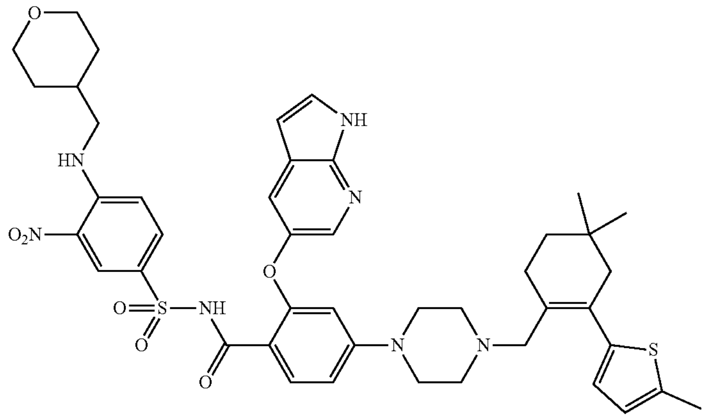
Molecular Weight: 854.05•TFA -continued
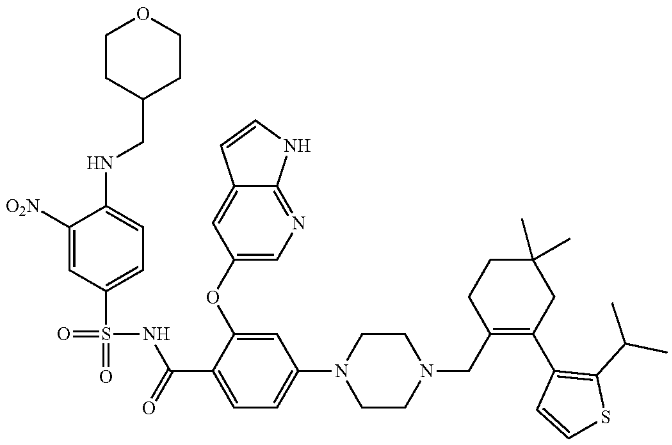
Molecular Weight: 882.10
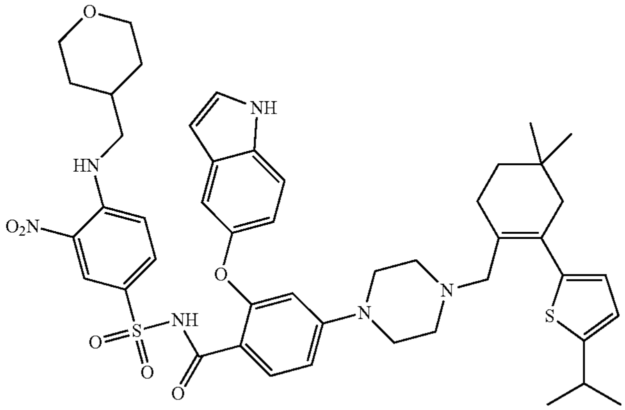
Molecular Weight: 882.10
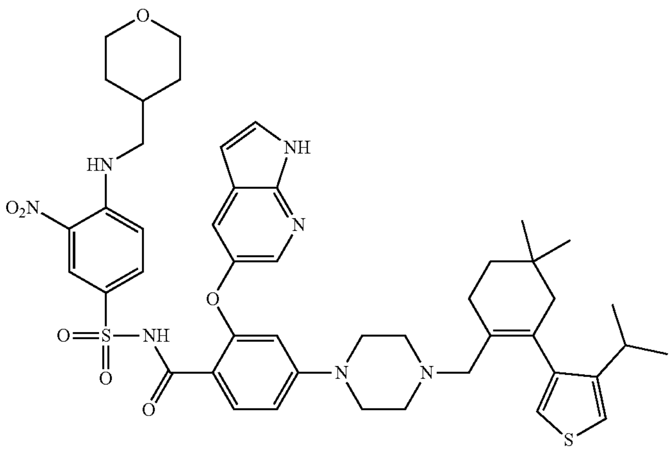
Molecular Weight: 882.10

-continued
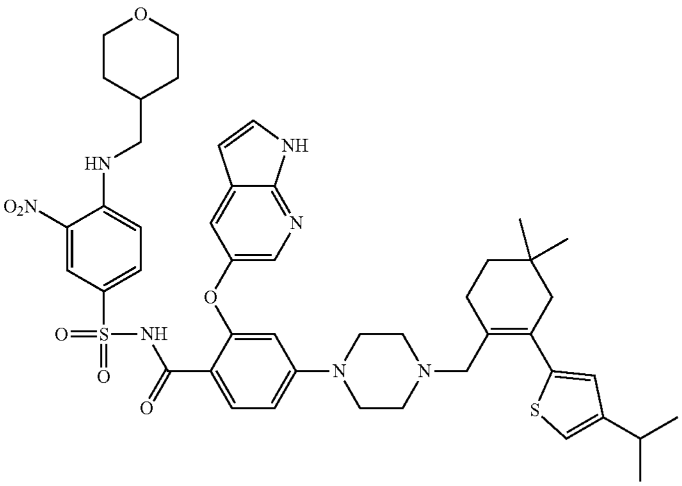
Molecular Weight: 882.10
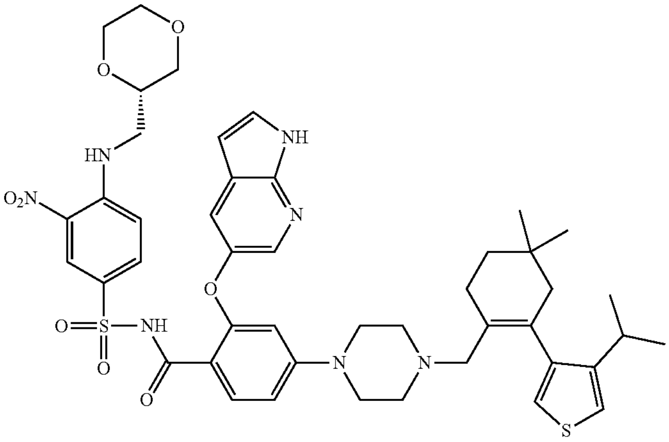
Molecular Weight: 884.07
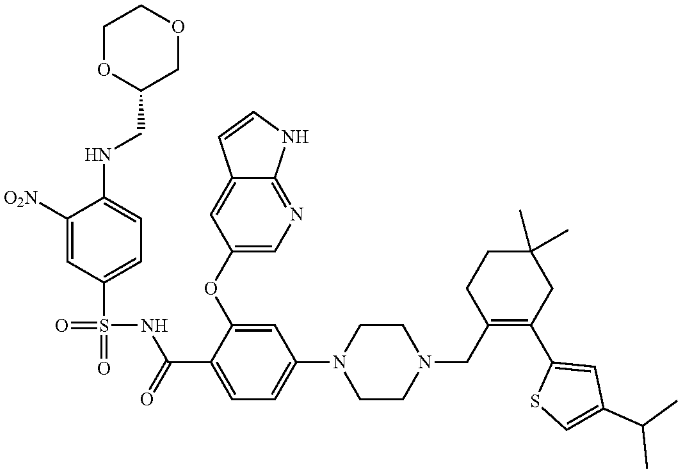
Molecular Weight: 884.07

-continued
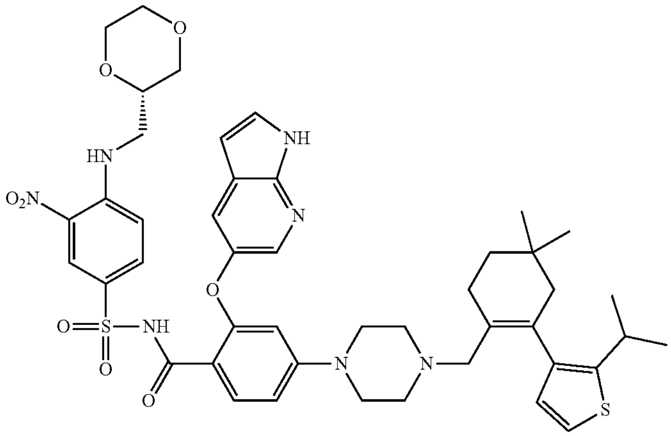
Molecular Weight: 884.07
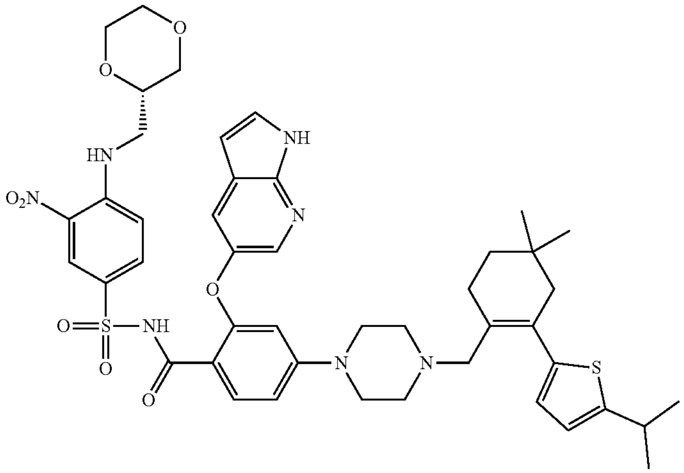
Molecular Weight: 884.07
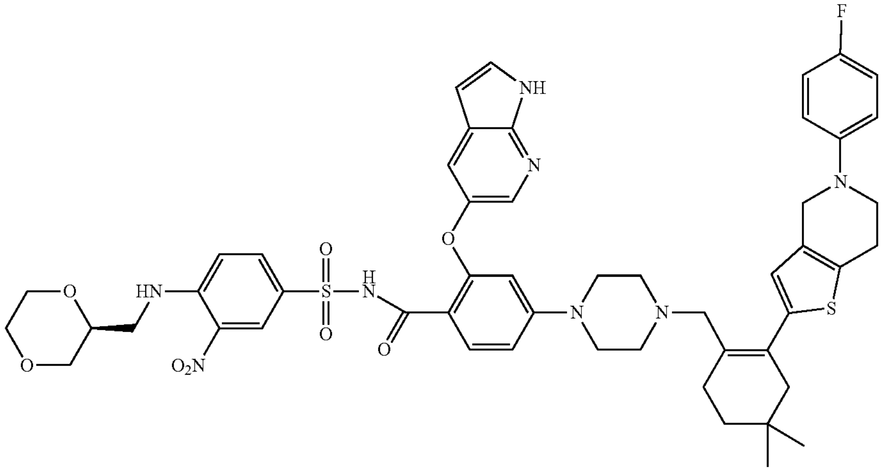
Molecular Weight: 991.16

-continued
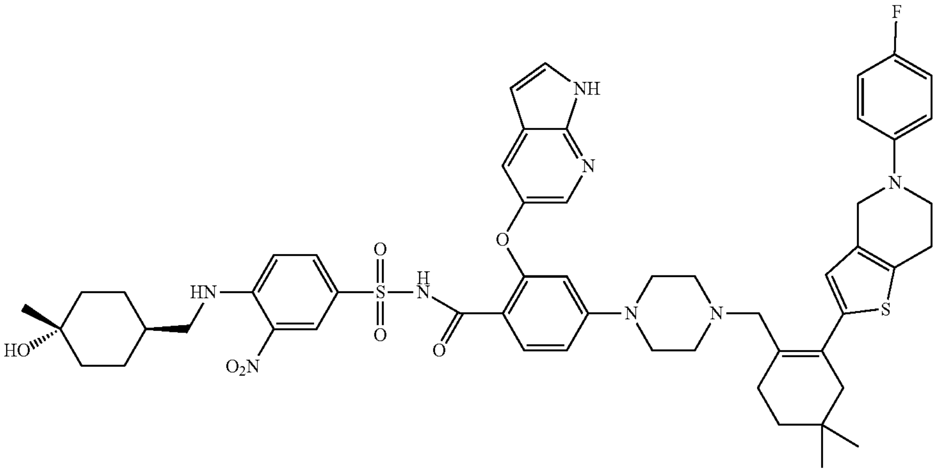
Molecular Weight: 1017.24
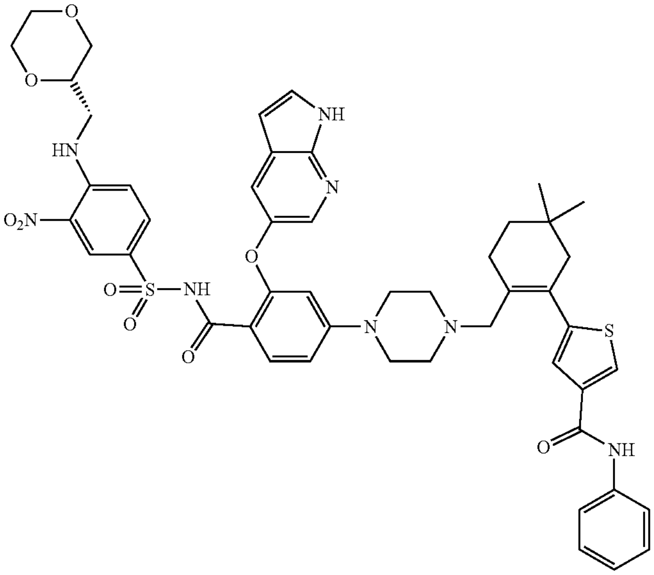
Molecular Weight: 961.12

-continued
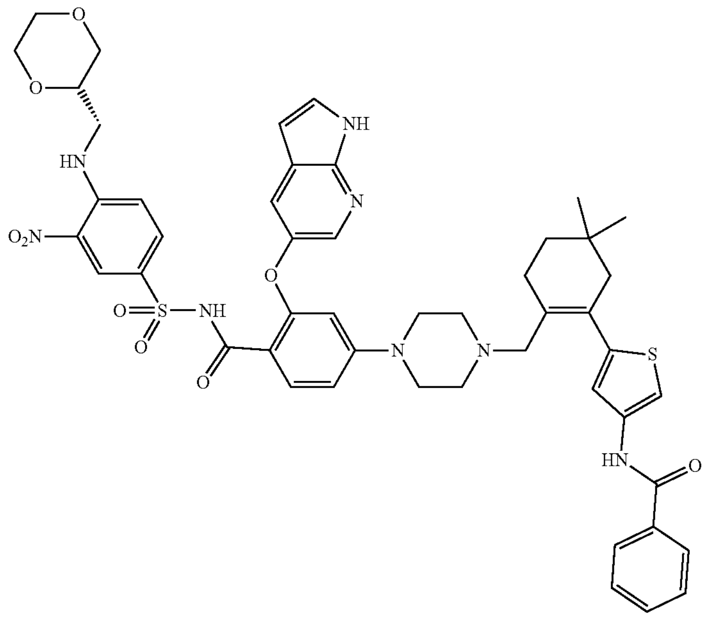
Molecular Weight: 961.12
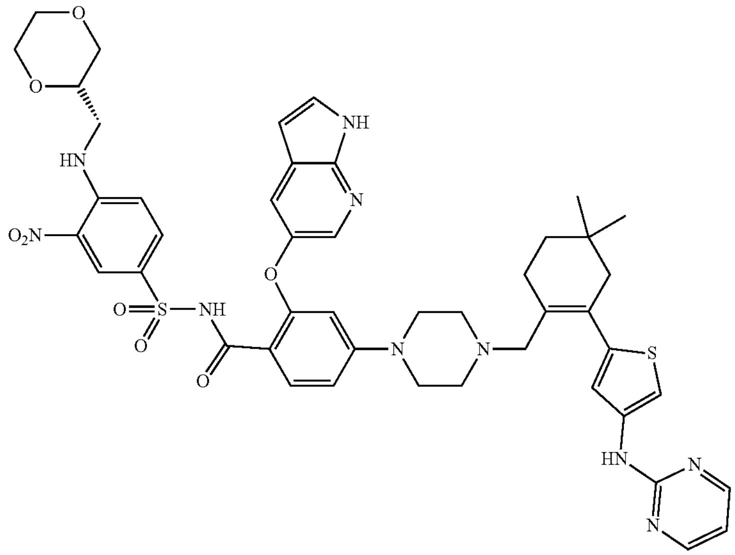
Molecular Weight: 935.08
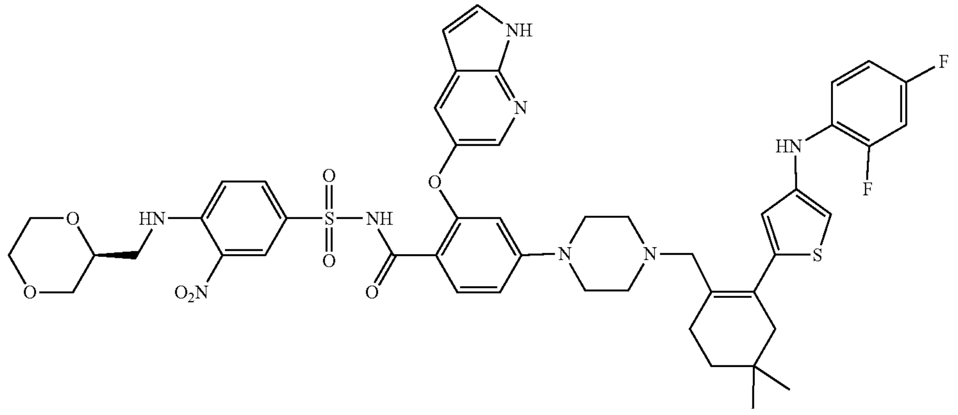
Molecular Weight: 969.09

-continued
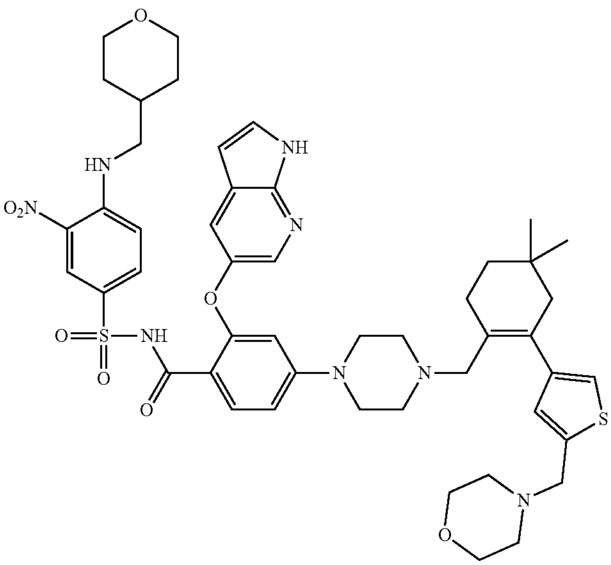
Molecular Weight: 939.15
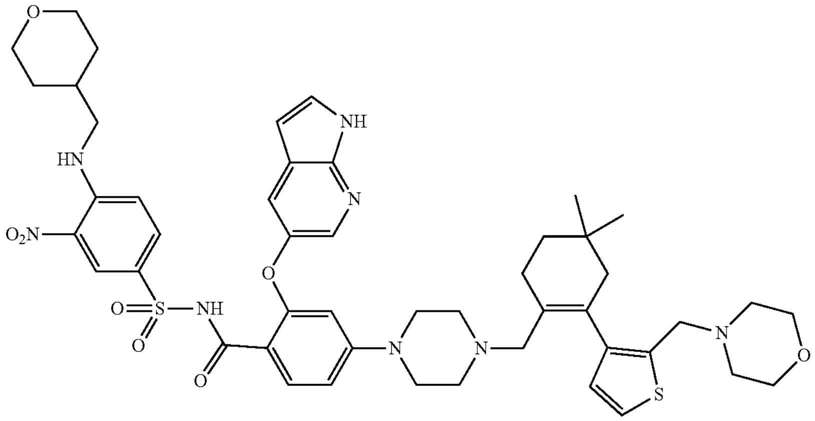
Molecular Weight: 939.15
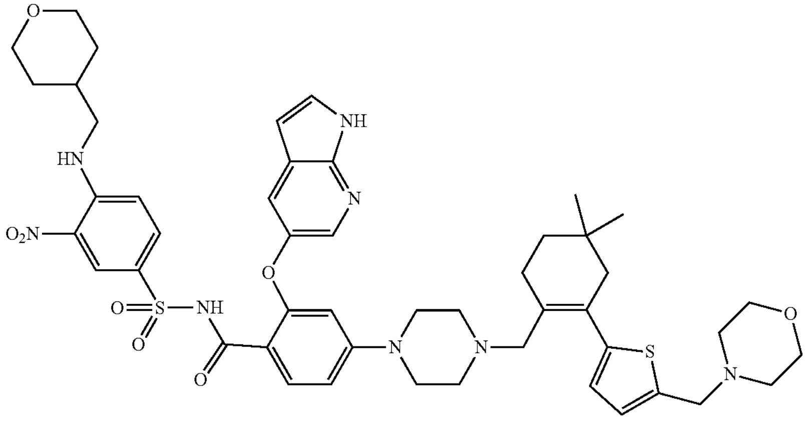
Molecular Weight: 939.15

-continued
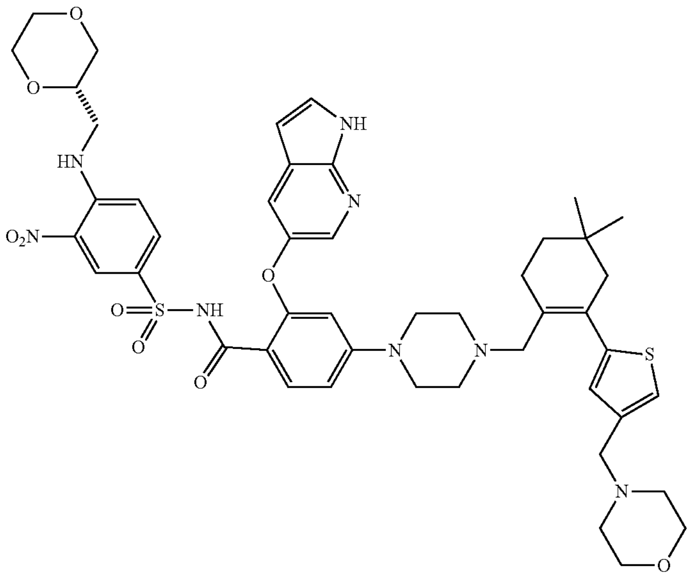
Molecular Weight: 941.13
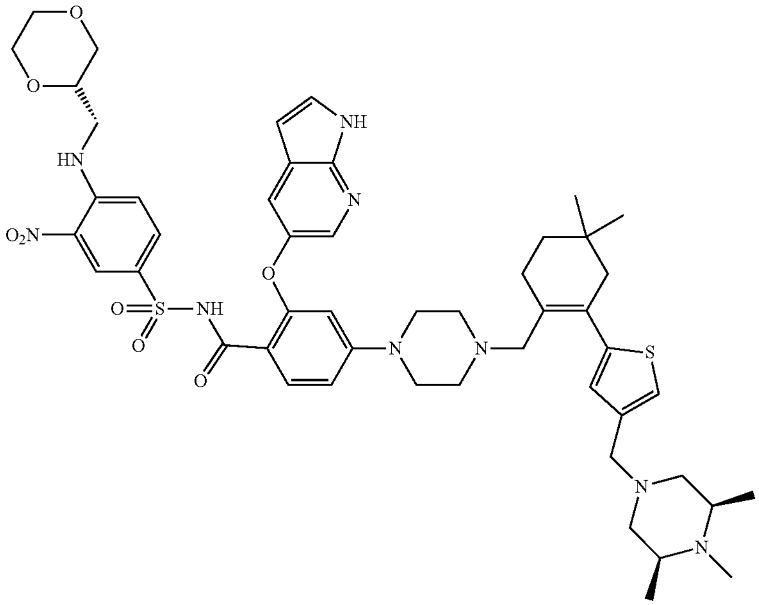
Molecular Weight: 982.22

-continued
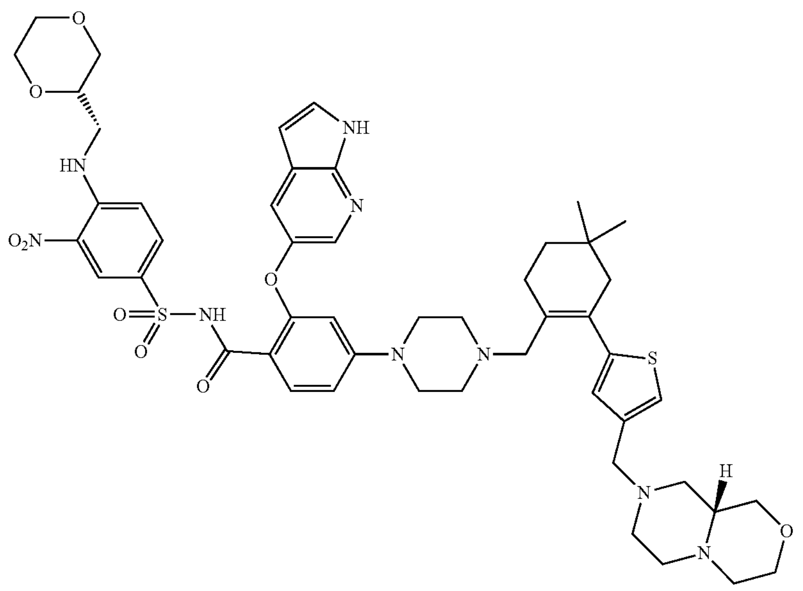
Molecular Weight: 996.20
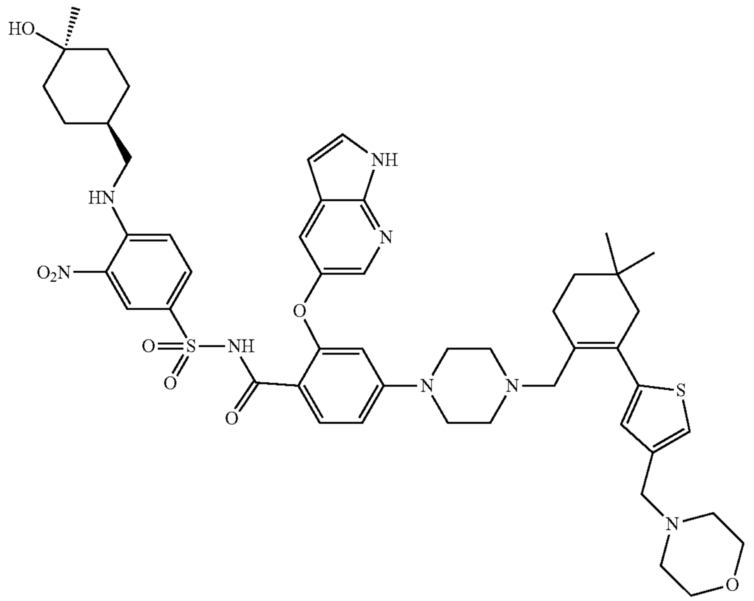
Molecular Weight: 967.21

-continued
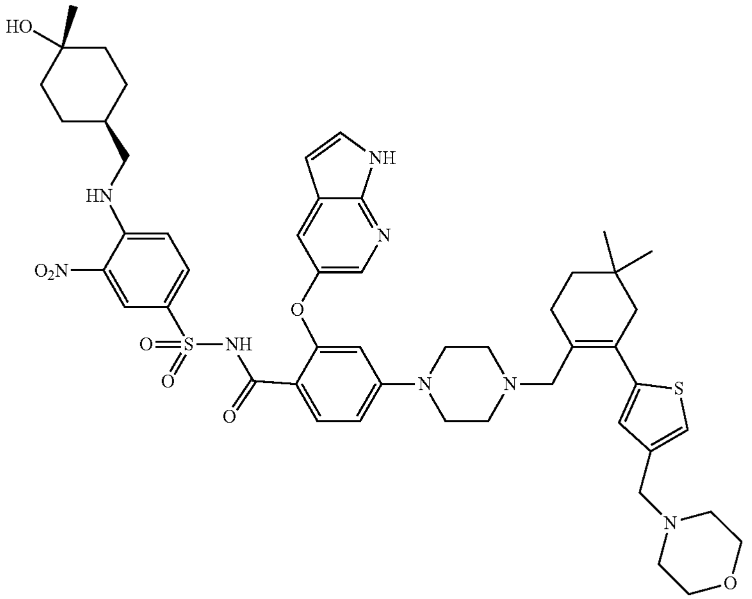
Molecular Weight: 967.21
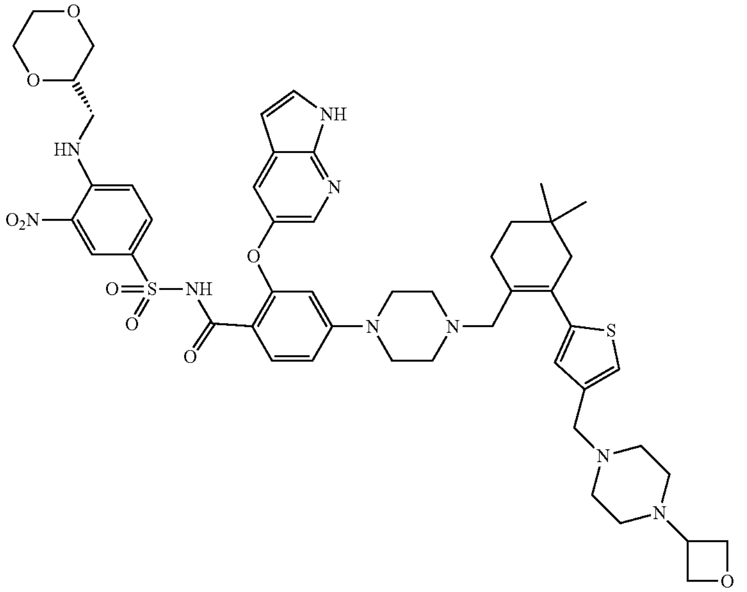
Molecular Weight: 996.20

-continued
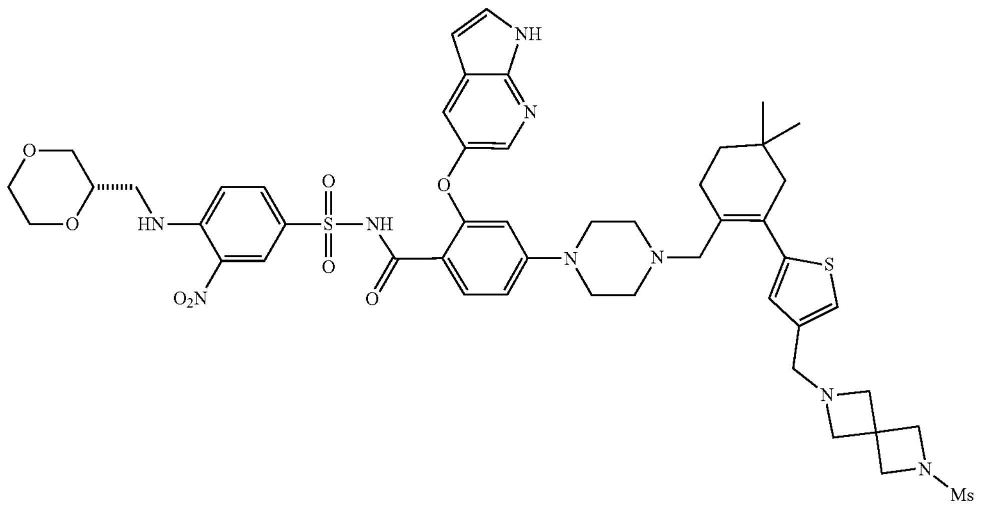
Molecular Weight: 1030.24
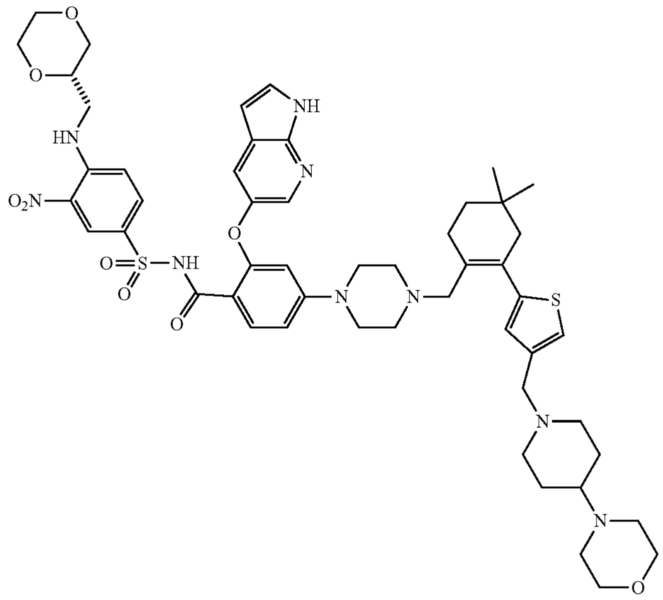
Molecular Weight: 1024.26

-continued
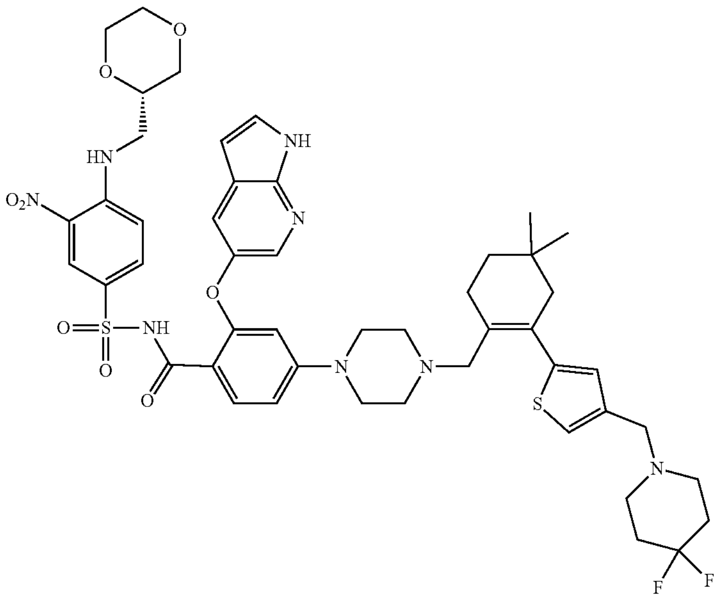
Molecular Weight: 975.13
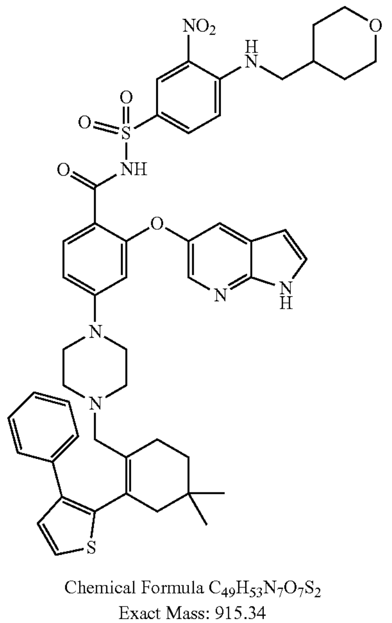
Chemical Formula $C_{49}H_{53}N_7O_7S_2$
Exact Mass: 915.34
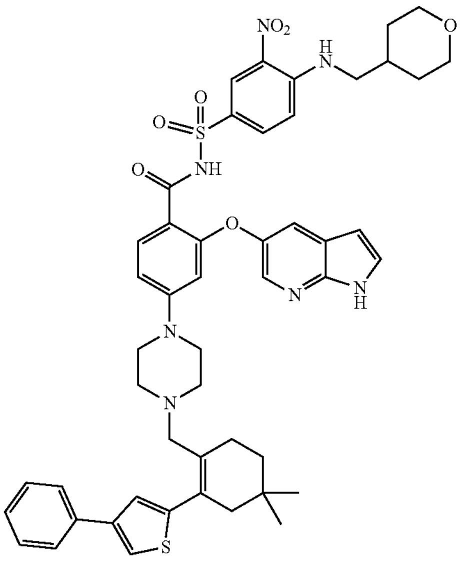
Chemical Formula $C_{49}H_{53}N_7O_7S_2$
Exact Mass: 915.34

-continued
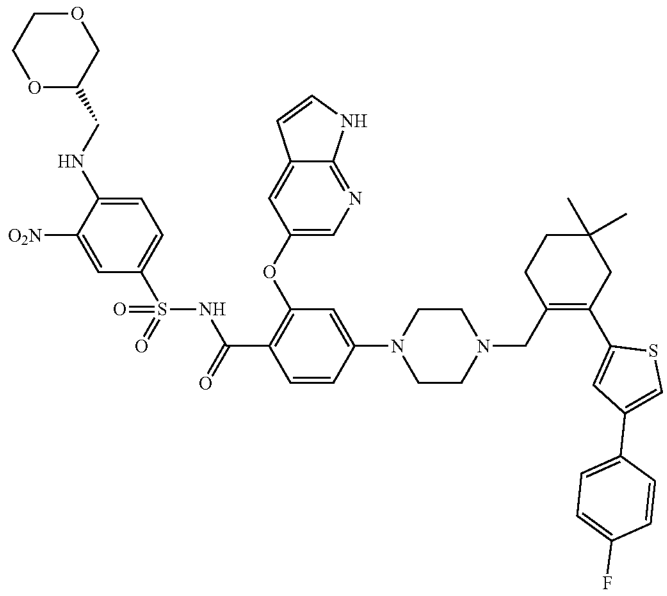
Molecular Weight: 936.08
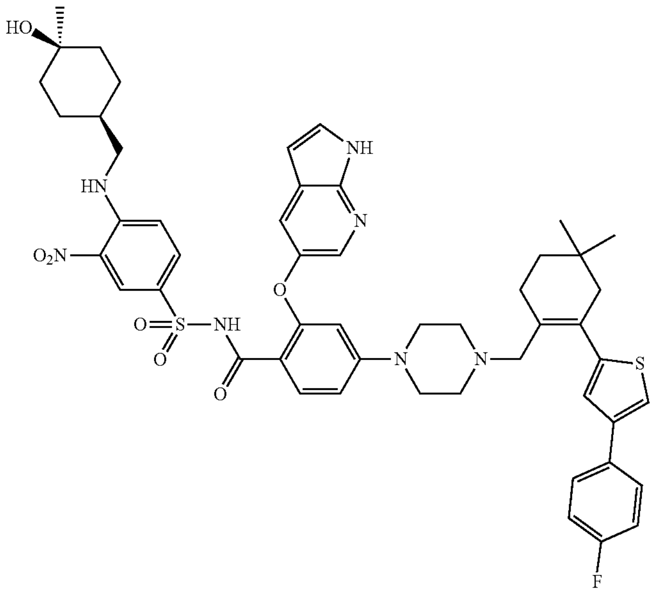
Molecular Weight: 962.16

-continued
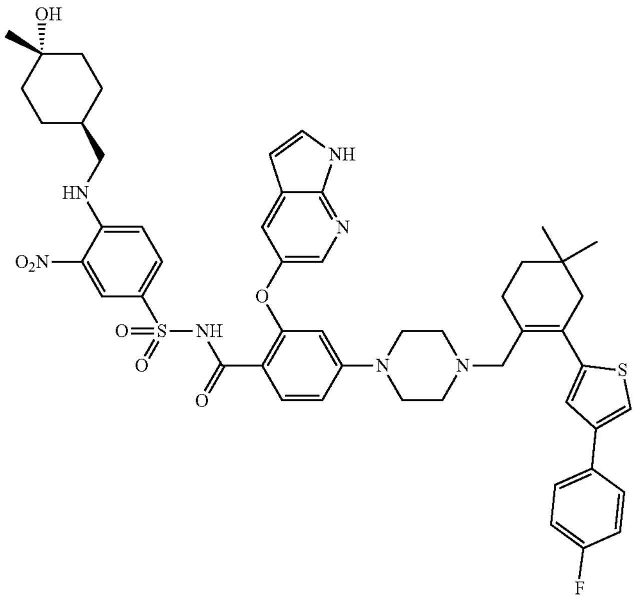
Molecular Weight: 962.16
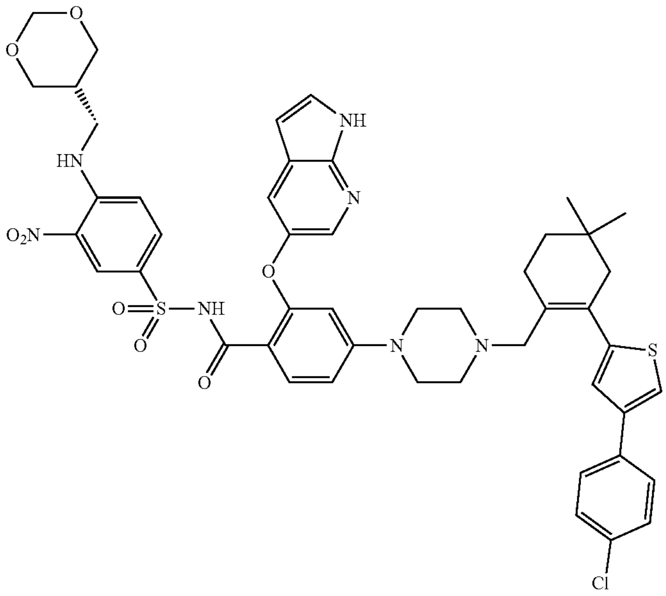
Molecular Weight: 952.54

-continued
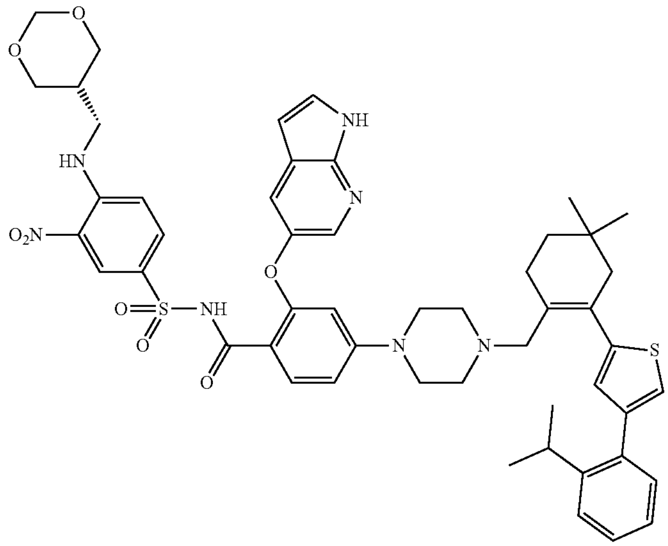
Molecular Weight: 960.17
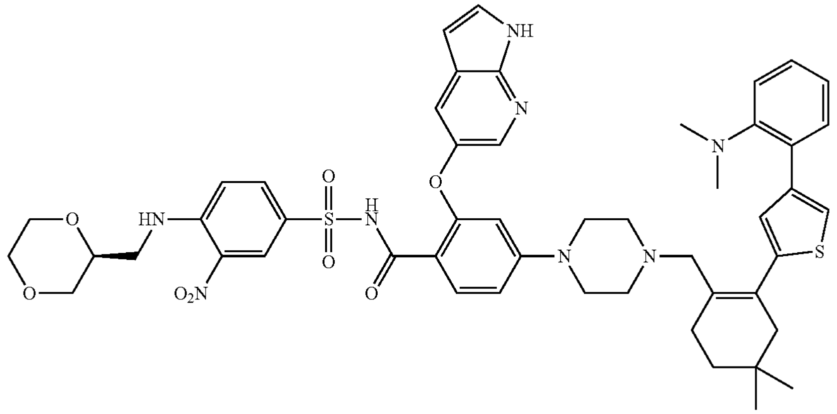
Molecular Weight: 961.16
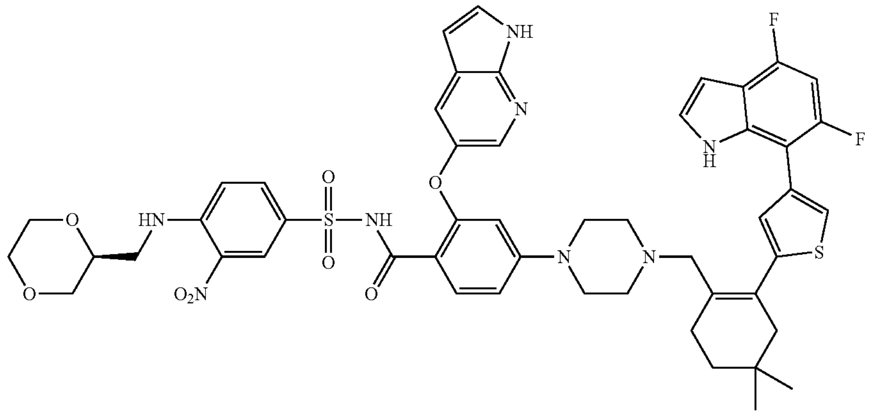
Molecular Weight: 993.11

-continued
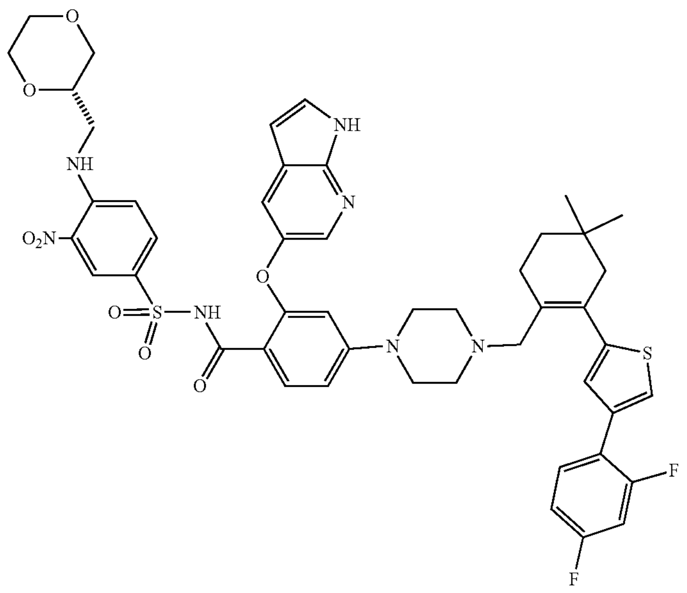
Molecular Weight: 954.07
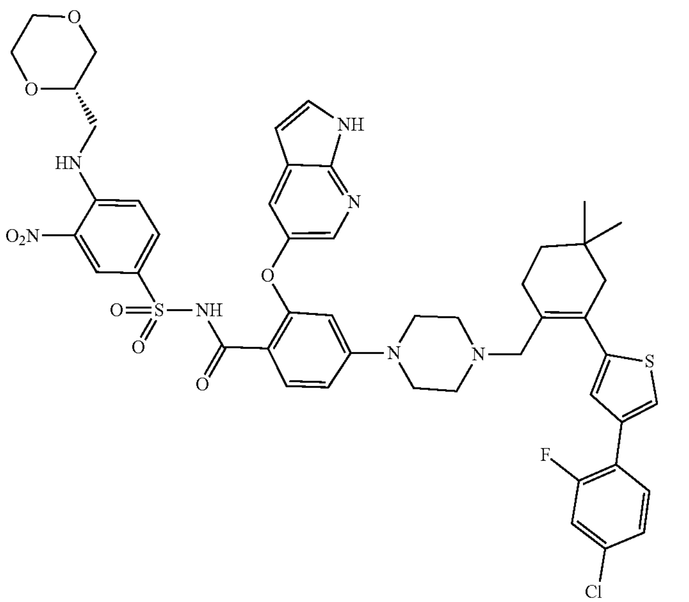
Molecular Weight: 970.53

-continued
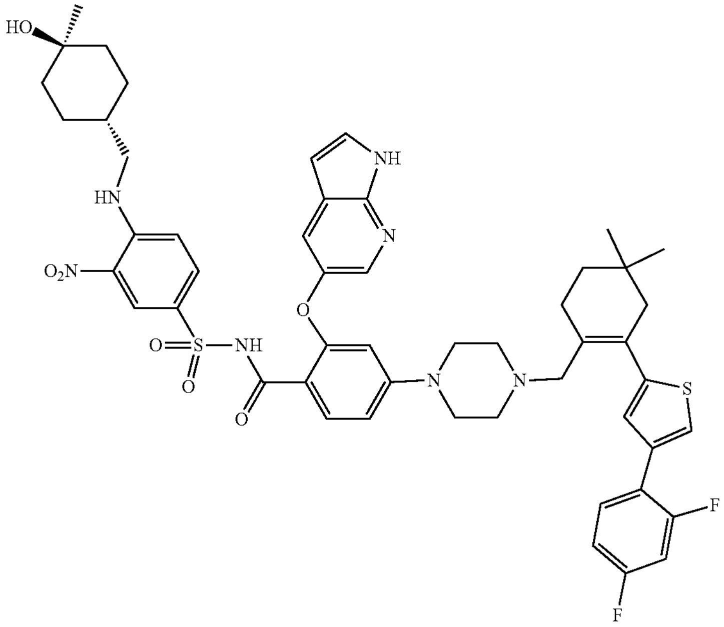
Molecular Weight: 980.15
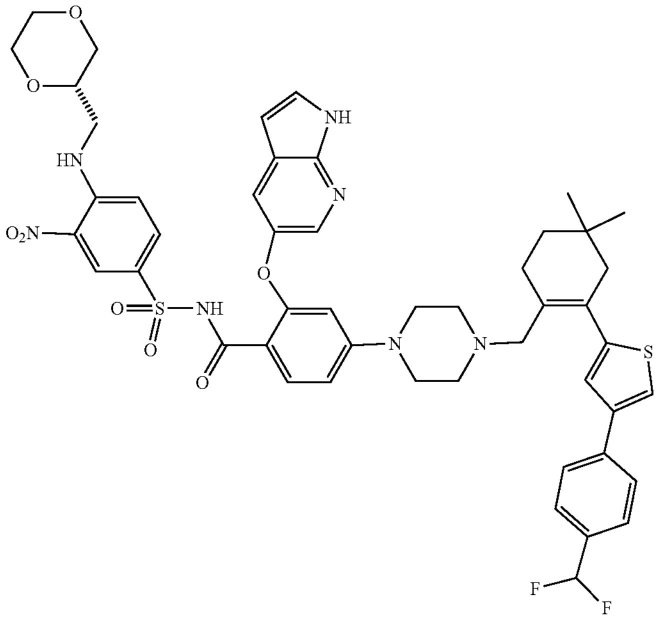
Molecular Weight: 968.10

-continued
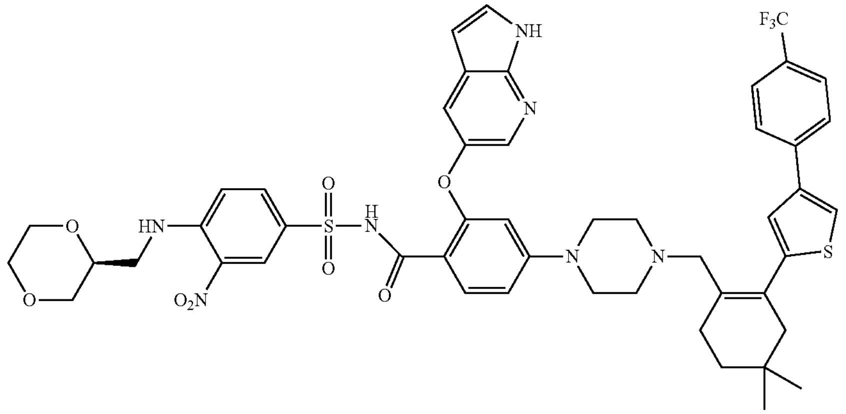
Molecular Weight: 986.09
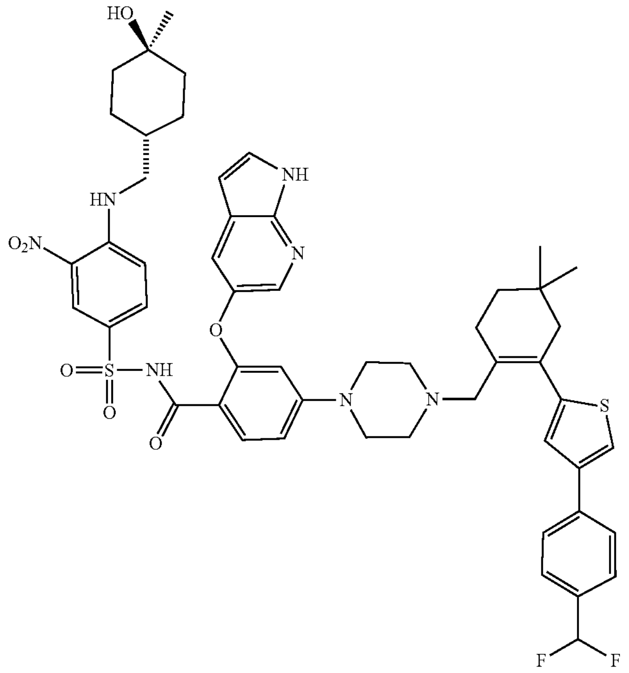
Molecular Weight: 994.18
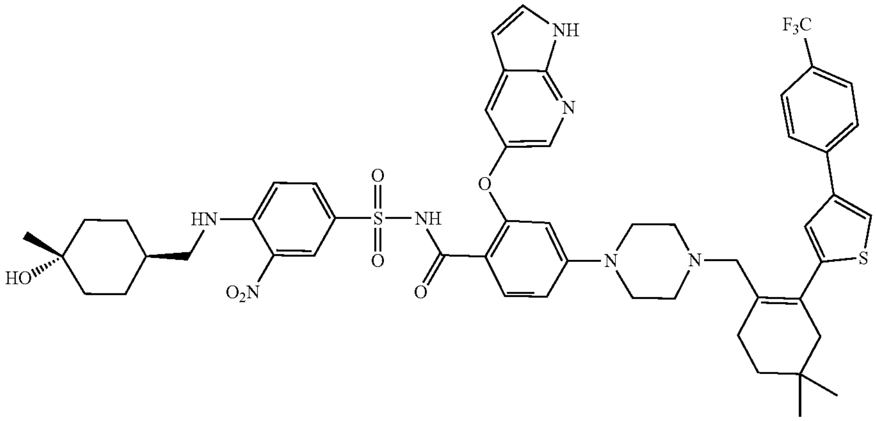
Molecular Weight: 1012.17

-continued
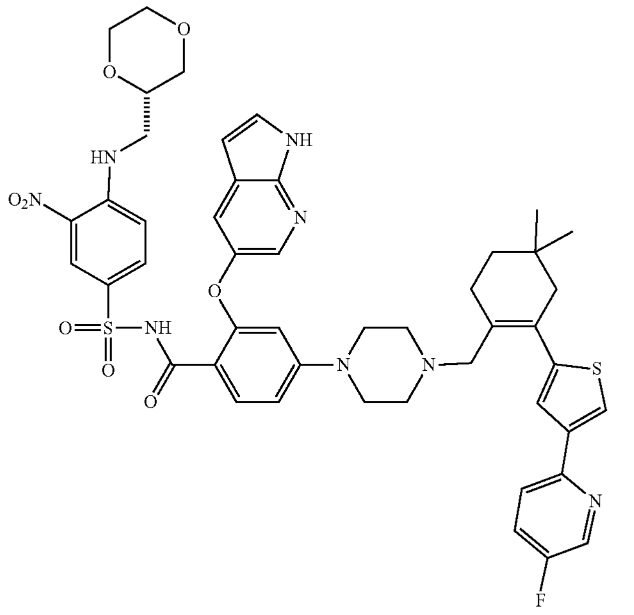
Molecular Weight: 937.07
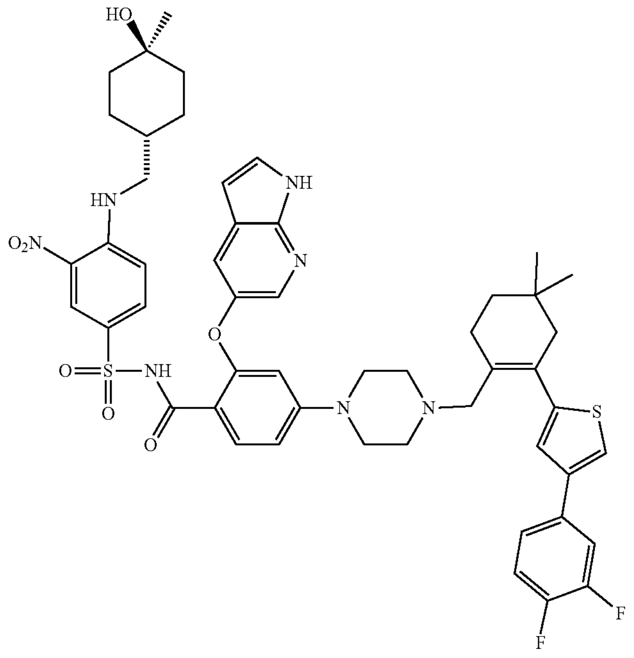
Molecular Weight: 980.15

-continued
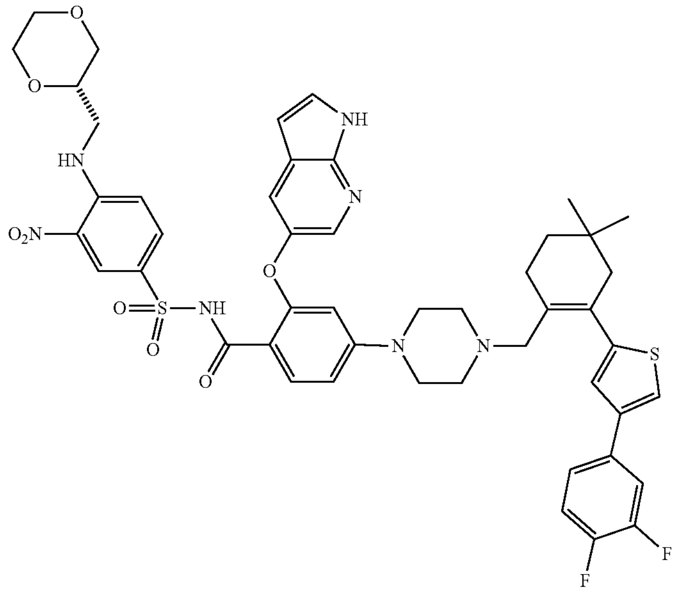
Molecular Weight: 954.07
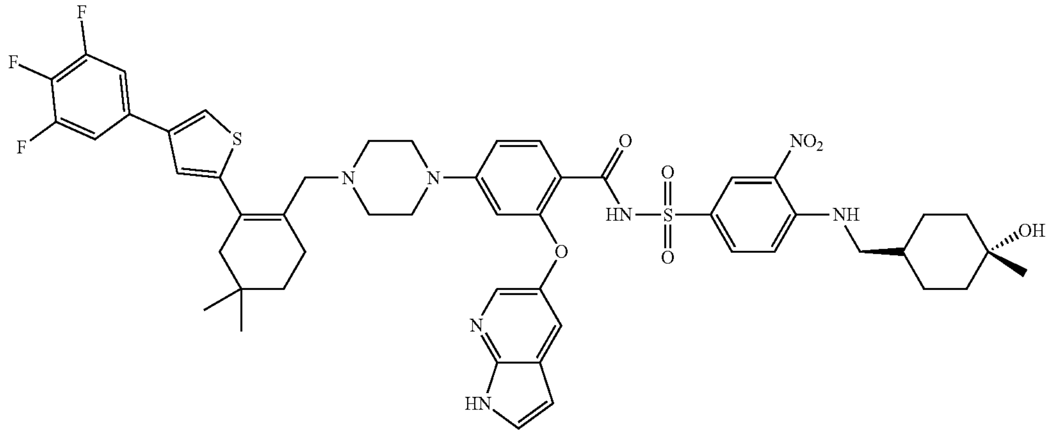
Molecular Weight: 998.15
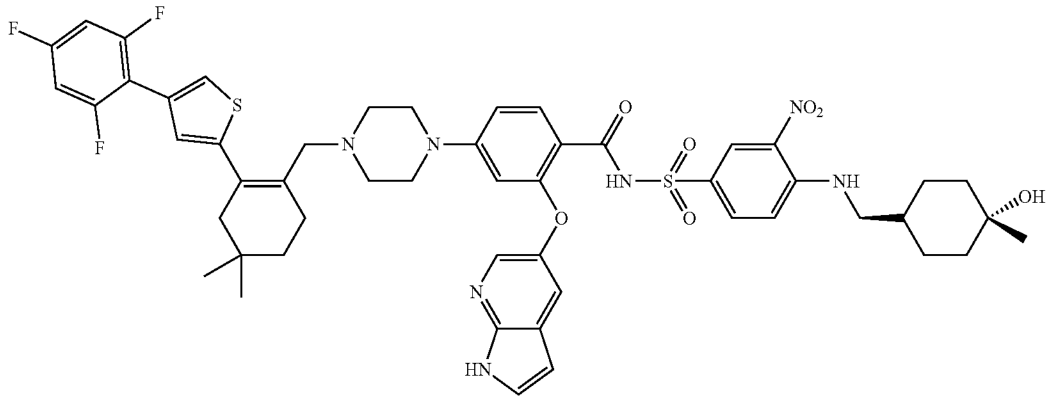
Molecular Weight: 998.15

-continued
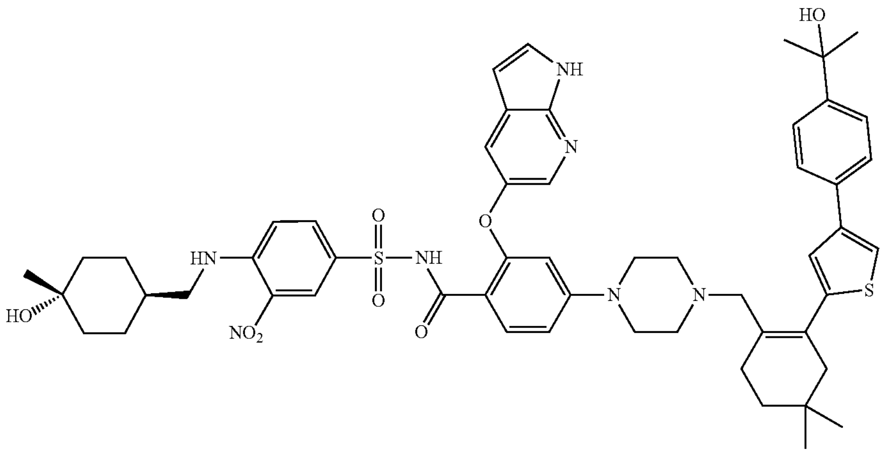
Molecular Weight: 1002.26
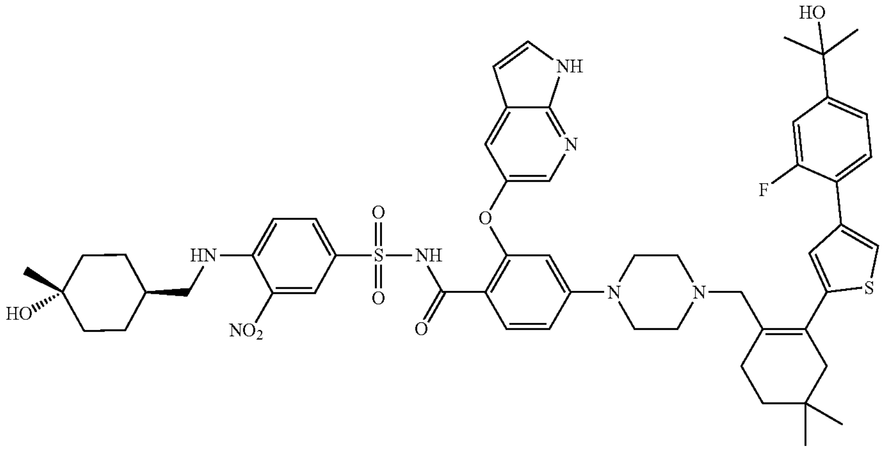
Molecular Weight: 1020.25
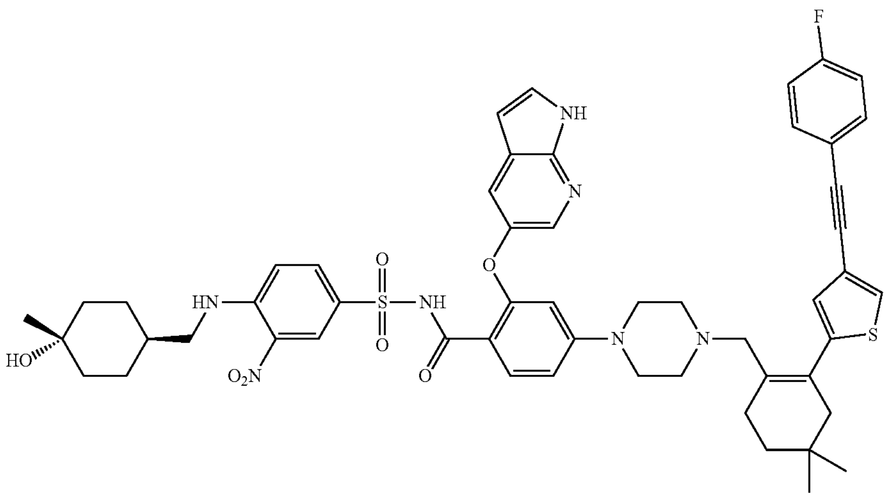
Molecular Weight: 986.19

-continued
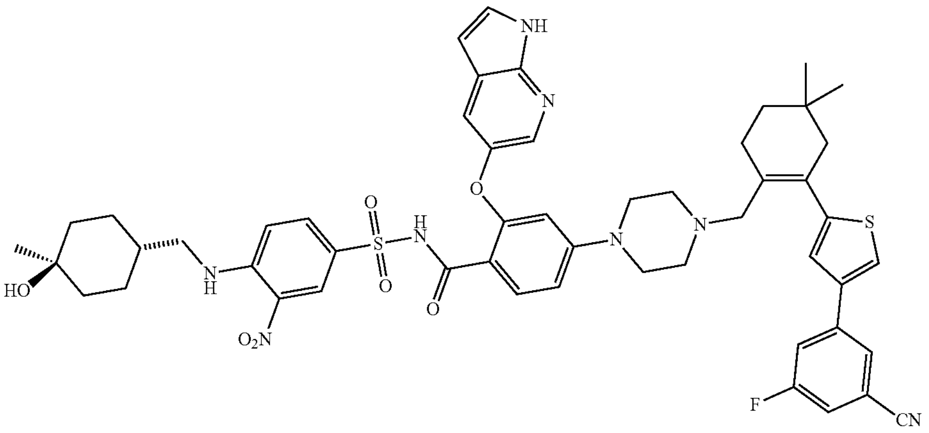
Molecular Weight: 987.18
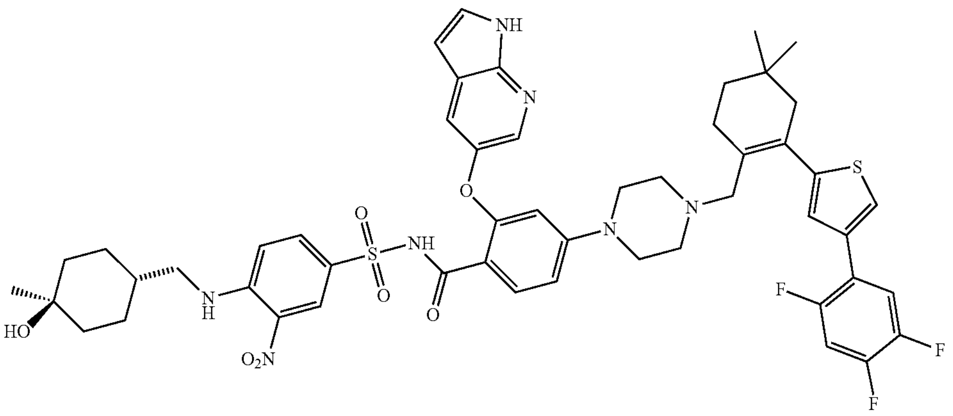
Molecular Weight: 998.15
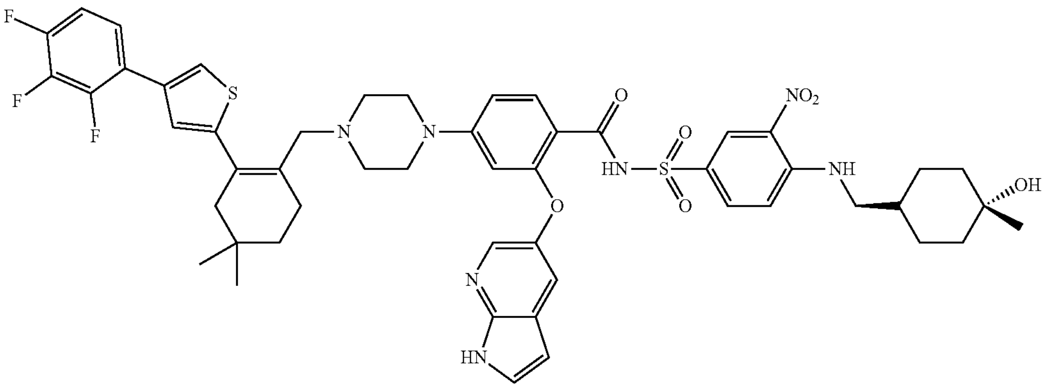
Molecular Weight: 998.15

-continued
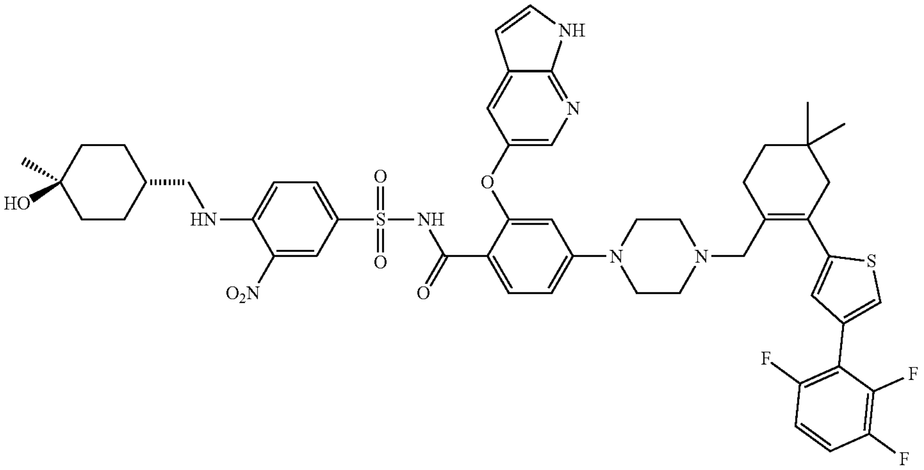
Molecular Weight: 998.15
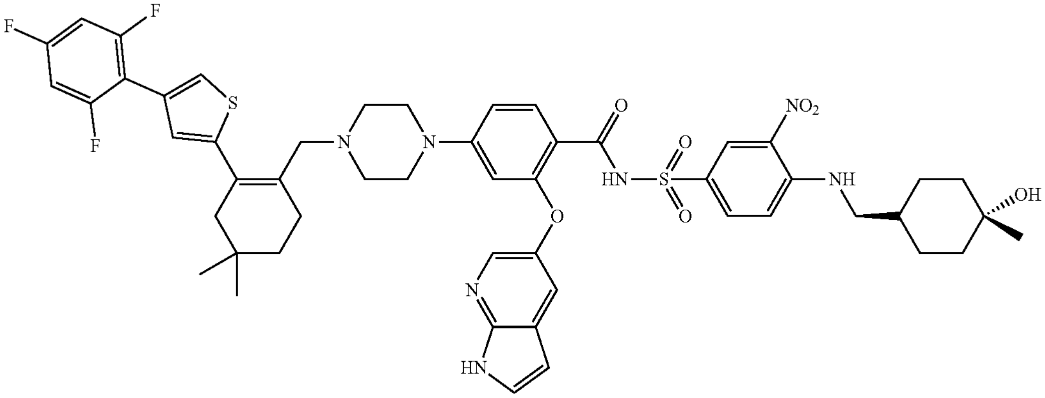
Molecular Weight: 998.15
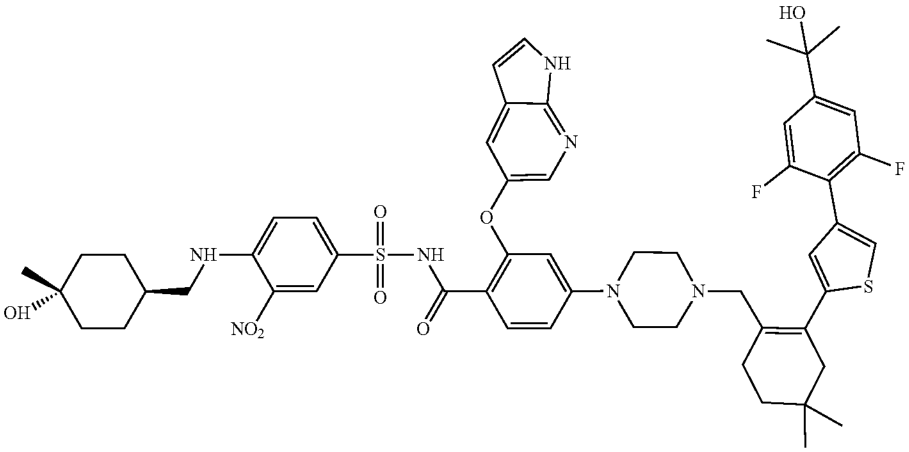
Molecular Weight: 1038.24

-continued
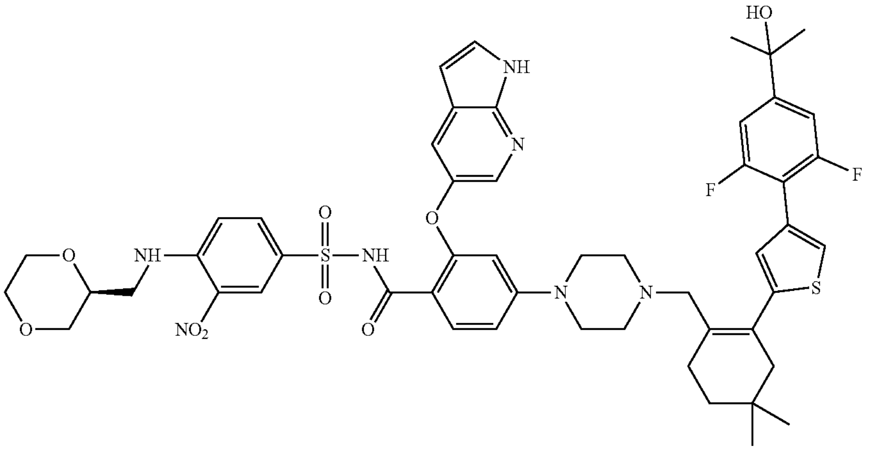
Molecular Weight: 1012.16
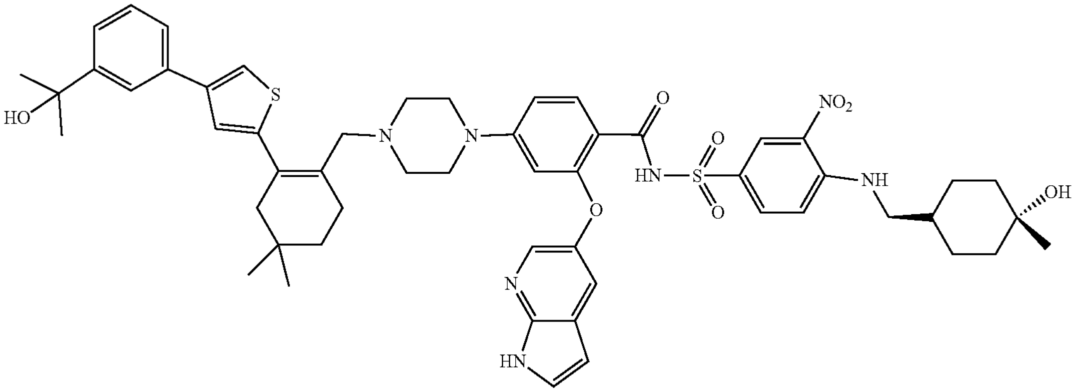
Molecular Weight: 1002.26
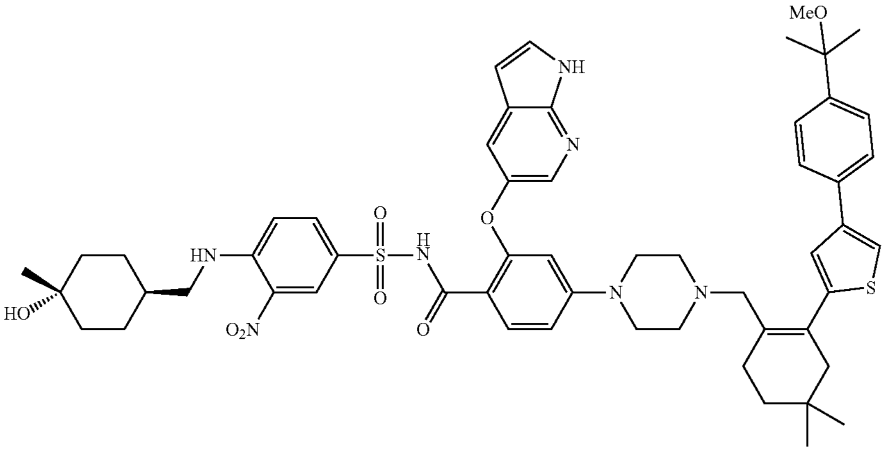
Molecular Weight: 1016.29

-continued
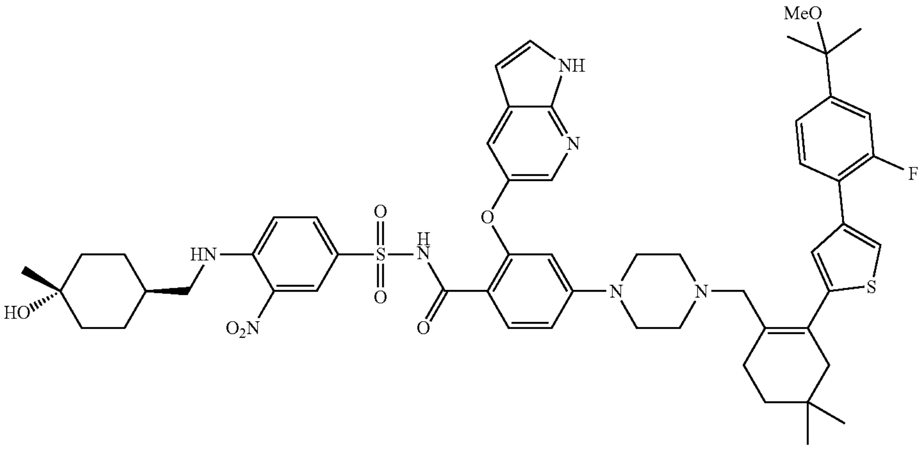
Molecular Weight: 1034.28
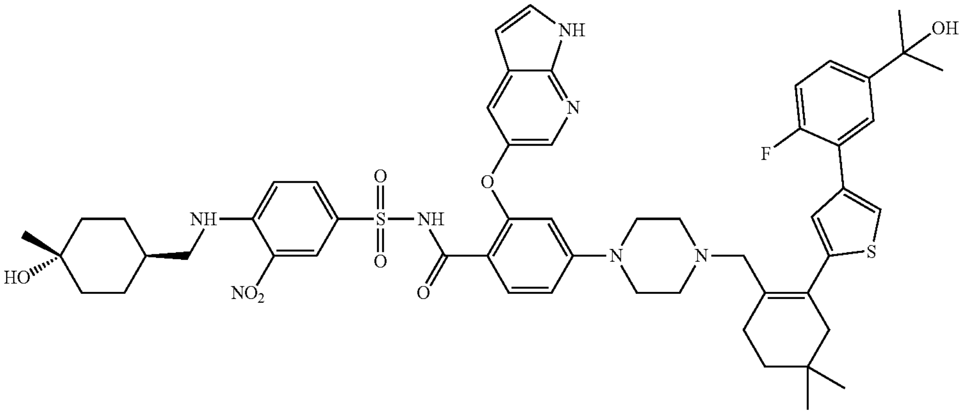
Molecular Weight: 1020.25
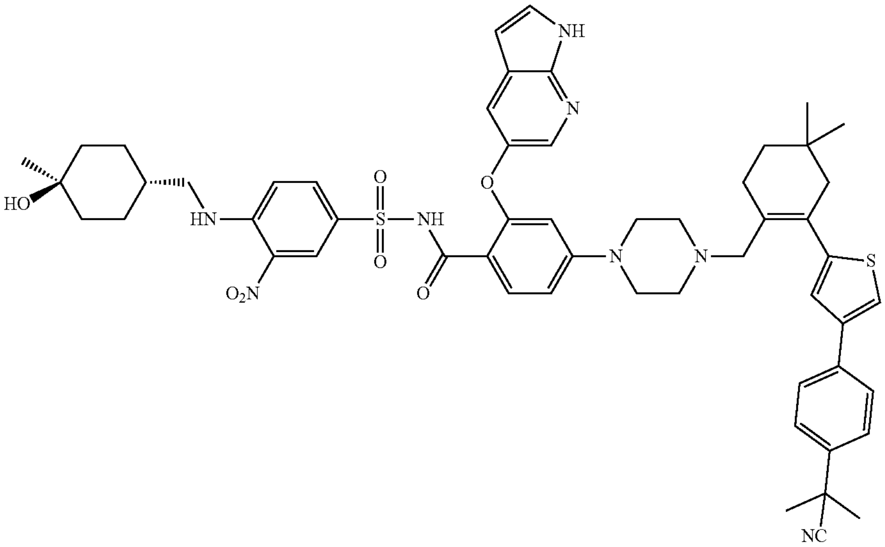
Molecular Weight: 1011.27

-continued
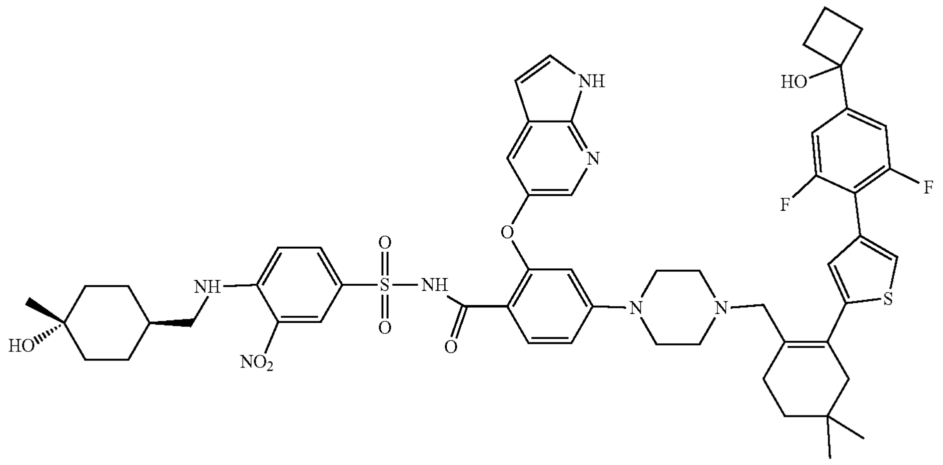
Molecular Weight: 1050.25
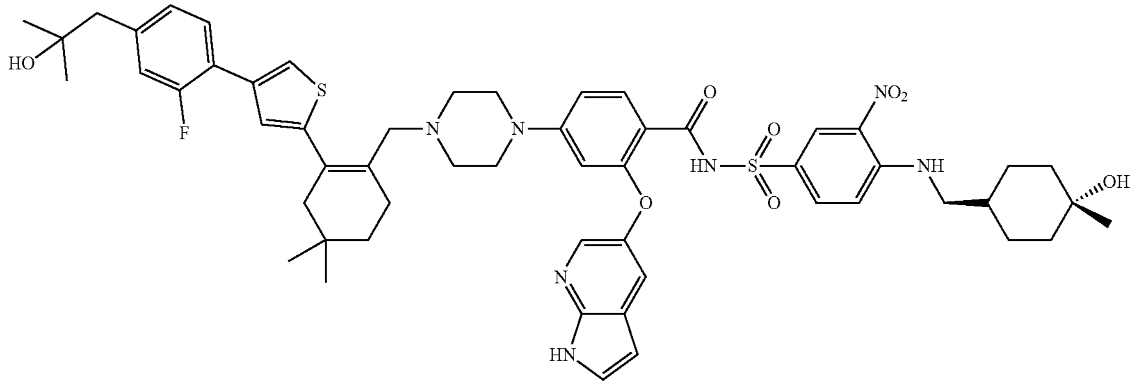
Molecular Weight: 1034.28
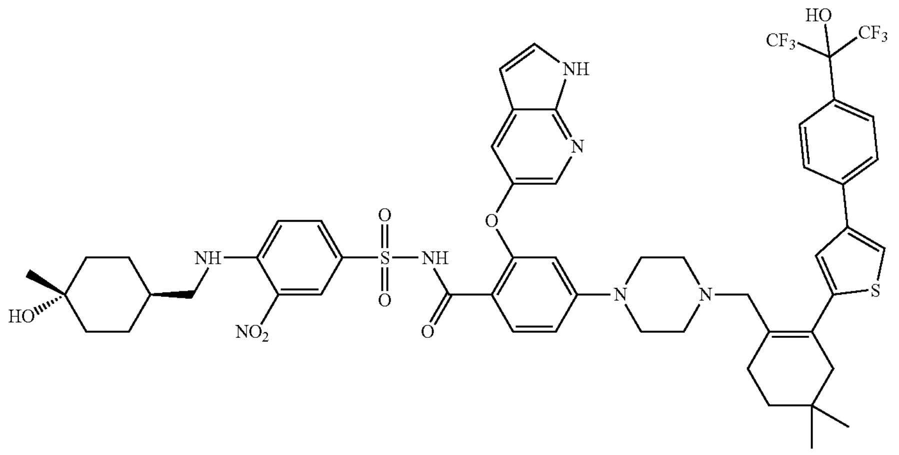
Molecular Weight: 1110.20

-continued
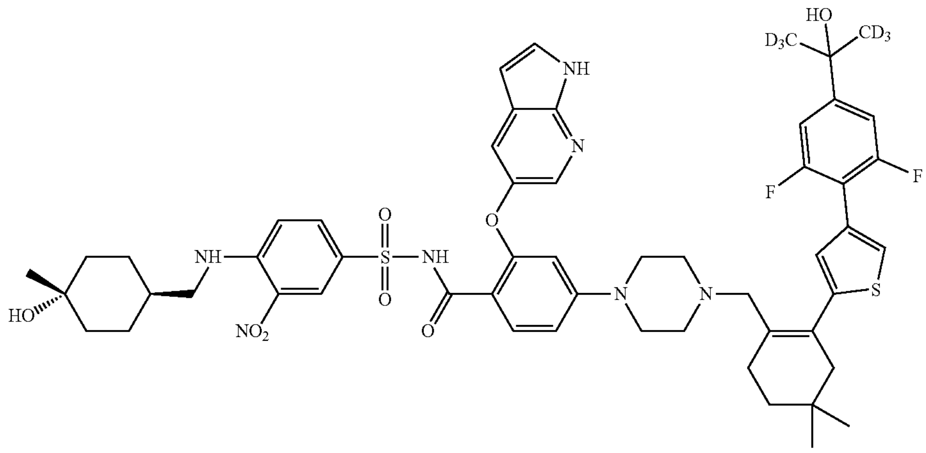
Molecular Weight: 1044.28
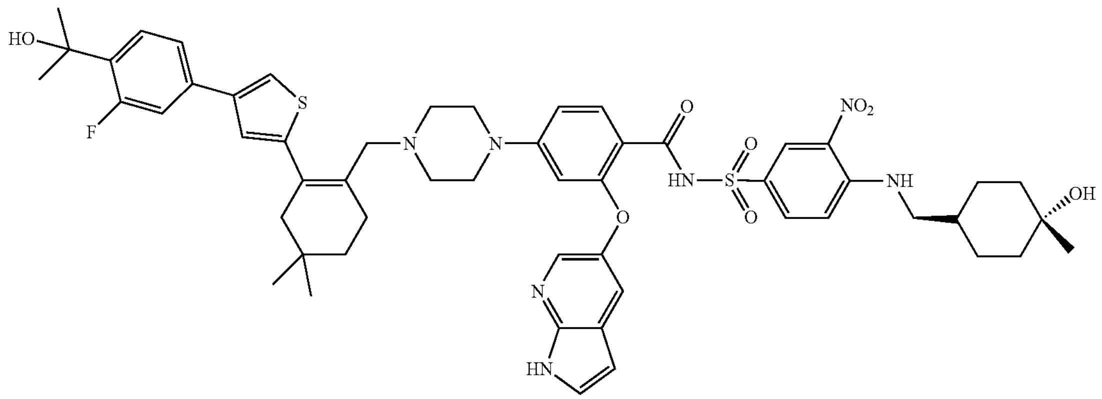
Molecular Weight: 1020.25
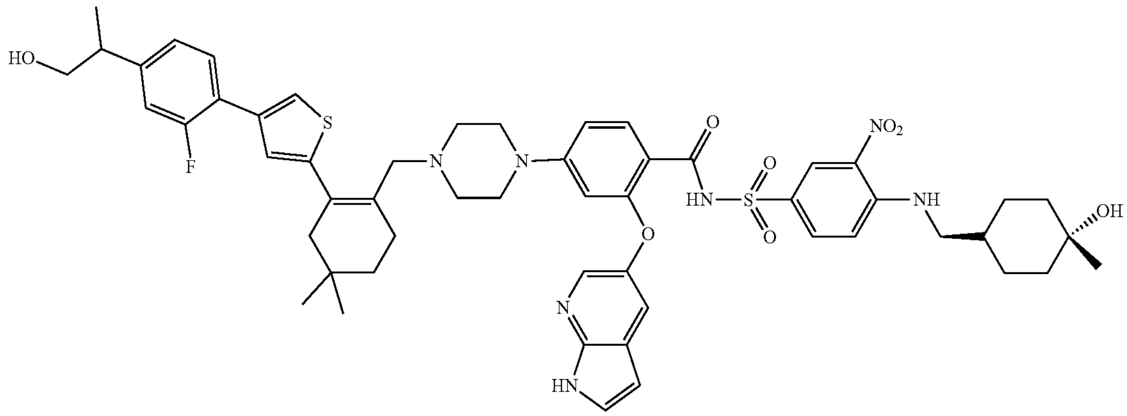
Molecular Weight: 1020.25

-continued
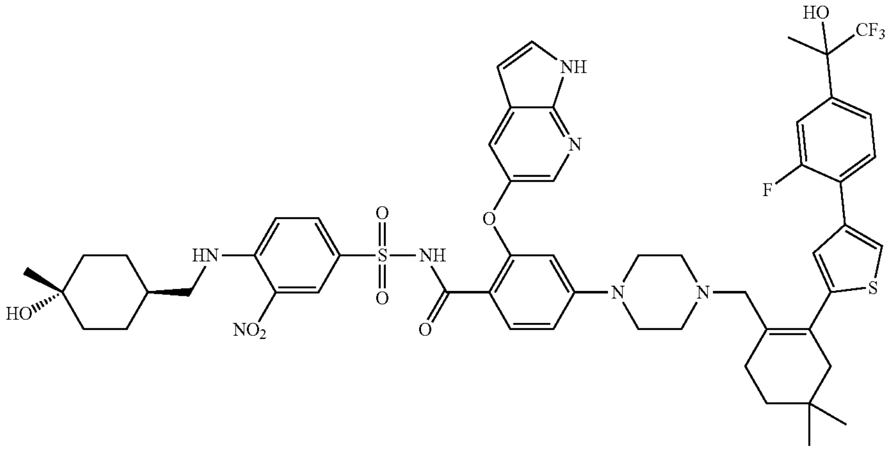
Molecular Weight: 1074.22
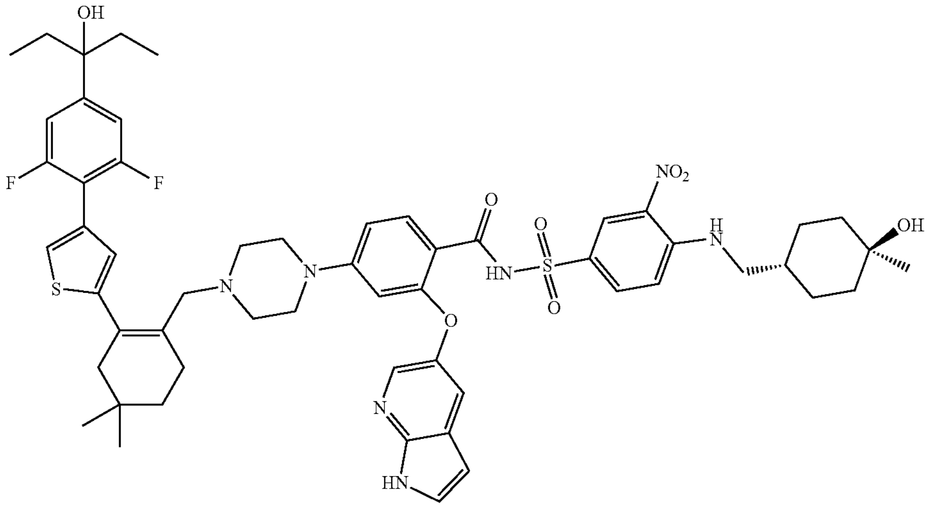
Molecular Weight: 1066.29
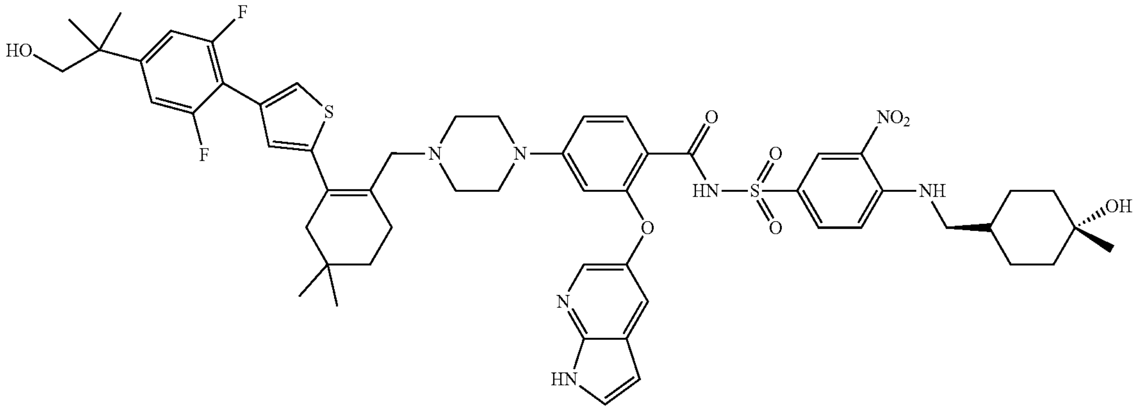
Molecular Weight:1052.27

-continued
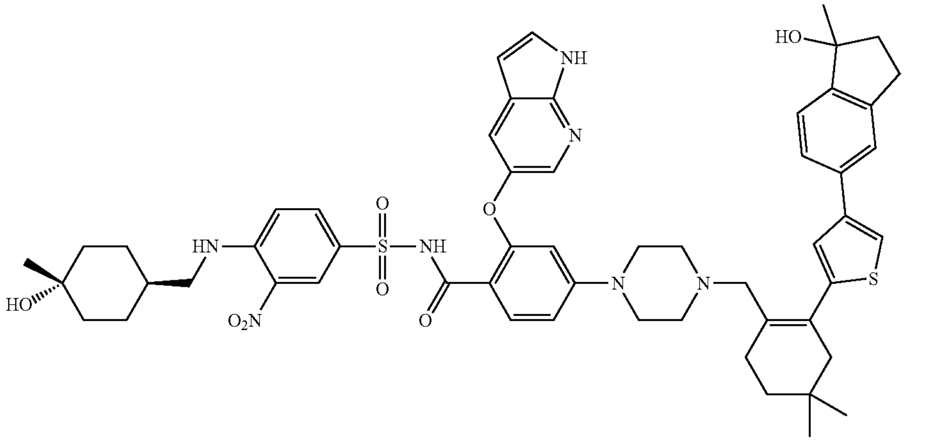
Molecular Weight:1014.27
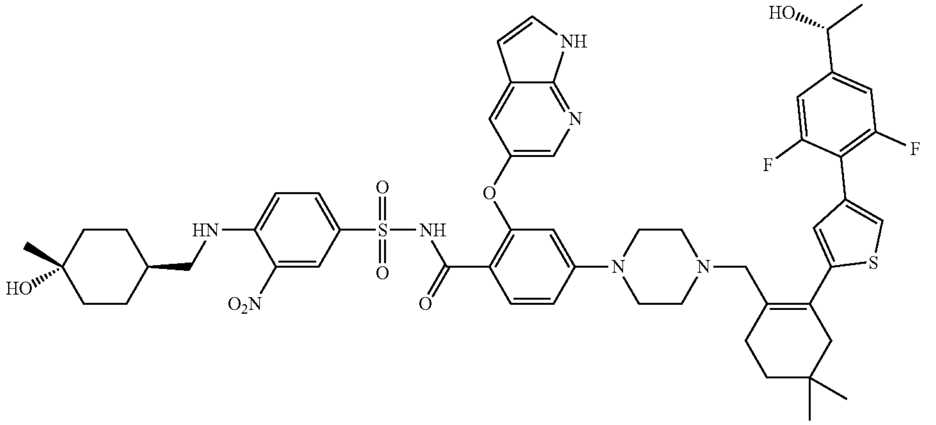
Molecular Weight:1024.21
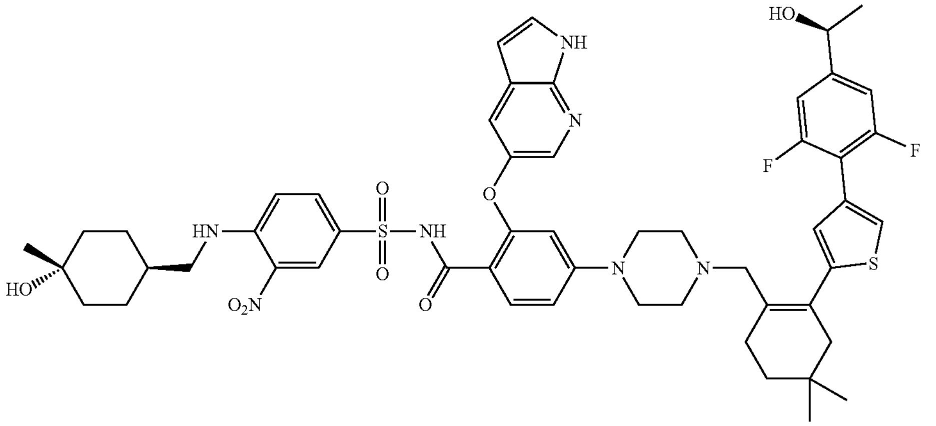
Molecular Weight: 1024.21

-continued
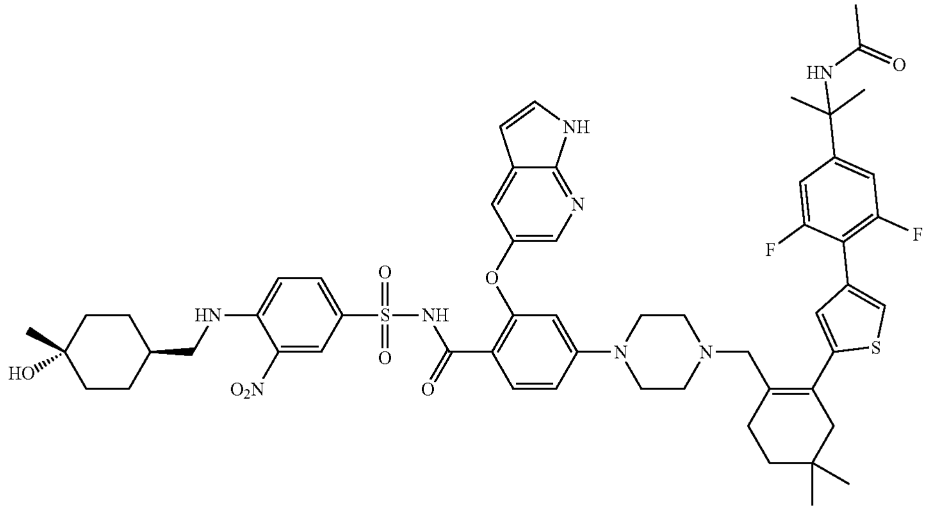
Molecular Weight: 1079.29
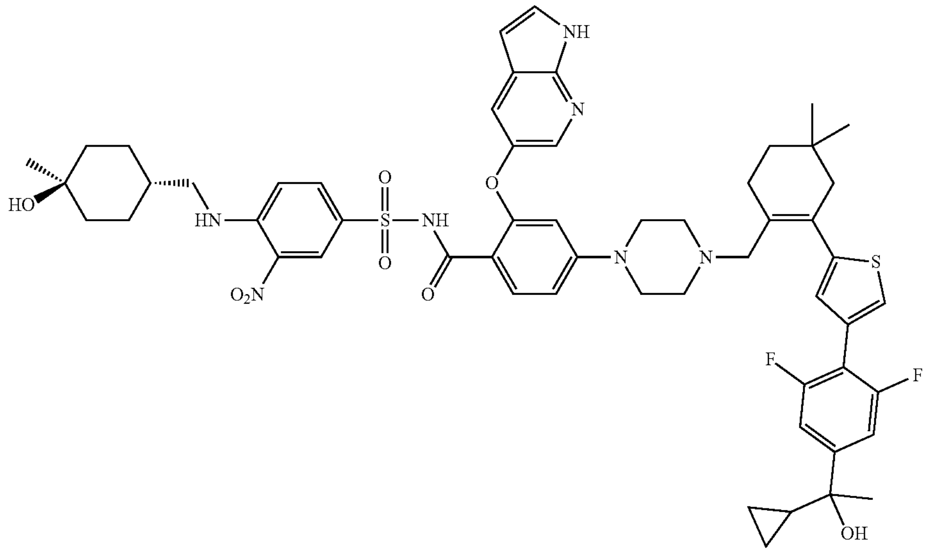
Molecular Weight: 1064.28
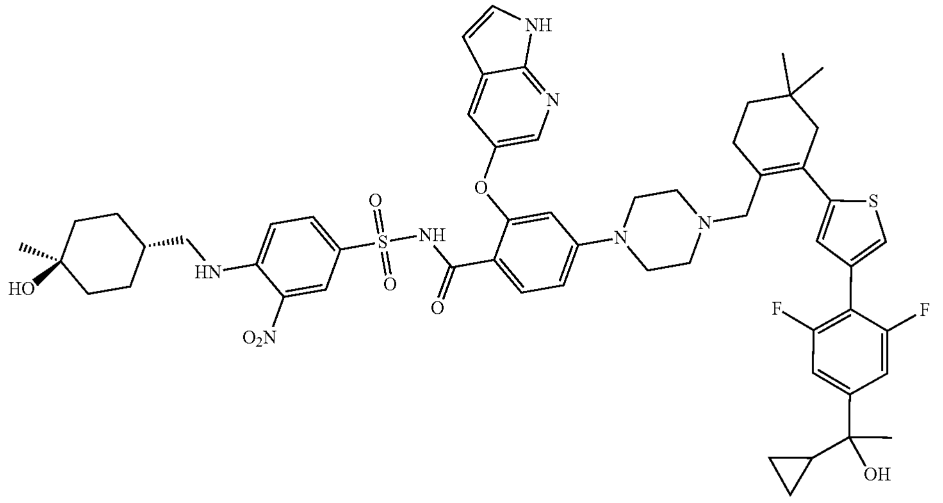
Molecular Weight: 1064.28

-continued
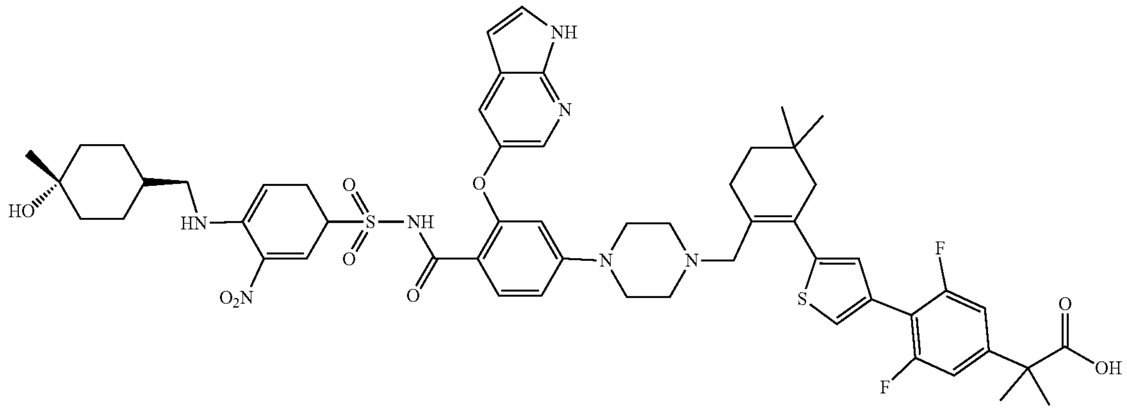
Molecular Weight: 1066.25
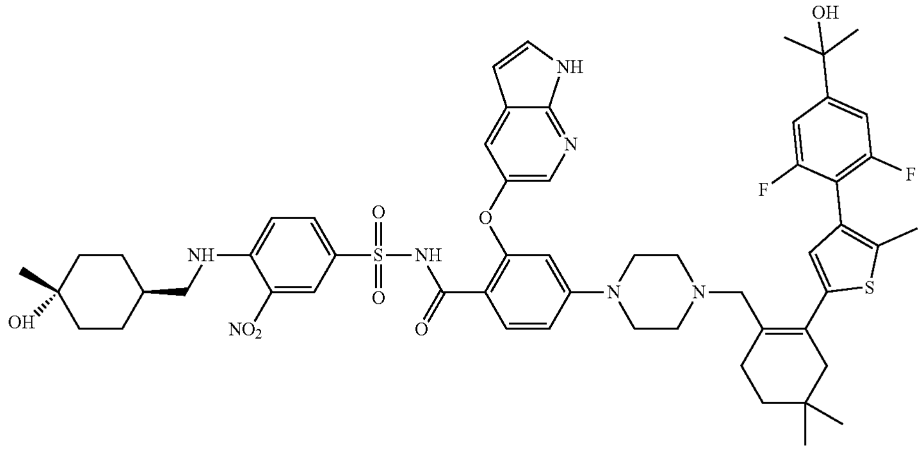
Molecular Weight: 1052.27
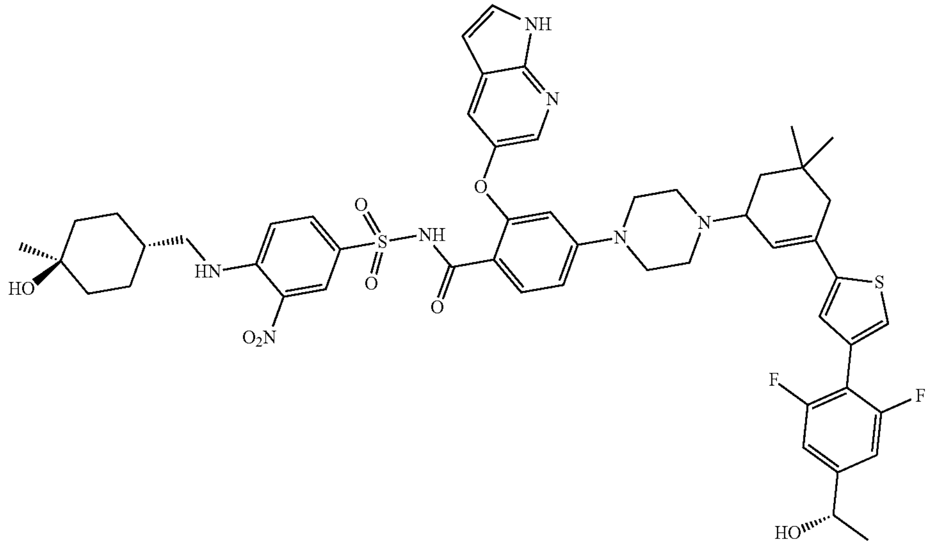
Molecular Weight: 1024.21

-continued

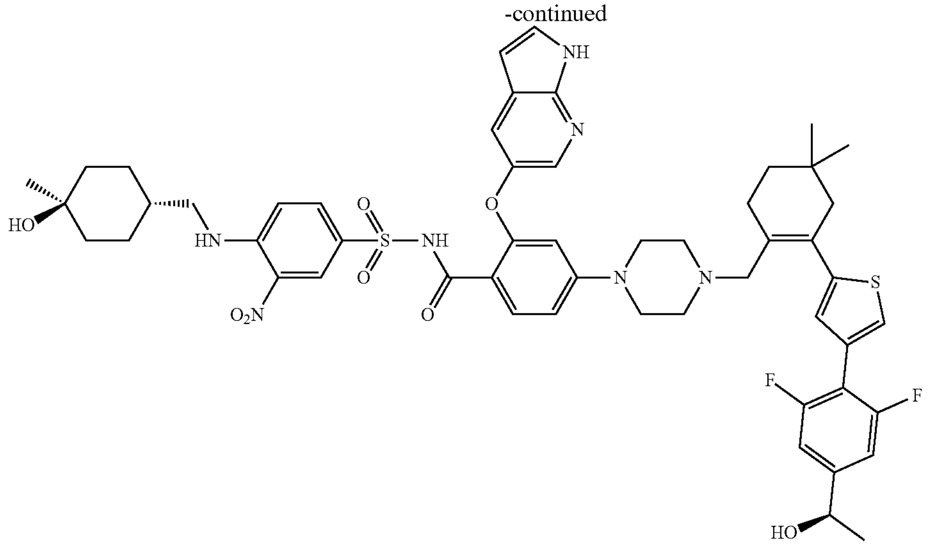

Molecular Weight: 1024.21

One embodiment of the present disclosure includes a compound of the present disclosure in a pharmaceutically acceptable salt form as a trifluoroacetate or formate.

One embodiment of the present disclosure includes a compound of the present disclosure, wherein at least one hydrogen atom is replaced with a deuterium atom.

One embodiment of the present disclosure includes a pharmaceutical composition comprising the compound of the present disclosure, or a pharmaceutically acceptable salt or solvate thereof, and a pharmaceutically acceptable carrier.

One embodiment of the present disclosure includes a method of treating a patient, the method comprising administering to the patient a therapeutically effective amount of the compound of the present disclosure, or a pharmaceutically acceptable salt or solvate thereof, wherein the patient has a hyperproliferative disease. The method of the present disclosure includes wherein the hyperproliferative disease is cancer. The method of the present disclosure includes wherein the cancer is selected from one or more of the cancers of Table 2. The method of the present disclosure includes wherein the cancer is selected from the group consisting of acute monocytic leukemia, acute myelogenous leukemia, chronic myelogenous leukemia, chronic lymphocytic leukemia mixed lineage leukaemia, NUT-midline carcinoma, multiple myeloma, small cell lung cancer, neuroblastoma, Burkitt's lymphoma, cervical cancer, esophageal cancer, ovarian cancer, colorectal cancer, prostate cancer, and breast cancer. The method of the present disclosure includes administering a therapeutically effective amount of a second therapeutic agent useful in the treatment of the disease.

One embodiment of the present disclosure includes a pharmaceutical composition comprising the compound of the present disclosure, or a pharmaceutically acceptable salt or solvate thereof, and a pharmaceutically acceptable carrier. One embodiment of the present disclosure includes a pharmaceutical composition of the present disclosure for use in treating a hyperproliferative disease. One embodiment of the present disclosure includes a pharmaceutical composition of the present disclosure wherein the hyperproliferative disease is cancer. One embodiment of the present disclosure includes a pharmaceutical composition of the present disclosure wherein the cancer is selected from one or more of the cancers of Table 2. One embodiment of the present disclosure includes a pharmaceutical composition of the present disclosure wherein the cancer is selected from the group consisting of acute monocytic leukemia, acute myelogenous leukemia, chronic myelogenous leukemia, chronic lymphocytic leukemia mixed lineage leukaemia, NUT-midline carcinoma, multiple myeloma, small cell lung cancer, neuroblastoma, Burkitt's lymphoma, cervical cancer, esophageal cancer, ovarian cancer, colorectal cancer, prostate cancer, and breast cancer.

One embodiment of the present disclosure includes a compound of the present disclosure or a pharmaceutically acceptable salt or solvate thereof, for use in treatment of a hyperproliferative disease. One embodiment includes wherein the hyperproliferative disease is cancer. One embodiment includes wherein the cancer is selected from one or more of the cancers of Table 2. One embodiment includes wherein the cancer is selected from the group consisting of acute monocytic leukemia, acute myelogenous leukemia, chronic myelogenous leukemia, chronic lymphocytic leukemia mixed lineage leukaemia, NUT-midline carcinoma, multiple myeloma, small cell lung cancer, neuroblastoma, Burkitt's lymphoma, cervical cancer, esophageal cancer, ovarian cancer, colorectal cancer, prostate cancer, and breast cancer.

One embodiment of the present disclosure includes the use of a compound of the present disclosure or a pharmaceutically acceptable salt or solvate thereof, for the manufacture of a medicament for treatment of a hyperproliferative disease. One embodiment of the present disclosure includes wherein the hyperproliferative disease is cancer. One embodiment of the present disclosure includes wherein the cancer is selected from one or more of the cancers of Table 2. One embodiment of the present disclosure includes wherein the cancer is selected from the group consisting of acute monocytic leukemia, acute myelogenous leukemia, chronic myelogenous leukemia, chronic lymphocytic leukemia mixed lineage leukaemia, NUT-midline carcinoma, multiple myeloma, small cell lung cancer, neuroblastoma, Burkitt's lymphoma, cervical cancer, esophageal cancer, ovarian cancer, colorectal cancer, prostate cancer, and breast cancer.

One embodiment of the present disclosure includes a kit comprising the compound of the present disclosure, or a pharmaceutically acceptable salt or solvate thereof, and instructions for administering the compound, or a pharmaceutically acceptable salt or solvate thereof, to a patient having a hyperproliferative disease. One embodiment of the present disclosure includes wherein the hyperproliferative disease is cancer. One embodiment of the present disclosure includes wherein the cancer is selected from one or more of the cancers of Table 2. One embodiment of the present disclosure includes wherein the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, neuroblastoma, Burkitt's lymphoma, cervical cancer, esophageal cancer, ovarian cancer, colorectal cancer, prostate cancer, and breast cancer. One embodiment of the present disclosure includes one or more additional therapeutic agents.

In another aspect, the present disclosure provides a pharmaceutical composition comprising a Compound of the Disclosure and one or more pharmaceutically acceptable carriers.

In another aspect, the present disclosure provides a method of inhibiting Bcl-2 proteins, e.g., Bcl-2, Bcl-2 WT, Bcl-xL, Mcl-1, and Bfl-1/A1, or any combination thereof, in a subject, e.g., a human, comprising administering to the subject an effective amount of at least one Compound of the Disclosure. In one embodiment, this aspect provides a method of inhibiting Bcl-2 WT. In one embodiment, this aspect provides a method of inhibiting the G101V mutant.

In another aspect, the present disclosure provides methods for treating or preventing diseases, disorders, or conditions, e.g., a hyperproliferative disease, e.g., cancer, e.g., small cell lung cancer, non-Hodgkin's lymphoma (NHL), acute myelogenous leukemia (AML), chronic lymphoid (or lymphocytic) leukemia (CLL), or acute lymphoblastic leukemia (ALL), in a subject responsive to inhibition of Bcl-2 proteins, e.g., Bcl-2 WT and/or Bcl-2 G101V, comprising administering to the subject a therapeutically effective amount of a Compound of the Disclosure.

In another aspect, the present disclosure provides the use of Compounds of the Disclosure as inhibitors of one or more Bcl-2 proteins, e.g., Bcl-2 WT and/or Bcl-2 G101V.

In another aspect, the present disclosure provides the use of Compounds of the Disclosure as inhibitors of Bcl-2 WT.

In another aspect, the present disclosure provides the use of Compounds of the Disclosure as inhibitors of Bcl-2 G101V.

In another aspect, the present disclosure provides a pharmaceutical composition for treating diseases, disorders, or conditions responsive to inhibition of Bcl-2 proteins, e.g., Bcl-2 WT and/or Bcl-2 G101V, wherein the pharmaceutical composition comprises a therapeutically effective amount of a Compound of the Disclosure optionally admixed with one or more pharmaceutically acceptable carriers.

In another aspect, the present disclosure provides Compounds of the Disclosure for use in treating or preventing a disease, disorder, or condition, e.g., a hyperproliferative disease, e.g., cancer, in a subject, e.g., a human.

In another aspect, the present disclosure provides a Compound of the Disclosure for use in the manufacture of a medicament for treating a disease, disorder, or condition, e.g., a hyperproliferative disease, e.g., cancer, in a subject, e.g., a human.

In another aspect, the present disclosure provides kit comprising a Compound of the Disclosure.

In another aspect, the present disclosure provides a kit comprising a Compound of the Disclosure and a second therapeutic agent useful in the treatment of a disease, disorder, or condition of interest, and a package insert containing directions for use in the treatment of that disease, disorder, or condition.

In another aspect, the present disclosure provides a composition comprising:

(a) a Compound of the Disclosure; (b) a second therapeutically active agent; and (c) optionally an excipient and/or pharmaceutically acceptable carrier.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Compounds of the Disclosure inhibit Bcl-2 proteins, e.g., Bcl-2 WT and/or Bcl-2 G101V. Compounds of the Disclosure are useful for treating or preventing diseases, disorders, or conditions, e.g., a hyperproliferative disease, e.g., cancer, responsive to the inhibition of Bcl-2 proteins in a subject. Cancers responsive to the inhibition of Bcl-2 proteins include, but are not limited to, small cell lung cancer, NHL, AML, CLL, and ALL.

In one embodiment, Compounds of the Disclosure are compounds having Formula I, and include Formulae Ix, Ixi, Iy, and Iyi.

In the present disclosure, the term "halogen" or "halo" as used by itself or as part of another group refers to —Cl, —F, —Br, or —I.

In the present disclosure, the term "nitro" as used by itself or as part of another group refers to $—NO_2$.

In the present disclosure, the term "cyano" as used by itself or as part of another group refers to —CN.

In the present disclosure, the term "hydroxy" as used by itself or as part of another group refers to —OH.

In the present disclosure, the term "amino" as used by itself or as part of another group refers to $—NH_2$.

In the present disclosure, the term "alkyl" as used by itself or as part of another group refers to unsubstituted straight- or branched-chain aliphatic hydrocarbons containing one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. In another embodiment, the alkyl group is a branched chain $C_{3-4}$ alkyl group. In another embodiment, the alkyl group is a straight or branched chain $C_{3-4}$ alkyl group. In another embodiment, the alkyl group is partially or completely deuterated, i.e., one or more hydrogen atoms of the alkyl group are replaced with deuterium atoms. Non-limiting exemplary $C_{1-12}$ alkyl groups include methyl, —$CD_3$, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$alkyl groups include methyl, ethyl, propyl, isopropyl, butyl, sec-butyl, tert-butyl, and iso-butyl. Non-limiting exemplary $C_{1-4}$ groups include methyl, ethyl, propyl, isopropyl, and tert-butyl.

In the present disclosure, the term "optionally substituted alkyl" as used by itself or as part of another group refers to an alkyl that is unsubstituted or substituted with one, two, or three substituents independently selected from the group consisting of halo, nitro, cyano, hydroxy, alkoxy, amino, alkylamino, dialkylamino, and optionally substituted aryl. In one embodiment, the optionally substituted alkyl is substituted with two substituents. In another embodiment, the optionally substituted alkyl is substituted with one substituent. In another embodiment, the optionally substituted alkyl is unsubstituted. Non-limiting exemplary optionally substituted alkyl groups include —$CH_2Ph$, —$CH_2CH_2NO_2$, —$CH_2CH_2OH$, —$CH_2CH_2OCH_3$, and —$CH_2CH_2F$.

In the present disclosure, the term "cycloalkyl" as used by itself or as part of another group refers to unsubstituted saturated or partially unsaturated, e.g., containing one or two double bonds, cyclic aliphatic hydrocarbons containing one to three rings having from three to twelve carbon atoms, i.e., $C_{3-12}$ cycloalkyl, or the number of carbons designated. In one embodiment, the cycloalkyl group has two rings. In one embodiment, the cycloalkyl group has one ring. In another embodiment, the cycloalkyl group is a $C_{3-8}$ cycloalkyl. In another embodiment, the cycloalkyl group is a $C_{3-6}$ cycloalkyl. In another embodiment, the cycloalkyl group is a $C_{3-5}$ cycloalkyl. The term "cycloalkyl" is meant to include groups wherein a ring —$CH_2$— is replaced with a —C(=O)—. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, cyclopentanone, spiro[3.3]heptane, and bicyclo[3.3.1]nonane.

In the present disclosure, the term "optionally substituted cycloalkyl" as used by itself or as part of another group refers to a cycloalkyl that is either unsubstituted or substituted with one, two, or three substituents independently selected from the group consisting of halo, nitro, cyano, hydroxy, alkyl, alkoxy, amino, alkylamino, dialkylamino, haloalkyl, and heterocyclo. In one embodiment, the optionally substituted cycloalkyl is substituted with two substituents. In another embodiment, the optionally substituted cycloalkyl is substituted with one substituent. In another embodiment, the optionally substituted cycloalkyl is unsubstituted.

In the present disclosure, the term "haloalkyl" as used by itself or as part of another group refers to an alkyl substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "alkoxy" as used by itself or as part of another group refers to an optionally substituted alkyl attached to a terminal oxygen atom. In one embodiment, the alkoxy group is a $C_{1-6}$ alkyl attached to a terminal oxygen atom. In another embodiment, the alkoxy group is a $C_{1-4}$ alkyl attached to a terminal oxygen atom. Non-limiting exemplary alkoxy groups include methoxy, ethoxy, and tert-butoxy.

In the present disclosure, the term "aryl" as used by itself or as part of another group refers to unsubstituted monocyclic or bicyclic aromatic ring systems having from six to fourteen carbon atoms, i.e., a $C_{6-14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl.

In the present disclosure, the term "optionally substituted aryl" as used herein by itself or as part of another group refers to an aryl that is either unsubstituted or substituted with one to five substituents independently selected from the group consisting of halo, nitro, cyano, hydroxy, alkyl, alkoxy, amino, alkylamino, dialkylamino, haloalkyl, and heterocyclo. In one embodiment, the optionally substituted aryl is an optionally substituted phenyl. In another embodiment, the optionally substituted phenyl has one substituent. In another embodiment, the optionally substituted phenyl is unsubstituted. Non-limiting exemplary substituted aryl groups include 2-methylphenyl, 2-methoxyphenyl, 2-fluorophenyl, and 4-chlorophenyl.

In the present disclosure, the term "heterocyclo" as used by itself or as part of another group refers to unsubstituted saturated and partially unsaturated, e.g., containing one or two double bonds, cyclic groups containing one, two, or three rings having from three to fourteen ring members, i.e., a 3- to 14-membered heterocyclo, wherein at least one carbon atom of one of the rings is replaced with a heteroatom. The term "heterocyclo" is meant to include cyclic ureido groups such as imidazolidinyl-2-one, cyclic amide groups such as β-lactam, γ-lactam, δ-lactam and ε-lactam, and cyclic carbamate groups such as oxazolidinyl-2-one. In one embodiment, the heterocyclo group is a 4-, 5-, 6-, 7- or 8-membered cyclic group containing one ring and one or two oxygen and/or nitrogen atoms. In one embodiment, the heterocyclo group is a 5- or 6-membered cyclic group containing one ring and one or two nitrogen atoms. In one embodiment, the heterocyclo group is an 8-, 9-, 10-, 11-, or 12-membered cyclic group containing two rings and one or two nitrogen atoms. In one embodiment, the heterocyclo group is a 4- or 5-membered cyclic group containing one ring and one oxygen atom. The heterocyclo can be optionally linked to the rest of the molecule through a carbon or nitrogen atom. Non-limiting exemplary heterocyclo groups include 1,4-dioxane, 2-oxopyrrolidin-3-yl, 2-imidazolidinone, piperidinyl, morpholinyl, piperazinyl, pyrrolidinyl, 8-azabicyclo[3.2.1]octane (nortropane), 6-azaspiro[2.5]octane, 6-azaspiro[3.4]octane, indolinyl, indolinyl-2-one, and 1,3-dihydro-2H-benzo[d]imidazol-2-one.

In the present disclosure, the term "optionally substituted heterocyclo" as used herein by itself or part of another group refers to a heterocyclo that is either unsubstituted or substituted with one, two, or three substituents independently selected from the group consisting of halo, nitro, cyano, hydroxy, alkyl, alkoxy, amino, alkylamino, dialkylamino, haloalkyl, and heterocyclo.

In the present disclosure, the term "alkylamino" as used by itself or as part of another group refers to —$NHR^{10}$, wherein $R^{10}$ is $C_{1-6}$ alkyl. In one embodiment, $R^{10}$ is $C_{1-4}$ alkyl. Non-limiting exemplary alkylamino groups include —$N(H)CH_3$ and —$N(H)CH_2CH_3$.

In the present disclosure, the term "dialkylamino" as used by itself or as part of another group refers to —$NR^{11a}R^{11b}$, wherein $R^{11a}$ and $R^{11b}$ are each independently $C_{1-6}$ alkyl. In one embodiment, $R^{11a}$ and $R^{11b}$ are each independently $C_{1-4}$ alkyl. Non-limiting exemplary dialkylamino groups include —$N(CH_3)_2$ and —$N(CH_3)CH_2CH(CH_3)_2$.

In the present disclosure, the term “(cycloalkyl)alkyl” as used by itself or as part of another group refers to an alkyl substituted with one optionally substituted cycloalkyl group. In one embodiment, the (cycloalkyl)alkyl is a $C_{1-4}$ alkyl substituted with one optionally substituted $C_{3-6}$ cycloalkyl.

In the present disclosure, the term “(heterocyclo)alkyl” as used by itself or as part of another group refers to an alkyl substituted with one optionally substituted heterocyclo group. In one embodiment, the (heterocyclo)alkyl is a $C_{1-4}$ alkyl substituted with one optionally substituted 4- to 6-membered heterocyclo group. The heterocyclo can be linked to the alkyl group through a carbon or nitrogen atom. Non-limiting exemplary (heterocyclo)alkyl groups include:

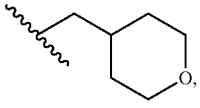
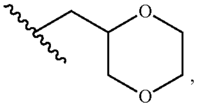
,
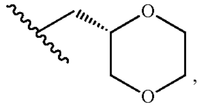
,
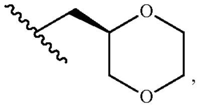
,
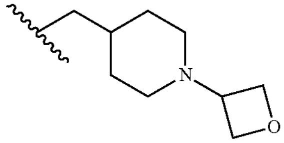
,
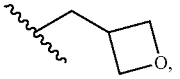
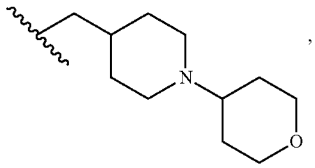
,
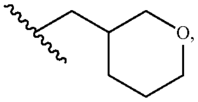
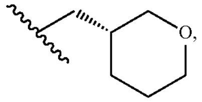
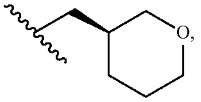
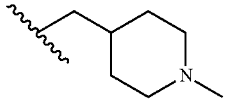
and
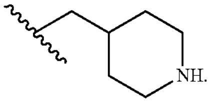

In the present disclosure, the term “heteroalkyl” as used by itself or part of another group refers to unsubstituted straight- or branched-chain aliphatic hydrocarbons containing from six to twelve chain atoms, i.e., 6- to 12-membered heteroalkyl, or the number of chain atoms designated, wherein at least two —$CH_2$— groups are independently replaced with —O—, —N(H)—, or —S—. The —O—, —N(H)—, or —S— can independently be placed at any interior position of the aliphatic hydrocarbon chain so long as each —O—, N(H)—, or —S— group is separated by at least two —$CH_2$— groups. In one embodiment, two —$CH_2$— groups are replaced with two —O— groups. In another embodiment, three —$CH_2$— groups are replaced with three —O— groups. Non-limiting exemplary heteroalkyl groups include —$CH_2CH_2OCH_2CH_2OCH_3$, —$CH_2CH_2OCH_2CH_2N(H)CH_3$, and —$CH_2CH_2OCH_2CH_2OCH_2CH_2OCH_3$.

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^{2}H$ (or deuterium (D)), $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, e.g., $^{3}H$, $^{11}C$, and $^{14}C$. In one embodiment, provided is a composition wherein substantially all of the atoms at a position within the Compound of the Disclosure are replaced by an atom having a different atomic mass or mass number. In another embodiment, provided is a composition wherein a portion of the atoms at a position within the Compound of the disclosure are replaced, i.e., the Compound of the Disclosure is enriched at a position with an atom having a different atomic mass or mass number. Isotopically-labelled Compounds of the Disclosure can be prepared by methods known in the art.

Compounds of the Disclosure may contain one or more asymmetric centers and may thus give rise to enantiomers, diastereomers, and other stereoisomeric forms. The present disclosure is meant to encompass the use of all such possible forms including racemic and resolved forms, and mixtures thereof. The individual stereoisomers, e.g., enantiomers, can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also intended to be encompassed by the present disclosure.

As used herein, the term “stereoisomers” or “stereoisomeric forms” are general terms for all isomers of individual molecules that differ only in the orientation of their atoms in space. It includes enantiomers and isomers of compounds with more than one chiral center that are not mirror images of one another (diastereomers).

The term “chiral center” or “asymmetric carbon atom” refers to a carbon atom to which four different groups are attached.

The terms “enantiomer” and “enantiomeric” refer to a molecule that cannot be superimposed on its mirror image and hence is optically active wherein the enantiomer rotates the plane of polarized light in one direction and its mirror image compound rotates the plane of polarized light in the opposite direction.

The term “racemic” refers to a mixture of equal parts of enantiomers and which mixture is optically inactive.

The term “absolute configuration” refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term “enantiomeric excess” or “ee” refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense. In one embodiment, Compounds of the Disclosure having one or more chiral centers are enantiopure.

The terms "enantiomerically enriched" or "enantioenriched" refer to a sample of a chiral substance whose enantiomeric excess is greater than 50%, e.g., about 60% or more, about 70% or more, about 80% or more, about 90% or more, about 95% or more, about 98% or more, or about 99% or more. Enantiomerically enriched compounds may be enantiomerically pure. In one embodiment, Compounds of the Disclosure having one or more chiral centers are enantioenriched.

The terms "a" and "an" refer to one or more.

The term "about," as used herein, includes the recited number±10%. Thus, "about 10" means 9 to 11.

The present disclosure encompasses the preparation and use of salts of the Compounds of the Disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparaginate, glutamate and the like. The term "pharmaceutically acceptable salt" as used herein, refers to any salt, e.g., obtained by reaction with an acid or a base, of a Compound of the Disclosure that is physiologically tolerated in the target patient (e.g., a mammal, e.g., a human).

Acid addition salts can be formed by mixing a solution of the particular Compound of the Disclosure with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g., a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure.

In one embodiment, the solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Compounds of the Disclosure are inhibitors of Bcl-2 proteins, such as Bcl-2 WT and/or Bcl-2 G101V, and thus a number of diseases, conditions, or disorders mediated by Bcl-2 proteins can be treated or prevented by administering these compounds to a subject. The present disclosure is thus directed generally to a method for treating or preventing a disease, condition, or disorder responsive to the inhibition of Bcl-2 proteins, such as Bcl-2 WT and/or Bcl-2 G101V, in an animal suffering from, or at risk of suffering from, the disease, condition, or disorder. The method comprises administering to the animal an effective amount of one or more Compounds of the Disclosure The present disclosure is further directed to a method of inhibiting Bcl-2 proteins in an animal, e.g., a human, in need thereof, the method comprising administering to the animal a therapeutically effective amount of at least one Compound of the Disclosure.

The present disclosure is further directed to a method of inhibiting Bcl-2 in an animal, e.g., a human, in need thereof, the method comprising administering to the animal a therapeutically effective amount of at least one Compound of the Disclosure.

The present disclosure is further directed to a method of inhibiting Bcl-2 WT in an animal, e.g., a human, in need thereof, the method comprising administering to the animal a therapeutically effective amount of at least one Compound of the Disclosure.

The present disclosure is further directed to a method of inhibiting Bcl-2 G101V in an animal, e.g., a human, in need thereof, the method comprising administering to the animal a therapeutically effective amount of at least one Compound of the Disclosure.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; modulate protein methylation in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

In the present disclosure, the term "Bcl-2 proteins" or "Bcl-2 family of proteins" refers to any one or more of the following proteins: Bax, Bak, Bid, Bcl-2, Bcl-xL, Mcl-1, Bcl-w or Bcl-2 WT, Bcl-2 G101V, Bfl-1/A1, Bim, Puma, Bad, Bik/Blk, Noxa, Bmf, Hrk/DP5, and Beclin-1.

The term "disease" or "condition" or "disorder" denotes disturbances and/or anomalies that as a rule are regarded as being pathological conditions or functions, and that can manifest themselves in the form of particular signs, symptoms, and/or malfunctions. Compounds of the Disclosure inhibit Bcl-2 proteins, such as Bcl-2 WT and/or Bcl-2 G101V, and can be used in treating or preventing diseases, conditions, or disorders such as hyperproliferative diseases, wherein inhibition of Bcl-2 proteins provides a benefit.

The term "hyperproliferative disease" refers to any condition in which a localized population of proliferating cells in an animal is not governed by the usual limitations of normal growth. In one embodiment, the hyperproliferative disease is cancer.

In some embodiments, the Compounds of the Disclosure can be used to treat a "Bcl-2 protein mediated disorder," e.g., a Bcl-2-mediated disorder, a Bcl-2 WT-mediated disorder, and/or a Bcl-2 G101V-mediated disorder. A Bcl-2 protein mediated disorder is any pathological condition in which a Bcl-2 protein is known to play a role. In one embodiment, a Bcl-2 mediated disorder is a hyperproliferative disease. In one embodiment, a Bcl-2 mediated disorder is cancer.

In one embodiment, Compounds of the Disclosure have a Bcl-2 WT and/or Bcl-2 G101V $IC_{50}$ of less than about 10 μM. In another embodiment, Compounds of the Disclosure have a Bcl-2 WT and/or Bcl-2 G101V $IC_{50}$ of less than about 5 μM. In another embodiment, Compounds of the Disclosure have a Bcl-2 WT and/or Bcl-2 G101V $IC_{50}$ of less than about 1 μM. In another embodiment, Compounds of the Disclosure have a Bcl-2 WT and/or Bcl-2 G101V $IC_{50}$ of less than about 0.5 μM. In another embodiment, Compounds of the Disclosure have a Bcl-2 WT and/or Bcl-2 G101V $IC_{50}$ of less than about 0.1 μM. In another embodiment, Compounds of the Disclosure have a Bcl-2 WT and/or Bcl-2 G101V $IC_{50}$ of less than about 0.05 μM. In another embodiment, Compounds of the Disclosure have a Bcl-2 WT and/or Bcl-2 G101V $IC_{50}$ of less than about 0.025 μM. In another embodiment, Compounds of the Disclosure have a Bcl-2 WT and/or Bcl-2 G101V $IC_{50}$ of less than about 0.010 μM. In another embodiment, Compounds of the Disclosure have a Bcl-2 WT and/or Bcl-2 G101V $IC_{50}$ of less than about 0.005 μM. In another embodiment, Compounds of the Disclosure have a Bcl-2 WT and/or Bcl-2 G101V $IC_{50}$ of less than about 0.0025 μM. In another embodiment, Compounds of the Disclosure have a Bcl-2 WT and/or Bcl-2 G101V $IC_{50}$ of less than about 0.001 μM.

In one embodiment, the present disclosure provides a method of treating or preventing a hyperproliferative disease in a subject, e.g., a human, comprising administering a therapeutically effective amount of a Compound of the Disclosure.

In another embodiment, the present disclosure provides a method of treating or preventing cancer in a subject comprising administering a therapeutically effective amount of a Compound of the Disclosure. While not being limited to a specific mechanism, in some embodiments, Compounds of the Disclosure can treat or prevent cancer by inhibiting Bcl-2 proteins, e.g., Bcl-2 WT and/or Bcl-2 G101V. Examples of treatable cancers include, but are not limited to, any one or more of the cancers of Table 2.

TABLE 2

| |
|---|
| adrenal cancer |
| acinic cell carcinoma |
| acoustic neuroma |
| acral lentigious melanoma |
| acrospiroma |
| acute eosinophilic leukemia |
| acute erythroid leukemia |
| acute lymphoblastic leukemia |
| acute megakaryoblastic leukemia |
| acute monocytic leukemia |
| acute promyelocytic leukemia |
| adenocarcinoma |
| adenoid cystic carcinoma |
| adenoma |
| adenomatoid odontogenic tumor |
| adenosquamous carcinoma |
| adipose tissue neoplasm |
| adrenocortical carcinoma |
| adult T-cell leukemia/lymphoma |
| aggressive NK-cell leukemia |
| AIDS-related lymphoma |

TABLE 2-continued

| |
|---|
| alveolar rhabdomyosarcoma |
| alveolar soft part sarcoma |
| ameloblastic fibroma |
| anaplastic large cell lymphoma |
| anaplastic thyroid cancer |
| angioimmunoblastic T-cell lymphoma, |
| angiomyolipoma |
| angiosarcoma |
| astrocytoma |
| atypical teratoid rhabdoid tumor |
| B-cell chronic lymphocytic leukemia |
| B-cell prolymphocytic leukemia |
| B-cell lymphoma |
| basal cell carcinoma |
| biliary tract cancer |
| bladder cancer |
| blastoma |
| bone cancer |
| Brenner tumor |
| Brown tumor |
| Burkitt's lymphoma |
| breast cancer |
| brain cancer |
| carcinoma |
| carcinoma in situ |
| carcinosarcoma |
| cartilage tumor |
| cementoma |
| myeloid sarcoma |
| chondroma |
| chordoma |
| choriocarcinoma |
| choroid plexus papilloma |
| clear-cell sarcoma of the kidney |
| craniopharyngioma |
| cutaneous T-cell lymphoma |
| cervical cancer |
| colorectal cancer |
| Degos disease |
| desmoplastic small round cell tumor |
| diffuse large B-cell lymphoma |
| dysembryoplastic neuroepithelial tumor, |
| dysgerminoma |
| embryonal carcinoma |
| endocrine gland neoplasm |
| endodermal sinus tumor |
| enteropathy-associated T-cell lymphoma |
| esophageal cancer |
| fetus in fetu |
| fibroma |
| fibrosarcoma |
| follicular lymphoma |
| follicular thyroid cancer |
| ganglioneuroma |
| gastrointestinal cancer |
| germ cell tumor |
| gestational choriocarcinoma |
| giant cell fibroblastoma |
| giant cell tumor of the bone |
| glial tumor |
| glioblastoma multiforme |
| glioma |
| gliomatosis cerebri |
| glucagonoma |
| gonadoblastoma |
| granulosa cell tumor |
| gynandroblastoma |
| gallbladder cancer |
| gastric cancer |
| hairy cell leukemia |
| hemangioblastoma |
| head and neck cancer |
| hemangiopericytoma |
| hematological malignancy |
| hepatoblastoma |
| hepatosplenic T-cell lymphoma |
| Hodgkin's lymphoma |
| non-Hodgkin's lymphoma |
| invasive lobular carcinoma |

TABLE 2-continued

| |
|---|
| intestinal cancer |
| kidney cancer |
| laryngeal cancer |
| lentigo maligna |
| lethal midline carcinoma |
| leukemia |
| leydig cell tumor |
| liposarcoma |
| lung cancer |
| lymphangioma |
| lymphangiosarcoma |
| lymphoepithelioma |
| lymphoma |
| acute lymphocytic leukemia |
| acute myelogeous leukemia |
| chronic lymphocytic leukemia |
| liver cancer |
| small cell lung cancer |
| non-small cell lung cancer |
| MALT lymphoma |
| malignant fibrous histiocytoma |
| malignant peripheral nerve sheath tumor |
| malignant triton tumor |
| mantle cell lymphoma |
| marginal zone B-cell lymphoma |
| mast cell leukemia |
| mediastinal germ cell tumor |
| medullary carcinoma of the breast |
| medullary thyroid cancer, |
| medulloblastoma |
| melanoma, |
| meningioma, |
| merkel cell cancer |
| mesothelioma |
| metastatic urothelial carcinoma |
| mixed Mullerian tumor |
| mucinous tumor |
| multiple myeloma |
| muscle tissue neoplasm |
| mycosis fungoides |
| myxoid liposarcoma |
| myxoma |
| myxosarcoma |
| nasopharyngeal carcinoma |
| neurinoma |
| neuroblastoma |
| neurofibroma |
| neuroma |
| nodular melanoma |
| ocular cancer |
| oligoastrocytoma |
| oligodendroglioma |
| oncocytoma |
| optic nerve sheath meningioma |
| optic nerve tumor |
| oral cancer |
| osteosarcoma |
| ovarian cancer |
| Pancoast tumor |
| papillary thyroid cancer |
| paraganglioma |
| pinealoblastoma |
| pineocytoma |
| pituicytoma |
| pituitary adenoma |
| pituitary tumor |
| plasmacytoma |
| polyembryoma |
| precursor T-lymphoblastic lymphoma |
| primary central nervous system lymphoma |
| primary effusion lymphoma |
| preimary peritoneal cancer |
| prostate cancer |
| pancreatic cancer |
| pharyngeal cancer |
| pseudomyxoma periotonei |
| renal cell carcinoma |
| renal medullary carcinoma |
| retinoblastoma |
| rhabdomyoma |

TABLE 2-continued

| |
|---|
| rhabdomyosarcoma |
| Richter's transformation |
| rectal cancer |
| sarcoma |
| Schwannomatosis |
| seminoma |
| Sertoli cell tumor |
| sex cord-gonadal stromal tumor |
| signet ring cell carcinoma |
| skin cancer |
| small blue round cell tumors |
| small cell carcinoma |
| soft tissue sarcoma |
| somatostatinoma |
| soot wart |
| spinal tumor |
| splenic marginal zone lymphoma |
| squamous cell carcinoma |
| synovial sarcoma |
| Sezary's disease |
| small intestine cancer |
| squamous carcinoma |
| stomach cancer |
| T-cell lymphoma |
| testicular cancer |
| thecoma |
| thyroid cancer |
| transitional cell carcinoma |
| throat cancer |
| urachal cancer |
| urogenital cancer |
| urothelial carcinoma |
| uveal melanoma |
| uterine cancer |
| verrucous carcinoma |
| visual pathway glioma |
| vulvar cancer |
| vaginal cancer |
| Waldenstrom's macroglobulinemia |
| Warthin's tumor |
| Wilms' tumor |

In another embodiment, the cancer is breast, cervix, colon, kidney, liver, head and neck, skin, pancreas, ovary, esophagus, or prostate cancer.

In another embodiment, the cancer is a hematologic malignancy such as acute myeloid leukemia (AML), B- and T-acute lymphoblastic leukemia (ALL), chronic lymphocytic leukemia (CLL), or mantle cell lymphoma (MCL).

In another embodiment, the cancer is esophageal squamous cell carcinoma (ESCC), bladder carcinoma, or cervical carcinoma.

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the cancer is adrenocortical carcinoma, bladder urothelial carcinoma, breast invasive carcinoma, colorectal adenocarcinoma, diffuse large B-cell lymphoma, head and neck squamous cell carcinoma, hepatocellular carcinoma, lung adenocarcinoma, lung squamous cell carcinoma, ovarian serous cystadenocarcinoma, pancreatic adenocarcinoma, prostate adenocarcinoma, renal clear cell carcinoma, skin cutaneous melanoma, stomach adenocarcinoma, uterine carcinosarcoma, or uterine corpus endometrial carcinoma.

In another embodiment, the present disclosure provides a therapeutic method of modulating gene expression, cell proliferation, cell differentiation and/or apoptosis in vivo in a cancer, e.g., in the cancers mentioned above, by administering a therapeutically effective amount of a Compound of the Disclosure to a subject in need of such therapy.

Compounds of the Disclosure can be administered to a subject in the form of a raw chemical without any other components present. Compounds of the Disclosure can also be administered to a subject as part of a pharmaceutical composition containing the compound combined with one or more suitable pharmaceutically acceptable carriers. Such carriers can be selected from pharmaceutically acceptable excipients and auxiliaries. The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, PA, 19th ed. 1995.

Pharmaceutical compositions within the scope of the present disclosure include all compositions where a Compound of the Disclosure is combined with one or more pharmaceutically acceptable carriers. In one embodiment, the Compound of the Disclosure is present in the composition in an amount that is effective to achieve its intended therapeutic purpose. While individual needs may vary, a determination of optimal ranges of effective amounts of each compound is within the skill of the art. Typically, a Compound of the Disclosure can be administered to a mammal, e.g., a human, orally at a dose of from about 0.0025 to about 1500 mg per kg body weight of the mammal, or an equivalent amount of a pharmaceutically acceptable salt or solvate thereof, per day to treat the particular disorder. A useful oral dose of a Compound of the Disclosure administered to a mammal is from about 0.0025 to about 50 mg per kg body weight of the mammal, or an equivalent amount of the pharmaceutically acceptable salt or solvate thereof. For intramuscular injection, the dose is typically about one-half of the oral dose.

A unit oral dose may comprise from about 0.01 mg to about 1 g of the Compound of the Disclosure, e.g., about 0.01 mg to about 500 mg, about 0.01 mg to about 250 mg, about 0.01 mg to about 100 mg, 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt or solvate thereof.

A Compound of the Disclosure or a pharmaceutical composition comprising a Compound of the Disclosure can be administered to any patient or subject that may experience the beneficial effects of a Compound of the Disclosure. Foremost among such patients or subject are mammals, e.g., humans and companion animals, although the disclosure is not intended to be so limited. In one embodiment, the patient or subject is a human.

A Compound of the Disclosure or a pharmaceutical composition comprising a Compound of the Disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a Compound of the Disclosure or a pharmaceutical composition comprising a Compound of the Disclosure can be administered orally. In another embodiment, a pharmaceutical composition of the present disclosure can be administered orally and is formulated into tablets, dragees, capsules, or an oral liquid preparation. In one embodiment, the oral formulation comprises extruded multiparticulates comprising the Compound of the Disclosure.

Alternatively, a Compound of the Disclosure or a pharmaceutical composition comprising a Compound of the Disclosure can be administered rectally, and is formulated in suppositories.

Alternatively, a Compound of the Disclosure or a pharmaceutical composition comprising a Compound of the Disclosure can be administered by injection.

Alternatively, a Compound of the Disclosure or a pharmaceutical composition comprising a Compound of the Disclosure can be administered transdermally.

Alternatively, a Compound of the Disclosure or a pharmaceutical composition comprising a Compound of the Disclosure can be administered by inhalation or by intranasal or transmucosal administration.

Alternatively, a Compound of the Disclosure or a pharmaceutical composition comprising a Compound of the Disclosure can be administered by the intravaginal route.

A pharmaceutical composition of the present disclosure can contain from about 0.01 to 99 percent by weight, e.g., from about 0.25 to 75 percent by weight, of a Compound of the Disclosure, e.g., about 1%, about 5%, about 10%, about 15%, about 20%, about 25%, about 30%, about 35%, about 40%, about 45%, about 50%, about 55%, about 60%, about 65%, about 70%, or about 75% by weight of a Compound of the Disclosure.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

In another embodiment, the present disclosure provides kits which comprise a Compound of the Disclosure (or a pharmaceutical composition comprising a Compound of the Disclosure) packaged in a manner that facilitates their use to practice methods of the present disclosure. In one embodiment, the kit includes a Compound of the Disclosure (or a pharmaceutical composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

In another embodiment, a Compound of the Disclosure is administered to a subject in conjunction with a second therapeutic agent. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

In some embodiments, the second therapeutic agent is an epigenetic drug. As used herein, the term “epigenetic drug” refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; *vinca* alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors (“MMP inhibitors”) include collagen peptidomimetic and nonpeptidomimetic inhibitors, tetracycline derivatives, batimastat, marimastat, prinomastat, metastat, BMS-279251, BAY 12-9566, TAA211, MM1270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DMI, cetuximab, bevacizumab, rituximab, PR064553, and 2C4. The term “antibody” is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SUIOI, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, CI-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Compound of the Disclosure, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, I-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a Compound of the Disclosure also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

SYNTHETIC EXAMPLES

Intermediate 1: Methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate

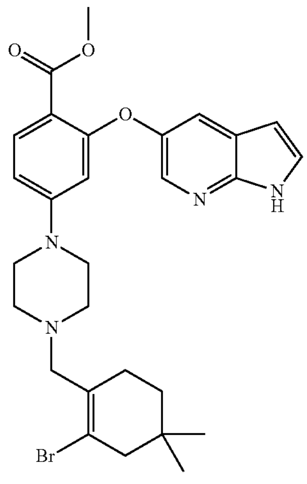 [SMILES: COC(=O)c1ccc(N2CCN(CC3=C(Br)CC(C)(C)CC3)CC2)cc1Oc1cnc2[nH]ccc2c1]

Step A: Methyl 2-((1H-pyrrolo[2,3-b]pyridin-5-yl)oxy)-4-(piperazin-1-yl)benzoate

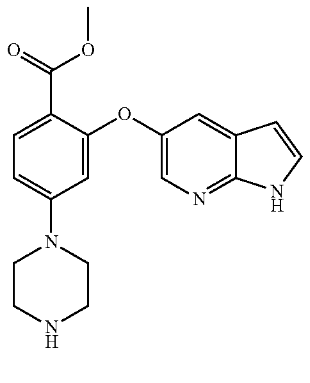 [SMILES: COC(=O)c1ccc(N2CCNCC2)cc1Oc1cnc2[nH]ccc2c1]

Under Ar, to a solution of methyl 2-((1H-pyrrolo[2,3-b]pyridin-5-yl)oxy)-4-fluorobenzoate (10.0 g, 34.9 mmol) in dry DMSO (100 mL) was added piperazine (9.0 g, 105 mmol) and dipotassium hydrogenphosphate (12.2 g, 69.9 mmol); then the reaction mixture was stirred at 100° C. for 4 h. After cooling down to room temperature, the resulting mixture was poured onto ice water and extracted with EA twice. The combined organic layers were washed with water and brine, dried over $Na_2SO_4$ and concentrated under reduced pressure to give the crude title compound (12 g) as a white solid, which was directly used for the next step without purification. MS: 353.2 $(M+H^+)$.

Step B: Methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1)

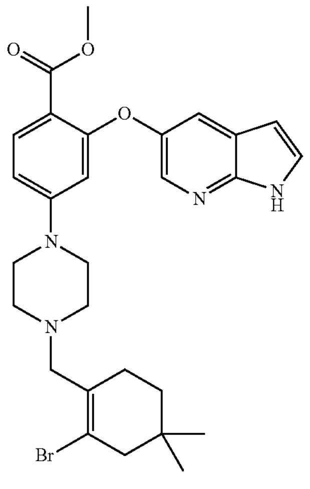 [SMILES: COC(=O)c1ccc(N2CCN(CC3=C(Br)CC(C)(C)CC3)CC2)cc1Oc1cnc2[nH]ccc2c1]

Under Ar, to a stirring solution of methyl 2-((1H-pyrrolo[2,3-b]pyridin-5-yl)oxy)-4-(piperazin-1-yl)benzoate (Step A, 4 g, 11.35 mmol) and 2-bromo-4,4-dimethylcyclohex-1-ene-1-carbaldehyde (4.4 g, 20.4 mmol) in dry DCE (100 mL) was added sodium triacetoxyborohydride (4.8 g, 22.7 mmol) at room temperature; then the reaction mixture was heated to 50° C. for 6 h. After cooling down to room temperature, the resulting mixture was washed with aq. $NaHCO_3$ and brine, dried over $Na_2SO_4$ and concentrated under reduced pressure to give a yellow oil, which was purified by silica gel column (MeOH:DCM, 1:35) to afford the title compound (4.8 g, 76% over 2 steps) as a white powder. MS: 553.2 ($M+H^+$).

Example 1: 2-((1H-pyrrolo[2,3-b]pyridin-5-yl)oxy)-4-(4-((4,4-dimethyl-2-(2-methylthiophen-3-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

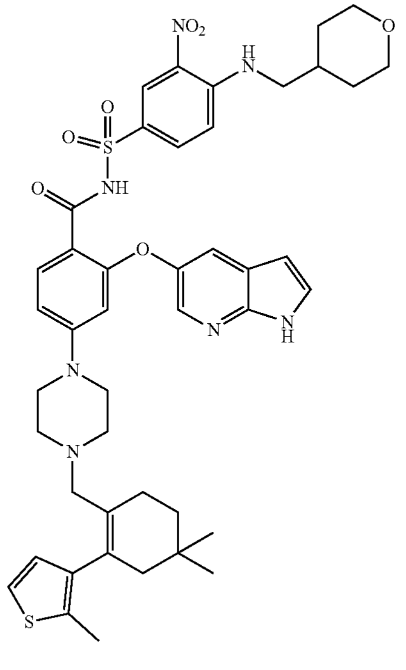 [SMILES: Cc1sccc1C1=C(CN2CCN(c3ccc(C(=O)NS(=O)(=O)c4ccc(NCC5CCOCC5)c([N+](=O)[O-])c4)c(Oc4cnc5[nH]ccc5c4)c3)CC2)CCC(C)(C)C1]

Step A: Methyl 2-((1H-pyrrolo[2,3-b]pyridin-5-yl)oxy)-4-(4-((4,4-dimethyl-2-(2-methylthiophen-3-yl)cyclohex-1-en-1-yl)methyl)piperazin-1-yl)benzoate

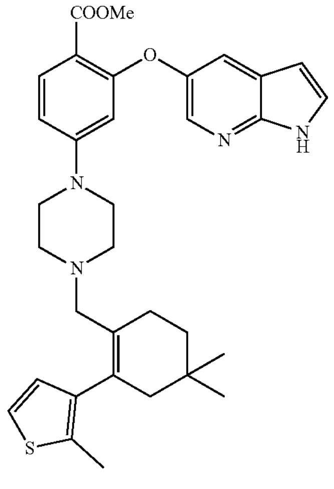 [SMILES: COC(=O)c1ccc(N2CCN(CC3=C(c4ccsc4C)CC(C)(C)CC3)CC2)cc1Oc1cnc2[nH]ccc2c1]

Under $N_2$, to a solution of methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 100 mg, 0.18 mmol) in a mixed solvent of DME (1.5 mL) and 2 M $Na_2CO_3$ (0.5 mL) was added 4,4,5,5-tetramethyl-2-(2-methylthiophen-3-yl)-1,3,2-dioxaborolane (61 mg, 0.27 mmol) and $PdCl_2(dppf)\cdot CH_2Cl_2$ (29.5 mg, 0.036 mmol). The mixture was stirred at 100° C. for 0.5 h with microwave assistance. After coiling down to room temperature, the mixture was diluted with ethyl acetate, and then washed with $H_2O$ and brine. The organic layer was dried over $Na_2SO_4$ and concentrated under reduced pressure to give a brown oil, which was loaded onto a silica gel column and eluted with ethyl acetate/hexane (hexane:ethyl acetate, 1:1) to afford the title compound (60 mg, 58%) as a yellow oil. MS: 571.3 ($M+H^+$).

Step B: 2-((1H-pyrrolo[2,3-b]pyridin-5-yl)oxy)-4-(4-((4,4-dimethyl-2-(2-methylthiophen-3-yl)cyclohex-1-en-1-yl)methyl)piperazin-1-yl)benzoic acid

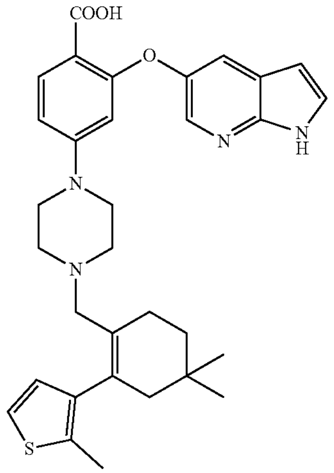 [SMILES: Cc1sccc1C1=C(CN2CCN(c3ccc(C(=O)O)c(Oc4cnc5[nH]ccc5c4)c3)CC2)CCC(C)(C)C1]

To a solution of methyl 2-((1H-pyrrolo[2,3-b]pyridin-5-yl)oxy)-4-(4-((4,4-dimethyl-2-(2-methylthiophen-3-yl)cyclohex-1-en-1-yl)methyl)piperazin-1-yl)benzoate (Step A, 60 mg, 0.11 mmol) in a mixed solvent of MeOH (1 mL), THF (1 mL) and/$H_2O$ (1 mL) was added sodium hydroxide (42 mg, 1.1 mmol). The mixture was stirred at 50° C. for 4 h. After cooling down to room temperature and removal of volatiles, the reaction mixture was acidified with 1 M HCl to adjust pH to 5-6 and extracted with ethyl acetate twice. The resulting organic layers were combined, dried over $Na_2SO_4$, and concentrated under reduced pressure to give the crude title compound (50 mg), which was directly used for the next step without purification. MS: 557.3 ($M+H^+$).

Step C: 2-((1H-pyrrolo[2,3-b]pyridin-5-yl)oxy)-4-(4-((4,4-dimethyl-2-(2-methylthiophen-3-yl)cyclohex-1-en-1-yl)methyl)piperazin-1-yl)-N-((3-nitro-4-(((tetrahydro-2H-pyran-4-yl)methyl)amino)phenyl)sulfonyl)benzamide (Example 1)

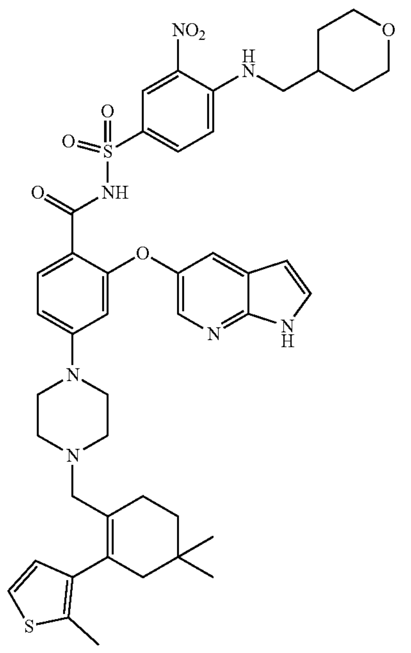 [SMILES: Cc1sccc1C1=C(CN2CCN(c3ccc(C(=O)NS(=O)(=O)c4ccc(NCC5CCOCC5)c([N+](=O)[O-])c4)c(Oc4cnc5[nH]ccc5c4)c3)CC2)CCC(C)(C)C1]

Under $N_2$, to a solution of the crude 2-((1H-pyrrolo[2,3-b]pyridin-5-yl)oxy)-4-(4-((4,4-dimethyl-2-(2-methylthiophen-3-yl)cyclohex-1-en-1-yl)methyl)piperazin-1-yl)benzoic acid (Step B, 50 mg) in dry DCM (3 mL) was added N,N-dimethylpyridin-4-amine (27 mg, 0.23 mmol), EDCl (25 mg, 0.14 mmol) and 3-nitro-4-(((tetrahydro-2H-pyran-4-yl)methyl)amino)benzenesulfonamide (28 mg, 0.09 mmol). The reaction mixture was stirred at 40° C. for 12 h. After cooling down to room temperature and removal of volatiles, the mixture was diluted with ethyl acetate and then washed with $H_2O$ and brine. The organic layer was separated, dried over $Na_2SO_4$, and concentrated under reduced pressure to give a yellow oil, which was purified by C18 prep-HPLC column to afford the title compound (15.9 mg, 21% over 2 steps) as a yellow solid. $^1H$ NMR (400 MHz, DMSO-$d_6$) δ 11.67 (s, 1H), 8.58 (t, J=5.6 Hz, 1H), 8.53 (d, J=2.0 Hz, 1H), 8.02 (d, J=2.5 Hz, 1H), 7.77 (dd, J=9.3, 1.5 Hz, 1H), 7.53-7.46 (m, 3H), 7.18 (d, J=5.1 Hz, 1H), 7.07 (d, J=9.3 Hz, 1H), 6.68 (dd, J=9.0, 1.9 Hz, 1H), 6.62 (d, J=5.1 Hz, 1H), 6.37 (dd, J=3.1, 1.8 Hz, 1H), 6.20 (d, J=1.9 Hz, 1H), 3.90-3.79 (m, 2H), 3.30-3.20 (m, 4H), 3.12-2.99 (m, 4H), 2.73-2.59 (m, 2H), 2.24-2.09 (m, 9H), 1.93-1.77 (m, 3H), 1.67-1.54 (m, 2H), 1.38 (t, J=6.3 Hz, 2H), 1.32-1.24 (m, 2H), 0.92 (s, 6H); MS: 854.3 (M+H$^+$).

Example 2: 2-((1H-pyrrolo[2,3-b]pyridin-5-yl)oxy)-4-(4-((4,4-dimethyl-2-(4-methylthiophen-3-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

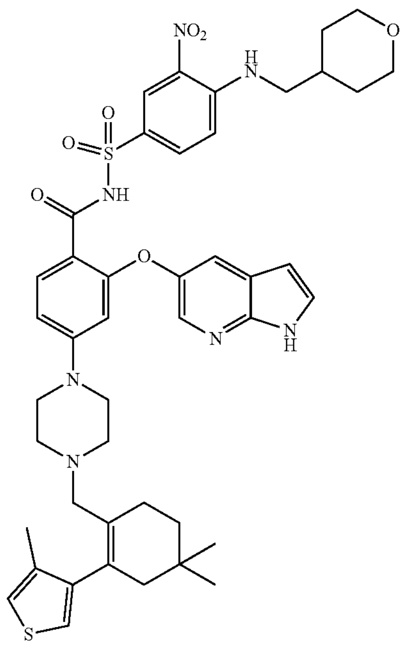 [SMILES: Cc1cscc1C1=C(CN2CCN(c3ccc(C(=O)NS(=O)(=O)c4ccc(NCC5CCOCC5)c([N+](=O)[O-])c4)c(Oc4cnc5[nH]ccc5c4)c3)CC2)CCC(C)(C)C1]

Essentially the same protocol of preparation of Example 1 was used to afford the example (30 mg) as a yellow solid. $^1H$ NMR (400 MHz, DMSO-$d_6$) δ 11.68 (s, 1H), 8.59 (t, J=5.7 Hz, 1H), 8.55 (d, J=2.1 Hz, 1H), 8.03 (d, J=2.5 Hz, 1H), 7.79 (dd, J=9.2, 1.9 Hz, 1H), 7.54-7.47 (m, 3H), 7.14-7.04 (m, 2H), 6.94 (d, J=3.1 Hz, 1H), 6.68 (dd, J=9.0, 1.9 Hz, 1H), 6.38 (dd, J=3.2, 1.8 Hz, 1H), 6.19 (d, J=1.8 Hz, 1H), 3.89-3.80 (m, 2H), 3.30-3.22 (m, 4H), 3.12-3.01 (m, 4H), 2.71-2.59 (m, 2H), 2.26-2.08 (m, 6H), 1.96 (s, 3H), 1.92-1.80 (m, 3H), 1.66-1.56 (m, 2H), 1.38 (t, J=6.3 Hz, 2H), 1.32-1.22 (m, 2H), 0.92 (s, 6H); MS: 854.2 (M+H$^+$).

Example 3: 2-((1H-pyrrolo[2,3-b]pyridin-5-yl)oxy)-4-(4-((4,4-dimethyl-2-(5-(trifluoromethyl)thiophen-3-yl)cyclohex-1-en-1-yl)methyl)piperazin-1-yl)-N-((3-nitro-4-(((tetrahydro-2H-pyran-4-yl)methyl) amino)phenyl)sulfonyl)benzamide

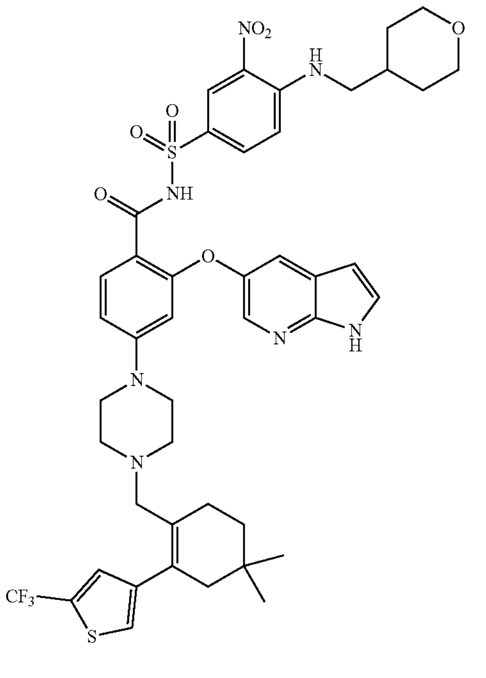 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2csc(C(F)(F)F)c2)C1]

Essentially the same protocol of preparation of Example 1 was used to afford the example (15 mg) as a yellow solid. $^1$H NMR (400 MHz, DMSO-$d_6$) δ 11.72 (s, 1H), 8.64 (t, J=5.8 Hz, 1H), 8.59 (d, J=2.2 Hz, 1H), 8.07 (d, J=2.6 Hz, 1H), 7.83 (dd, J=9.2, 2.0 Hz, 1H), 7.64 (d, J=1.4 Hz, 1H), 7.60-7.58 (m, 1H), 7.56 (d, J=2.4 Hz, 1H), 7.55-7.50 (m, 2H), 7.14 (d, J=9.4 Hz, 1H), 6.72 (dd, J=9.0, 2.0 Hz, 1H), 6.42 (dd, J=3.3, 1.9 Hz, 1H), 6.23 (d, J=2.0 Hz, 1H), 3.88 (dd, J=11.3, 3.0 Hz, 2H), 3.33-3.23 (m, 3H), 3.17-3.03 (m, 4H), 2.88 (s, 2H), 2.33-2.21 (m, 4H), 2.21-2.14 (m, 2H), 2.05 (s, 2H), 1.97-1.85 (m, 1H), 1.64 (d, J=11.4 Hz, 2H), 1.39 (t, J=6.3 Hz, 2H), 1.35-1.21 (m, 3H), 0.95 (s, 6H); MS: 908.9 (M+H$^+$).

Example 4: 2-((1H-pyrrolo[2,3-b]pyridin-5-yl)oxy)-4-(4-((4,4-dimethyl-2-(3-methylthiophen-2-yl)cyclohex-1-en-1-yl)methyl)piperazin-1-yl)-N-((3-nitro-4-(((tetrahydro-2H-pyran-4-yl)methyl)amino)phenyl) sulfonyl)benzamide

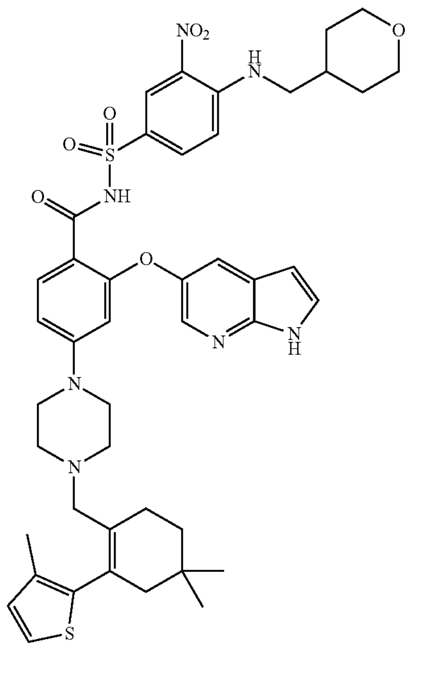 [SMILES: Cc1ccsc1C1=C(CN2CCN(c3ccc(C(=O)NS(=O)(=O)c4ccc(NCC5CCOCC5)c([N+](=O)[O-])c4)c(Oc4cnc5[nH]ccc5c4)c3)CC2)CCC(C)(C)C1]

Essentially the same protocol of preparation of Example 1 was used to afford the example (3.7 mg) as a yellow solid. $^1$H NMR (400 MHz, DMSO-$d_6$) δ 8.52 (d, J=2.2 Hz, 1H), 7.98 (d, J=1.9 Hz, 1H), 7.77 (dd, J=9.3, 2.1 Hz, 1H), 7.52-7.46 (m, 3H), 7.34 (d, J=5.0 Hz, 1H), 7.06 (d, J=9.4 Hz, 1H), 6.83 (d, J=5.1 Hz, 1H), 6.74 (d, J=9.3 Hz, 1H), 6.38 (d, J=3.4 Hz, 1H), 6.28-6.24 (m, 1H), 3.87-3.81 (m, 6H), 3.62-3.51 (m, 2H), 3.31-3.19 (m, 4H), 2.23-2.13 (m, 2H), 2.03-1.94 (m, 6H), 1.92 (s, 3H), 1.88-1.78 (m, 1H), 1.63-1.54 (m, 2H), 1.43 (t, J=6.2 Hz, 2H), 1.30-1.26 (m, 2H), 0.91 (s, 6H); MS: 854.3 (M+H$^+$).

Example 5: 2-((1H-pyrrolo[2,3-b]pyridin-5-yl)oxy)-4-(4-((4,4-dimethyl-2-(4-methylthiophen-2-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

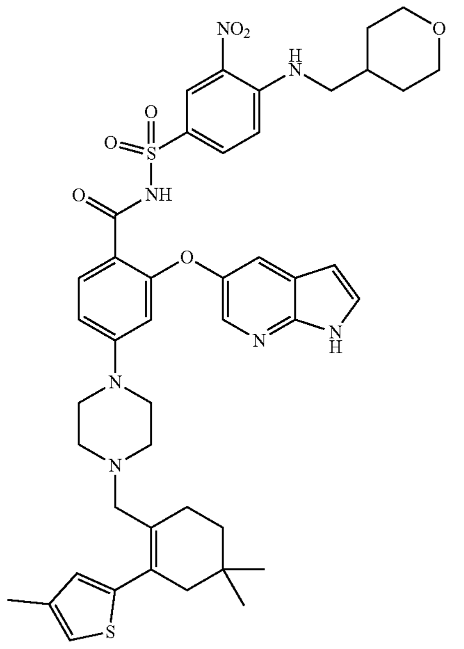 [SMILES: Cc1csc(C2=C(CN3CCN(c4ccc(C(=O)NS(=O)(=O)c5ccc(NCC6CCOCC6)c([N+](=O)[O-])c5)c(Oc5cnc6[nH]ccc6c5)c4)CC3)CCC(C)(C)C2)c1]

Essentially the same protocol of preparation of Example 1 was used to afford the example (4.5 mg) as a yellow solid. $^1$H NMR (400 MHz, DMSO-$d_6$) δ 8.52-8.45 (m, 1H), 8.02-7.93 (m, 1H), 7.73 (d, J=9.5 Hz, 1H), 7.53-7.40 (m, 3H), 7.01 (d, J=9.7 Hz, 1H), 6.94 (s, 1H), 6.69 (d, J=8.2 Hz, 1H), 6.61 (s, 1H), 6.36 (d, J=3.2 Hz, 1H), 6.25-6.15 (m, 1H), 3.86-3.79 (m, 2H), 3.31-3.19 (m, 4H), 3.16-2.95 (m, 6H), 2.35-2.23 (m, 4H), 2.17-2.13 (m, 2H), 2.12 (s, 3H), 2.01-1.98 (m, 2H), 1.91-1.79 (m, 1H), 1.63-1.54 (m, 2H), 1.33 (t, J=6.0 Hz, 2H), 1.29-1.24 (m, 2H), 0.88 (s, 6H); MS: 854.0 (M+H$^+$).

Example 6: 2-((1H-pyrrolo[2,3-b]pyridin-5-yl)oxy)-4-(4-((4,4-dimethyl-2-(5-methylthiophen-2-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

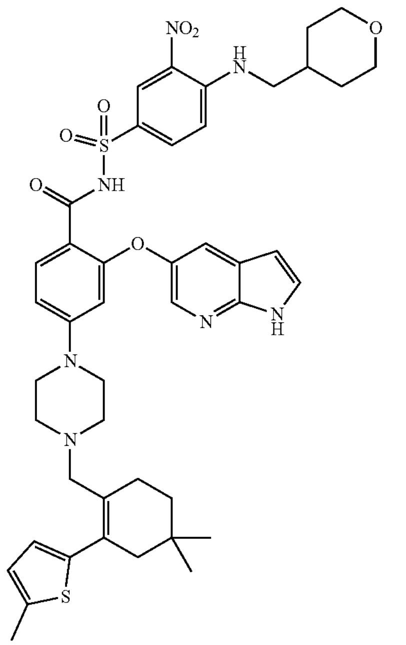 [SMILES: Cc1ccc(C2=C(CN3CCN(c4ccc(C(=O)NS(=O)(=O)c5ccc(NCC6CCOCC6)c([N+](=O)[O-])c5)c(Oc5cnc6[nH]ccc6c5)c4)CC3)CCC(C)(C)C2)s1]

Essentially the same protocol of preparation of Example 1 was used to afford the example (6.6 mg) as a yellow solid. $^1$H NMR (400 MHz, DMSO-$d_6$) δ 8.51-8.44 (m, 1H), 8.00-7.94 (m, 1H), 7.71 (d, J=8.8 Hz, 1H), 7.52-7.41 (m, 3H), 6.98 (d, J=8.3 Hz, 1H), 6.69 (d, J=8.8 Hz, 1H), 6.63-6.59 (m, 1H), 6.56 (d, J=3.1 Hz, 1H), 6.35 (d, J=2.8 Hz, 1H), 6.26-6.16 (m, 1H), 3.94-3.88 (m, 2H), 3.25-3.21 (m, 4H), 3.17-3.00 (m, 6H), 2.42-2.27 (m, 7H), 2.18-2.08 (m, 2H), 1.99-1.96 (m, 2H), 1.90-1.78 (m, 1H), 1.62-1.51 (m, 2H), 1.32 (t, J=6.0 Hz, 2H), 1.28-1.21 (m, 2H), 0.86 (s, 6H); MS: 854.2 (M+H$^+$).

Examples 7 and 8: 2-((1H-pyrrolo[2,3-b]pyridin-5-yl)oxy)-4-(4-((2-(4-isopropylthiophen-3-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide (Example 7) and 2-((1H-pyrrolo[2,3-b]pyridin-5-yl)oxy)-4-(4-((2-(4-isopropylthiophen-2-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide (Example 8)

Example 7

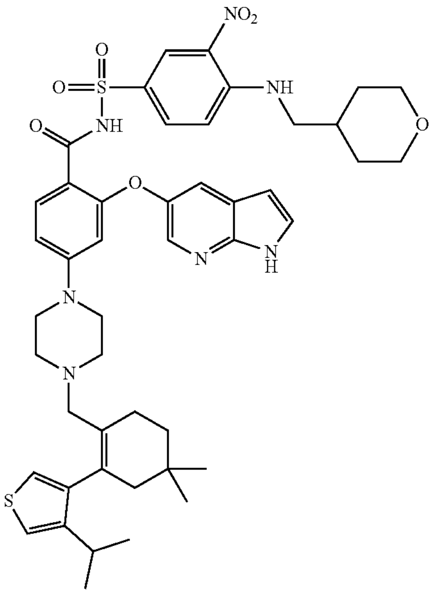

and

Example 8

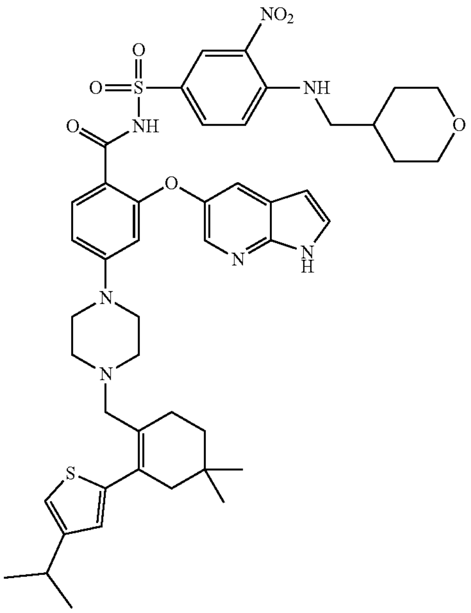

Step A: 2-(4-Bromothiophen-3-yl)propan-2-ol

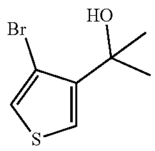

Under $N_2$, to a solution of methyl 4-bromothiophene-3-carboxylate (4 g, 18.1 mmol) in dry THF (100 mL) was added MeMgBr (14 mL, 3 M in 2-MeTHF, 41.6 mmol) at 0° C.; The reaction mixture was stirred at room temperature for 20 h. The mixture was quenched by sat. $NH_4Cl$, diluted with ethyl acetate (100 mL) and then washed with $H_2O$ (100 mL) and brine (100 mL). The organic layer was separated, dried over $Na_2SO_4$, and concentrated under reduced pressure to give a yellow oil, which was loaded onto a silica gel column and eluted with ethyl acetate and hexane (1:1) to afford the title compound (3.3 g, 82%) as a colorless oil. $^1$H NMR (400 MHz, DMSO-$d_6$) δ 7.61 (d, J=3.7 Hz, 1H), 7.43 (d, J=3.7 Hz, 1H), 5.20 (s, 1H), 1.51 (s, 6H).

Step B: 3-Bromo-4-isopropylthiophene

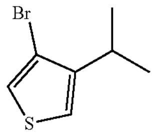

Under $N_2$, to a solution of 2-(4-bromothiophen-3-yl)propan-2-ol (Step A, 1.6 g, 7.24 mmol) in dry DCM (70 mL) was added triethylsilane (2.52 g, 21.71 mmol) and 2,2,2-trifluoroacetic acid (4.13 g, 36.2 mmol); the mixture was stirred at room temperature for 3 h. After removal of volatiles, the resulting mixture was loaded onto a silica gel column and eluted with ethyl acetate and hexane (1:10) to afford the title compound (1.05 g, 71%) as a colorless oil. $^1$H NMR (400 MHz, DMSO-$d_6$) δ 7.65 (d, J=3.3 Hz, 1H), 7.35 (d, J=3.3 Hz, 1H), 2.98-2.86 (m, 1H), 1.20 (d, J=6.9 Hz, 6H).

Step C: (4-Isopropylthiophen-3-yl)boronic acid and (4-isopropylthiophen-2-yl)boronic acid

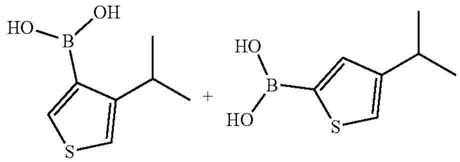

Under $N_2$, to a solution of 3-bromo-4-isopropylthiophene (Step B, 900 mg, 4.39 mmol) in dry THF (30 mL) was added nBuLi (2.6 mL, 2.5 M in hexane, 6.59 mmol) dropwise at −78° C., and the mixture was stirred at −78° C. for 20 min. Triisopropyl borate (1.65 g, 8.78 mmol) was added; the reaction mixture was stirred at −78° C. for 2 h, allowed to warm up to room temperature and stirred for 12 h. The mixture was quenched by 2 M HCl, diluted with ethyl acetate, and then washed with $H_2O$ and brine. The organic layer was separated, dried over $Na_2SO_4$, and concentrated under reduced pressure to give a yellow oil, which was loaded onto a silica gel column and was eluted with MeOH and DCM (1:20) to afford the mixed title compounds (570 mg, 76%) as a yellow oil. MS: 171.1 (M+H$^+$).

Step D: Methyl 2-((1H-pyrrolo[2,3-b]pyridin-5-yl)oxy)-4-(4-((2-(4-isopropylthiophen-3-yl)-4,4-dimethylcyclohex-1-en-1-yl)methyl)piperazin-1-yl)benzoate and methyl 2-((1H-pyrrolo[2,3-b]pyridin-5-yl)oxy)-4-(4-((2-(4-isopropylthiophen-2-yl)-4,4-dimethylcyclohex-1-en-1-yl)methyl)piperazin-1-yl)benzoate

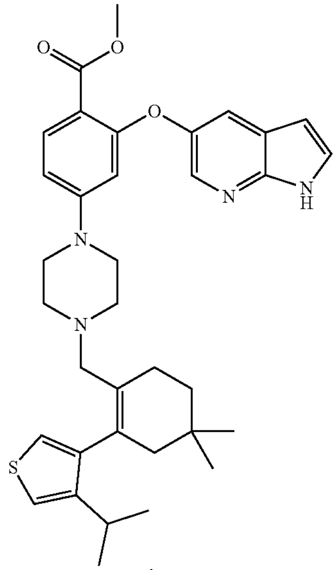

+

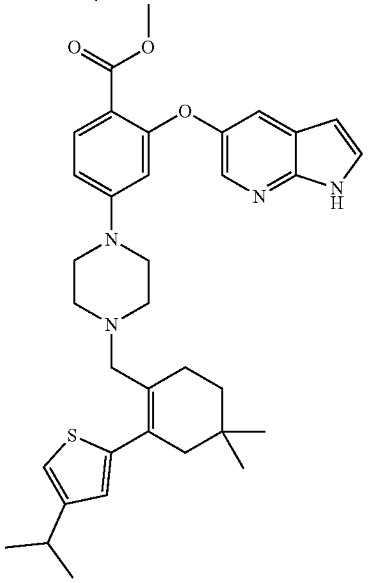

Under $N_2$, to a solution of methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 70 mg, 0.13 mmol) in DME (1.5 mL) and 2 M $Na_2CO_3$ (0.5 mL) was added a mixture of (4-isopropylthiophen-3-yl)boronic acid and (4-isopropylthiophen-2-yl)boronic acid (Step C, 32.3 mg, 0.19 mmol) and $PdCl_2$(dppf)·$CH_2Cl_2$ (20.7 mg, 0.02 mmol); the reaction mixture was stirred at 100° C. for 0.5 h with microwave assistance. After coiling down to room temperature, the mixture was diluted with ethyl acetate and then washed with $H_2O$ and brine. The organic layer was separated, dried over $Na_2SO_4$, and concentrated under reduced pressure to give a yellow oil, which was loaded onto a silica gel column and eluted with ethyl acetate and hexane (1:1) to afford the mixed title compounds (50 mg, 66%) as a yellow oil. MS: 599.3 (M+H$^+$).

Step E: 2-((1H-pyrrolo[2,3-b]pyridin-5-yl)oxy)-4-(4-((2-(4-isopropylthiophen-3-yl)-4,4-dimethylcyclohex-1-en-1-yl)methyl)piperazin-1-yl)benzoic acid and 2-((1H-pyrrolo[2,3-b]pyridin-5-yl)oxy)-4-(4-((2-(4-isopropylthiophen-2-yl)-4,4-dimethylcyclohex-1-en-1-yl)methyl)piperazin-1-yl)benzoic acid

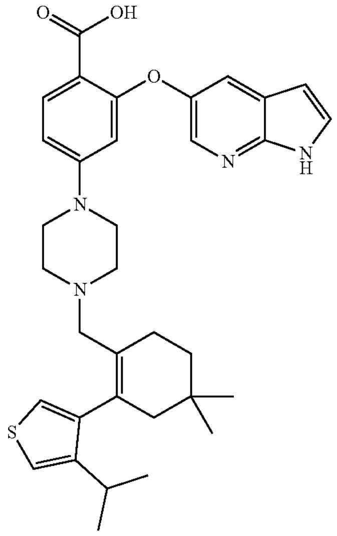

+

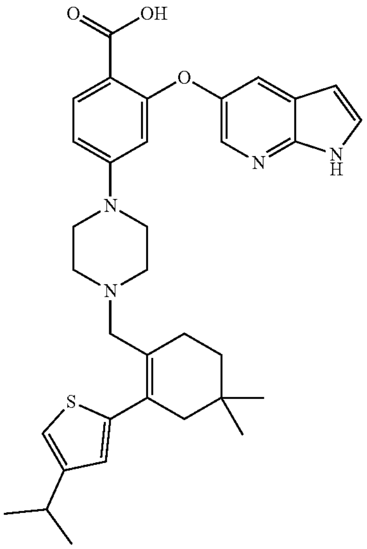

To a solution of a mixture of methyl 2-((1H-pyrrolo[2,3-b]pyridin-5-yl)oxy)-4-(4-((2-(4-isopropylthiophen-3-yl)-4,4-dimethylcyclohex-1-en-1-yl)methyl)piperazin-1-yl)benzoate and methyl 2-((1H-pyrrolo[2,3-b]pyridin-5-yl)oxy)-4-(4-((2-(4-isopropylthiophen-2-yl)-4,4-dimethylcyclohex-1-en-1-yl)methyl)piperazin-1-yl)benzoate (Step D, 76 mg, 0.13 mmol) in a mixed solvent of MeOH (1 mL), THF (1 mL) and $H_2O$ (1 mL) was added NaOH (51 mg, 1.3 mmol); the reaction mixture was stirred at 50° C. for 4 h. After coiling down to room temperature, the mixture was acidified with 1 M HCl to adjust pH 4-5 and then extracted with ethyl acetate twice. The combined organic layer was dried over $Na_2SO_4$, and concentrated under reduced pressure to give the crude title compounds (72 mg) as a yellow oil, which was directly used for the next step without purification. MS: 585.3 (M+$H^+$).

Step F: 2-((1H-pyrrolo[2,3-b]pyridin-5-yl)oxy)-4-(4-((2-(4-isopropylthiophen-3-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide (Example 7) and 2-((1H-pyrrolo[2,3-b]pyridin-5-yl)oxy)-4-(4-((2-(4-isopropylthiophen-2-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide (Example 8)

Example 7

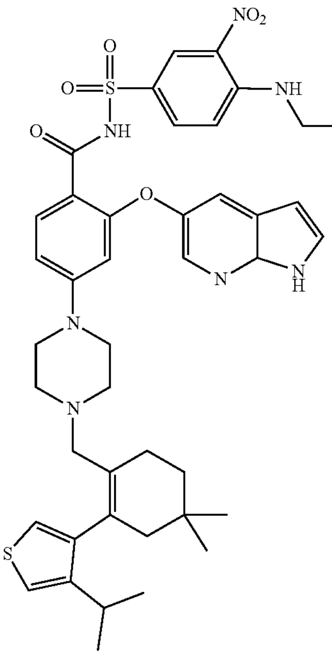

and

-continued

Example 8

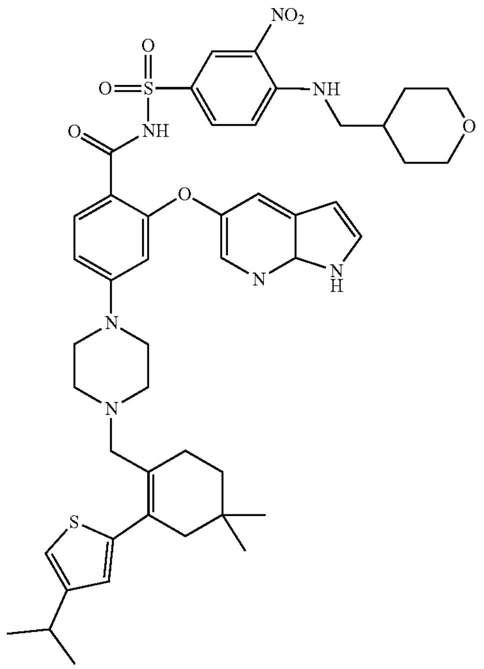

Under $N_2$, to a solution of a mixture of 2-((1H-pyrrolo[2,3-b]pyridin-5-yl)oxy)-4-(4-((2-(4-isopropylthiophen-3-yl)-4,4-dimethylcyclohex-1-en-1-yl)methyl)piperazin-1-yl)benzoic acid and 2-((1H-pyrrolo[2,3-b]pyridin-5-yl)oxy)-4-(4-((2-(4-isopropylthiophen-2-yl)-4,4-dimethylcyclohex-1-en-1-yl)methyl)piperazin-1-yl)benzoic acid (Step E, 36 mg, 0.06 mmol) in dry DCM (2 mL) was added N,N-dimethylpyridin-4-amine (18.8 mg, 0.15 mmol), EDCl (17.7 mg, 0.09 mmol) and 3-nitro-4-(((tetrahydro-2H-pyran-4-yl)methyl)amino)benzenesulfonamide (19.4 mg, 0.06 mmol); the reaction mixture was stirred at 40° C. for 12 h. After cooling down to room temperature, the mixture was diluted with ethyl acetate and washed with $H_2O$ and brine. The organic layer was dried over $Na_2SO_4$ and concentrated under reduced pressure to give a yellow oil, which was purified by C18 prep-HPLC column to afford the title compounds (Example 7: 17 mg, 31% over 2 steps; Example 8: 4 mg, 7% over 2 steps) as yellow solid.

Example 7: $^1H$ NMR (400 MHz, DMSO-$d_6$) 511.69 (s, 1H), 11.48 (s, 1H), 8.61 (t, J=5.5 Hz, 1H), 8.55 (d, J=1.9 Hz, 1H), 8.03 (d, J=2.5 Hz, 1H), 7.79 (dd, J=9.1, 1.4 Hz, 1H), 7.56-7.46 (m, 3H), 7.15 (d, J=3.0 Hz, 1H), 7.10 (d, J=9.1 Hz, 1H), 6.93 (d, J=3.1 Hz, 1H), 6.68 (dd, J=8.9, 1.8 Hz, 1H), 6.41-6.36 (m, 1H), 6.18 (d, J=1.5 Hz, 1H), 3.88-3.81 (m, 2H), 3.32-3.22 (m, 4H), 3.12-3.00 (m, 4H), 2.76-2.53 (m, 3H), 2.35-2.20 (m, 4H), 2.21-2.09 (m, 2H), 2.02-1.97 (m, 1H), 1.92-1.84 (m, 2H), 1.65-1.57 (m, 2H), 1.38 (t, J=6.4 Hz, 2H), 1.31-1.24 (m, 2H), 1.12-1.06 (m, 6H), 0.92 (s, 6H); MS: 882.4 (M+$H^+$).

Example 8: $^1$H NMR (400 MHz, DMSO-$d_6$) δ11.68 (s, 1H), 11.50 (s, 1H), 8.60 (t, J=5.5 Hz, 1H), 8.54 (d, J=2.0 Hz, 1H), 8.03 (d, J=2.5 Hz, 1H), 7.77 (d, J=10.4 Hz, 1H), 7.56-7.46 (m, 3H), 7.08 (d, J=9.2 Hz, 1H), 6.98 (s, 1H), 6.79 (s, 1H), 6.70 (dd, J=9.0, 1.8 Hz, 1H), 6.37 (dd, J=3.1, 1.8 Hz, 1H), 6.23 (d, J=1.6 Hz, 1H), 3.88-3.81 (m, 2H), 3.32-3.22 (m, 4H), 3.13-3.05 (m, 4H), 3.02-2.94 (m, 2H), 2.89-2.77 (m, 1H), 2.32-2.23 (m, 4H), 2.21-2.12 (m, 2H), 2.07-2.02 (m, 2H), 1.95-1.81 (m, 1H), 1.66-1.55 (m, 2H), 1.35 (t, J=6.2 Hz, 2H), 1.31-1.24 (m, 2H), 1.15 (d, J=6.8 Hz, 6H), 0.90 (s, 6H); MS: 882.4 (M+H$^+$).

Examples 9 and 10: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-isopropylthiophen-3-yl)-4,4-dimethylcyclohex-1-en-1-yl)methyl)piperazin-1-yl)benzamide (Example 9) and (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-isopropylthiophen-2-yl)-4,4-dimethylcyclohex-1-en-1-yl)methyl)piperazin-1-yl)benzamide (Example 10)

Example 9

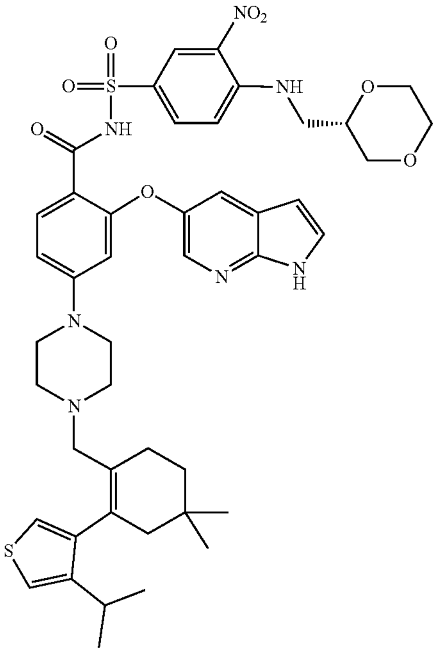

and

-continued

Example 10

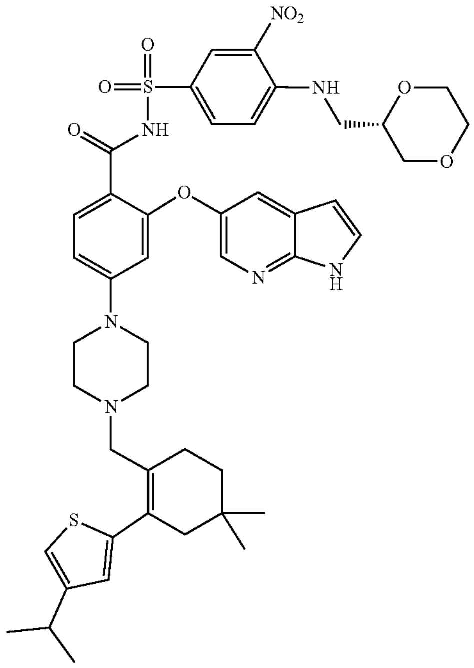

Essentially the same protocol of preparation of Examples 7 and 8 was used to afford the examples (Example 9: 3.6 mg; Example 10: 9.6 mg) as yellow solid.

Example 9: $^1$H NMR (400 MHz, DMSO-$d_6$) δ11.67 (s, 1H), 8.60-8.49 (m, 2H), 8.06-7.97 (m, 1H), 7.78 (d, J=9.1 Hz, 1H), 7.52-7.46 (m, 3H), 7.16 (d, J=3.0 Hz, 1H), 7.05 (d, J=10.3 Hz, 1H), 6.93 (d, J=3.0 Hz, 1H), 6.72-6.64 (m, 1H), 6.40-6.34 (m, 1H), 6.25-6.15 (m, 1H), 3.84-3.75 (m, 3H), 3.69-3.57 (m, 2H), 3.54-3.44 (m, 2H), 3.33-3.28 (m, 2H), 3.12-3.00 (m, 4H), 2.75-2.60 (m, 3H), 2.36-2.20 (m, 2H), 2.17-2.09 (m, 2H), 2.06-1.94 (m, 4H), 1.38 (t, J=6.2 Hz, 2H), 1.11-1.06 (m, 6H), 0.92 (s, 6H); MS: 884.4 (M+H$^+$).

Example 10: $^1$H NMR (400 MHz, DMSO-$d_6$) δ11.67 (s, 1H), 11.51 (s, 1H), 8.62-8.50 (m, 2H), 8.02 (d, J=2.3 Hz, 1H), 7.79 (d, J=9.0 Hz, 1H), 7.54-7.45 (m, 3H), 7.07 (d, J=9.2 Hz, 1H), 6.98 (s, 1H), 6.79 (s, 1H), 6.70 (dd, J=8.9, 1.3 Hz, 1H), 6.39-6.34 (m, 1H), 6.28-6.18 (m, 1H), 3.86-3.74 (m, 3H), 3.69-3.55 (m, 2H), 3.54-3.43 (m, 2H), 3.33-3.27 (m, 2H), 3.14-3.04 (m, 4H), 3.02-2.94 (m, 2H), 2.88-2.79 (m, 1H), 2.35-2.22 (m, 4H), 2.21-2.12 (m, 2H), 2.08-2.02 (m, 2H), 1.35 (t, J=6.1 Hz, 2H), 1.15 (d, J=6.8 Hz, 6H), 0.90 (s, 6H); MS: 884.4 (M+H$^+$).

Examples 11 and 12: 2-((1H-pyrrolo[2,3-b]pyridin-5-yl)oxy)-4-(4-((2-(2-isopropylthiophen-3-yl)-4,4-dimethylcyclohex-1-en-1-yl)-methyl)piperazin-1-yl)-N-((3-nitro-4-(((tetrahydro-2H-pyran-4-yl)methyl)amino)-phenyl)sulfonyl)benzamide (Example 11) and 2-((1H-pyrrolo[2,3-b]pyridin-5-yl)oxy)-4-(4-((2-(5-isopropylthiophen-2-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide (Example 12)

Example 11

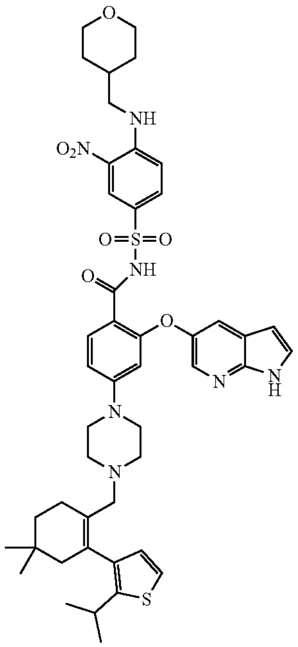

and

Example 12

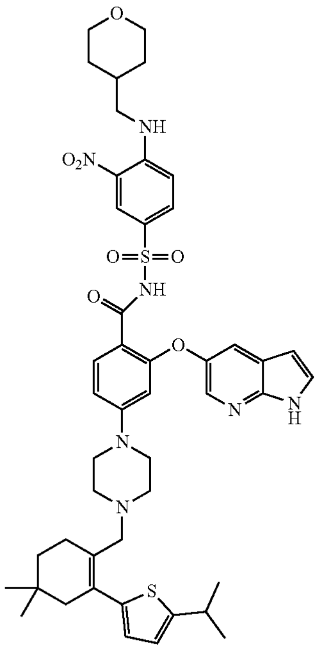

Step A: (2-Isopropylthiophen-3-yl)boronic acid and (5-isopropylthiophen-2-yl)boronic acid

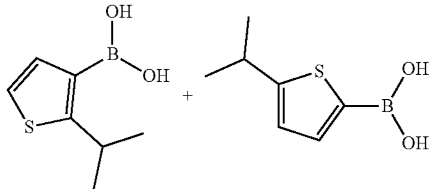

In a flame-dried over 100 mL round-bottomed flask, 3-bromo-2-isopropylthiophene (0.6 g, 2.93 mmol) was dissolved into dry THF (10 mL) under argon to give a solution. nBuLi (1.4 mL, 2.5 M in n-Hexane, 3.51 mmol) was added to the reaction mixture at −78° C. After stirred at −78° C. for 30 min, triisopropyl borate (0.825 g, 4.39 mmol) was added. The reaction mixture was stirred at −78° C. for 2 h and then at room temperature for overnight. 1 N HCl (10 mL) was added to the reaction mixture followed by extraction with ethyl acetate (10 mL×2). The combined organic layers were dried over $Na_2SO_4$, and concentrated under reduced pressure to give a yellow oil, which was loaded onto a silica gel column and was eluted with methanol and dichloromethane (1:50) to afford the mixed title compounds (0.4 g, 80%) as a light yellow oil.

Step B: Methyl 2-((1H-pyrrolo[2,3-b]pyridin-5-yl)oxy)-4-(4-((2-(2-isopropylthiophen-3-yl)-4,4-dimethylcyclohex-1-en-1-yl)methyl)piperazin-1-yl)benzoate and methyl 2-((1H-pyrrolo[2,3-b]pyridin-5-yl)oxy)-4-(4-((2-(5-isopropylthiophen-2-yl)-4,4-dimethylcyclohex-1-en-1-yl)methyl)piperazin-1-yl)benzoate

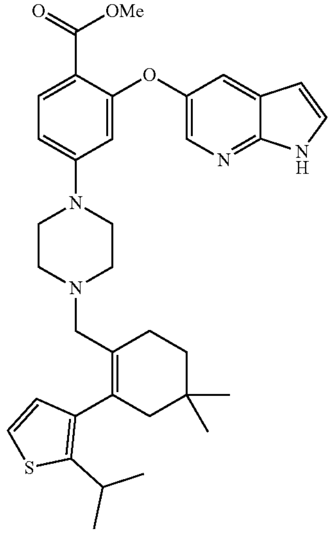

+

-continued

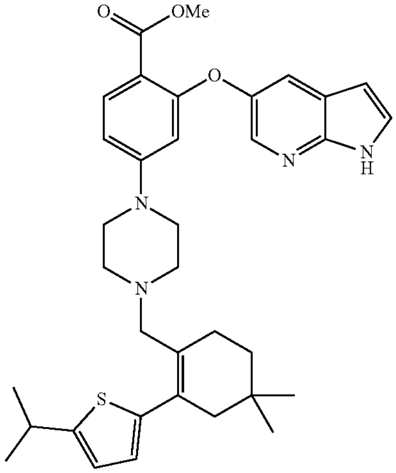

In a flame-dried over 100 mL round-bottomed flask, methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (50 mg, 0.09 mmol), a mixture of (2-isopropylthiophen-3-yl)boronic acid and (5-isopropylthiophen-2-yl)boronic acid (Step A, 46.1 mg, 0.27 mmol), $K_2CO_3$ (44.9 mg, 0.325 mmol) and $Pd(Ph_3P)_4$ (20.88 mg, 0.018 mmol) were dissolved into a mixed solvent of 1,4-dioxane (6 mL) and water (2 mL) under argon to give a solution; then the reaction mixture was stirred at room temperature for 10 min, and then stirred at 100° C. for 5 h. Sat. $NaHCO_3$ (10 mL) was added to the reaction mixture followed by extraction with ethyl acetate (10 mL×2). The combined organic layers were dried over $Na_2SO_4$, and concentrated under reduced pressure to give a yellow oil, which was loaded onto a silica gel column and eluted with methanol and dichloromethane (1:40) to afford the mixed title compounds (40 mg, 74%) as a light yellow oil. MS: 599.8 (M+H$^+$).

Step C: 2-((1H-pyrrolo[2,3-b]pyridin-5-yl)oxy)-4-(4-((2-(2-isopropylthiophen-3-yl)-4,4-dimethylcyclohex-1-en-1-yl)methyl)piperazin-1-yl)benzoic acid and 2-((1H-pyrrolo[2,3-b]pyridin-5-yl)oxy)-4-(4-((2-(5-isopropylthiophen-2-yl)-4,4-dimethylcyclohex-1-en-1-yl)methyl)piperazin-1-yl)benzoic acid

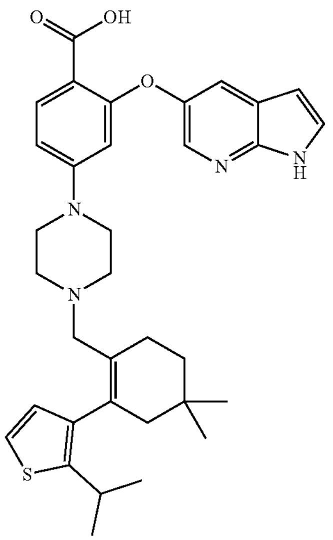

+

-continued

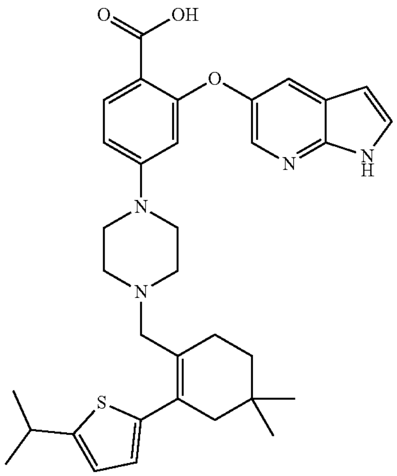

In a flame-dried over 100 mL round-bottomed flask, a mixture of methyl 2-((1H-pyrrolo[2,3-b]pyridin-5-yl)oxy)-4-(4-((2-(2-isopropylthiophen-3-yl)-4,4-dimethylcyclohex-1-en-1-yl)meth-yl)piperazin-1-yl)benzoate and methyl 2-((1H-pyrrolo[2,3-b]pyridin-5-yl)oxy)-4-(4-((2-(5-isopropylthiophen-2-yl)-4,4-dimethylcyclohex-1-en-1-yl)methyl)piperazin-1-yl)benzoate (Step B, 70 mg, 0.117 mmol) was dissolved into a mixed solvent of THF (2 mL), water (1 mL) and MeOH (1 mL) under argon to give a solution; Sodium hydroxide (80 mg, 2.0 mmol) was added and the reaction mixture was stirred at 40° C. for 5 h. After cooling down to room temperature, 1 N HCl (2 mL) was added to the reaction mixture followed by extraction with ethyl acetate (10 mL×2). The combined organic layers were dried over $Na_2SO_4$, and concentrated under reduced pressure to give a yellow oil, which was loaded onto a silica gel column and eluted with methanol and dichloromethane (1:50) to afford the mixed title compounds (68 mg, 99%) as a light yellow oil. MS: 585.5 (M+H$^+$).

Step D: 2-((1H-pyrrolo[2,3-b]pyridin-5-yl)oxy)-4-(4-((2-(2-isopropylthiophen-3-yl)-4,4-dimethylcyclohex-1-en-1-yl)-methyl)piperazin-1-yl)-N-((3-nitro-4-(((tetrahydro-2H-pyran-4-yl)methyl)amino)-phenyl)sulfonyl)benzamide (Example 11) and 2-((1H-pyrrolo[2,3-b]pyridin-5-yl)oxy)-4-(4-((2-(5-isopropylthiophen-2-yl)-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide (Example 12)

Example 11

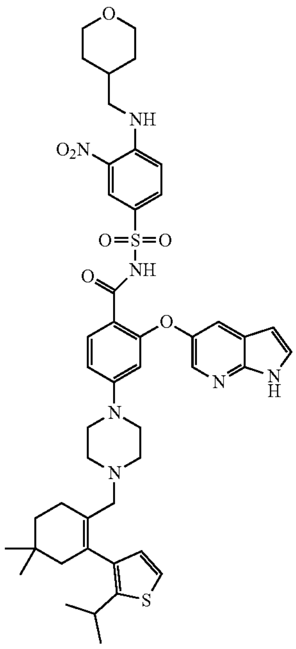

and

Example 12

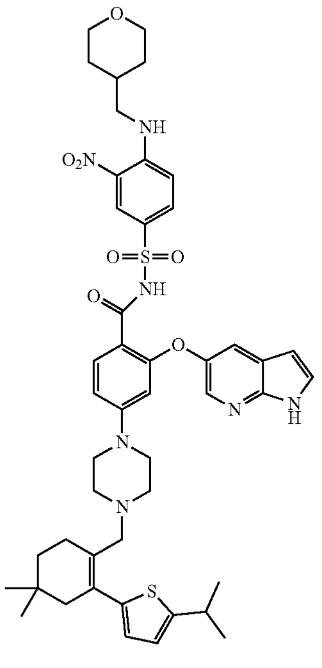

In a flame-dried over 100 mL round-bottomed flask, a mixture of 2-((1H-pyrrolo[2,3-b]pyridin-5-yl)oxy)-4-(4-((2-(2-isopropylthiophen-3-yl)-4,4-dimethylcyclohex-1-en-1-yl)methyl)-piperazin-1-yl)benzoic acid and 2-((1H-pyrrolo[2,3-b]pyridin-5-yl)oxy)-4-(4-((2-(5-isopropylthiophen-2-yl)-4,4-dimethylcyclohex-1-en-1-yl)methyl)piperazin-1-yl)benzoic acid (Step C, 50 mg, 0.086 mmol), 3-nitro-4-(((tetrahydro-2H-pyran-4-yl)methyl)amino) benzenesulfonamide (40.4 mg, 0.128 mmol), N,N-dimethylpyridin-4-amine (31.3 mg, 0.257 mmol) were dissolved into dry $CH_2Cl_2$ (10 mL) under argon to give a solution; 3-(((ethylimino)methylene)amino)-N,N-dimethyl-propan-1-amine hydrochloride (32.8 mg, 0.171 mmol) was added at 0° C. and the reaction mixture was stirred at 0° C. for 1 h and then at room temperature for 16 h. Sat. $NaHCO_3$ (10 mL) was added to the reaction mixture followed by extraction with dichloromethane (10 mL×2). The combined organic layers were dried over $Na_2SO_4$, and concentrated under reduced pressure to give a yellow oil, which was purified by C18 prep-HPLC to afford the title compounds (Example 11: 4 mg, 7%; Example 12: 4 mg, 7%) as a yellow solid.

Example 11: $^1$H NMR (400 MHz, DMSO-$d_6$) δ 11.72 (s, 1H), 8.63 (brs, 1H), 8.56 (s, 1H), 8.05 (d, J=2.2 Hz, 1H), 7.80 (d, J=9.0 Hz, 1H), 7.57-7.48 (m, 3H), 7.27 (d, J=5.1 Hz, 1H), 7.11 (d, J=9.0 Hz, 1H), 6.71 (dd, J=9.0, 1.9 Hz, 1H), 6.61 (d, J=5.1 Hz, 1H), 6.43-6.38 (m, 1H), 6.22 (d, J=1.7 Hz, 1H), 3.87 (dd, J=11.0, 3.2 Hz, 2H), 3.35-3.24 (m, 4H), 3.17-3.05 (m, 4H), 3.03-2.94 (m, 1H), 2.82-2.72 (m, 1H), 2.67-2.59 (m, 1H), 2.34-2.20 (m, 3H), 2.19-2.11 (m, 2H), 2.10-1.99 (m, 1H), 1.99-1.86 (m, 2H), 1.85-1.74 (m, 1H), 1.64 (d, J=12.3 Hz, 2H), 1.41 (t, J=6.3 Hz, 2H), 1.34-1.27 (m, 2H), 1.18 (d, J=6.6 Hz, 6H), 0.95 (s, 6H); MS: 883.2 ($M+H^+$).

Example 12: $^1$H NMR (400 MHz, DMSO-$d_6$) δ 11.69 (s, 1H), 8.69-8.50 (m, 2H), 8.04 (s, 1H), 7.77 (s, 1H), 7.59-7.47 (m, 3H), 7.24 (s, 1H), 6.77-6.68 (m, 2H), 6.65 (d, J=3.5 Hz, 1H), 6.39 (s, 1H), 6.26 (s, 1H), 3.87 (dd, J=10.9, 3.6 Hz, 2H), 3.35-3.24 (m, 4H), 3.16-3.05 (m, 5H), 3.02 (s, 2H), 2.34-2.24 (m, 4H), 2.24-2.16 (m, 2H), 2.05 (s, 2H), 1.96-1.83 (m, 1H), 1.63 (d, J=11.5 Hz, 2H), 1.37 (t, J=6.0 Hz, 2H), 1.34-1.28 (m, 2H), 1.24 (s, 6H), 0.93 (s, 6H); MS: 883.2 ($M+H^+$).

Examples 13 and 14: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(2-isopropylthiophen-3-yl)-4,4-dimethylcyclohex-1-en-1-yl)methyl)piperazin-1-yl)benzamide (Example 13) and (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(5-isopropylthiophen-2-yl)-4,4-dimethylcyclohex-1-en-1-yl)methyl)piperazin-1-yl)benzamide (Example 14)

Example 13

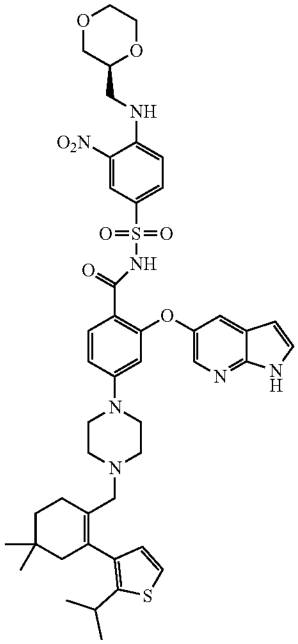

and

Example 14

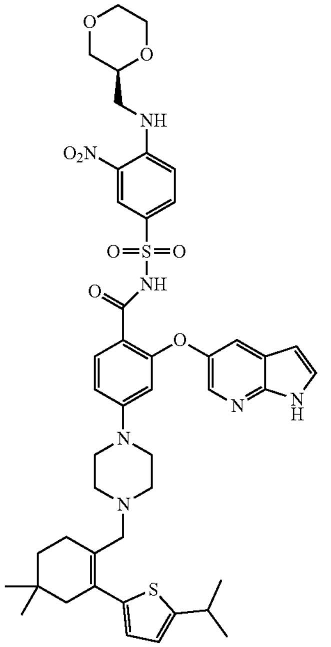

Essentially the same protocol of preparation of Examples 11 and 12 was used to afford the examples (Example 13: 1.4 mg; Example 14: 0.5 mg) as yellow solid.

Example 13: $^1$H NMR (400 MHz, DMSO-$d_6$) δ 11.60 (s, 1H), 8.57-8.38 (m, 2H), 7.97 (s, 1H), 7.72 (s, 1H), 7.52 (d, J=9.0 Hz, 1H), 7.46 (s, 1H), 7.31-7.14 (m, 2H), 6.71-6.62 (m, 1H), 6.62-6.53 (m, 2H), 6.34 (s, 1H), 6.22 (s, 1H), 3.85-3.73 (m, 3H), 3.70-3.57 (m, 2H), 3.56-3.40 (m, 4H), 3.10-2.97 (m, 7H), 2.30-2.18 (m, 4H), 2.17-2.08 (m, 2H), 1.97 (s, 2H), 1.42-1.34 (m, 2H), 1.15 (d, J=4.0 Hz, 6H), 0.92 (s, 6H); MS: 885.2 (M+H$^+$).

Example 14: $^1$H NMR (400 MHz, DMSO-$d_6$) δ 11.58 (s, 1H), 8.53-8.37 (m, 2H), 7.96 (s, 1H), 7.68 (s, 1H), 7.54 (d, J=8.8 Hz, 1H), 7.44 (s, 1H), 7.35 (s, 1H), 7.21 (s, 1H), 6.71-6.65 (m, 2H), 6.63 (d, J=3.5 Hz, 1H), 6.32 (s, 1H), 6.26 (s, 1H), 3.84-3.73 (m, 3H), 3.70-3.56 (m, 2H), 3.52-3.42 (m, 4H), 3.10-3.04 (m, 5H), 3.00 (s, 2H), 2.32-2.23 (m, 4H), 2.22-2.12 (m, 2H), 2.02 (s, 2H), 1.40-1.31 (m, 2H), 1.23-1.19 (m, 6H), 0.90 (s, 6H); MS: 884.6 (M+H$^+$).

Example 15: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(5-(4-fluorophenyl)-4,5,6,7-tetrahydrothieno[3,2-c]pyridin-2-yl)-4,4-dimethylcyclohex-1-en-1-yl)methyl)piperazin-1-yl)benzamide

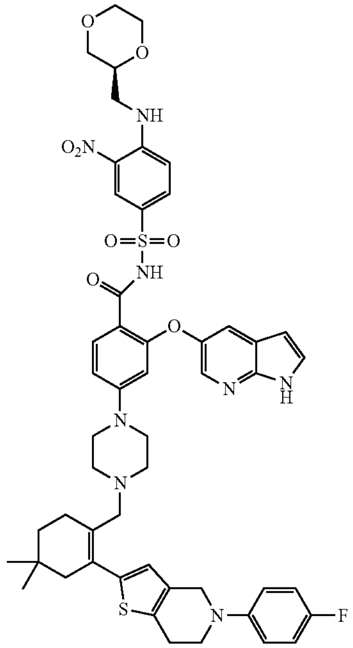 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc3c(s2)CCN(c2ccc(F)cc2)C3)C1]

Step A: 5-(4-Fluorophenyl)-4,5,6,7-tetrahydrothieno[3,2-c]pyridine

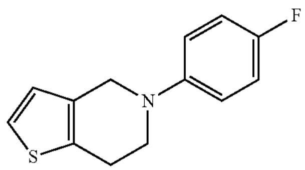 [SMILES: Fc1ccc(N2CCc3sccc3C2)cc1]

In a flame-dried over 100 mL round-bottomed flask, 4,5,6,7-tetrahydrothieno[3,2-c]pyridine (1 g, 7.18 mmol)

and (4-fluorophenyl)boronic acid (2.010 g, 14.37 mmol) were dissolved into dry $CH_2Cl_2$ (5 mL) under argon to give a solution; Diacetoxycopper hydrate (1.43 g, 7.18 mmol) and triethylamine (2.18 g, 21.55 mmol) were added at room temperature and the reaction mixture was stirred at room temperature for 16 h. After removal of volatiles, the residue was loaded onto a silica gel column and eluted with ethyl acetate and hexane (1:3) to afford the title compound (1.2 g, 72%) as a light yellow solid. $^1$H NMR (400 MHz, DMSO-$d_6$) δ 7.32 (d, J=5.1 Hz, 1H), 7.09-6.99 (m, 4H), 6.90 (d, J=5.1 Hz, 1H), 4.22 (s, 2H), 3.53 (t, J=5.7 Hz, 2H), 2.89 (t, J=5.6 Hz, 2H); MS: 233.6 (M+H$^+$).

Step B: (5-(4-fluorophenyl)-4,5,6,7-tetrahydrothieno[3,2-c]pyridin-2-yl)boronic acid

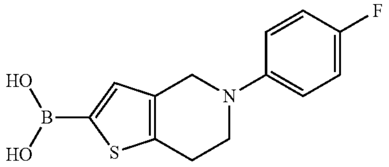 [SMILES: OB(O)c1cc2c(s1)CCN(c1ccc(F)cc1)C2]

In a flame-dried over 100 mL round-bottomed flask, 5-(4-fluorophenyl)-4,5,6,7-tetrahydrothieno[3,2-c]pyridine (Step A, 250 mg, 1.1 mmol) was dissolved in dry THF (10 mL) under argon at −78° C. to give a solution; LDA (1.1 mL, 2 M in THF, 2.14 mmol) was added at −78° C., the mixture was stirred at −78° C. for 1 h and then triisopropyl borate (443 mg, 2.36 mmol) was followed dropwise over 30 min; the reaction mixture was stirred at −78° C. for 30 min, allowed to gradually warm up to room temperature and stirred for another 1 h. MeOH (10 mL) was added to quench the reaction. After removal of volatiles, the residue was directly used for the next step without further purifications. MS: 277.3 (M+H$^+$).

Step C: Methyl 2-((1H-pyrrolo[2,3-b]pyridin-5-yl)oxy)-4-(4-((2-(5-(4-fluorophenyl)-4,5,6,7-tetrahydrothieno[3,2-c]pyridin-2-yl)-4,4-dimethylcyclohex-1-en-1-yl)methyl)piperazin-1-yl benzoate

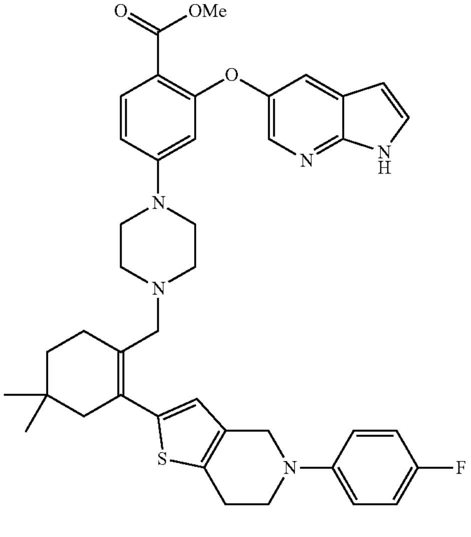 [SMILES: COC(=O)c1ccc(N2CCN(CC3=C(c4cc5c(s4)CCN(c4ccc(F)cc4)C5)CC(C)(C)CC3)CC2)cc1Oc1cnc2[nH]ccc2c1]

In a flame-dried over 100 mL round-bottomed flask, the crude (5-(4-fluorophenyl)-4,5,6,7-tetrahydrothieno[3,2-c]pyridin-2-yl)boronic acid (Step B), methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 297 mg, 0.536 mmol), $PdCl_2(dppf)\cdot CH_2Cl_2$ (175 mg, 0.214 mmol) and $Na_2CO_3$ (568 mg, 5.36 mmol) were dissolved into a mixed solvent of 1,4-dioxane (7.5 mL) and water (1.5 mL) under argon to give a solution. $Na_2CO_3$ (568 mg, 5.36 mmol) was added at room temperature; and the reaction mixture was stirred at 100° C. for 12 h. After cooling down to room temperature, sat. $NaHCO_3$ (10 mL) was added to the reaction mixture followed by extraction with dichloromethane (10 mL×2). The combined organic layers were dried over $Na_2SO_4$, and concentrated under reduced pressure to give a yellow oil, which was loaded onto a silica gel column and eluted with methanol and dichloromethane (1:50) to afford the title compound (300 mg, 40% over 2 steps) as a light yellow solid. $^1$H NMR (400 MHz, DMSO-$d_6$) δ 11.61 (s, 1H), 7.99 (d, J=2.4 Hz, 1H), 7.75 (d, J=9.0 Hz, 1H), 7.49-7.44 (m, 1H), 7.41 (d, J=2.6 Hz, 1H), 7.08-6.96 (m, 4H), 6.76 (dd, J=9.0, 2.3 Hz, 1H), 6.61 (s, 1H), 6.40-6.34 (m, 2H), 4.13 (s, 2H), 3.64 (s, 3H), 3.50 (t, J=5.6 Hz, 2H), 3.21-3.10 (m, 4H), 3.04 (s, 2H), 2.88-2.78 (m, 2H), 2.37-2.26 (m, 4H), 2.26-2.13 (m, 2H), 2.03 (s, 2H), 1.36 (t, J=6.3 Hz, 2H), 0.91 (s, 6H); MS: 706.0 (M+H$^+$).

Step D: 2-((1H-pyrrolo[2,3-b]pyridin-5-yl)oxy)-4-(4-((2-(5-(4-fluorophenyl)-4,5,6,7-tetrahydrothieno[3,2-c]pyridin-2-yl)-4,4-dimethylcyclohex-1-en-1-yl)methyl)piperazin-1-yl)benzoic acid

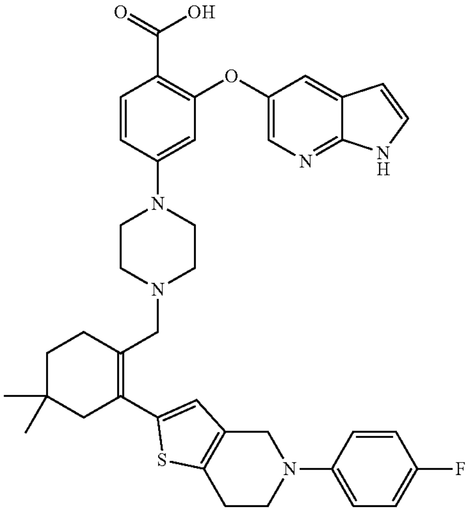 [SMILES: CC1(C)CCC(CN2CCN(c3ccc(C(=O)O)c(Oc4cnc5[nH]ccc5c4)c3)CC2)=C(c2cc3c(s2)CCN(c2ccc(F)cc2)C3)C1]

In a flame-dried over 100 mL round-bottomed flask, methyl 2-((1H-pyrrolo[2,3-b]pyridin-5-yl)oxy)-4-(4-((2-(5-(4-fluorophenyl)-4,5,6,7-tetrahydrothieno[3,2-c]pyridin-2-yl)-4,4-dimethylcyclohex-1-en-1-yl)methyl)piperazin-1-yl)benzoate (Step C, 300 mg, 0.43 mmol) was dissolved into a mixed solvent of water (2 mL), THF (4 mL) and MeOH (2 mL) under argon to give a solution. Sodium hydroxide (170 mg, 4.25 mmol) was added at room temperature; and the reaction mixture was stirred at 45° C. for 16 h. 1 N HCl (4 mL) was added to the reaction mixture and the resulting mixture was concentrated under reduced pressure to give the crude product as pale solid, which was directly used in the next step without purification. MS: 693.3 ($M+H^+$).

Step E: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(5-(4-fluorophenyl)-4,5,6,7-tetrahydrothieno[3,2-c]pyridin-2-yl)-4,4-dimethylcyclohex-1-en-1-yl)methyl)piperazin-1-yl)benzamide (Example 15)

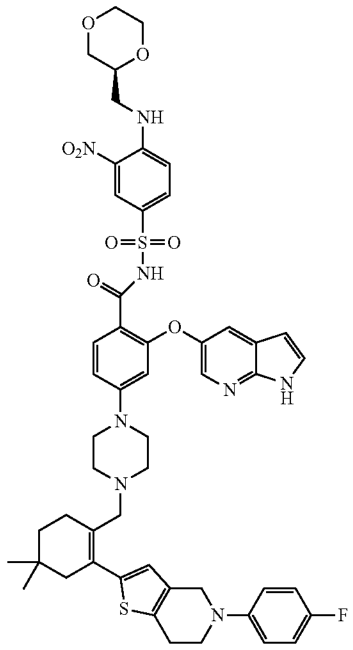 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc3c(s2)CCN(c2ccc(F)cc2)C3)C1]

In a flame-dried over 100 mL round-bottomed flask, the crude 2-((1H-pyrrolo[2,3-b]pyridin-5-yl)oxy)-4-(4-((2-(5-(4-fluorophenyl)-4,5,6,7-tetrahydrothieno[3,2-c]pyridin-2-yl)-4,4-dimethylcyclohex-1-en-1-yl)methyl)piperazin-1-yl)benzoic acid (Step D, 60 mg), N,N-dimethylpyridin-4-amine (53.0 mg, 0.43 mmol), (S)-4-(((1,4-dioxan-2-yl)methyl)amino)-3-nitrobenzenesulfonamide (27.5 mg, 0.087 mmol) were dissolved into dry $CH_2Cl_2$ (10 mL) under argon to give a solution; 3-(((ethylimino)methylene)amino)-N,N-dimethylpropan-1-amine hydrochloride (49.9 mg, 0.26 mmol) was added at room temperature and the reaction mixture was stirred at 40° C. for 12 h. After cooling down to room temperature, sat. $NaHCO_3$ (10 mL) was added to the reaction mixture followed by extraction with dichloromethane (10 mL×2). The combined organic layers were dried over $Na_2SO_4$, and concentrated under reduced pressure to give a yellow oil, which was purified by C18 prep-HPLC to afford the title compound (15 mg, 18% over 2 steps) as a yellow solid. $^1H$ NMR (400 MHz, DMSO-$d_6$) δ 11.59 (s, 1H), 8.56-8.39 (m, 2H), 7.99 (s, 1H), 7.75 (d, J=8.5 Hz, 1H), 7.53 (d, J=8.8 Hz, 1H), 7.49-7.37 (m, 2H), 7.09-6.92 (m, 5H), 6.69 (d, J=7.3 Hz, 1H), 6.60 (s, 1H), 6.35 (s, 1H), 6.25 (s, 1H), 4.14 (s, 2H), 3.84-3.74 (m, 4H), 3.64 (t, J=10.2 Hz, 2H), 3.54-3.42 (m, 4H), 3.40-3.32 (m, 1H), 3.13-3.06 (m, 4H), 3.03 (s, 2H), 2.87-2.78 (m, 2H), 2.36-2.26 (m, 4H), 2.22-2.13 (m, 2H), 2.03 (s, 2H), 1.36 (t, J=6.2 Hz, 2H), 0.91 (s, 6H); MS: 991.8 ($M+H^+$).

Example 16: 2-((1H-pyrrolo[2,3-b]pyridin-5-yl)oxy)-4-(4-((2-(5-(4-fluorophenyl)-4,5,6,7-tetrahydrothieno[3,2-c]pyridin-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

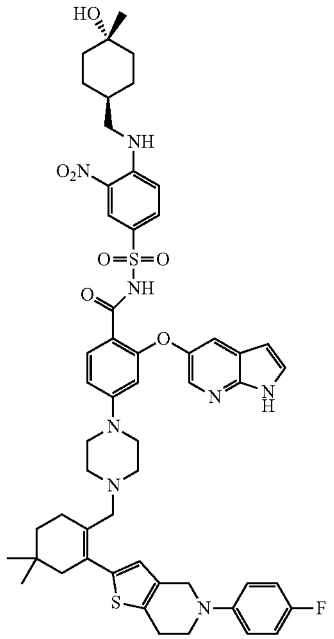 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc3c(s2)CCN(c2ccc(F)cc2)C3)C1]

Essentially the same protocol of preparation of Example 15 was used to afford the example (5 mg) as a yellow solid. $^1H$ NMR (400 MHz, DMSO-$d_6$) δ 11.63 (s, 1H), 8.59-8.40 (m, 2H), 8.02 (s, 1H), 7.76 (d, J=8.1 Hz, 1H), 7.57-7.43 (m, 3H), 7.11-6.95 (m, 5H), 6.69 (d, J=9.1 Hz, 1H), 6.60 (s, 1H), 6.36 (s, 1H), 6.24 (s, 1H), 4.21 (s, 1H), 4.13 (s, 2H), 3.50 (t, J=5.5 Hz, 2H), 3.28-3.21 (m, 2H), 3.14-3.08 (m, 4H), 3.03 (s, 2H), 2.89-2.75 (m, 2H), 2.34-2.24 (m, 4H), 2.23-2.14 (m, 2H), 2.03 (s, 2H), 1.73-1.59 (m, 3H), 1.58-1.50 (m, 2H), 1.39-1.29 (m, 4H), 1.19-1.06 (m, 5H), 0.91 (s, 6H); MS: 1018.2 ($M+H^+$).

Example 17: (S)-5-(2-((4-(4-(((4-(((1,4-dioxan-2-yl)methyl)amino)-3-nitrophenyl)sulfonyl)carbamoyl)-3-((1H-pyrrolo[2,3-b]pyridin-5-yl)oxy)phenyl)piperazin-1-yl)methyl)-5,5-dimethylcyclohex-1-en-1-yl)-N-phenylthiophene-3-carboxamide

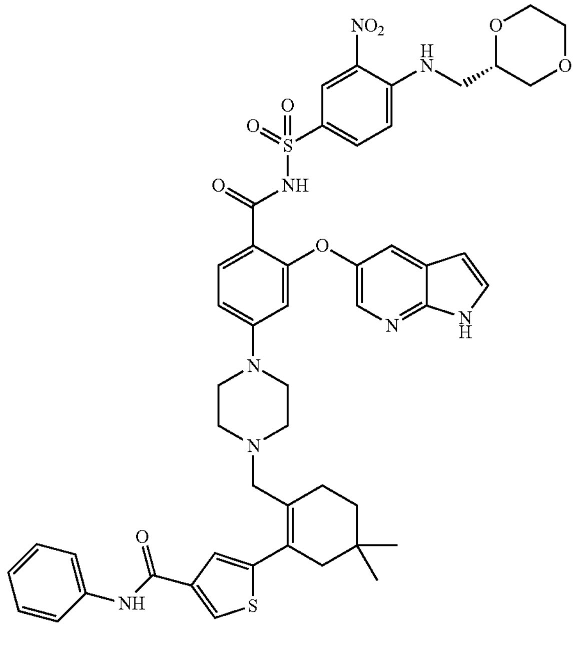 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(C(=O)Nc3ccccc3)cs2)C1]

Step A: 5-Bromo-N-phenylthiophene-3-carboxamide

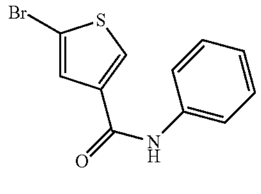 [SMILES: O=C(Nc1ccccc1)c1csc(Br)c1]

Under Ar, to a solution of 5-bromothiophene-3-carboxylic acid (1.0 g, 4.83 mmol) in dry DCM (25 mL) was added aniline (0.45 g, 4.83 mmol), EDCl (1.39 g, 7.24 mmol) and DMAP (1.18 g, 9.66 mmol); and the reaction mixture was stirred at 40° C. for 2 h. After cooling down to room temperature, the mixture was washed with 1 N HCl and brine, dried over $Na_2SO_4$ and concentrated under reduced pressure to give the crude title compound (800 mg) as a gray solid, which was directly used for the next step without purification. MS: 283.9 ($M+H^+$).

Step B: N-phenyl-5-(4,4,5,5-tetramethyl-1,3,2-dioxaborolan-2-yl)thiophene-3-carboxamide

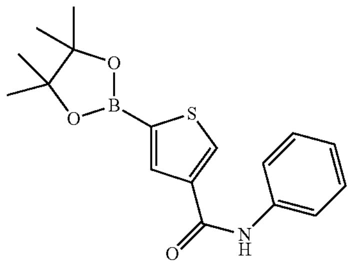 [SMILES: CC1(C)OB(c2cc(C(=O)Nc3ccccc3)cs2)OC1(C)C]

Under Ar, to a solution of the crude 5-bromo-N-phenylthiophene-3-carboxamide (Step A, 100 mg) in dry dioxane (8 mL) was added 4,4,4',4',5,5,5',5'-octamethyl-2,2'-bi(1,3,2-dioxaborolane) (108 mg, 0.425 mmol), potassium acetate (104 mg, 1.063 mmol) and $PdCl_2(dppf)$ (25.9 mg, 0.035 mmol); the reaction mixture was heated to 100° C. for 6 h. After cooling down to room temperature, the resulting mixture was filtered off through celite and the filtrate was concentrated under reduced pressure to give the crude title compound as a yellow oil, which was directly used for the next step without purification. MS: 330.1 ($M+H^+$).

Step C: Methyl 2-((1H-pyrrolo[2,3-b]pyridin-5-yl)oxy)-4-(4-((4,4-dimethyl-2-(4-(phenylcarbamoyl)thiophen-2-yl)cyclohex-1-en-1-yl)methyl)piperazin-1-yl)benzoate

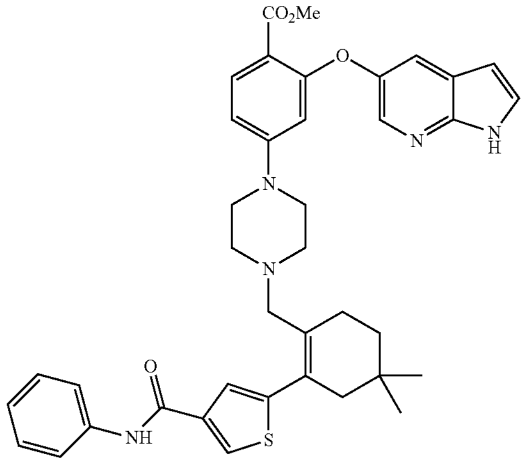 [SMILES: COC(=O)c1ccc(N2CCN(CC3=C(c4cc(C(=O)Nc5ccccc5)cs4)CC(C)(C)CC3)CC2)cc1Oc1cnc2[nH]ccc2c1]

Under Ar, to a solution of methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 98 mg, 0.178 mmol) in a mixed solvent of dioxane (10 mL) and water (2 mL) was added the crude N-phenyl-5-(4,4,5,5-tetramethyl-1,3,2-dioxaborolan-2-yl)thiophene-3-carboxamide (Step B, 117 mg), $Na_2CO_3$ (113 mg, 1.066 mmol) and $PdCl_2(dppf)$ (26 mg, 0.036 mmol); the reaction mixture was stirred at 90° C. for 16 h. After cooling down to room temperature and removal of volatiles, the residue was purified by silica gel column (hexane:EA, 1:1) to afford the title compound (80 mg, 33% over 3 steps) as a yellow oil. MS: 676.9 ($M+H^+$).

Step D: 2-((1H-pyrrolo[2,3-b]pyridin-5-yl)oxy)-4-(4-((4,4-dimethyl-2-(4-(phenylcarbamoyl)thiophen-2-yl)cyclohex-1-en-1-yl)methyl)piperazin-1-yl)benzoic acid

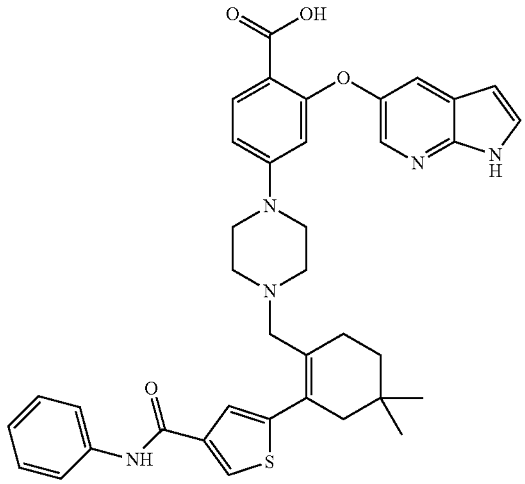 [SMILES: CC1(C)CCC(CN2CCN(c3ccc(C(=O)O)c(Oc4cnc5[nH]ccc5c4)c3)CC2)=C(c2cc(C(=O)Nc3ccccc3)cs2)C1]

To a solution of methyl 2-((1H-pyrrolo[2,3-b]pyridin-5-yl)oxy)-4-(4-((4,4-dimethyl-2-(4-(phenylcarbamoyl)thiophen-2-yl)cyclohex-1-en-1-yl)methyl)piperazin-1-yl)benzoate (Step C, 80 mg, 0.12 mmol) in a mixed solvent of THF (4 mL) and MeOH (4 mL) was added 3 N NaOH (4 mL); the reaction mixture was stirred at 40° C. for 16 h. After cooling down to room temperature, the mixture was adjusted to pH 3-4 with 1 N HCl. The resulting mixture was extracted with EA twice. The combined organic layer was washed with brine, dried over $Na_2SO_4$ and concentrated under reduced pressure to give the crude title compound (60 mg) as a yellow solid, which was directly used for the next step without purification. MS: 663.0 ($M+H^+$).

Step E: (S)-5-(2-((4-(4-(((4-(((1,4-dioxan-2-yl)methyl)amino)-3-nitrophenyl)sulfonyl)carbamoyl)-3-((1H-pyrrolo[2,3-b]pyridin-5-yl)oxy)phenyl)piperazin-1-yl)methyl)-5,5-dimethylcyclohex-1-en-1-yl)-N-phenylthiophene-3-carboxamide Example (17)

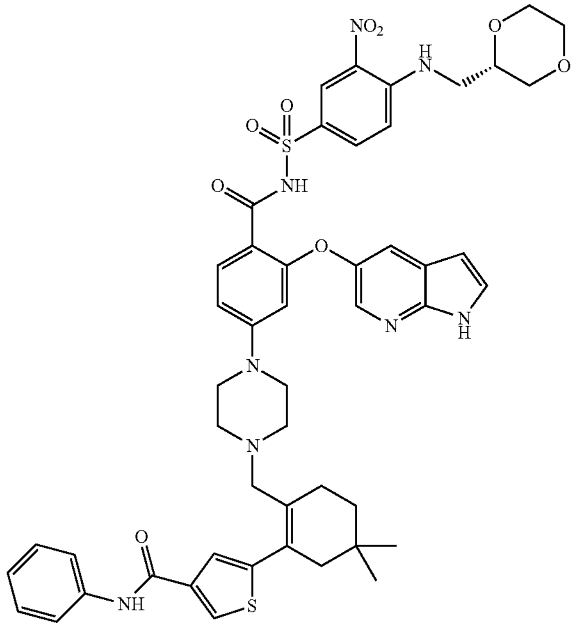 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(C(=O)Nc3ccccc3)cs2)C1]

Under Ar, to a solution of the crude 2-((1H-pyrrolo[2,3-b]pyridin-5-yl)oxy)-4-(4-((4,4-dimethyl-2-(4-(phenylcarbamoyl)thiophen-2-yl)cyclohex-1-en-1-yl)methyl)piperazin-1-yl)benzoic acid (Step D, 60 mg) in a mixed solvent of dry DMF (2 mL) and DCM (10 mL) was added (S)-4-(((1,4-dioxan-2-yl)methyl)amino)-3-nitrobenzenesulfonamide (28.8 mg, 0.091 mmol), DMAP (27.7 mg, 0.227 mmol) and EDCl (26.1 mg, 0.136 mmol); the reaction mixture was stirred at 40° C. for 16 h. After cooling down to room temperature, the resulting mixture was diluted with DCM, washed with 1 N HCl and brine, dried over $Na_2SO_4$ and concentrated under reduced pressure to give a yellow oil, which was purified by C18 prep-HPLC column to afford the title compound (15 mg, 17% over 2 steps) as a yellow solid. $^1H$ NMR (400 MHz, DMSO-$d_6$) δ 11.72 (s, 1H), 10.01 (s, 1H), 8.61 (brs, 1H), 8.57 (s, 1H), 8.25 (d, J=1.0 Hz, 1H), 8.06 (d, J=2.4 Hz, 1H), 7.82 (d, J=9.3 Hz, 1H), 7.74 (d, J=7.8 Hz, 2H), 7.57-7.48 (m, 3H), 7.41-7.31 (m, 3H), 7.11 (t, J=7.3 Hz, 2H), 6.74 (d, J=7.5 Hz, 1H), 6.40 (s, 1H), 6.26 (s, 1H), 3.88-3.76 (m, 3H), 3.71-3.58 (m, 2H), 3.56-3.45 (m, 3H), 3.37-3.28 (m, 2H), 3.21-3.09 (m, 4H), 3.08-2.98 (m, 2H), 2.37-2.27 (m, 4H), 2.26-2.19 (m, 2H), 2.17-2.08 (m, 2H), 1.41 (t, J=6.0 Hz, 2H), 0.97 (s, 6H); MS: 962.1 ($M+H^+$).

Example 18: (S)—N-((4-(((1,4-dioxan-2-yl)methyl) amino)-3-nitrophenyl)sulfonyl)-2-((1H-pyrrolo[2,3-b]pyridin-5-yl)oxy)-4-(4-((2-(4-benzamidothiophen-2-yl)-4,4-dimethylcyclohex-1-en-1-yl)methyl) piperazin-1-yl)benzamide

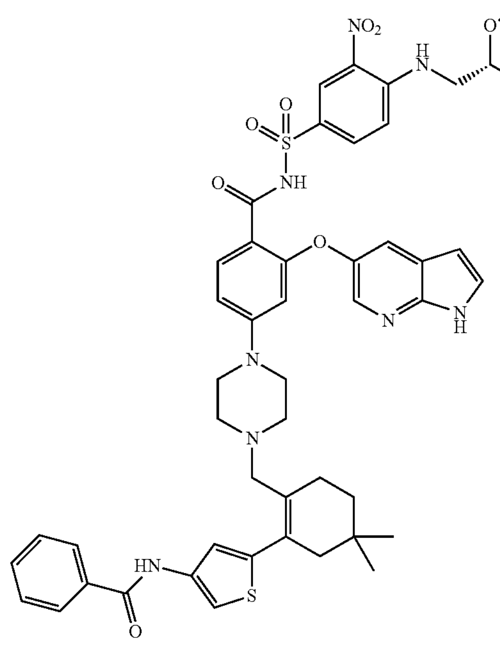

Step A: 5-Bromothiophen-3-amine

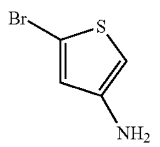

Under Ar, to a solution of tert-butyl (5-bromothiophen-3-yl)carbamate (200 mg, 0.719 mmol) in DCM (3 mL) was added TFA (3 mL), and the reaction mixture was stirred at room temperature for 16 h. After removal of volatiles, the resulting yellow oil as the crude title compound (128 mg, TFA salt)) was directly used for the next step without purification. MS: 179.7 (M+H$^+$).

Step B: N-(5-bromothiophen-3-yl)benzamide

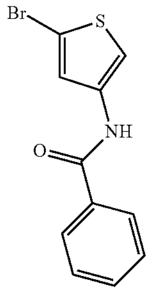 [SMILES: O=C(Nc1csc(Br)c1)c1ccccc1]

Under Ar, to a solution of the crude 5-bromothiophen-3-amine (Step A, 128 mg) in dry DCM (5 mL) was added $Et_3N$ (727 mg, 7.19 mmol) and benzoyl chloride (101 mg, 0.719 mmol) at 0° C.; then the reaction mixture was stirred at room temperature for 1 h. The resulting mixture was diluted with DCM, washed with aq. $NaHCO_3$ and brine, dried over $Na_2SO_4$ and concentrated under reduced pressure to give a yellow oil, which was purified by silica gel column (DCM: MeOH, 20:1) to afford the title compound (150 mg, 74% over 2 steps) as a yellow oil. MS: 283.9 (M+H$^+$).

Step C: N-(5-(4,4,5,5-tetramethyl-1,3,2-dioxaborolan-2-yl)thiophen-3-yl)benzamide

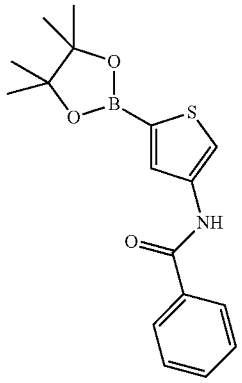 [SMILES: CC1(C)OB(c2cc(NC(=O)c3ccccc3)cs2)OC1(C)C]

Under Ar, to solution of N-(5-bromothiophen-3-yl)benzamide (Step B, 150 mg, 0.532 mmol) in dry dioxane (10 mL) was added 4,4,4',4',5,5,5',5'-octamethyl-2,2'-bi(1,3,2-dioxaborolane) (203 mg, 0.797 mmol), $PdCl_2$(dppf) (38.9 mg, 0.053 mmol) and potassium acetate (157 mg, 1.595 mmol); then the reaction mixture was stirred at 100° C. for 6 h. After cooling down to room temperature, the resulting mixture was filtered off through celite and the filtrate was concentrated under reduced pressure to give the crude title compound as a yellow oil, which was directly used for the next step without purification. MS: 330.2 (M+H$^+$).

Step D: Methyl 2-((1H-pyrrolo[2,3-b]pyridin-5-yl)oxy)-4-(4-((2-(4-benzamidothiophen-2-yl)-4,4-dimethylcyclohex-1-en-1-yl)methyl)piperazin-1-yl)benzoate

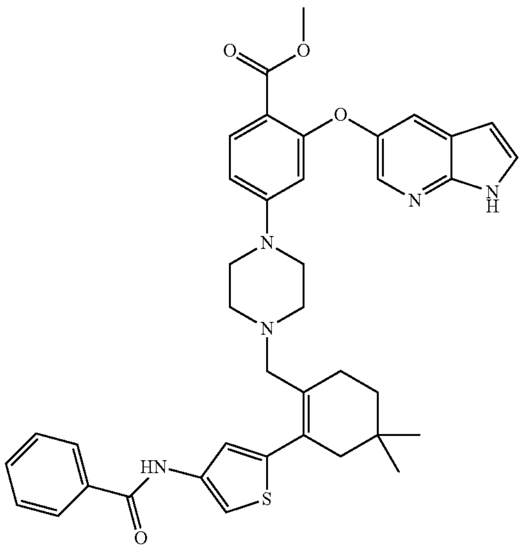 [SMILES: COC(=O)c1ccc(N2CCN(CC3=C(c4cc(NC(=O)c5ccccc5)cs4)CC(C)(C)CC3)CC2)cc1Oc1cnc2[nH]ccc2c1]

Under Ar, to a solution of the crude N-(5-(4,4,5,5-tetramethyl-1,3,2-dioxaborolan-2-yl)thiophen-3-yl)benzamide (Step C, 175 mg) in a mixed solvent of dioxane (15 mL) and water (3 mL) was added methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 88 mg, 0.159 mmol), $PdCl_2$(dppf) (38.9 mg, 0.053 mmol) and $Na_2CO_3$ (169 mg, 1.595 mmol); then the reaction mixture was stirred at 100° C. for 16 h. After cooling down to room temperature and removal of volatiles, the residue was purified by silica gel column (hexane:EA, 1:1) to afford the title compound (13 mg, 4% over 2 steps) as a yellow oil. MS: 676.6 ($M+H^+$).

Step E: 2-((1H-pyrrolo[2,3-b]pyridin-5-yl)oxy)-4-(4-((2-(4-benzamidothiophen-2-yl)-4,4-dimethylcyclohex-1-en-1-yl)methyl)piperazin-1-yl)benzoic acid

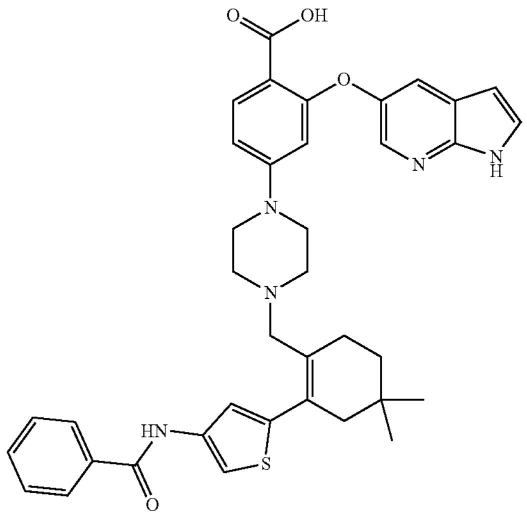 [SMILES: CC1(C)CCC(CN2CCN(c3ccc(C(=O)O)c(Oc4cnc5[nH]ccc5c4)c3)CC2)=C(c2cc(NC(=O)c3ccccc3)cs2)C1]

To a solution of methyl 2-((1H-pyrrolo[2,3-b]pyridin-5-yl)oxy)-4-(4-((2-(4-benzamidothiophen-2-yl)-4,4-dimethylcyclohex-1-en-1-yl)methyl)piperazin-1-yl)benzoate (Step D, 13 mg, 0.019 mmol) in a mixed solvent of MeOH (3 mL) and THF (3 mL) was added 3M NaOH (3 mL); then the reaction mixture was stirred at 40° C. for 16 h. After cooling down to room temperature, the resulting mixture was adjusted to pH 3-4 with 1 N HCl. The resulting mixture was extracted with EA twice, the combined organic layer was washed with brine, dried over $Na_2SO_4$ and concentrated under reduced pressure to give the crude title compound (10 mg) as a yellow solid, which was directly used for the next step without purifications. MS: 662.5 ($M+H^+$).

Step F: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-benzamidothiophen-2-yl)-4,4-dimethylcyclohex-1-en-1-yl)methyl)piperazin-1-yl)benzamide (Example 18)

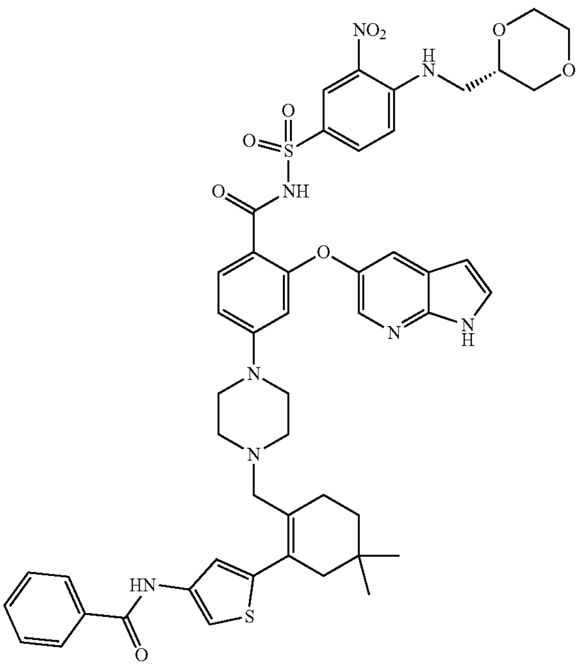 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(NC(=O)c3ccccc3)cs2)C1]

Under Ar, to solution of the crude 2-((1H-pyrrolo[2,3-b]pyridin-5-yl)oxy)-4-(4-((2-(4-benzamidothiophen-2-yl)-4,4-dimethylcyclohex-1-en-1-yl)methyl)piperazin-1-yl)benzoic acid (Step E, 10 mg) in a mixed solvent of dry DMF (2 mL) and dry DCM (10 mL) was added (S)-4-(((1,4-dioxan-2-yl)methyl)amino)-3-nitrobenzenesulfonamide (4.79 mg, 0.015 mmol), DMAP (4.61 mg, 0.038 mmol) and EDCl (4.34 mg, 0.023 mmol); then the reaction mixture was stirred at 40° C. for 16 h. After cooling down to room temperature, the resulting mixture was diluted with DCM, washed with 1 N HCl and brine, dried over $Na_2SO_4$ and concentrated under reduced pressure to give a yellow oil, which was purified by C18 prep-HPLC column to afford the title compound (6 mg, 41% over 2 steps) as a yellow solid. $^1H$ NMR (400 MHz, DMSO-$d_6$) δ 11.70 (s, 1H), 10.62 (s, 1H), 8.60 (brs, 1H), 8.57 (s, 1H), 8.06 (d, J=2.3 Hz, 1H), 8.00-7.90 (m, 2H), 7.82 (d, J=9.2 Hz, 1H), 7.67-7.48 (m, 7H), 7.14-7.04 (m, 2H), 6.74 (d, J=8.9 Hz, 1H), 6.40 (s, 1H), 6.27 (s, 1H), 3.86-3.78 (m, 3H), 3.71-3.60 (m, 2H), 3.56-3.49 (m, 2H), 3.36-3.31 (m, 2H), 3.19-3.11 (m, 4H), 3.11-3.04 (m, 2H), 2.41-2.28 (m, 4H), 2.27-2.19 (m, 2H), 2.11-2.06 (m, 2H), 1.41 (t, J=6.1 Hz, 2H), 0.96 (s, 6H); MS: 962.3 (M+H$^+$).

Example 19: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-(pyrimidin-2-ylamino)thiophen-2-yl)cyclohex-1-en-1-yl)methyl)piperazin-1-yl)benzamide

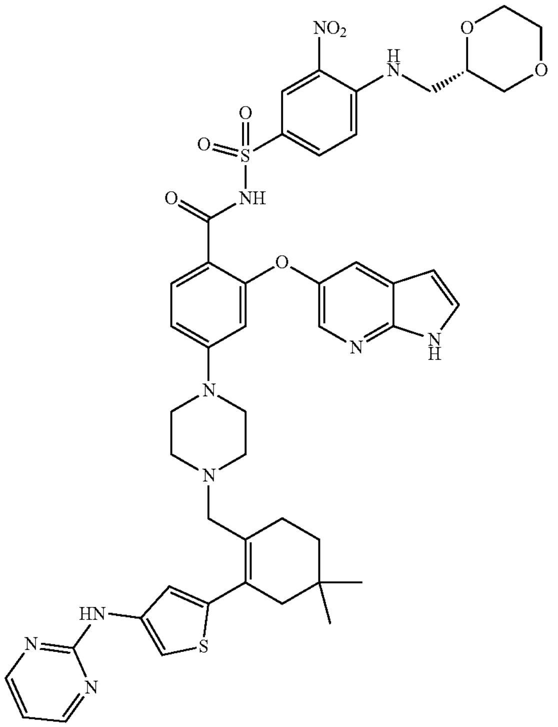 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(Nc3ncccn3)cs2)C1]

Step A: (4-((tert-Butoxycarbonyl)amino)thiophen-2-yl)boronic acid

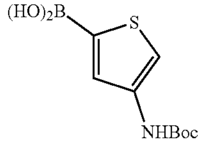 [SMILES: CC(C)(C)OC(=O)Nc1csc(B(O)O)c1]

Under Ar, to solution of 4,4,4',4',5,5,5',5'-octamethyl-2,2'-bi(1,3,2-dioxaborolane) (1.1 g, 4.31 mmol) in dry dioxane (15 mL) was added tert-butyl (5-bromothiophen-3-yl)carbamate (1 g, 3.6 mmol), $PdCl_2(dppf)$ (0.263 g, 0.36 mmol) and potassium acetate (1.06 g, 10.8 mmol); the reaction mixture was stirred at 100° C. for 6 h. After cooling down to room temperature, the resulting mixture was filtered off through celite and the filtrate was concentrated under reduced pressure to give the crude title compound as a light yellow oil, which was directly used for the next step without purification. MS: 244.2 (M+H$^+$).

Step B: Methyl 2-((1H-pyrrolo[2,3-b]pyridin-5-yl)oxy)-4-(4-((2-(4-((tert-butoxycarbonyl)amino)thiophen-2-yl)-4,4-dimethylcyclohex-1-en-1-yl)methyl)piperazin-1-yl)benzoate

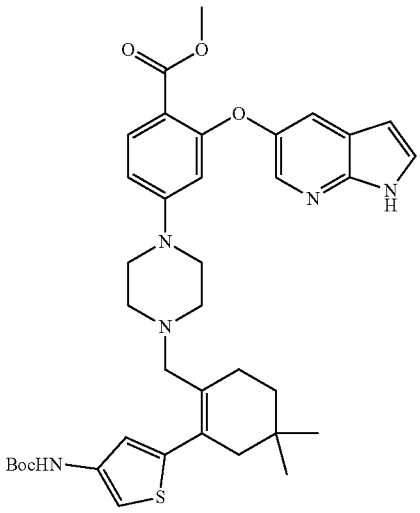 [SMILES: COC(=O)c1ccc(N2CCN(CC3=C(c4cc(NC(=O)OC(C)(C)C)cs4)CC(C)(C)CC3)CC2)cc1Oc1cnc2[nH]ccc2c1]

Under Ar, to a solution of methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 660 mg, 1.192 mmol) in a mixed solvent of dioxane (20 mL) and water (4 mL) was added the crude (4-((tert-butoxycarbonyl)amino)thiophen-2-yl)boronic acid (Step A, 580 mg), $PdCl_2$(dppf) (87 mg, 0.119 mmol) and $Na_2CO_3$ (379 mg, 3.58 mmol); then the reaction mixture was stirred at 100° C. for 16 h. After cooling down to room temperature and removal of volatiles, the residue was filtered off through a short silica gel column (DCM:MeOH, 15:1) to give the crude title compound (1.2 g) as a yellow oil, which was directly used for the next step without further purification. MS: 672.9 ($M+H^+$).

Step C: Methyl 4-(4-((2-(4-((tert-butoxycarbonyl)amino)thiophen-2-yl)-4,4-dimethylcyclohex-1-en-1-yl)methyl)piperazin-1-yl)-2-((1-tosyl-1H-pyrrolo[2,3-b]pyridin-5-yl)oxy)benzoate

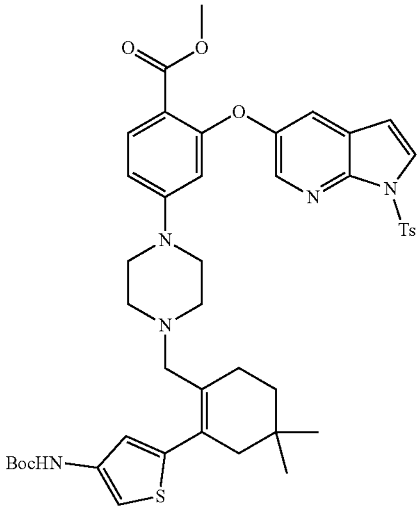 [SMILES: COC(=O)c1ccc(N2CCN(CC3=C(c4cc(NC(=O)OC(C)(C)C)cs4)CC(C)(C)CC3)CC2)cc1Oc1cnc2c(ccn2S(=O)(=O)c2ccc(C)cc2)c1]

Under Ar, to a solution of the crude methyl 2-((1H-pyrrolo[2,3-b]pyridin-5-yl)oxy)-4-(4-((2-(4-((tert-butoxycarbonyl)amino)thiophen-2-yl)-4,4-dimethylcyclohex-1-en-1-yl)methyl)piperazin-1-yl)benzoate (Step B, 1.2 g) in dry THF (30 mL) was added NaH (90 mg, 2.14 mmol) at 0-10° C. slowly, and the mixture was stirred at 0-10° C. for 15 min. TsCl (0.34 g, 1.79 mmol) was then added and the reaction mixture was stirred for 2 h. The resulting mixture was poured onto ice water, and then extracted with EA twice. The combined organic layers were washed with brine, dried over $Na_2SO_4$ and concentrated under reduced pressure to give a yellow oil, which was purified by silica gel column (hexane: EA, 1:1) to afford the title compound (700 mg, 47% over 3 steps) as a yellow oil. MS: 827.1 ($M+H^+$).

Step D: Methyl 4-(4-((2-(4-aminothiophen-2-yl)-4,4-dimethylcyclohex-1-en-1-yl)methyl)piperazin-1-yl)-2-((1-tosyl-1H-pyrrolo[2,3-b]pyridin-5-yl)oxy)benzoate

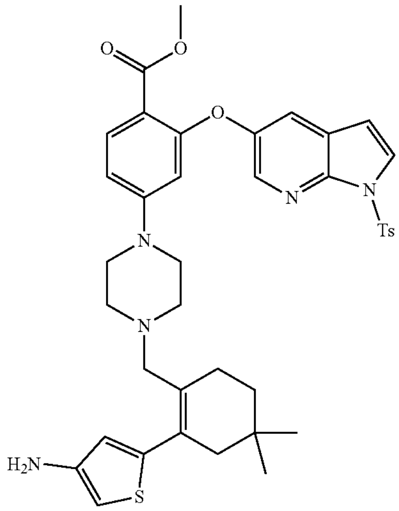 [SMILES: COC(=O)c1ccc(N2CCN(CC3=C(c4cc(N)cs4)CC(C)(C)CC3)CC2)cc1Oc1cnc2c(ccn2S(=O)(=O)c2ccc(C)cc2)c1]

Under Ar, to a solution of methyl 4-(4-((2-(4-((tert-butoxycarbonyl)amino)thiophen-2-yl)-4,4-dimethylcyclohex-1-en-1-yl)methyl)piperazin-1-yl)-2-((1-tosyl-1H-pyrrolo[2,3-b]pyridin-5-yl)oxy)benzoate (Step C, 700 mg, 0.85 mmol) in DCM (5 mL) was added TFA (5 mL); then the reaction mixture was stirred at 15-20° C. for 16 h. After removal of volatiles, the resulting mixture was diluted with DCM, washed with aq. $NaHCO_3$ and brine, dried over $Na_2SO_4$ and concentrated under reduced pressure to give a yellow oil, which was purified by silica gel column (DCM:MeOH, 20:1) to afford the title compound (400 mg, 65%) as a yellow oil. MS: 726.5 ($M+H^+$).

Step E: Methyl 4-(4-((4,4-dimethyl-2-(4-(pyrimidin-2-ylamino)thiophen-2-yl)cyclohex-1-en-1-yl)methyl)piperazin-1-yl)-2-((1-tosyl-1H-pyrrolo[2,3-b]pyridin-5-yl)oxy)benzoate

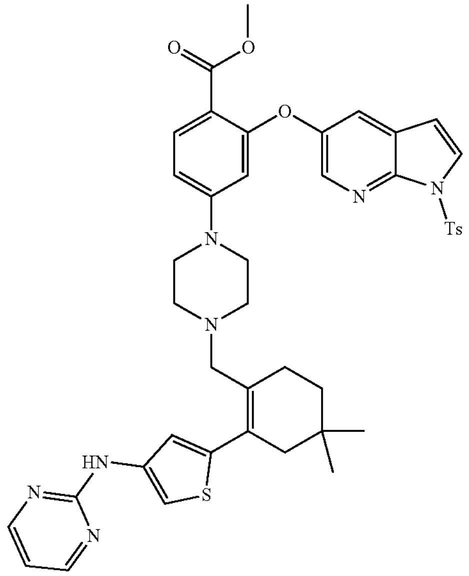 [SMILES: COC(=O)c1ccc(N2CCN(CC3=C(c4cc(Nc5ncccn5)cs4)CC(C)(C)CC3)CC2)cc1Oc1cnc2c(ccn2S(=O)(=O)c2ccc(C)cc2)c1]

Under Ar, to a solution of methyl 4-(4-((2-(4-aminothiophen-2-yl)-4,4-dimethylcyclohex-1-en-1-yl)methyl)piperazin-1-yl)-2-((1-tosyl-1H-pyrrolo[2,3-b]pyridin-5-yl)oxy)benzoate (Step D, 150 mg, 0.21 mmol) in dry dioxane (10 mL) was added 2-bromopyrimidine (49.3 mg, 0.31 mmol), $Cs_2CO_3$ (202 mg, 0.62 mmol), $Pd_2(dba)_3$ (18.92 mg, 0.021 mmol) and Xantphos (11.96 mg, 0.021 mmol); then the reaction mixture was stirred at 100° C. for 6 h. After cooling down to room temperature and removal of volatiles, the residue was purified by silica gel column (DCM:MeOH, 20:1) to afford the title compound (90 mg, 54%) as a yellow oil. MS: 805.1 ($M+H^+$).

Step F: 2-((1H-pyrrolo[2,3-b]pyridin-5-yl)oxy)-4-(4-((4,4-dimethyl-2-(4-(pyrimidin-2-ylamino)thiophen-2-yl)cyclohex-1-en-1-yl)methyl)piperazin-1-yl)benzoic acid

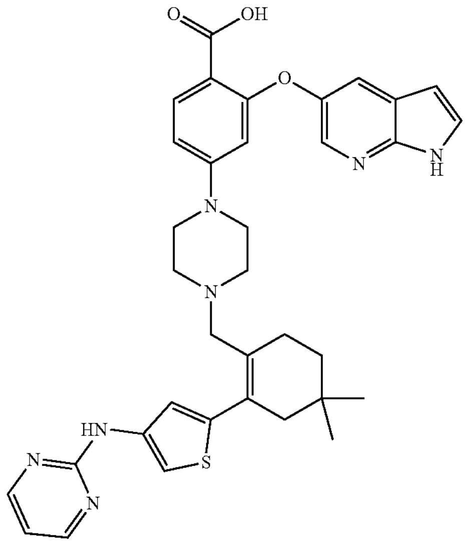 [SMILES: CC1(C)CCC(CN2CCN(c3ccc(C(=O)O)c(Oc4cnc5[nH]ccc5c4)c3)CC2)=C(c2cc(Nc3ncccn3)cs2)C1]

To a solution of methyl 4-(4-((4,4-dimethyl-2-(4-(pyrimidin-2-ylamino)thiophen-2-yl)cyclohex-1-en-1-yl)methyl)piperazin-1-yl)-2-((1-tosyl-1H-pyrrolo[2,3-b]pyridin-5-yl)oxy)benzoate (Step E, 90 mg, 0.112 mmol) in a mixed solvent of THF (5 mL) and MeOH (2 mL) was added 3N NaOH (5 mL); then the reaction mixture was stirred at 50° C. for 6 h. After cooling down to room temperature, the resulting mixture was diluted with water, adjusted to pH 4-5 with 1 N HCl, and extracted with DCM twice. The combined organic layers were washed with brine, dried over $Na_2SO_4$ and concentrated under reduced pressure to afford the crude title compound (70 mg) as a yellow solid, which was directly used for the next step without purification. MS: 636.5 ($M+H^+$).

Step G: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-(pyrimidin-2-ylamino)thiophen-2-yl)cyclohex-1-en-1-yl)methyl)piperazin-1-yl)benzamide (Example 19)

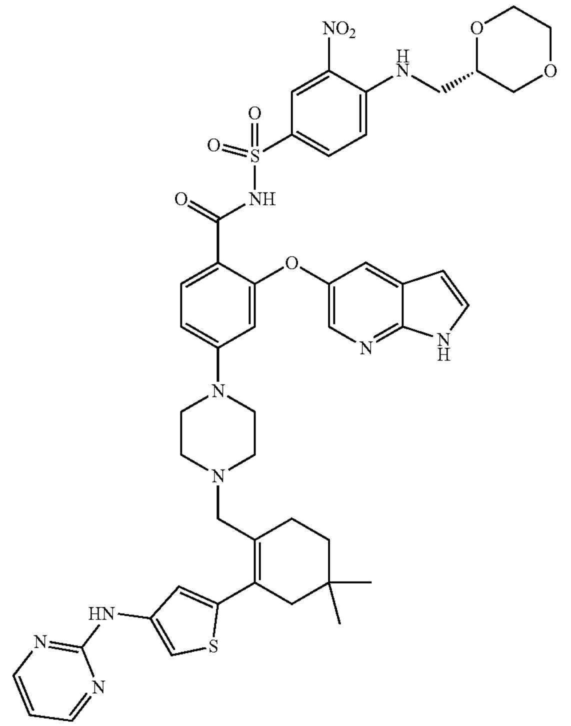 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(Nc3ncccn3)cs2)C1]

Under Ar, to a solution of the crude 2-((1H-pyrrolo[2,3-b]pyridin-5-yl)oxy)-4-(4-((4,4-dimethyl-2-(4-(pyrimidin-2-ylamino)thiophen-2-yl)cyclohex-1-en-1-yl)methyl)piperazin-1-yl)benzoic acid (Step F, 70 mg) in a mixed solvent of dry DMF (2 mL) and DCM (10 mL) was added (S)-4-(((1,4-dioxan-2-yl)methyl)amino)-3-nitrobenzenesulfonamide (34.9 mg, 0.11 mmol), DMAP (33.6 mg, 0.28 mmol) and EDCI (31.7 mg, 0.17 mmol); then the reaction mixture was stirred at 40° C. for 16 h. After cooling down to room temperature, the resulting mixture was diluted with DCM, washed with 1 N HCl and brine, dried over $Na_2SO_4$ and concentrated under reduced pressure to give a yellow oil, which was purified by C18 prep-HPLC to afford the title compound (20 mg, 19% over 2 steps) as a yellow solid. $^1$H NMR (400 MHz, DMSO-$d_6$) δ 11.67 (s, 1H), 9.88 (s, 1H), 8.60-8.51 (m, 2H), 8.46 (d, J=4.8 Hz, 2H), 8.04 (d, J=2.6 Hz, 1H), 7.80 (d, J=9.3 Hz, 1H), 7.57-7.46 (m, 4H), 7.07 (d, J=9.1 Hz, 1H), 6.96 (d, J=4.7 Hz, 1H), 6.80 (t, J=4.8 Hz, 1H), 6.72 (dd, J=9.0, 2.0 Hz, 1H), 6.38 (dd, J=3.3, 1.9 Hz, 1H), 6.26 (d, J=1.9 Hz, 1H), 3.86-3.74 (m, 3H), 3.70-3.57 (m, 2H), 3.55-3.45 (m, 2H), 3.44-3.37 (m, 2H), 3.16-3.08 (m, 4H), 3.07-3.01 (m, 2H), 2.39-2.29 (m, 4H), 2.25-2.17 (m, 2H), 2.09-2.04 (m, 2H), 1.38 (t, J=6.3 Hz, 2H), 0.94 (s, 6H); MS: 936.2 (M+H$^+$).

Example 20: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-((2,4-difluorophenyl)amino)thiophen-2-yl)-4,4-dimethylcyclohex-1-en-1-yl)methyl)piperazin-1-yl)benzamide

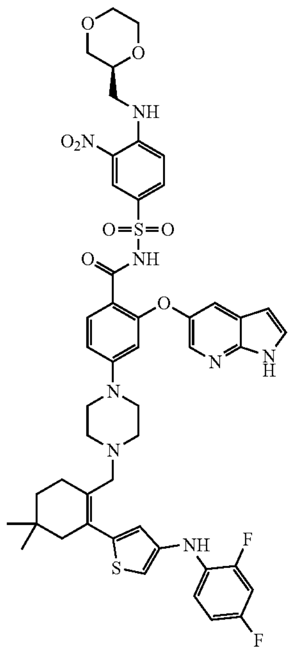 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(Nc3ccc(F)cc3F)cs2)C1]

Essentially the same protocol of preparation of Example 19 was used to afford the example (2 mg) as a yellow solid. $^1$H NMR (400 MHz, DMSO-$d_6$) δ 11.59 (s, 1H), 8.55-8.41 (m, 2H), 7.99 (s, 1H), 7.88 (s, 1H), 7.74 (d, J=10.5 Hz, 1H), 7.53 (d, J=8.8 Hz, 1H), 7.46 (s, 1H), 7.29-7.12 (m, 2H), 6.93-6.87 (m, 1H), 6.73 (s, 1H), 6.71-6.62 (m, 3H), 6.60 (s, 1H), 6.34 (s, 1H), 6.24 (s, 1H), 3.84-3.75 (m, 3H), 3.69-3.57 (m, 2H), 3.53-3.32 (m, 4H), 3.11-3.05 (m, 4H), 3.03 (s, 2H), 2.36-2.24 (m, 4H), 2.22-2.12 (m, 2H), 2.05 (s, 2H), 1.40-1.31 (m, 2H), 0.91 (s, 6H); MS: 970.1 (M+H$^+$).

Example 21: 2-((1H-pyrrolo[2,3-b]pyridin-5-yl)oxy)-4-(4-((4,4-dimethyl-2-(5-(morpholinomethyl)thiophen-3-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

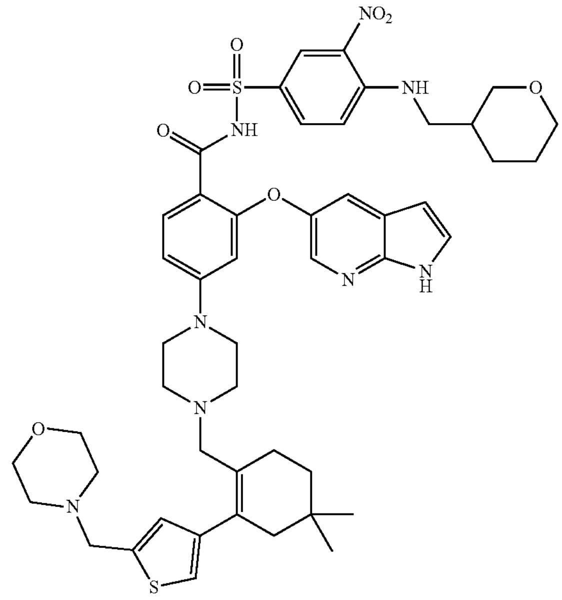 [SMILES: CC1(C)CCC(CN2CCN(c3ccc(C(=O)NS(=O)(=O)c4ccc(NCC5CCCOC5)c([N+](=O)[O-])c4)c(Oc4cnc5[nH]ccc5c4)c3)CC2)=C(c2csc(CN3CCOCC3)c2)C1]

Step A: 2-((1H-pyrrolo[2,3-b]pyridin-5-yl)oxy)-4-(4-((2-bromo-4,4-dimethylcyclohex-1-en-1-yl)methyl)piperazin-1-yl)benzoic acid

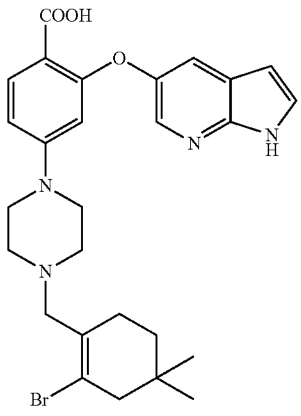 [SMILES: CC1(C)CCC(CN2CCN(c3ccc(C(=O)O)c(Oc4cnc5[nH]ccc5c4)c3)CC2)=C(Br)C1]

To a solution of methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 150 mg, 0.27 mmol) in a mixed solvent of MeOH (1 mL), THF (1 mL) and $H_2O$ (1 mL) was added sodium hydroxide (108 mg, 2.71 mmol); then the reaction mixture was stirred at 50° C. for 4 h. After cooling down to room temperature, the resulting mixture was acidified with 1 M HCl to adjust pH 4-5 and extracted with ethyl acetate twice. The combined organic layer was dried over $Na_2SO_4$, and concentrated under reduced pressure to give the crude title compound (131 mg), which was directly used for the next step without purification. MS: 539.2 $(M+H^+)$.

Step B: 2-((1H-pyrrolo[2,3-b]pyridin-5-yl)oxy)-4-(4-((2-bromo-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide

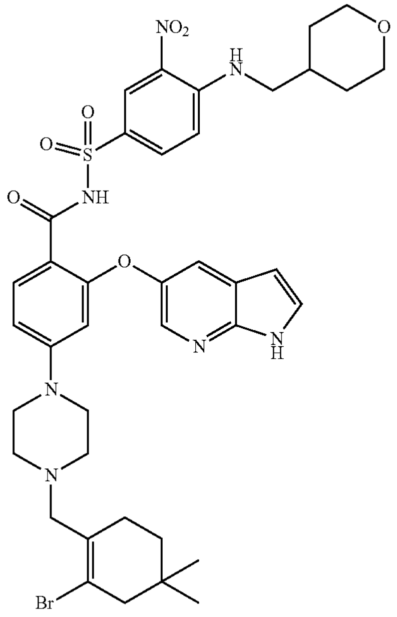 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(Br)C1]

Under Ar, to a solution of the crude 2-((1H-pyrrolo[2,3-b]pyridin-5-yl)oxy)-4-(4-((2-bromo-4,4-dimethylcyclohex-1-en-1-yl)methyl)piperazin-1-yl)benzoic acid (Step A, 131 mg) in dry DMF (3 mL) was added N,N-dimethylpyridin-4-amine (74.2 mg, 0.61 mmol), EDCl (69.8 mg, 0.36 mmol) and 3-nitro-4-(((tetrahydro-2H-pyran-4-yl)methyl)amino)benzenesulfonamide (77.0 mg, 0.24 mmol); then the reaction mixture was stirred at 40° C. for 12 h. After cooling down to room temperature, the resulting mixture was diluted with ethyl acetate and then washed with $H_2O$ and brine. The organic layer was dried over $Na_2SO_4$ and concentrated under reduced pressure to give a yellow oil, which was loaded onto a silica gel column and eluted with methanol and dichloromethane (1:20) to afford the title compound (126 mg, 62% over 2 steps) as a yellow solid. MS: 836.2 $(M+H^+)$.

Step C: 2-((1H-pyrrolo[2,3-b]pyridin-5-yl)oxy)-4-(4-((4,4-dimethyl-2-(5-(morpholinomethyl)thiophen-3-yl)cyclohex-1-en-1-yl)methyl)piperazin-1-yl)-N-((3-nitro-4-(((tetrahydro-2H-pyran-4-yl)methyl)amino)phenyl)sulfonyl)benzamide (Example 21)

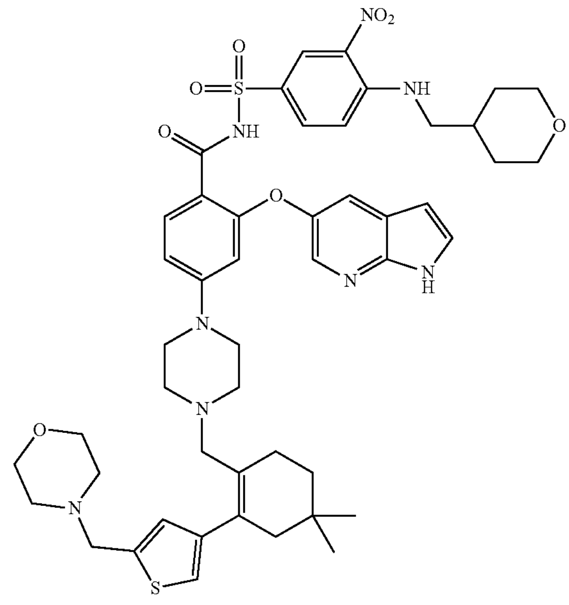 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2csc(CN3CCOCC3)c2)C1]

Under Ar, to a solution of 2-((1H-pyrrolo[2,3-b]pyridin-5-yl)oxy)-4-(4-((2-bromo-4,4-dimethylcyclohex-1-en-1-yl)methyl)piperazin-1-yl)-N-((3-nitro-4-(((tetrahydro-2H-pyran-4-yl)methyl)amino)phenyl)sulfonyl)benzamide (Step B, 42 mg, 0.05 mmol) in a mixed solvent of DME (1.5 mL) and 2M $Na_2CO_3$ (0.5 mL) was added (5-(morpholinomethyl)thiophen-3-yl)boronic acid (11.4 mg, 0.05 mmol) and $PdCl_2$(dppf)·$CH_2Cl_2$ (8.2 mg, 10 μmol), then the reaction mixture was stirred at 100° C. for 0.5 h with microwave assistance. After cooling down to room temperature, the resulting mixture was diluted with ethyl acetate and then washed with $H_2O$ and brine. The organic layer was dried over $Na_2SO_4$ and concentrated under reduced pressure to give a yellow oil, which was purified by C18 prep-HPLC to afford the title compound (7.9 mg, 17%) as a yellow solid. $^1$H NMR (400 MHz, DMSO-$d_6$) δ11.68 (s, 1H), 8.59 (t, J=5.2 Hz, 1H), 8.54 (d, J=2.1 Hz, 1H), 8.03 (d, J=2.6 Hz, 1H), 7.78 (dd, J=9.3, 1.8 Hz, 1H), 7.53-7.47 (m, 3H), 7.09 (d, J=9.4 Hz, 1H), 7.04 (s, 1H), 6.76 (s, 1H), 6.68 (dd, J=9.1, 2.1 Hz, 1H), 6.38 (dd, J=3.2, 1.9 Hz, 1H), 6.21 (d, J=1.8 Hz, 1H), 3.91-3.79 (m, 2H), 3.62 (s, 2H), 3.57-3.49 (m, 4H), 3.30-3.23 (m, 4H), 3.13-3.03 (m, 4H), 2.94-2.79 (m, 2H), 2.41-2.33 (m, 4H), 2.29-2.18 (m, 4H), 2.15-2.09 (m, 2H), 1.99-1.96 (m, 2H), 1.93-1.81 (m, 1H), 1.66-1.55 (m, 2H), 1.35 (t, J=6.2 Hz, 2H), 1.31-1.25 (m, 2H), 0.90 (s, 6H); MS: 939.4 (M+H$^+$).

Example 22: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-(morpholinomethyl)thiophen-2-yl)cyclohex-1-en-1-yl)methyl)piperazin-1-yl)benzamide

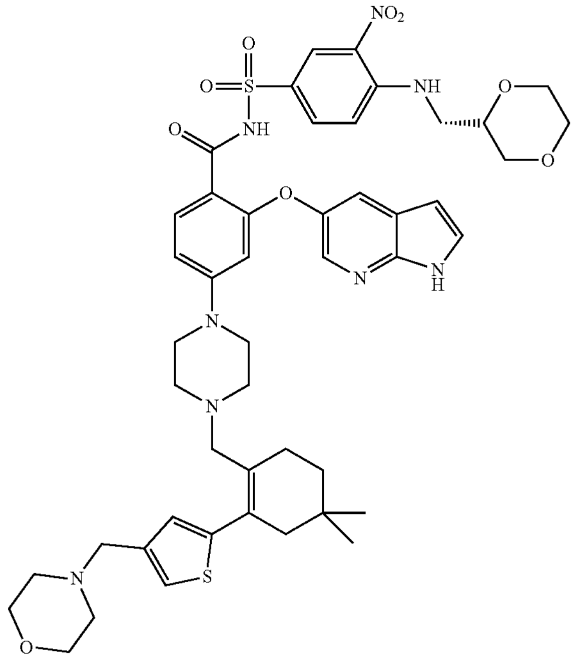

Step A: Methyl 2-((1H-pyrrolo[2,3-b]pyridin-5-yl)oxy)-4-(4-((4,4-dimethyl-2-(4,4,5,5-tetramethyl-1,3,2-dioxaborolan-2-yl)cyclohex-1-en-1-yl)methyl)piperazin-1-yl)benzoate

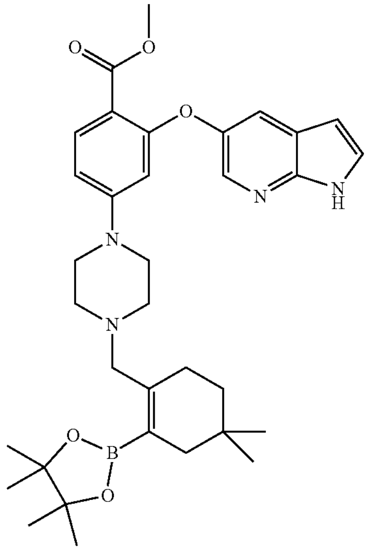 [SMILES: COC(=O)c1ccc(N2CCN(CC3=C(B4OC(C)(C)C(C)(C)O4)CC(C)(C)CC3)CC2)cc1Oc1cnc2[nH]ccc2c1]

To a solution of methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 0.4 g, 0.72 mmol) in dry 1,4-Dioxane (7 mL) was added 4,4,4',4',5,5,5',5'-octamethyl-2,2'-bi(1,3,2-dioxaborolane) (0.28 g, 1.08 mmol), potassium acetate (0.21 g, 2.17 mmol) and $PdCl_2$(dppf) (0.053 g, 0.072 mmol); then the reaction mixture was filled with $N_2$ three times and stirred at 100° C. for 12 h. After cooling down to room temperature, the resulting mixture was diluted with ethyl acetate and then washed with $H_2O$ and brine. The organic layer was dried over $Na_2SO_4$ and concentrated under reduced pressure to give a yellow oil, which was loaded onto a silica gel column and eluted with DCM and MeOH (30:1) to afford the title compound (0.33 g, 76%) as a yellow oil. MS: 601.4 ($M+H^+$).

Step B: Methyl 2-((1H-pyrrolo[2,3-b]pyridin-5-yl)oxy)-4-(4-((4,4-dimethyl-2-(4-(morpholinomethyl)thiophen-2-yl)cyclohex-1-en-1-yl)methyl)piperazin-1-yl)benzoate

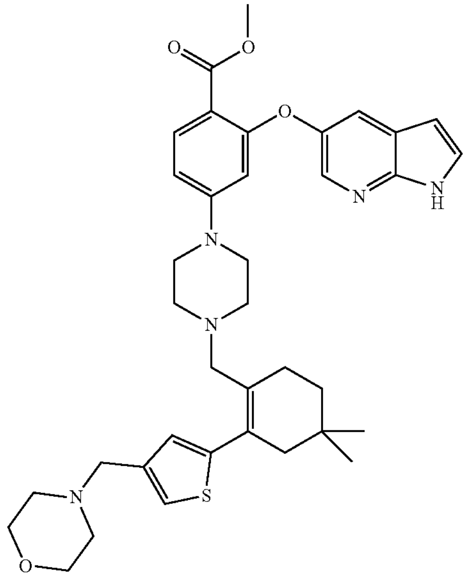 [SMILES: COC(=O)c1ccc(N2CCN(CC3=C(c4cc(CN5CCOCC5)cs4)CC(C)(C)CC3)CC2)cc1Oc1cnc2[nH]ccc2c1]

To a solution of methyl 2-((1H-pyrrolo[2,3-b]pyridin-5-yl)oxy)-4-(4-((4,4-dimethyl-2-(4,4,5,5-tetramethyl-1,3,2-dioxaborolan-2-yl)cyclohex-1-en-1-yl)methyl)piperazin-1-yl)benzoate (Step A, 130 mg, 0.22 mmol) in a mixed solvent of 1,4-dioxane (2.4 mL) and water (0.4 mL) was added 4-((5-bromothiophen-3-yl)methyl)morpholine (85 mg, 0.33 mmol), $K_2CO_3$ (90 mg, 0.66 mmol) and $PdCl_2$(dppf) (15.8 mg, 0.022 mmol); then the reaction mixture was filled with $N_2$ three times and stirred at 100° C. for 45 min with microwave assistance. After cooling down to room temperature, the resulting mixture was diluted with ethyl acetate and then washed with $H_2O$ and brine. The organic layer was dried over $Na_2SO_4$, and concentrated under reduced pressure to afford a yellow oil, which was loaded onto a silica gel column and eluted with DCM and MeOH (30:1) to afford the title compound (45 mg, 32%) as a yellow oil. MS: 656.3 ($M+H^+$).

Step C: 2-((1H-pyrrolo[2,3-b]pyridin-5-yl)oxy)-4-(4-((4,4-dimethyl-2-(4-(morpholinomethyl)thiophen-2-yl)cyclohex-1-en-1-yl)methyl)piperazin-1-yl)benzoic acid

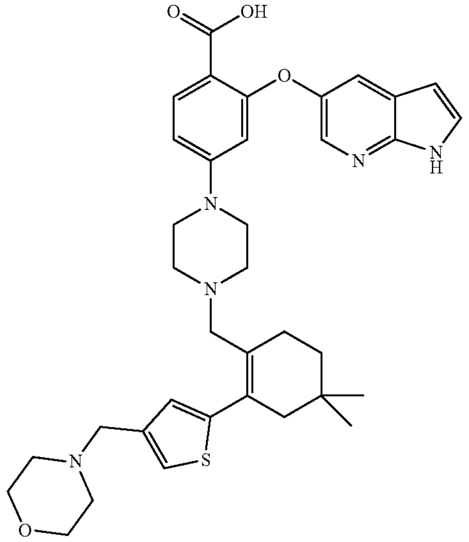 [SMILES: CC1(C)CCC(CN2CCN(c3ccc(C(=O)O)c(Oc4cnc5[nH]ccc5c4)c3)CC2)=C(c2cc(CN3CCOCC3)cs2)C1]

To a solution of methyl 2-((1H-pyrrolo[2,3-b]pyridin-5-yl)oxy)-4-(4-((4,4-dimethyl-2-(4-(morpholinomethyl)thiophen-2-yl)cyclohex-1-en-1-yl)methyl)piperazin-1-yl)benzoate (Step B, 45 mg, 0.07 mmol) in a mixed solvent of MeOH (1 mL) and THF (1 mL) was added a solution of sodium hydroxide (21.9 mg, 0.57 mmol) in water (0.5 mL); then the reaction mixture was stirred at 45° C. for 4 h. After cooling down to room temperature, the resulting mixture was acidified with 1 N HCl to adjust pH 4-5 and extracted with ethyl acetate twice. The combined organic layer was dried over $Na_2SO_4$, and concentrated under reduced pressure to give the crude title compound product (40 mg, 91%) as a yellow solid, which was directly used for the next step without purification. MS: 642.3 ($M+H^+$).

Step D: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-(morpholinomethyl)thiophen-2-yl)cyclohex-1-en-1-yl)methyl)piperazin-1-yl)benzamide (Example 22)

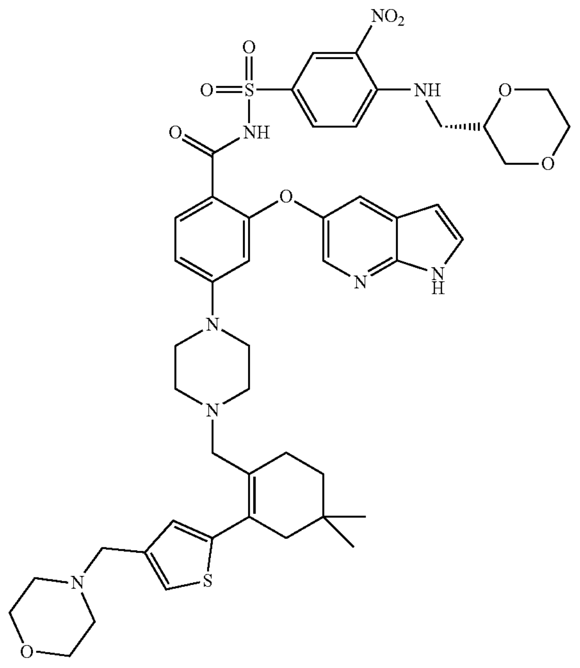

Under Ar, to a solution of the crude 2-((1H-pyrrolo[2,3-b]pyridin-5-yl)oxy)-4-(4-((4,4-dimethyl-2-(4-(morpholinomethyl)thiophen-2-yl)cyclohex-1-en-1-yl)methyl)piperazin-1-yl)benzoic acid (Step C, 40 mg) in a mixed solvent of dry DCM (1.5 mL) and dry DMF (1.5 mL) was added N,N-dimethylpyridin-4-amine (19.0 mg, 0.16 mmol), EDCl (17.9 mg, 0.09 mmol) and (S)-4-(((1,4-dioxan-2-yl)methyl)amino)-3-nitrobenzenesulfonamide (19.8 mg, 0.06 mmol); then the reaction mixture was stirred at 40° C. for 12 h. After cooling down to room temperature, the resulting mixture was diluted with ethyl acetate and then washed with $H_2O$ and brine. The organic layer was dried over $Na_2SO_4$, and concentrated under reduced pressure to give a yellow solid, which was purified by C18 prep-HPLC to afford the title compound (6.6 mg, 11% over 2 steps) as a yellow solid. $^1H$ NMR (400 MHz, DMSO-d) δ 11.66 (s, 1H), 8.59-8.48 (m, 2H), 8.03-8.01 (m, 1H), 7.78 (d, J=9.9 Hz, 1H), 7.54-7.46 (m, 3H), 7.20 (s, 1H), 7.05 (d, J=9.0 Hz, 1H), 6.79 (s, 1H), 6.69 (d, J=8.3 Hz, 1H), 6.41-6.33 (m, 1H), 6.26-6.19 (m, 1H), 3.85-3.74 (m, 3H), 3.69-3.61 (m, 2H), 3.59-3.42 (m, 10H), 3.13-3.05 (m, 4H), 3.01-2.94 (m, 2H), 2.39-2.32 (m, 4H), 2.30-2.23 (m, 4H), 2.22-2.15 (m, 2H), 2.07-2.02 (m, 2H), 1.40-1.32 (m, 2H), 0.91 (s, 6H); MS: 941.4 ($M+H^+$).

Example 23: 2-((1H-pyrrolo[2,3-b]pyridin-5-yl)oxy)-4-(4-((4,4-dimethyl-2-(4-(morpholinomethyl)thiophen-2-yl)cyclohex-1-en-1-yl)methyl)piperazin-1-yl)-N-((4-((((1s,4s)-4-hydroxy-4-methylcyclohexyl)methyl)amino)-3-nitrophenyl)sulfonyl)benzamide

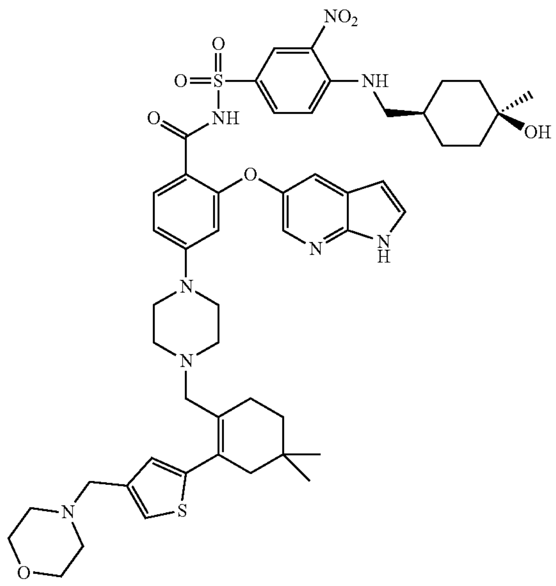 [SMILES: CC1(C)CCC(CN2CCN(c3ccc(C(=O)NS(=O)(=O)c4ccc(NC[C@H]5CC[C@@](C)(O)CC5)c([N+](=O)[O-])c4)c(Oc4cnc5[nH]ccc5c4)c3)CC2)=C(c2cc(CN3CCOCC3)cs2)C1]

Essentially the same protocol of preparation of Example 22 was used to afford the example (7.5 mg) as a yellow solid. $^1H$ NMR (400 MHz, DMSO-$d_6$) δ 11.66 (s, 1H), 8.56 (t, J=5.1 Hz, 1H), 8.52 (d, J=1.2 Hz, 1H), 8.02 (d, J=2.3 Hz, 1H), 7.74 (d, J=9.0 Hz, 1H), 7.52-7.47 (m, 3H), 7.19 (s, 1H), 7.01 (d, J=9.2 Hz, 1H), 6.79 (s, 1H), 6.69 (dd, J=8.8, 1.3 Hz, 1H), 6.39-6.34 (m, 1H), 6.22 (d, J=1.2 Hz, 1H), 3.97 (s, 1H), 3.53-3.50 (m, 4H), 3.43-3.42 (m, 2H), 3.25 (t, J=6.1 Hz, 2H), 3.10-3.07 (m, 4H), 2.98-2.95 (m, 2H), 2.36-2.32 (m, 4H), 2.27-2.24 (m, 4H), 2.20-2.16 (m, 2H), 2.06-2.04 (m, 2H), 1.56-1.46 (m, 5H), 1.39-1.33 (m, 4H), 1.27-1.24 (m, 2H), 1.08 (s, 3H), 0.91 (s, 6H); MS: 967.4 ($M+H^+$).

Example 24: 2-((1H-pyrrolo[2,3-b]pyridin-5-yl)oxy)-4-(4-((4,4-dimethyl-2-(4-(morpholinomethyl)thiophen-2-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

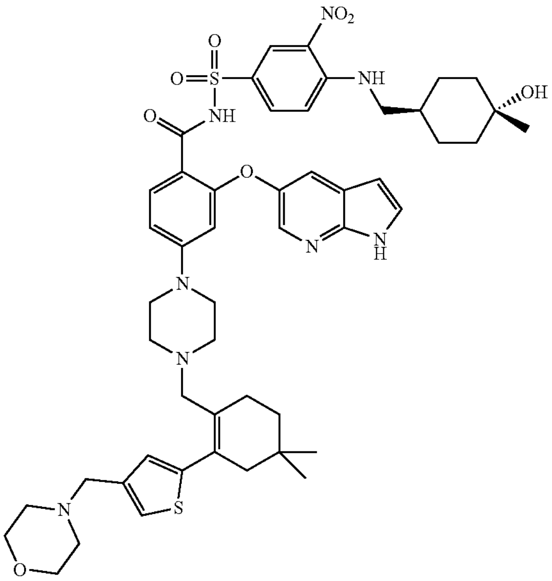 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(CN3CCOCC3)cs2)C1]

Essentially the same protocol of preparation of Example 22 was used to afford the example (15.7 mg) as a yellow solid. $^1$H NMR (400 MHz, DMSO-$d_6$) δ 11.67 (s, 1H), 8.55-8.52 (m, 2H), 8.02 (d, J=2.4 Hz, 1H), 7.75 (d, J=9.3 Hz, 1H), 7.53-7.47 (m, 3H), 7.19 (s, 1H), 7.03 (d, J=9.3 Hz, 1H), 6.79 (s, 1H), 6.69 (dd, J=8.9, 1.4 Hz, 1H), 6.39-6.36 (m, 1H), 6.22 (d, J=1.3 Hz, 1H), 4.26 (s, 1H), 3.53-3.50 (m, 4H), 3.45-3.41 (m, 2H), 3.29-3.25 (m, 2H), 3.13-3.05 (m, 4H), 2.97-2.95 (m, 2H), 2.39-2.30 (m, 4H), 2.28-2.22 (m, 4H), 2.20-2.14 (m, 2H), 2.05-2.03 (m, 2H), 1.70-1.62 (m, 3H), 1.52-1.51 (m, 2H), 1.36-1.29 (m, 4H), 1.15-1.13 (m, 2H), 1.09 (s, 3H), 0.91 (s, 6H); MS: 967.3 ($M+H^+$).

Example 25: 2-((1H-pyrrolo[2,3-b]pyridin-5-yl)oxy)-4-(4-((4,4-dimethyl-2-(2-(morpholinomethyl)thiophen-3-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

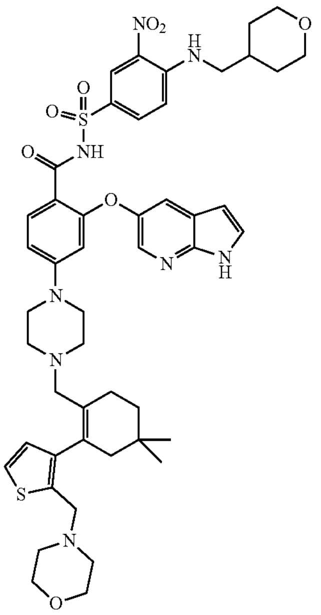 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccsc2CN2CCOCC2)C1]

Essentially the same protocol of preparation of Example 22 was used to afford the example (6 mg) as a yellow solid. $^1$H NMR (400 MHz, DMSO-$d_6$) δ 11.70 (s, 1H), 8.61 (s, 1H), 8.55 (s, 1H), 8.04 (s, 1H), 7.78 (d, J=7.1 Hz, 1H), 7.57-7.46 (m, 3H), 7.36 (d, J=5.0 Hz, 1H), 7.14-7.02 (m, 1H), 6.71 (d, J=8.2 Hz, 1H), 6.66 (d, J=5.1 Hz, 1H), 6.40 (s, 1H), 6.23 (s, 1H), 3.92-3.82 (m, 2H), 3.63-3.50 (m, 4H), 3.36-3.23 (m, 8H), 3.14-3.01 (m, 4H), 2.41-2.29 (m, 4H), 2.28-2.04 (m, 5H), 1.97-1.78 (m, 2H), 1.69-1.58 (m, 2H), 1.46-1.37 (m, 2H), 1.34-1.21 (m, 4H), 0.95 (s, 6H); MS: 940.8 ($M+H^+$).

Example 26: 2-((1H-pyrrolo[2,3-b]pyridin-5-yl)oxy)-4-(4-((4,4-dimethyl-2-(5-(morpholinomethyl)thiophen-2-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

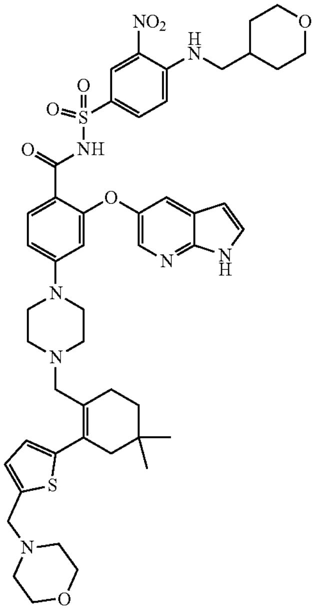 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(CN3CCOCC3)s2)C1]

Essentially the same protocol of preparation of Example 22 was used to afford the example (6 mg) as a yellow solid. $^{1}$H NMR (400 MHz, DMSO-$d_6$) δ 11.72 (s, 1H), 8.64 (t, J=5.8 Hz, 1H), 8.57 (d, J=2.0 Hz, 1H), 8.06 (d, J=2.4 Hz, 1H), 7.81 (d, J=9.0 Hz, 1H), 7.57-7.48 (m, 3H), 7.12 (d, J=9.3 Hz, 1H), 6.82 (d, J=3.2 Hz, 1H), 6.73 (d, J=9.2 Hz, 1H), 6.68 (d, J=3.3 Hz, 1H), 6.41 (s, 1H), 6.25 (s, 1H), 3.87 (d, J=8.3 Hz, 2H), 3.71-3.62 (m, 2H), 3.60-3.50 (m, 4H), 3.32-3.24 (m, 2H), 3.17-3.06 (m, 4H), 3.07-2.98 (m, 2H), 2.47-2.36 (m, 4H), 2.34-2.25 (m, 4H), 2.24-2.15 (m, 2H), 2.10-2.02 (m, 2H), 1.97-1.84 (m, 1H), 1.64 (d, J=12.4 Hz, 2H), 1.37 (t, J=6.2 Hz, 2H), 1.32-1.19 (m, 4H), 0.90 (s, 6H); MS: 940.7 (M+H).

Example 27: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-((6-(methylsulfonyl)-2,6-diazaspiro[3.3]heptan-2-yl)methyl)thiophen-2-yl)cyclohexan-1-yl)methyl)piperazin-1-yl)benzamide

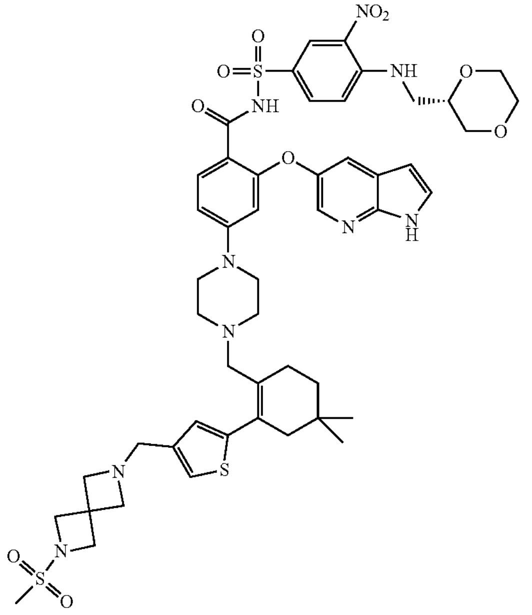 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(CN3CC4(C3)CN(S(C)(=O)=O)C4)cs2)C1]

Step A: (4-Formylthiophen-2-yl)boronic acid

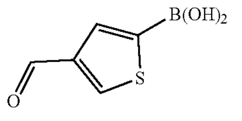

Under Ar, to solution of 5-bromothiophene-3-carbaldehyde (2 g, 10.47 mmol) in dry dioxane (25 mL) was added 4,4,4',4',5,5,5',5'-octamethyl-2,2'-bi(1,3,2-dioxaborolane) (3.99 g, 15.70 mmol), potassium acetate (3.08 g, 31.4 mmol) and $PdCl_2$(dppf) (766 mg, 1.047 mmol); then the reaction mixture was stirred at 70° C. for 16 h. After cooling down to room temperature, the resulting mixture was filtered off through celite and the filtrate was under reduced pressure to give the crude title compound as a yellow oil, which was used directly for the next step without purification. MS: 156.9 (M+H$^+$).

Step B: Methyl 2-((1H-pyrrolo[2,3-b]pyridin-5-yl)oxy)-4-(4-((2-(4-formylthiophen-2-yl)-4,4-dimethylcyclohex-1-en-1-yl)methyl)piperazin-1-yl)benzoate

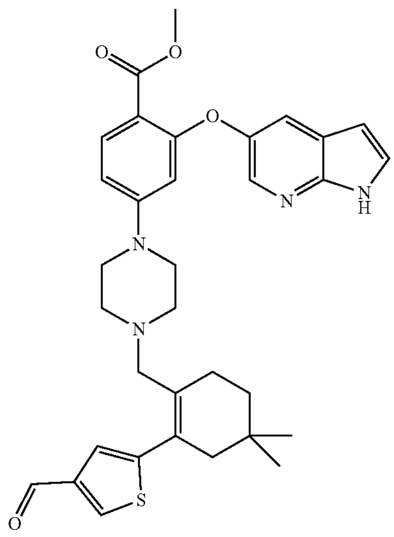 [SMILES: COC(=O)c1ccc(N2CCN(CC3=C(c4cc(C=O)cs4)CC(C)(C)CC3)CC2)cc1Oc1cnc2[nH]ccc2c1]

Under Ar, to a solution of the crude (4-formylthiophen-2-yl)boronic acid (Step A, 500 mg) in a mixed solvent of dioxane (40 mL) and water (8 mL) was added methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 887 mg, 1.6 mmol), $PdCl_2$(dppf) (235 mg, 0.32 mmol) and $Na_2CO_3$ (1.02 g, 9.62 mmol); then the reaction mixture was stirred at 100° C. for 16 h. After cooling down to room temperature and removal of volatiles, the residue was purified by silica gel column (hexane:ethyl acetate, 1:1) to afford the title compound (600 mg, 32% over 2 steps) as a yellow oil. MS: 585.9 (M+H$^+$).

Step C: tert-Butyl 6-((5-(2-((4-(3-((1H-pyrrolo[2,3-b]pyridin-5-yl)oxy)-4-(methoxycarbonyl)phenyl)piperazin-1-yl)methyl)-5,5-dimethylcyclohex-1-en-1-yl)thiophen-3-yl)methyl)-2,6-diazaspiro[3.3]heptane-2-carboxylate

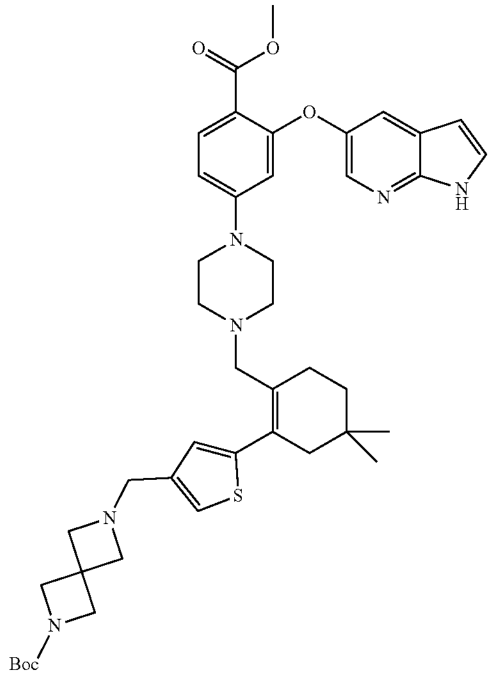 [SMILES: COC(=O)c1ccc(N2CCN(CC3=C(c4cc(CN5CC6(C5)CN(C(=O)OC(C)(C)C)C6)cs4)CC(C)(C)CC3)CC2)cc1Oc1cnc2[nH]ccc2c1]

Under Ar, to a solution of methyl 2-((1H-pyrrolo[2,3-b]pyridin-5-yl)oxy)-4-(4-((2-(4-formylthiophen-2-yl)-4,4-dimethylcyclohex-1-en-1-yl)methyl)piperazin-1-yl)benzoate (Step B, 40 mg, 0.07 mmol) in 1,2-dichloroethane (2 mL) was added tert-butyl 2,6-diazaspiro[3.3]heptane-2-carboxylate (27.1 mg, 0.14 mmol) and NaBH(OAc)$_3$ (29.0 mg, 0.14 mmol); then the reaction mixture was stirred at room temperature for 12 h. The resulting mixture was diluted with dichloromethane and then washed with $H_2O$ and brine. The organic layer was dried over $Na_2SO_4$, and concentrated under reduced pressure to give a yellow oil, which was loaded onto a silica gel column and eluted with methanol and dichloromethane (1:30) to afford the title compound (41 mg, 78%) as a yellow oil. MS: 767.4 (M+H$^+$).

Step D: Methyl 2-((1H-pyrrolo[2,3-b]pyridin-5-yl)oxy)-4-(4-((2-(4-((2,6-diazaspiro[3.3]heptan-2-yl)methyl)thiophen-2-yl)-4,4-dimethylcyclohexan-1-yl)methyl)piperazin-1-yl)benzoate

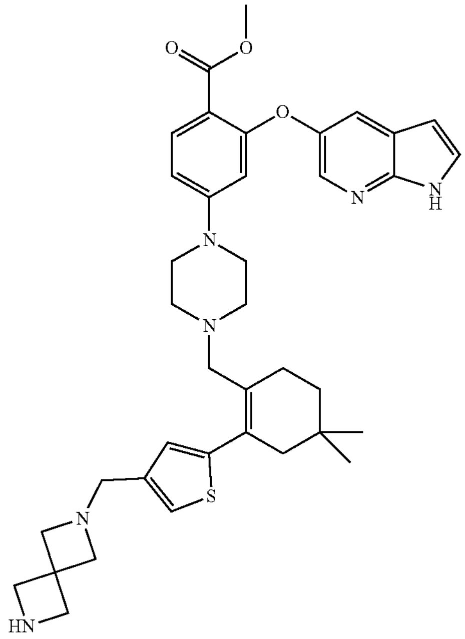 [SMILES: COC(=O)c1ccc(N2CCN(CC3=C(c4cc(CN5CC6(CNC6)C5)cs4)CC(C)(C)CC3)CC2)cc1Oc1cnc2[nH]ccc2c1]

To a solution of tert-butyl 6-((5-(2-((4-(3-((1H-pyrrolo[2,3-b]pyridin-5-yl)oxy)-4-(methoxycarbonyl)phenyl)piperazin-1-yl)methyl)-5,5-dimethylcyclohex-1-en-1-yl)thiophen-3-yl)methyl)-2,6-diazaspiro[3.3]heptane-2-carboxylate (Step C, 41 mg, 0.05 mmol) in DCM (5 mL) was added TFA (0.5 mL); then the reaction mixture was stirred at room temperature for 1 h. After removal of volatiles, the crude title compound (35 mg) as a yellow oil was directly used for the next step without purification. MS: 667.3 (M+H$^+$).

Step E: Methyl 2-((1H-pyrrolo[2,3-b]pyridin-5-yl)oxy)-4-(4-((4,4-dimethyl-2-(4-((6-(methylsulfonyl)-2,6-diazaspiro[3.3]heptan-2-yl)methyl)thiophen-2-yl)cyclohexan-1-yl)methyl)piperazin-1-yl)benzoate

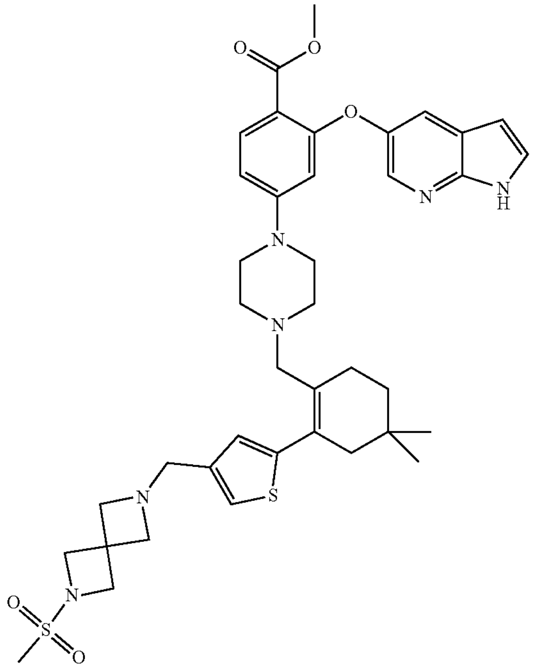 [SMILES: COC(=O)c1ccc(N2CCN(CC3=C(c4cc(CN5CC6(C5)CN(S(C)(=O)=O)C6)cs4)CC(C)(C)CC3)CC2)cc1Oc1cnc2[nH]ccc2c1]

Under Ar, to a solution of the crude methyl 2-((1H-pyrrolo[2,3-b]pyridin-5-yl)oxy)-4-(4-((2-(4-((2,6-diazaspiro[3.3]heptan-2-yl)methyl)thiophen-2-yl)-4,4-dimethylcyclohexan-1-yl)methyl)piperazin-1-yl)benzoate (Step D, 35 mg) in dry DCM (2 mL) was added triethylamine (53.1 mg, 0.5 mmol) and MsCl (9.0 mg, 0.08 mmol); then the reaction mixture was stirred at room temperature for 2 h. The resulting mixture was diluted with DCM and then washed with $H_2O$ and brine. The organic layer was dried over $Na_2SO_4$, and concentrated under reduced pressure to give a yellow oil, which was loaded onto a silica gel column and eluted with methanol and dichloromethane (1:40) to afford the title compound (29 mg, 74% over 2 steps) as a yellow oil. MS: 745.3 (M+H$^+$).

Step F: 2-((1H-pyrrolo[2,3-b]pyridin-5-yl)oxy)-4-(4-((4,4-dimethyl-2-(4-((6-(methylsulfonyl)-2,6-diazaspiro[3.3]heptan-2-yl)methyl)thiophen-2-yl)cyclohexan-1-yl)methyl)piperazin-1-yl)benzoic acid

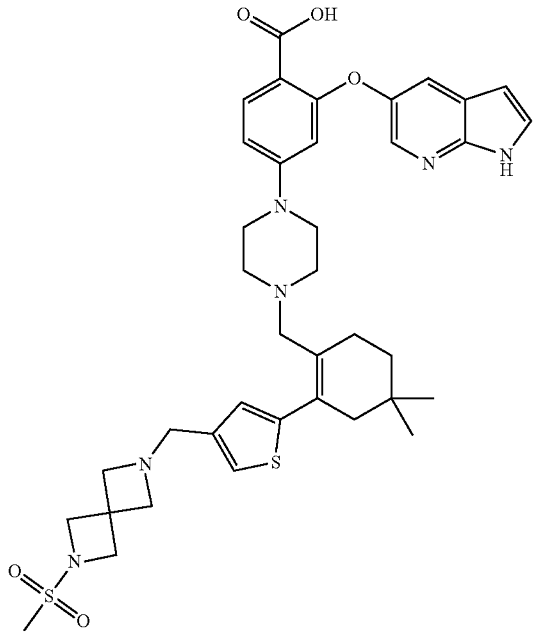 [SMILES: CC1(C)CCC(CN2CCN(c3ccc(C(=O)O)c(Oc4cnc5[nH]ccc5c4)c3)CC2)=C(c2cc(CN3CC4(C3)CN(S(C)(=O)=O)C4)cs2)C1]

To a solution of methyl 2-((1H-pyrrolo[2,3-b]pyridin-5-yl)oxy)-4-(4-((4,4-dimethyl-2-(4-((6-(methylsulfonyl)-2,6-diazaspiro[3.3]heptan-2-yl)methyl)thiophen-2-yl)cyclohexan-1-yl)methyl)piperazin-1-yl)benzoate (Step E, 29 mg, 0.03 mmol) in a mixed solvent of MeOH (2 mL), THF (2 mL) and $H_2O$ (2 mL) was added sodium hydroxide (12.5 mg, 0.3 mmol); then the reaction mixture was stirred at 40° C. for 8 h. After cooling down to room temperature, the resulting mixture was acidified with 1 N HCl to adjust pH 4-5 and extracted with ethyl acetate twice. The combined organic layers was dried over $Na_2SO_4$, and concentrated under reduced pressure to give the crude title compound as a yellow solid, which was directly used for the next step without purification. MS: 731.3 (M+H$^+$).

Step G: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-((6-(methylsulfonyl)-2,6-diazaspiro[3.3]heptan-2-yl)methyl)thiophen-2-yl)cyclohexan-1-yl)methyl)piperazin-1-yl)benzamide (Example 27)

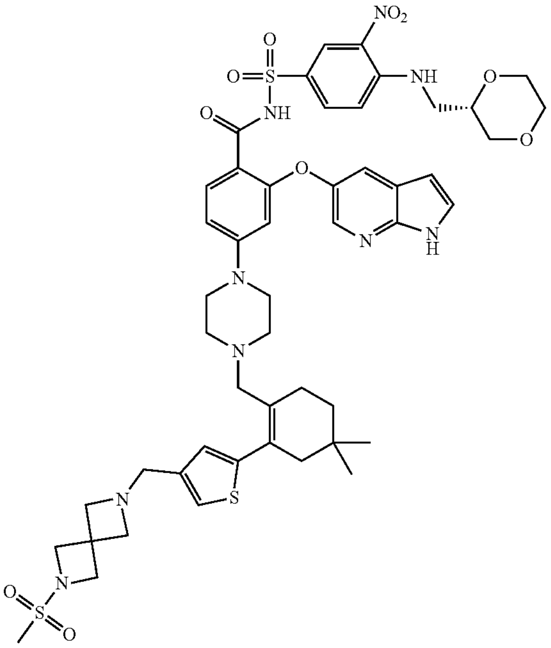 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(CN3CC4(C3)CN(S(C)(=O)=O)C4)cs2)C1]

Under Ar, to a solution of the crude 2-((1H-pyrrolo[2,3-b]pyridin-5-yl)oxy)-4-(4-((4,4-dimethyl-2-(4-((6-(methylsulfonyl)-2,6-diazaspiro[3.3]heptan-2-yl)methyl)thiophen-2-yl)cyclohexan-1-yl)methyl)piperazin-1-yl)benzoic acid (Step F, 29 mg) in a mixed solvent of dry DCM (1.5 mL) and dry DMF (1.5 mL) was added N,N-dimethylpyridin-4-amine (12.1 mg, 0.10 mmol), EDCl (11.4 mg, 0.06 mmol) and (S)-4-(((1,4-dioxan-2-yl)methyl)amino)-3-nitrobenzenesulfonamide (12.6 mg, 0.04 mmol); then the reaction mixture was stirred at 40° C. for 12 h. After cooling down to room temperature, the resulting mixture was diluted with ethyl acetate and then washed with $H_2O$ and brine. The organic layer was dried over $Na_2SO_4$, and concentrated under reduced pressure to give a yellow oil, which was purified by C18 prep-HPLC to afford the title compound (2.6 mg, 6% over 2 steps) as a yellow solid. $^1$H NMR (400 MHz, DMSO-$d_6$) δ 11.59 (s, 1H), 8.46-8.44 (m, 2H), 7.96 (d, J=2.3 Hz, 1H), 7.69 (d, J=8.4 Hz, 1H), 7.54 (d, J=8.8 Hz, 1H), 7.45 (t, J=2.7 Hz, 1H), 7.38-7.36 (m, 1H), 7.30-7.19 (m, 1H), 6.93 (d, J=8.9 Hz, 1H), 6.75 (s, 1H), 6.67 (dd, J=9.1, 1.5 Hz, 2H), 6.33-6.32 (m, 1H), 6.25 (d, J=1.5 Hz, 1H), 3.95 (s, 2H), 3.83-3.75 (m, 3H), 3.70-3.55 (m, 6H), 3.54-3.43 (m, 8H), 3.10-3.06 (m, 4H), 2.98-2.99 (m, 2H), 2.94 (s, 3H), 2.28-2.26 (m, 4H), 2.18 (t, J=7.4 Hz, 2H), 2.04-2.02 (m, 2H), 1.35 (t, J=7.7 Hz, 2H), 0.91 (s, 6H); MS: 1030.4 (M+H$^+$).

Example 28: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-((4-morpholinopiperidin-1-yl)methyl)thiophen-2-yl)cyclohex-1-en-1-yl)methyl)piperazin-1-yl)benzamide

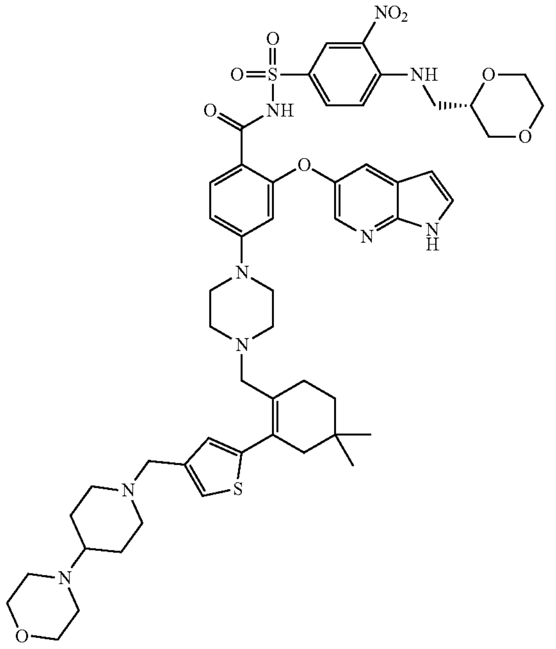 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(CN3CCC(N4CCOCC4)CC3)cs2)C1]

Step A: Methyl 2-((1H-pyrrolo[2,3-b]pyridin-5-yl)oxy)-4-(4-((4,4-dimethyl-2-(4-((4-morpholinopiperidin-1-yl)methyl)thiophen-2-yl)cyclohex-1-en-1-yl)methyl)piperazin-1-yl)benzoate

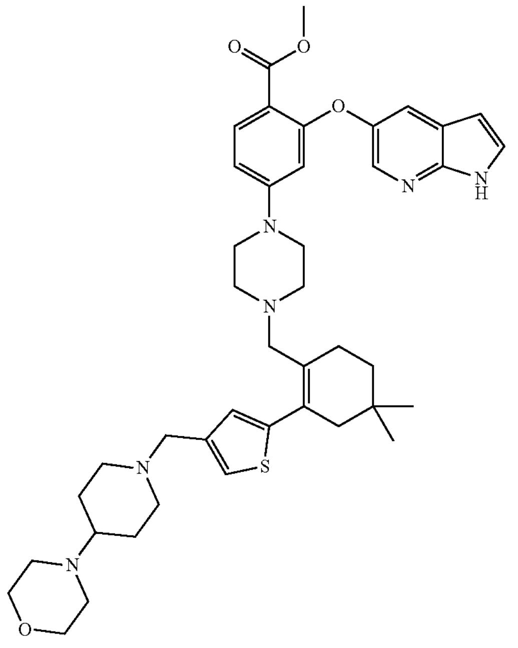 [SMILES: COC(=O)c1ccc(N2CCN(CC3=C(c4cc(CN5CCC(N6CCOCC6)CC5)cs4)CC(C)(C)CC3)CC2)cc1Oc1cnc2[nH]ccc2c1]

Under Ar, to a solution of methyl 2-((1H-pyrrolo[2,3-b]pyridin-5-yl)oxy)-4-(4-((2-(4-formylthiophen-2-yl)-4,4-dimethylcyclohex-1-en-1-yl)methyl)piperazin-1-yl)benzoate (Step B of Example 27, 35 mg, 0.06 mmol) in 1,2-dichloroethane (2 mL) was added 4-(piperidin-4-yl)morpholine (20.4 mg, 0.12 mmol) and $NaBH(OAc)_3$ (25.4 mg, 0.12 mmol); then the reaction mixture was stirred at room temperature for 12 h. The resulting mixture was diluted with DCM and then washed with $H_2O$ and brine. The organic layer was dried over $Na_2SO_4$, and concentrated under reduced pressure to give a yellow oil, which was loaded onto a silica gel column and eluted with methanol and dichloromethane (1:40) to afford the title compound (31 mg, 70% over 2 steps) as a yellow solid. MS: 739.4 ($M+H^+$).

Step B: 2-((1H-pyrrolo[2,3-b]pyridin-5-yl)oxy)-4-(4-((4,4-dimethyl-2-(4-((4-morpholinopiperidin-1-yl)methyl)thiophen-2-yl)cyclohex-1-en-1-yl)methyl)piperazin-1-yl)benzoic acid

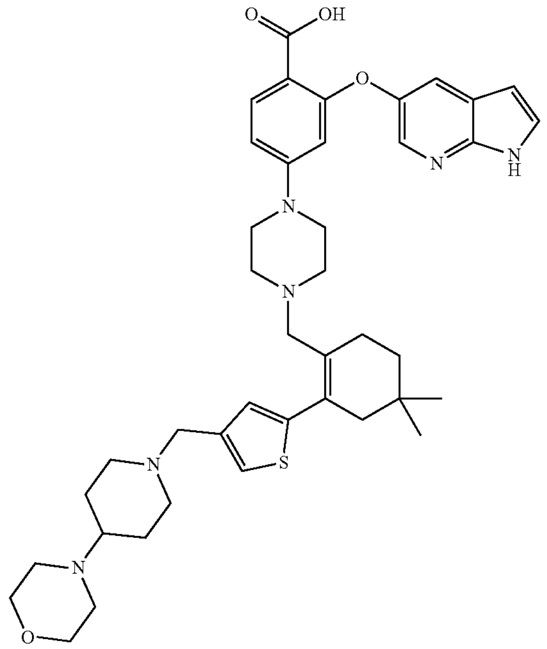 [SMILES: CC1(C)CCC(CN2CCN(c3ccc(C(=O)O)c(Oc4cnc5[nH]ccc5c4)c3)CC2)=C(c2cc(CN3CCC(N4CCOCC4)CC3)cs2)C1]

To a solution of methyl 2-((1H-pyrrolo[2,3-b]pyridin-5-yl)oxy)-4-(4-((4,4-dimethyl-2-(4-((4-morpholinopiperidin-1-yl)methyl)thiophen-2-yl)cyclohex-1-en-1-yl)methyl)piperazin-1-yl)benzoate (Step A, 31 mg, 0.04 mmol) in a mixed solvent of MeOH (2 mL), THF (2 mL) and $H_2O$ (2 mL) was added sodium hydroxide (13.4 mg, 0.33 mmol); then the reaction mixture was stirred at 45° C. for 8 h. After cooling down to room temperature, the resulting mixture was acidified with 1 N HCl to adjust pH 4-5 and extracted with ethyl acetate twice. The combined organic layer was dried over $Na_2SO_4$, and concentrated under reduced pressure to give the crude title compound (30 mg) as a yellow oil, which was directly used for the next step without purification. MS: 725.4 ($M+H^+$).

Step C: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-((4-morpholinopiperidin-1-yl)methyl)thiophen-2-yl)cyclohex-1-en-1-yl)methyl)piperazin-1-yl)benzamide (Example 28)

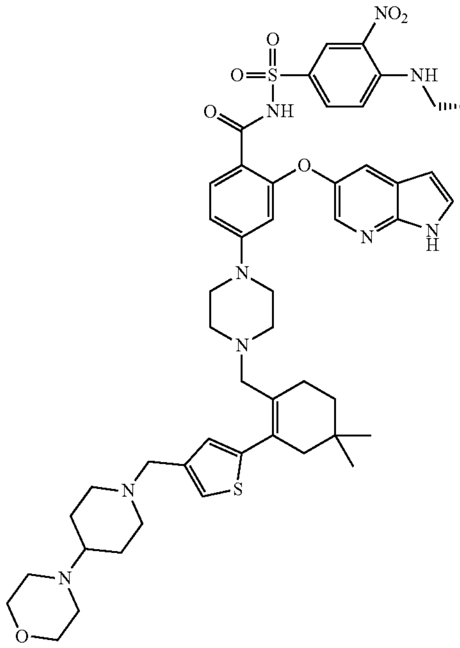

Under Ar, to a solution of the crude 2-((1H-pyrrolo[2,3-b]pyridin-5-yl)oxy)-4-(4-((4,4-dimethyl-2-(4-((4-morpholinopiperidin-1-yl)methyl)thiophen-2-yl)cyclohex-1-en-1-yl)methyl)piperazin-1-yl)benzoic acid (Step B, 30 mg) in a mixed solvent of dry DCM (1.5 mL) and dry DMF (1.5 mL) was added N,N-dimethylpyridin-4-amine (12.6 mg, 0.10 mmol), EDCl (11.9 mg, 0.06 mmol) and (S)-4-(((1,4-dioxan-2-yl)methyl)amino)-3-nitrobenzenesulfonamide (13.1 mg, 0.04 mmol); then the reaction mixture was stirred at 40° C. for 12 h. After cooling down to room temperature, the resulting mixture was diluted with ethyl acetate and then washed with $H_2O$ and brine. The organic layer was dried over $Na_2SO_4$, and concentrated under reduced pressure to give a yellow oil, which was purified by C18 prep-HPLC to afford the title compound (20 mg, 47% over 2 steps) as a yellow solid. $^1$H NMR (400 MHz, DMSO-$d_6$) δ 11.59 (s, 1H), 8.45-8.42 (m, 2H), 7.96 (d, J=2.6 Hz, 1H), 7.69 (dd, J=9.1, 1.7 Hz, 1H), 7.54 (d, J=8.8 Hz, 1H), 7.45 (t, J=2.9 Hz, 1H), 7.36 (d, J=2.1 Hz, 1H), 7.30 (s, 1H), 6.91 (d, J=9.3 Hz, 1H), 6.83 (s, 1H), 6.66 (dd, J=8.9, 1.9 Hz, 1H), 6.33-6.32 (m, 1H), 6.24 (d, J=1.8 Hz, 1H), 3.84-3.73 (m, 4H), 3.70-3.56 (m, 6H), 3.50-3.47 (m, 6H), 3.09-3.02 (m, 4H), 2.99-2.93 (m, 4H), 2.47-2.38 (m, 4H), 2.32-2.14 (m, 8H), 2.06-2.04 (m, 2H), 1.77-1.74 (m, 2H), 1.49-1.42 (m, 2H), 1.36 (t, J=6.2 Hz, 2H), 0.91 (s, 6H); MS: 1024.4 (M+H$^+$).

Example 29: N-((4-((((S)-1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-(((3S,5R)-3,4,5-trimethylpiperazin-1-yl)methyl)thiophen-2-yl)cyclohex-1-en-1-yl)methyl)piperazin-1-yl)benzamide

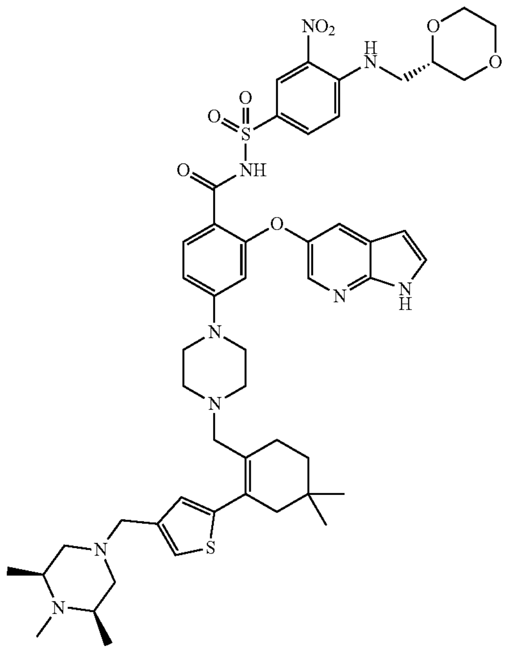 [SMILES: C[C@@H]1CN(Cc2csc(C3=C(CN4CCN(c5ccc(C(=O)NS(=O)(=O)c6ccc(NC[C@H]7COCCO7)c([N+](=O)[O-])c6)c(Oc6cnc7[nH]ccc7c6)c5)CC4)CCC(C)(C)C3)c2)C[C@H](C)N1C]

Essentially the same protocol of preparation of Example 28 was used to afford the example (8 mg) as a yellow solid. $^1$H NMR (400 MHz, DMSO-$d_6$) δ 11.58 (s, 1H), 8.45 (d, J=1.7 Hz, 1H), 8.41 (brs, 1H), 7.97 (d, J=2.4 Hz, 1H), 7.66 (d, J=8.3 Hz, 1H), 7.56 (d, J=8.7 Hz, 1H), 7.46 (s, 1H), 7.32 (s, 1H), 7.22 (s, 1H), 6.86 (d, J=9.3 Hz, 1H), 6.79 (s, 1H), 6.70 (d, J=8.7 Hz, 1H), 6.32 (s, 2H), 3.87-3.76 (m, 3H), 3.71-3.61 (m, 2H), 3.55-3.46 (m, 4H), 3.33-3.24 (m, 4H), 3.19-3.08 (m, 4H), 3.00-2.91 (m, 2H), 2.88-2.75 (m, 3H), 2.50-2.42 (m, 2H), 2.33-2.25 (m, 4H), 2.24-2.17 (m, 2H), 2.10-2.05 (m, 2H), 2.04-1.93 (m, 2H), 1.44-1.35 (m, 2H), 1.08 (d, J=5.8 Hz, 6H), 0.94 (s, 6H); MS: 983.1 (M+H$^+$).

Example 30: N-((4-((((S)-1,4-dioxan-2-yl)methyl)amino)-3-nitrophenyl)sulfonyl)-2-((1H-pyrrolo[2,3-b]pyridin-5-yl)oxy)-4-(4-((2-(4-(((R)-hexahydropyrazino[2,1-c][1,4]oxazin-8(1H)-yl)methyl)thiophen-2-yl)-4,4-dimethylcyclohex-1-en-1-yl)methyl)piperazin-1-yl)benzamide

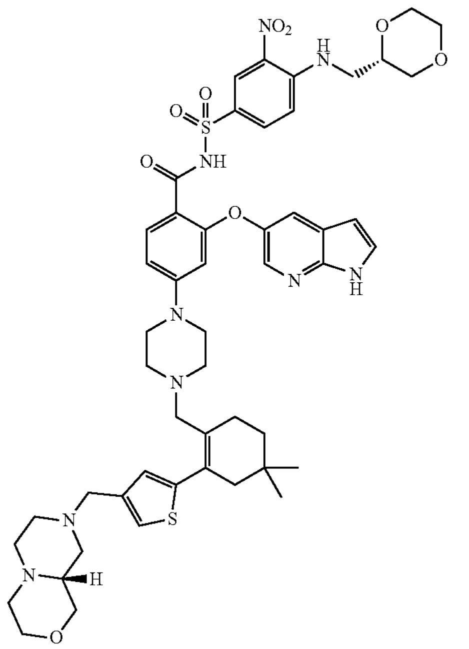 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(CN3CCN4CCOC[C@H]4C3)cs2)C1]

Essentially the same protocol of preparation of Example 28 was used to afford the example (13 mg) as a yellow solid. $^1$H NMR (400 MHz, DMSO-$d_6$) δ 11.67 (s, 1H), 8.54 (s, 2H), 8.04 (s, 1H), 7.79 (d, J=8.2 Hz, 1H), 7.55 (d, J=8.9 Hz, 1H), 7.50 (d, J=8.4 Hz, 2H), 7.21 (s, 1H), 7.05 (d, J=9.4 Hz, 1H), 6.81 (s, 1H), 6.71 (d, J=8.2 Hz, 1H), 6.39 (s, 1H), 6.26 (s, 1H), 3.89-3.76 (m, 3H), 3.75-3.59 (m, 4H), 3.59-3.48 (m, 6H), 3.17-2.92 (m, 8H), 2.79-2.57 (m, 4H), 2.36-2.26 (m, 4H), 2.24-2.02 (m, 8H), 1.78-1.65 (m, 1H), 1.44-1.33 (m, 2H), 0.94 (s, 6H); MS: 997.9 ($M+H^+$).

Example 31: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-((4-(oxetan-3-yl)piperazin-1-yl)methyl)thiophen-2-yl)cyclohex-1-en-1-yl)methyl)piperazin-1-yl)benzamide

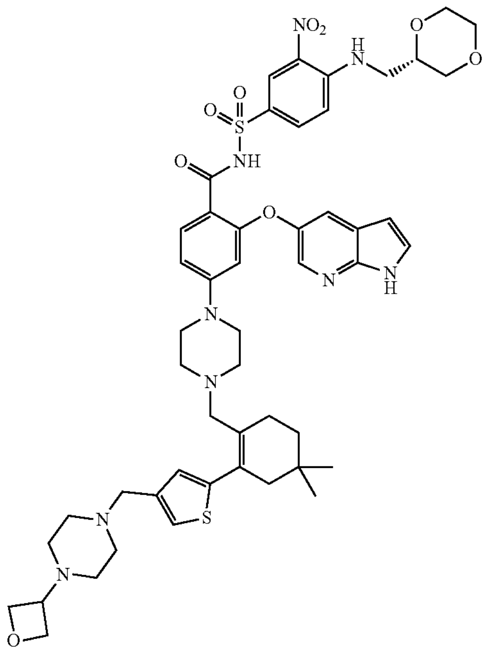 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(CN3CCN(C4COC4)CC3)cs2)C1]

Essentially the same protocol of preparation of Example 28 was used to afford the example (10 mg) as a yellow solid. $^1$H NMR (400 MHz, DMSO-$d_6$) δ 11.67 (s, 1H), 8.54 (s, 2H), 8.03 (d, J=2.0 Hz, 1H), 7.79 (d, J=8.5 Hz, 1H), 7.55 (d, J=8.8 Hz, 1H), 7.50 (d, J=10.1 Hz, 2H), 7.25 (s, 1H), 7.05 (d, J=9.3 Hz, 1H), 6.83 (s, 1H), 6.71 (d, J=8.4 Hz, 1H), 6.39 (s, 1H), 6.25 (s, 1H), 4.48 (t, J=6.4 Hz, 2H), 4.36 (t, J=5.9 Hz, 2H), 3.86-3.78 (m, 3H), 3.72-3.43 (m, 16H), 3.38-3.23 (m, 15H), 3.14-3.07 (m, 4H), 3.03-2.94 (m, 2H), 2.49-2.13 (m, 12H), 2.11-2.04 (m, 2H), 1.42-1.33 (m, 2H), 0.94 (s, 6H); MS: 997.3 ($M+H^+$).

Example 32: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-((4,4-difluoropiperidin-1-yl)methyl)thiophen-2-yl)-4,4-dimethylcyclohex-1-en-1-yl)methyl)piperazin-1-yl)benzamide

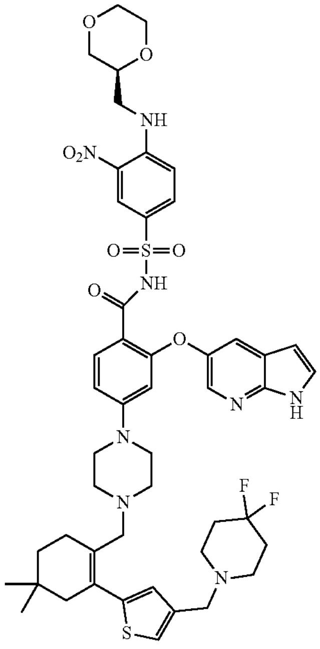 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(CN3CCC(F)(F)CC3)cs2)C1]

Essentially the same protocol of preparation of Example 28 was used to afford the example (13 mg) as a yellow solid. $^1$H NMR (400 MHz, DMSO-$d_6$) δ 11.63 (s, 1H), 8.60-8.40 (m, 2H), 8.00 (d, J=2.2 Hz, 1H), 7.75 (d, J=8.4 Hz, 1H), 7.51 (d, J=8.8 Hz, 1H), 7.49-7.46 (m, 1H), 7.44 (s, 1H), 7.19 (s, 1H), 7.07-6.94 (m, 1H), 6.77 (s, 1H), 6.73-6.64 (m, 1H), 6.35 (dd, J=2.8, 1.6 Hz, 1H), 6.23 (d, J=1.7 Hz, 1H), 3.85-3.75 (m, 3H), 3.69-3.56 (m, 2H), 3.52-3.43 (m, 4H), 3.41-3.30 (m, 2H), 3.13-3.02 (m, 4H), 2.97 (s, 2H), 2.47-2.39 (m, 4H), 2.30-2.22 (m, 4H), 2.21-2.13 (m, 2H), 2.05 (s, 2H), 1.97-1.81 (m, 4H), 1.35 (t, J=6.3 Hz, 2H), 0.91 (s, 6H); MS: 975.7 (M+H$^+$).

Example 33: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(4-fluorophenyl)thiophen-2-yl)-4,4-dimethylcyclohex-1-en-1-yl)methyl)piperazin-1-yl)benzamide

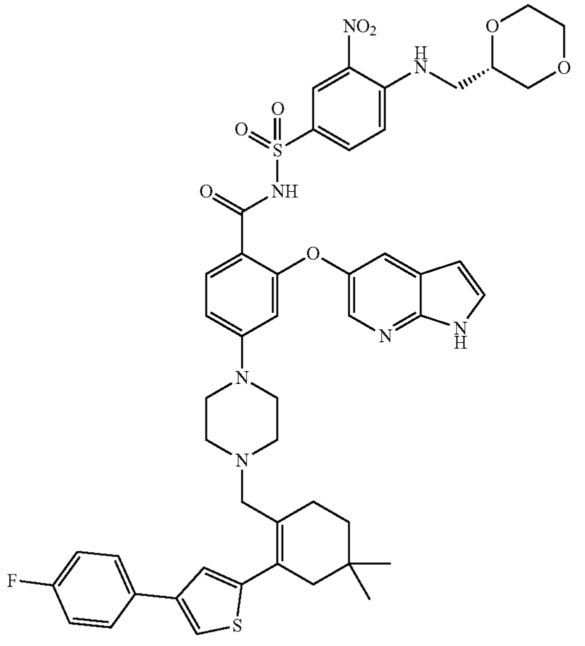 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3ccc(F)cc3)cs2)C1]

Step A: 3-(4-Fluorophenyl)thiophene

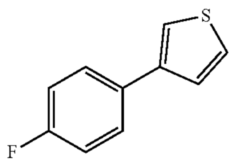 [SMILES: Fc1ccc(-c2ccsc2)cc1]

Under Ar, to a solution of 3-bromothiophene (1 g, 6.13 mmol) in a mixed solvent of dioxane (20 mL) and water (4 mL) was added (4-fluorophenyl)boronic acid (1.03 g, 7.36 mmol), $PdCl_2$(dppf) (0.449 g, 0.613 mmol) and $Na_2CO_3$ (1.95 g, 18.4 mmol); then the reaction mixture was stirred at 100° C. for 3 h. After cooling down to room temperature and removal of volatiles, the residue was purified by silica gel column (hexane:EA, 20:1) to afford the title compound (700 mg, 64%) as a light yellow solid.

$^1$H NMR (400 MHz, DMSO-$d_6$) δ 7.92-7.86 (m, 1H), 7.83-7.76 (m, 2H), 7.70-7.65 (m, 1H), 7.61-7.54 (m, 1H), 7.31-7.22 (m, 2H).

Step B: (4-(4-Fluorophenyl)thiophen-2-yl)boronic acid

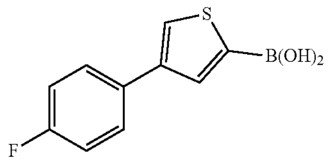 [SMILES: OB(O)c1cc(-c2ccc(F)cc2)cs1]

Under Ar, to a solution of 3-(4-fluorophenyl)thiophene (Step A, 500 mg, 2.81 mmol) in dry THF (10 mL) was added LDA (2.8 mL, 2 M in THF, 5.61 mmol) at 0° C.; and the mixture was stirred for 0.5 h. Triisopropyl borate (1.06 g, 5.61 mmol) was added slowly; then the reaction mixture was allowed to warm up to room temperature gradually and stirred for 1 h. The reaction was quenched with aq. $NH_4Cl$ and extracted with EA twice. The combined organic layer was washed with brine, dried over $Na_2SO_4$ and concentrated to give a yellow oil, which was purified by silica gel column (hexane:EA, 3:1) to afford the title compound (400 mg, 64%) as a yellow solid. $^1H$ NMR (400 MHz, DMSO-$d_6$) δ 8.33 (s, 2H), 8.06 (d, J=4.5 Hz, 2H), 7.76-7.69 (m, 2H), 7.33-7.25 (m, 2H).

Step C: methyl 2-((1H-pyrrolo[2,3-b]pyridin-5-yl)oxy)-4-(4-((2-(4-(4-fluorophenyl)thiophen-2-yl)-4,4-dimethylcyclohex-1-en-1-yl)methyl)piperazin-1-yl)benzoate

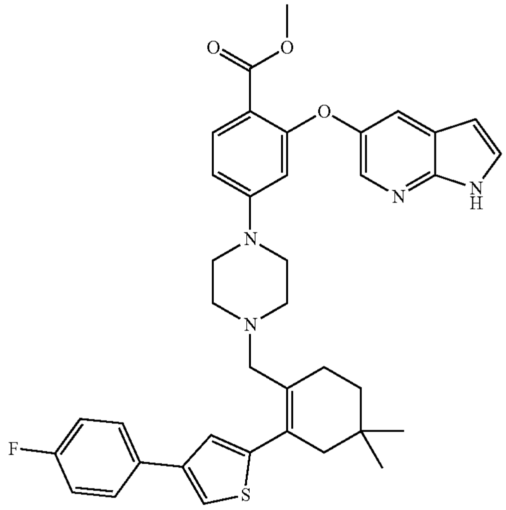 [SMILES: COC(=O)c1ccc(N2CCN(CC3=C(c4cc(-c5ccc(F)cc5)cs4)CC(C)(C)CC3)CC2)cc1Oc1cnc2[nH]ccc2c1]

Under Ar, to a solution of methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 100 mg, 0.181 mmol) in a mixed solvent of dioxane (10 mL) and water (2 mL) was added (4-(4-fluorophenyl)thiophen-2-yl)boronic acid (Step B, 80 mg, 0.361 mmol), $PdCl_2$(dppf) (132 mg, 0.181 mmol) and $Na_2CO_3$ (19.15 mg, 0.181 mmol); then the reaction mixture was stirred at 100° C. for 16 h. After cooling down to room temperature and removal of volatiles, the residue was purified by silica gel column (DCM:MeOH, 25:1) to afford the title compound (60 mg, 51%) as a yellow oil. MS: 651.5 (M+H$^+$).

Step D: 2-((1H-pyrrolo[2,3-b]pyridin-5-yl)oxy)-4-(4-((2-(4-(4-fluorophenyl)thiophen-2-yl)-4,4-dimethylcyclohex-1-en-1-yl)methyl)piperazin-1-yl)benzoic acid

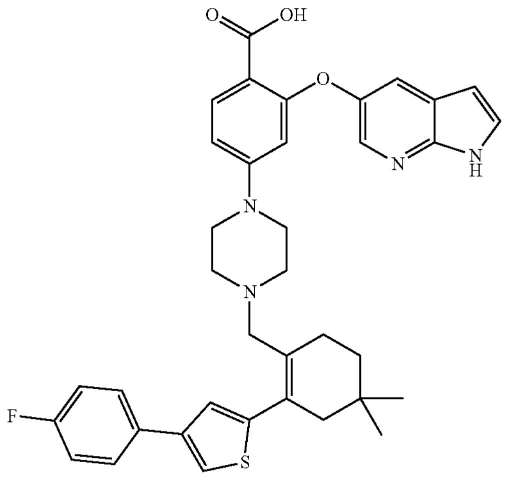 [SMILES: CC1(C)CCC(CN2CCN(c3ccc(C(=O)O)c(Oc4cnc5[nH]ccc5c4)c3)CC2)=C(c2cc(-c3ccc(F)cc3)cs2)C1]

To a solution of methyl 2-((1H-pyrrolo[2,3-b]pyridin-5-yl)oxy)-4-(4-((2-(4-(4-fluorophenyl)thiophen-2-yl)-4,4-dimethylcyclohex-1-en-1-yl)methyl)piperazin-1-yl)benzoate (Step C, 60 mg, 0.092 mmol) in a mixed solvent of MeOH (3 mL) and THF (3 mL) was added 3 N NaOH (3 mL); then the reaction mixture was stirred at 40° C. for 16 h. After cooling down to room temperature, the mixture was adjusted to pH 3-4 with 1 N HCl, and extracted with EA twice. The combined organic layer was washed with brine, dried over $Na_2SO_4$ and concentrated under reduced pressure to give the crude title compound (50 mg) as a yellow solid, which was directly used for the next step without purification. MS: 637.5 (M+H$^+$).

Step E: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(4-fluorophenyl)thiophen-2-yl)-4,4-dimethylcyclohex-1-en-1-yl)methyl)piperazin-1-yl)benzamide (Example 33)

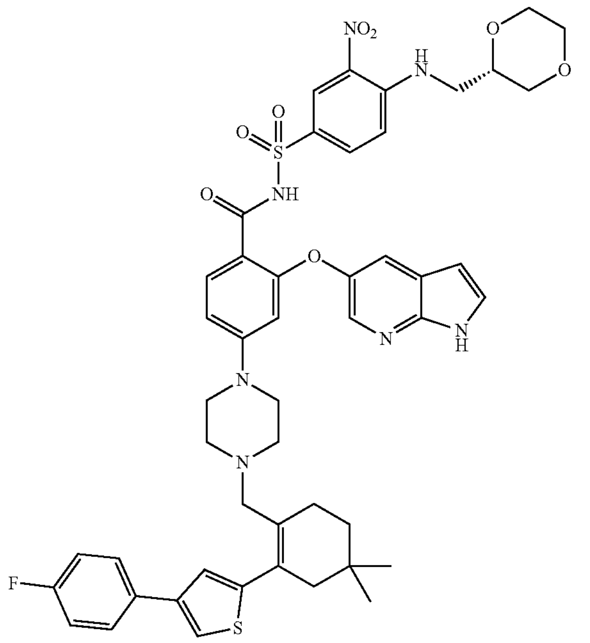 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3ccc(F)cc3)cs2)C1]

Under Ar, to a solution of the crude 2-((1H-pyrrolo[2,3-b]pyridin-5-yl)oxy)-4-(4-((2-(4-(4-fluorophenyl)thiophen-2-yl)-4,4-dimethylcyclohex-1-en-1-yl)methyl)piperazin-1-yl)benzoic acid (Step D, 50 mg) in a mixed solvent of dry DMF (2 mL) and DCM (10 mL) was added (S)-4-(((1,4-dioxan-2-yl)methyl)amino)-3-nitrobenzenesulfonamide (24.92 mg, 0.079 mmol), DMAP (23.98 mg, 0.196 mmol) and EDCl (22.58 mg, 0.118 mmol); then the reaction mixture was stirred at 40° C. for 16 h. After cooling down to room temperature, the resulting mixture was diluted with DCM, washed with 1 N HCl and brine, dried over $Na_2SO_4$ and concentrated under reduced pressure to give a yellow oil, which was purified by C18 prep-HPLC to afford the title compound (14 mg, 19% over 2 steps) as a yellow solid. $^1H$ NMR (400 MHz, DMSO-$d_6$) δ 11.71 (s, 1H), 8.63-8.58 (m, 1H), 8.56 (d, J=1.6 Hz, 1H), 8.05 (d, J=2.4 Hz, 1H), 7.81 (d, J=8.6 Hz, 1H), 7.78-7.67 (m, 3H), 7.58-7.45 (m, 3H), 7.32 (s, 1H), 7.24 (t, J=8.8 Hz, 2H), 7.09 (d, J=9.2 Hz, 1H), 6.73 (d, J=7.8 Hz, 1H), 6.40 (s, 1H), 6.26 (s, 1H), 3.90-3.75 (m, 3H), 3.73-3.58 (m, 2H), 3.61-3.48 (m, 2H), 3.38-3.28 (m, 2H), 3.19-3.10 (m, 4H), 3.10-2.99 (m, 2H), 2.39-2.26 (m, 4H), 2.27-2.18 (m, 2H), 2.17-2.09 (m, 2H), 1.40 (t, J=6.1 Hz, 2H), 0.98 (s, 6H); MS: 937.1 ($M+H^+$).

Example 34: 2-((1H-pyrrolo[2,3-b]pyridin-5-yl)oxy)-4-(4-((4,4-dimethyl-2-(4-phenylthiophen-2-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

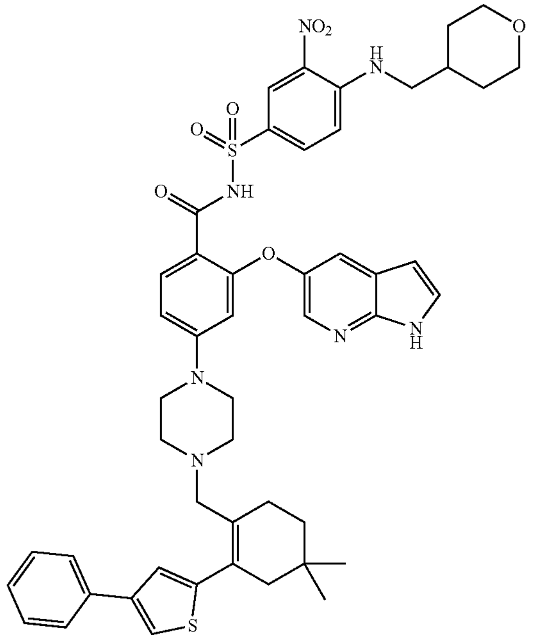 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2cc(-c3ccccc3)cs2)C1]

Essentially the same protocol of preparation of Example 33 was used to afford the example (7 mg) as a yellow solid. $^1H$ NMR (400 MHz, DMSO-$d_6$) δ 11.69 (s, 1H), 8.60 (brs, 1H), 8.54 (s, 1H), 8.04 (s, 1H), 7.78 (s, 2H), 7.69 (d, J=7.7 Hz, 2H), 7.58-7.45 (m, 3H), 7.43-7.24 (m, 4H), 7.14-7.02 (m, 1H), 6.72 (d, J=7.7 Hz, 1H), 6.39 (s, 1H), 6.26 (s, 1H), 3.87 (d, J=8.5 Hz, 2H), 3.32-3.26 (m, 2H), 3.18-3.08 (m, 4H), 3.07-3.00 (m, 2H), 2.39-2.28 (m, 4H), 2.27-2.19 (m, 2H), 2.14 (s, 2H), 1.96-1.81 (m, 1H), 1.70-1.58 (m, 2H), 1.45-1.36 (m, 2H), 1.31-1.24 (m, 4H), 0.96 (s, 6H); MS: 917.2 ($M+H^+$).

Example 35: 2-((1H-pyrrolo[2,3-b]pyridin-5-yl)oxy)-4-(4-((4,4-dimethyl-2-(2-phenylthiophen-3-yl)cyclohex-1-en-1-yl)methyl)piperazin-1-yl)-N-((3-nitro-4-(((tetrahydro-2H-pyran-4-yl)methyl)amino)phenyl)sulfonyl)benzamide

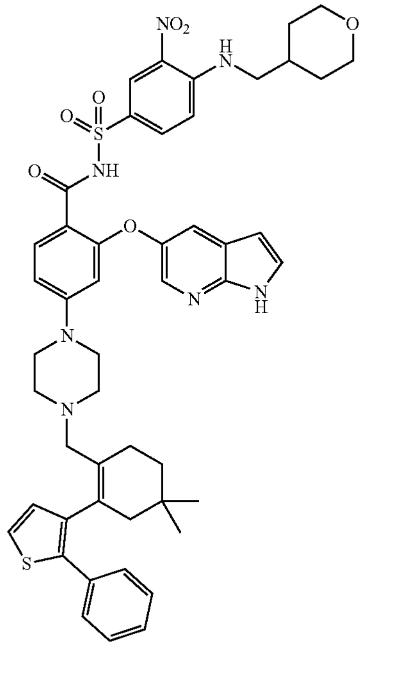 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccsc2-c2ccccc2)C1]

Essentially the same protocol of preparation of Example 33 was used to afford the example (7 mg) as a yellow solid. $^1$H NMR (400 MHz, DMSO-$d_6$) δ 11.75 (s, 1H), 8.66 (t, J=5.8 Hz, 1H), 8.59 (d, J=2.1 Hz, 1H), 8.09 (d, J=2.5 Hz, 1H), 7.83 (d, J=9.4 Hz, 1H), 7.62-7.49 (m, 4H), 7.40-7.30 (m, 4H), 7.28-7.18 (m, 2H), 7.15 (d, J=9.4 Hz, 1H), 6.70 (dd, J=9.1, 2.0 Hz, 1H), 6.44 (dd, J=3.2, 1.9 Hz, 1H), 6.20 (s, 1H), 3.88 (dd, J=11.2, 3.0 Hz, 2H), 3.37-3.23 (m, 7H), 3.14-3.00 (m, 4H), 2.32-2.06 (m, 4H), 2.01-1.84 (m, 2H), 1.65 (d, J=11.8 Hz, 2H), 1.41-1.18 (m, 6H), 0.95-0.66 (m, 6H); MS: 917.2 (M+H$^+$).

Example 36: 2-((1H-pyrrolo[2,3-b]pyridin-5-yl)oxy)-4-(4-((2-(4-(4-fluorophenyl)thiophen-2-yl)-4,4-dimethylcyclohex-1-en-1-yl)methyl)piperazin-1-yl)-N-((4-((((1s,4s)-4-hydroxy-4-methylcyclohexyl)methyl)amino)-3-nitrophenyl)sulfonyl)benzamide

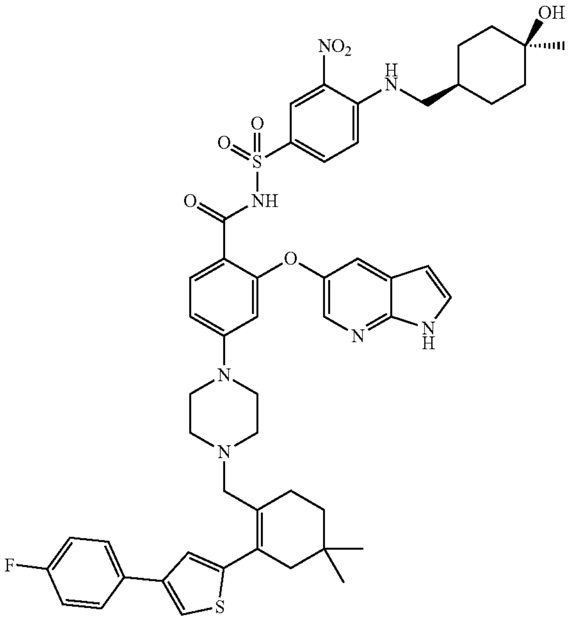 [SMILES: CC1(C)CCC(CN2CCN(c3ccc(C(=O)NS(=O)(=O)c4ccc(NC[C@H]5CC[C@@](C)(O)CC5)c([N+](=O)[O-])c4)c(Oc4cnc5[nH]ccc5c4)c3)CC2)=C(c2cc(-c3ccc(F)cc3)cs2)C1]

Essentially the same protocol of preparation of Example 33 was used to afford the example (10 mg) as a yellow solid. $^1$H NMR (400 MHz, DMSO-$d_6$) δ 11.72 (s, 1H), 8.63 (brs, 1H), 8.57 (d, J=1.8 Hz, 1H), 8.07 (d, J=2.5 Hz, 1H), 7.80 (d, J=9.1 Hz, 1H), 7.77-7.70 (m, 3H), 7.57-7.49 (m, 3H), 7.32 (s, 1H), 7.24 (t, J=8.8 Hz, 2H), 7.09 (d, J=9.3 Hz, 1H), 6.73 (d, J=8.9 Hz, 1H), 6.41 (s, 1H), 6.25 (s, 1H), 4.00 (s, 1H), 3.31-3.25 (m, 2H), 3.19-3.01 (m, 6H), 2.39-2.28 (m, 4H), 2.27-2.19 (m, 2H), 2.18-2.11 (m, 2H), 1.64-1.20 (m, 11H), 1.11 (s, 3H), 0.96 (s, 6H); MS: 963.3 (M+H).

Example 37: 2-((1H-pyrrolo[2,3-b]pyridin-5-yl)oxy)-4-(4-((2-(4-(4-fluorophenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

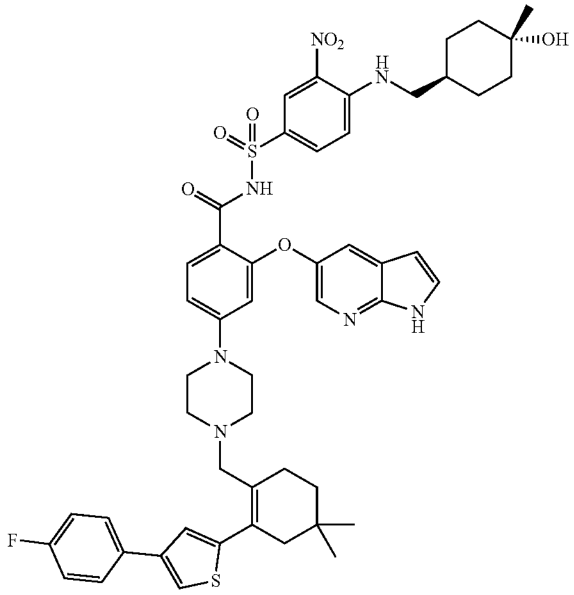 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(F)cc3)cs2)C1]

Essentially the same protocol of preparation of Example 33 was used to afford the example (10 mg) as a yellow solid. $^1$H NMR (400 MHz, DMSO-$d_6$) δ 11.68 (s, 1H), 8.55 (s, 2H), 8.05 (s, 1H), 7.82-7.68 (m, 4H), 7.56-7.44 (m, 3H), 7.31 (s, 1H), 7.28-7.18 (m, 2H), 7.05 (d, J=8.9 Hz, 1H), 6.72 (d, J=9.9 Hz, 1H), 6.39 (s, 1H), 6.26 (s, 1H), 4.28 (s, 1H), 3.31-3.25 (m, 2H), 3.16-3.02 (m, 6H), 2.38-2.28 (m, 4H), 2.26-2.19 (m, 2H), 2.17-2.09 (m, 2H), 1.80-1.15 (m, 11H), 1.12 (s, 3H), 0.96 (s, 6H); MS: 963.4 (M+H$^+$).

Example 38: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(4-chlorophenyl)thiophen-2-yl)-4,4-dimethylcyclohex-1-en-1-yl)methyl)piperazin-1-yl)benzamide

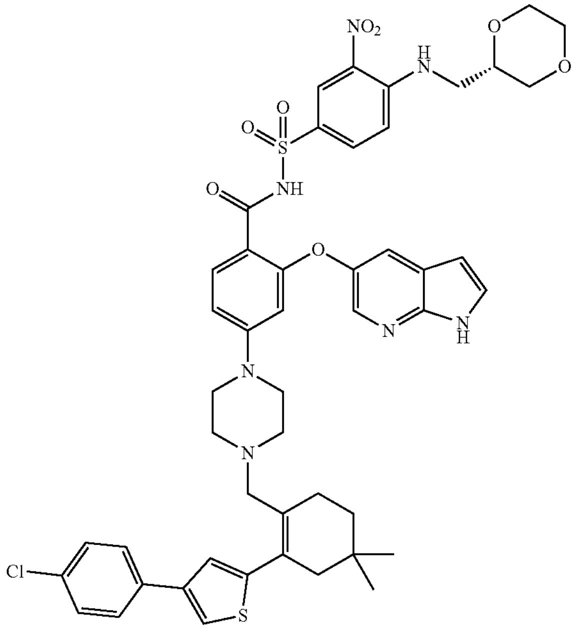 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3ccc(Cl)cc3)cs2)C1]

Essentially the same protocol of preparation of Example 33 was used to afford the example (26 mg) as a yellow solid. $^1$H NMR (400 MHz, DMSO-$d_6$) δ 11.68 (s, 1H), 8.57 (s, 2H), 8.05 (s, 1H), 7.87-7.64 (m, 4H), 7.59-7.41 (m, 5H), 7.34 (s, 1H), 7.09 (d, J=8.6 Hz, 1H), 6.72 (d, J=8.0 Hz, 1H), 6.40 (s, 1H), 6.26 (s, 1H), 3.92-3.76 (m, 3H), 3.73-3.58 (m, 2H), 3.59-3.41 (m, 4H), 3.18-3.01 (m, 6H), 2.39-2.19 (m, 6H), 2.17-2.07 (m, 2H), 1.49-1.35 (m, 2H), 0.96 (s, 6H); MS: 953.5 (M+H$^+$).

Example 39: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(2-isopropylphenyl)thiophen-2-yl)-4,4-dimethylcyclohex-1-en-1-yl)methyl)piperazin-1-yl)benzamide

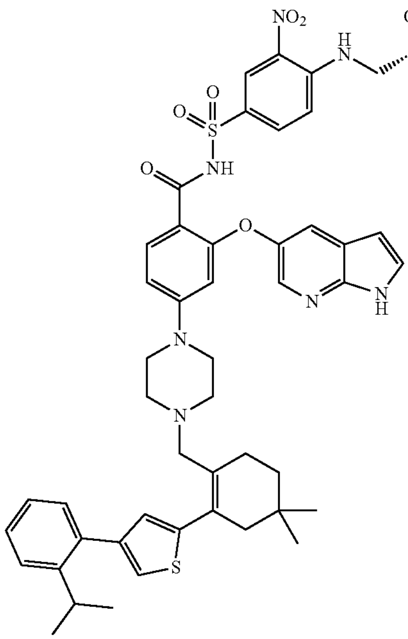

Essentially the same protocol of preparation of Example 33 was used to afford the example (35 mg) as a yellow solid. $^1$H NMR (400 MHz, DMSO-$d_6$) δ 11.70 (s, 1H), 8.64-8.52 (m, 2H), 8.05 (d, J=1.9 Hz, 1H), 7.83 (d, J=8.4 Hz, 1H), 7.58-7.49 (m, 3H), 7.40-7.26 (m, 3H), 7.19 (d, J=3.5 Hz, 2H), 7.10 (d, J=9.4 Hz, 1H), 6.83 (s, 1H), 6.71 (d, J=7.9 Hz, 1H), 6.40 (s, 1H), 6.24 (s, 1H), 3.89-3.75 (m, 3H), 3.72-3.59 (m, 2H), 3.58-3.48 (m, 2H), 3.46-3.40 (m, 2H), 3.16-3.03 (m, 7H), 2.36-2.18 (m, 6H), 2.16-2.08 (m, 2H), 1.48-1.34 (m, 2H), 1.07 (d, J=6.8 Hz, 6H), 0.96 (s, 6H); MS: 961.2 (M+H$^+$).

Example 40: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((4,4-dimethyl-2-(4-(4-(trifluoromethyl)phenyl)thiophen-2-yl)cyclohex-1-en-1-yl)methyl)piperazin-1-yl)benzamide

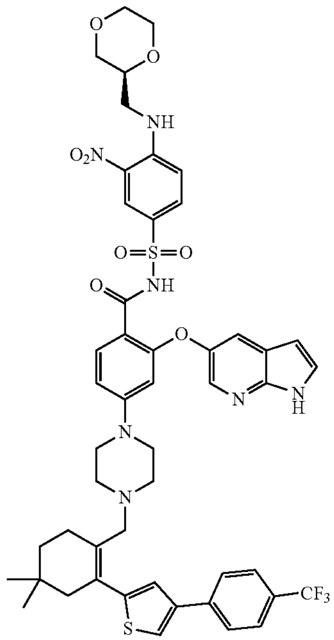 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3ccc(C(F)(F)F)cc3)cs2)C1]

Essentially the same protocol of preparation of Example 33 was used to afford the example (11 mg) as a yellow solid. $^1$H NMR (400 MHz, DMSO-$d_6$) δ 11.63 (s, 1H), 8.62-8.46 (m, 2H), 8.02 (d, J=2.5 Hz, 1H), 7.95 (d, J=1.3 Hz, 1H), 7.91 (s, 1H), 7.89 (s, 1H), 7.80 (d, J=9.1 Hz, 1H), 7.73 (d, J=8.3 Hz, 2H), 7.54-7.45 (m, 3H), 7.39 (d, J=1.3 Hz, 1H), 7.06 (d, J=9.1 Hz, 1H), 6.70 (dd, J=9.0, 2.0 Hz, 1H), 6.37 (dd, J=3.2, 1.8 Hz, 1H), 6.23 (d, J=1.9 Hz, 1H), 3.85-3.74 (m, 3H), 3.69-3.57 (m, 2H), 3.53-3.44 (m, 2H), 3.42-3.32 (m, 2H), 3.16-3.07 (m, 4H), 3.04 (s, 2H), 2.36-2.25 (m, 4H), 2.26-2.17 (m, 2H), 2.12 (s, 2H), 1.39 (t, J=6.3 Hz, 2H), 0.94 (s, 6H); MS: 987.1 (M+H$^+$).

Example 41: 2-((1H-pyrrolo[2,3-b]pyridin-5-yl)oxy)-4-(4-((4,4-dimethyl-2-(4-(4-(trifluoromethyl)phenyl)thiophen-2-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

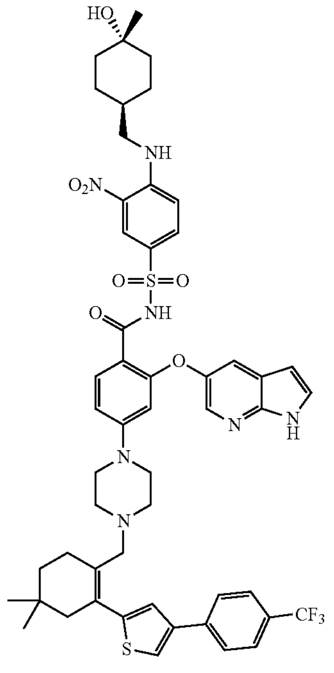 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(F)(F)F)cc3)cs2)C1]

Essentially the same protocol of preparation of Example 33 was used to afford the example (9 mg) as a yellow solid. $^1$H NMR (400 MHz, DMSO-$d_6$) δ 11.65 (s, 1H), 8.53 (s, 2H), 8.02 (d, J=2.4 Hz, 1H), 7.95 (d, J=1.3 Hz, 1H), 7.90 (d, J=8.2 Hz, 2H), 7.77 (d, J=8.2 Hz, 1H), 7.73 (d, J=8.3 Hz, 2H), 7.55-7.44 (m, 3H), 7.39 (d, J=1.4 Hz, 1H), 7.04 (d, J=8.7 Hz, 1H), 6.69 (dd, J=9.0, 2.1 Hz, 1H), 6.40-6.33 (m, 1H), 6.23 (d, J=1.9 Hz, 1H), 4.22 (s, 1H), 3.29-3.24 (d, J=6.7 Hz, 2H), 3.11 (s, 4H), 3.04 (s, 2H), 2.30 (s, 4H), 2.22 (s, 2H), 2.12 (s, 2H), 1.74-1.59 (m, 3H), 1.58-1.49 (m, 2H), 1.39 (t, J=6.4 Hz, 2H), 1.32 (dd, J=12.6, 3.5 Hz, 2H), 1.18-1.10 (m, 2H), 1.10 (s, 3H), 0.94 (s, 6H); MS: 1013.3 (M+H$^+$).

Example 42: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(2,4-difluorophenyl)thiophen-2-yl)-4,4-dimethylcyclohex-1-en-1-yl)methyl)piperazin-1-yl)benzamide

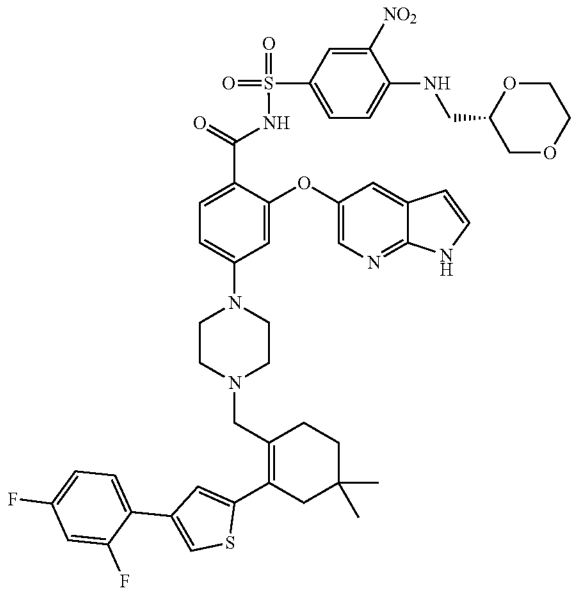 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3ccc(F)cc3F)cs2)C1]

Step A: 2-Chloro-4-(2,4-difluorophenyl)thiophene

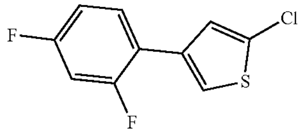 [SMILES: Fc1ccc(-c2csc(Cl)c2)c(F)c1]

Under Ar, to a solution of 4-bromo-2-chlorothiophene (800 mg, 4.0 mmol) in a mixed solvent of DME (12 mL) and 2 M $Na_2CO_3$ (4 mL) was added (2,4-difluorophenyl)boronic acid (960 mg, 6 mmol) and $PdCl_2(dppf)\cdot CH_2Cl_2$ (331 mg, 0.4 mmol); then the reaction mixture was stirred at 100° C. for 0.5 h. After cooling down to room temperature, the resulting mixture was diluted with ethyl acetate and then washed with $H_2O$ and brine. The organic layer was dried over $Na_2SO_4$, and concentrated under reduced pressure to give a light yellow oil, which was loaded onto a silica gel column and eluted with ethyl acetate and hexane (1:10) to afford the title compound (850 mg, 91%) as a colorless oil. $^1$H NMR (400 MHz, $CD_3OD$) δ 7.63-7.55 (m, 1H), 7.48-7.44 (m, 1H), 7.29-7.26 (m, 1H), 7.06-6.95 (m, 2H).

Step B: Methyl 2-((1H-pyrrolo[2,3-b]pyridin-5-yl)oxy)-4-(4-((2-(4-(2,4-difluorophenyl)thiophen-2-yl)-4,4-dimethylcyclohex-1-en-1-yl)methyl)piperazin-1-yl)benzoate

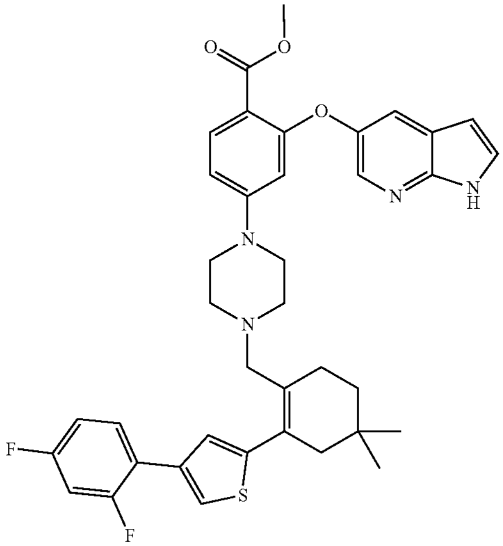 [SMILES: COC(=O)c1ccc(N2CCN(CC3=C(c4cc(-c5ccc(F)cc5F)cs4)CC(C)(C)CC3)CC2)cc1Oc1cnc2[nH]ccc2c1]

Under Ar, to a solution of methyl 2-((1H-pyrrolo[2,3-b]pyridin-5-yl)oxy)-4-(4-((4,4-dimethyl-2-(4,4,5,5-tetramethyl-1,3,2-dioxaborolan-2-yl)cyclohex-1-en-1-yl)methyl)piperazin-1-yl)benzoate (Step A of Example 22, 270 mg, 0.45 mmol) in a mixed solvent of 1,4-dioxane (24 mL) and $H_2O$ (4 mL) was added 2-chloro-4-(2,4-difluorophenyl)thiophene (Step A, 156 mg, 0.67 mmol), $K_2CO_3$ (186 mg, 1.35 mmol) and $PdCl_2$(dppf) (32.9 mg, 0.045 mmol); then the reaction mixture was stirred at 100° C. for 45 min with microwave assistance. After cooling down to room temperature, the resulting mixture was diluted with ethyl acetate and then washed with $H_2O$ and brine. The organic layer was dried over $Na_2SO_4$, and concentrated under reduced pressure to give a yellow oil, which was loaded onto a silica gel column and eluted with DCM and MeOH (40:1) to afford the title compound (100 mg, 33%) as a yellow oil. MS: 669.3 ($M+H^+$).

Step C: 2-((1H-pyrrolo[2,3-b]pyridin-5-yl)oxy)-4-(4-((2-(4-(2,4-difluorophenyl)thiophen-2-yl)-4,4-dimethylcyclohex-1-en-1-yl)methyl)piperazin-1-yl)benzoic acid

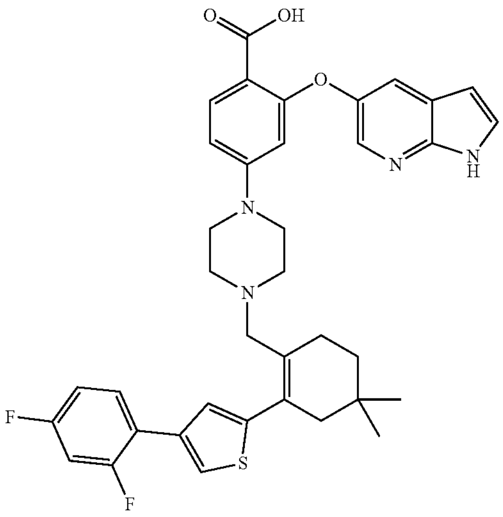 [SMILES: CC1(C)CCC(CN2CCN(c3ccc(C(=O)O)c(Oc4cnc5[nH]ccc5c4)c3)CC2)=C(c2cc(-c3ccc(F)cc3F)cs2)C1]

To a solution of methyl 2-((1H-pyrrolo[2,3-b]pyridin-5-yl)oxy)-4-(4-((2-(4-(2,4-difluorophenyl)thiophen-2-yl)-4,4-dimethylcyclohex-1-en-1-yl)methyl)piperazin-1-yl)benzoate (Step B, 100 mg, 0.15 mmol) in a mixed solvent of MeOH (2 mL), THF (2 mL) and $H_2O$ (2 mL) was added sodium hydroxide (47.8 mg, 1.19 mmol); then the reaction mixture was stirred at 45° C. for 8 h. After cooling down to room temperature, the resulting mixture was acidified with 1 N HCl to adjust pH 4-5 and extracted with ethyl acetate twice. The combined organic layers were dried over $Na_2SO_4$, and concentrated under reduced pressure to give the crude title compound (65 mg) as a yellow oil, which was directly used for the next step without purification. MS: 655.3 ($M+H^+$).

Step D: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(2,4-difluorophenyl)thiophen-2-yl)-4,4-dimethylcyclohex-1-en-1-yl)methyl)piperazin-1-yl)benzamide (Example 42)

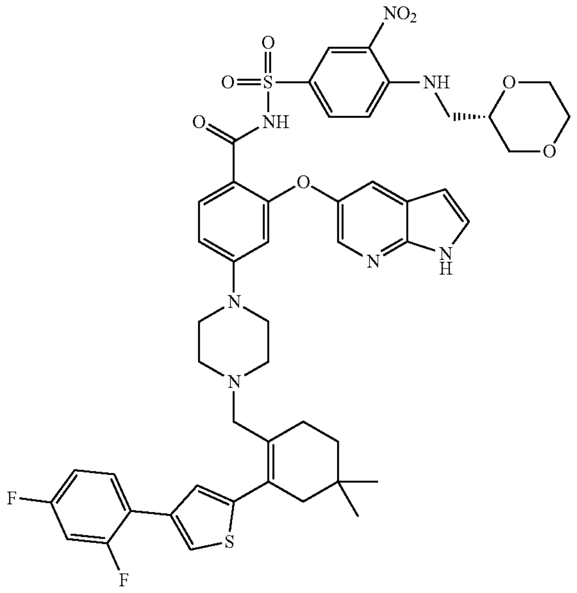 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3ccc(F)cc3F)cs2)C1]

Under Ar, to a solution of the crude 2-((1H-pyrrolo[2,3-b]pyridin-5-yl)oxy)-4-(4-((2-(4-(2,4-difluorophenyl)thiophen-2-yl)-4,4-dimethylcyclohex-1-en-1-yl)methyl)piperazin-1-yl)benzoic acid (Step C, 65 mg) in a mixed solvent of dry DCM (2.5 mL) and dry DMF (0.5 mL) was added N,N-dimethylpyridin-4-amine (30.3 mg, 0.25 mmol), EDCl (28.5 mg, 0.15 mmol) and (S)-4-(((1,4-dioxan-2-yl)methyl)amino)-3-nitrobenzenesulfonamide (31.5 mg, 0.10 mmol); then the reaction mixture was stirred at 40° C. for 12 h. After cooling down to room temperature, the resulting mixture was diluted with ethyl acetate and then washed with $H_2O$ and brine. The organic layer was dried over $Na_2SO_4$, and concentrated under reduced pressure to give a yellow oil, which was purified by C18 prep-HPLC column to afford the title compound (10.5 mg, 11% over 2 steps) as a yellow solid. $^1$H NMR (400 MHz, DMSO-$d_6$) δ 11.48 (s, 1H), 8.44-8.24 (m, 2H), 7.90 (d, J=2.4 Hz, 1H), 7.78-7.71 (m, 2H), 7.70 (s, 1H), 7.60-7.56 (m, 2H), 7.40-7.39 (m, 1H), 7.33-7.28 (m, 1H), 7.22 (s, 1H), 7.15-7.10 (m, 1H), 6.78-6.76 (m, 1H), 6.65 (dd, J=8.9, 2.0 Hz, 1H), 6.30-6.25 (m, 2H), 3.82-3.75 (m, 3H), 3.66-3.58 (m, 2H), 3.51-3.43 (m, 4H), 3.09-3.03 (m, 6H), 2.38-2.32 (m, 4H), 2.22 (t, J=6.2 Hz, 2H), 2.12-2.10 (m, 2H), 1.38 (t, J=6.2 Hz, 2H), 0.94 (s, 6H); MS: 954.3 (M+H$^+$).

Example 43: 2-((1H-pyrrolo[2,3-b]pyridin-5-yl)oxy)-4-(4-((2-(4-(2,4-difluorophenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

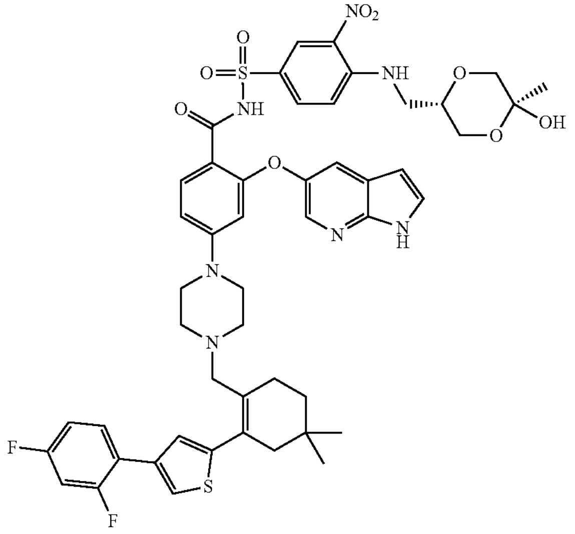 [SMILES: CC1(C)CCC(CN2CCN(c3ccc(C(=O)NS(=O)(=O)c4ccc(NC[C@H]5CO[C@](C)(O)CO5)c([N+](=O)[O-])c4)c(Oc4cnc5[nH]ccc5c4)c3)CC2)=C(c2cc(-c3ccc(F)cc3F)cs2)C1]

Essentially the same protocol of preparation of Example 42 was used to afford the example (9 mg) as a yellow solid. $^1$H NMR (400 MHz, DMSO-$d_6$) δ 11.66 (s, 1H), 8.54-8.53 (m, 2H), 8.03 (d, J=2.5 Hz, 1H), 7.78-7.71 (m, 2H), 7.70 (s, 1H), 7.56-7.44 (m, 3H), 7.33-7.28 (m, 1H), 7.22 (s, 1H), 7.12 (td, J=8.4, 2.3 Hz, 1H), 7.06-7.03 (m, 1H), 6.70 (dd, J=8.9, 1.7 Hz, 1H), 6.37-6.36 (m, 1H), 6.22 (d, J=1.5 Hz, 1H), 4.25 (s, 1H), 3.28-3.26 (m, 2H), 3.15-3.06 (m, 4H), 3.04-3.02 (m, 2H), 2.33-2.25 (m, 4H), 2.24-2.17 (m, 2H), 2.11-2.09 (m, 2H), 1.69-1.62 (m, 3H), 1.56-1.52 (m, 2H), 1.39-1.29 (m, 4H), 1.16-1.13 (m, 2H), 1.09 (s, 3H), 0.93 (s, 6H); MS: 980.4 (M+H$^+$).

Example 44: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(4-chloro-2-fluorophenyl)thiophen-2-yl)-4,4-dimethylcyclohex-1-en-1-yl)methyl)piperazin-1-yl)benzamide

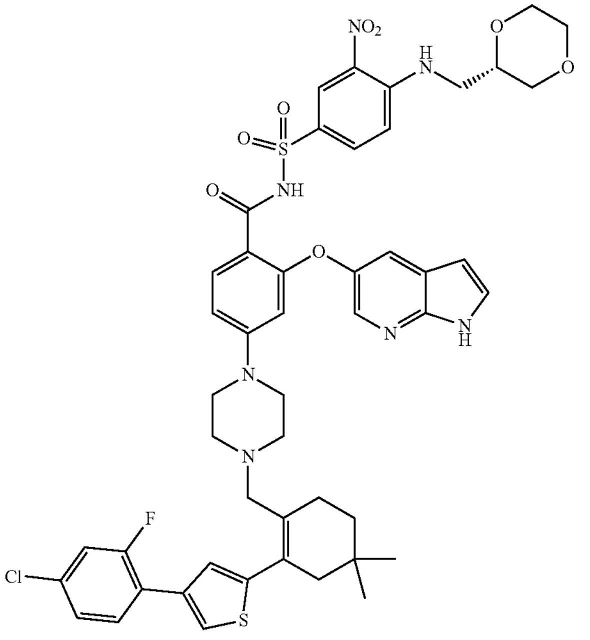 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3ccc(Cl)cc3F)cs2)C1]

Essentially the same protocol of preparation of Example 42 was used to afford the example (6 mg) as a yellow solid. $^{1}H$ NMR (400 MHz, DMSO-$d_6$) δ 11.67 (s, 1H), 8.61-8.52 (m, 2H), 8.05 (d, J=2.3 Hz, 1H), 7.85-7.78 (m, 2H), 7.78-7.73 (m, 1H), 7.55-7.48 (m, 4H), 7.35 (dd, J=8.4, 1.9 Hz, 1H), 7.28 (s, 1H), 7.08 (d, J=9.2 Hz, 1H), 6.73 (d, J=10.6 Hz, 1H), 6.39 (s, 1H), 6.26 (s, 1H), 3.87-3.77 (m, 3H), 3.72-3.60 (m, 2H), 3.56-3.48 (m, 2H), 3.46-3.41 (m, 2H), 3.17-3.01 (m, 6H), 2.38-2.20 (m, 6H), 2.18-2.09 (m, 2H), 1.45-1.38 (m, 2H), 0.96 (s, 6H); MS: 971.6 ($M+H^+$).

Example 45: 2-((1H-pyrrolo[2,3-b]pyridin-5-yl)oxy)-4-(4-((4,4-dimethyl-2-(4-(3,4,5-trifluorophenyl)thiophen-2-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

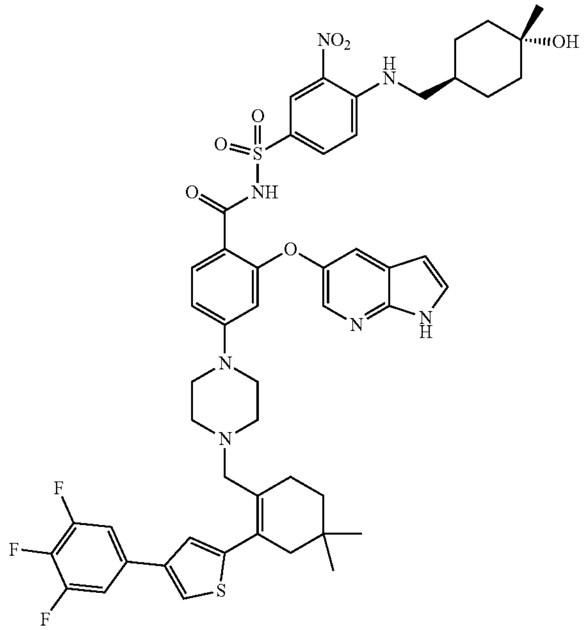 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3cc(F)c(F)c(F)c3)cs2)C1]

Essentially the same protocol of preparation of Example 42 was used to afford the example (5.5 mg) as a yellow solid. $^{1}H$ NMR (400 MHz, DMSO-$d_6$) δ 11.68 (s, 1H), 8.61-8.51 (m, 2H), 8.06 (d, J=2.6 Hz, 1H), 7.94 (d, J=1.0 Hz, 1H), 7.81 (dd, J=9.2, 2.1 Hz, 1H), 7.71 (dd, J=9.6, 6.8 Hz, 2H), 7.57-7.48 (m, 3H), 7.39 (d, J=1.2 Hz, 1H), 7.09 (d, J=9.4 Hz, 1H), 6.71 (dd, J=9.0, 2.1 Hz, 1H), 6.40 (dd, J=3.3, 1.9 Hz, 1H), 6.23 (d, J=2.0 Hz, 1H), 4.25 (s, 1H), 3.31-3.24 (m, 2H), 3.18-2.97 (m, 6H), 2.38-2.18 (m, 6H), 2.16-2.07 (m, 2H), 1.75-1.51 (m, 5H), 1.43-1.21 (m, 6H), 1.12 (s, 3H), 0.95 (s, 6H); MS: 999.2 ($M+H^+$).

Example 46: 2-((1H-pyrrolo[2,3-b]pyridin-5-yl)oxy)-4-(4-((4,4-dimethyl-2-(4-(2,3,4-trifluorophenyl)thiophen-2-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

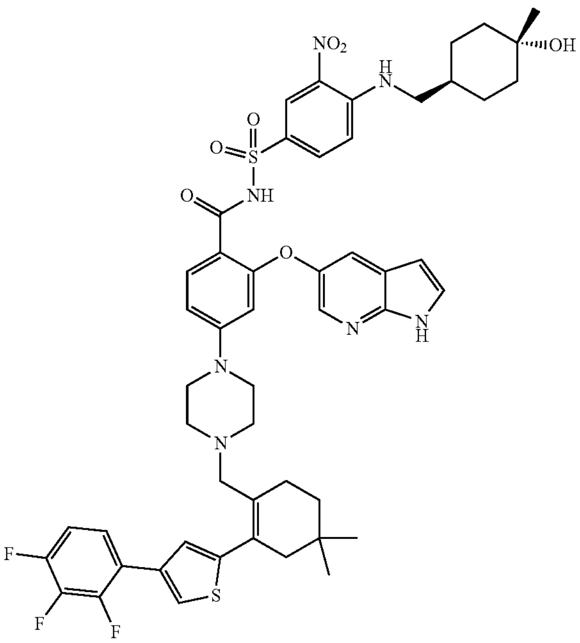 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(F)c(F)c3F)cs2)C1]

Essentially the same protocol of preparation of Example 42 was used to afford the example (13 mg) as a yellow solid. $^1H$ NMR (400 MHz, DMSO-$d_6$) δ 11.68 (s, 1H), 8.62-8.52 (m, 2H), 8.07 (d, J=2.4 Hz, 1H), 7.85-7.78 (m, 2H), 7.60-7.49 (m, 4H), 7.43-7.33 (m, 1H), 7.27 (s, 1H), 7.10 (d, J=9.2 Hz, 1H), 6.73 (d, J=7.5 Hz, 1H), 6.41 (s, 1H), 6.26 (s, 1H), 4.26 (s, 1H), 3.32-3.27 (m, 2H), 3.21-3.02 (m, 6H), 2.40-2.19 (m, 6H), 2.18-2.10 (m, 2H), 1.78-1.54 (m, 5H), 1.44-1.28 (m, 6H), 1.13 (s, 3H), 0.97 (s, 6H); MS: 999.3 (M+H$^+$).

Example 47: 2-((1H-pyrrolo[2,3-b]pyridin-5-yl)oxy)-4-(4-((4,4-dimethyl-2-(4-(2,4,6-trifluorophenyl)thiophen-2-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

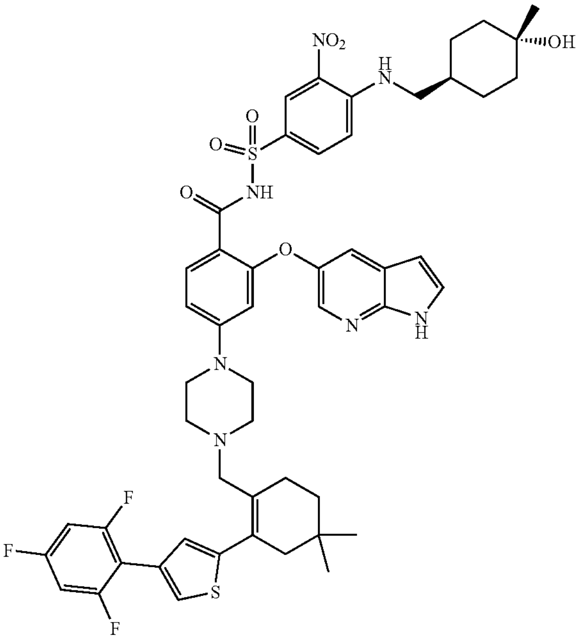 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(F)cc3F)cs2)C1]

Essentially the same protocol of preparation of Example 42 was used to afford the example (25 mg) as a yellow solid. $^1H$ NMR (400 MHz, DMSO-$d_6$) δ 11.70 (s, 1H), 8.58 (s, 2H), 8.07 (s, 1H), 7.83 (d, J=8.7 Hz, 1H), 7.68 (s, 1H), 7.61-7.47 (m, 3H), 7.29 (t, J=8.8 Hz, 2H), 7.15-7.04 (m, 2H), 6.73 (d, J=8.3 Hz, 1H), 6.41 (s, 1H), 6.25 (s, 1H), 4.26 (s, 1H), 3.31-3.23 (m, 2H), 3.19-2.99 (m, 6H), 2.41-2.18 (m, 6H), 2.16-2.08 (m, 2H), 1.75-1.53 (m, 5H), 1.43-1.25 (m, 6H), 1.13 (s, 3H), 0.96 (s, 6H); MS: 999.3 (M+H$^+$).

Example 48: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(4-(difluoromethyl)phenyl)thiophen-2-yl)-4,4-dimethylcyclohex-1-en-1-yl)methyl)piperazin-1-yl)benzamide

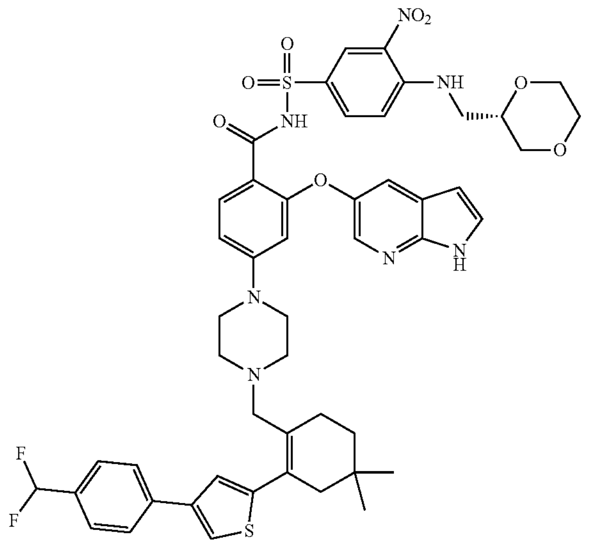 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3ccc(C(F)F)cc3)cs2)C1]

Essentially the same protocol of preparation of Example 42 was used to afford the example (18.8 mg) as a yellow solid. $^1$H NMR (400 MHz, DMSO-$d_6$) δ 11.63 (s, 1H), 8.63-8.49 (m, 2H), 8.02 (d, J=2.5 Hz, 1H), 7.86 (d, J=0.7 Hz, 1H), 7.82-7.78 (m, 3H), 7.58-7.56 (m, 2H), 7.51-7.47 (m, 3H), 7.36 (d, J=1.1 Hz, 1H), 7.18-6.87 (m, 2H), 6.70 (dd, J=8.9, 1.9 Hz, 1H), 6.37 (dd, J=3.2, 1.8 Hz, 1H), 6.23 (d, J=1.8 Hz, 1H), 3.82-3.75 (m, 3H), 3.67-3.59 (m, 2H), 3.53-3.44 (m, 2H), 3.42-3.34 (m, 2H), 3.15-3.09 (m, 4H), 3.05-3.03 (m, 2H), 2.33-2.27 (m, 4H), 2.25-2.18 (m, 2H), 2.13-2.11 (m, 2H), 1.38 (t, J=6.1 Hz, 2H), 0.94 (s, 6H); MS: 968.3 (M+H$^+$).

Example 49: 2-((1H-pyrrolo[2,3-b]pyridin-5-yl)oxy)-4-(4-((2-(4-(4-(difluoromethyl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

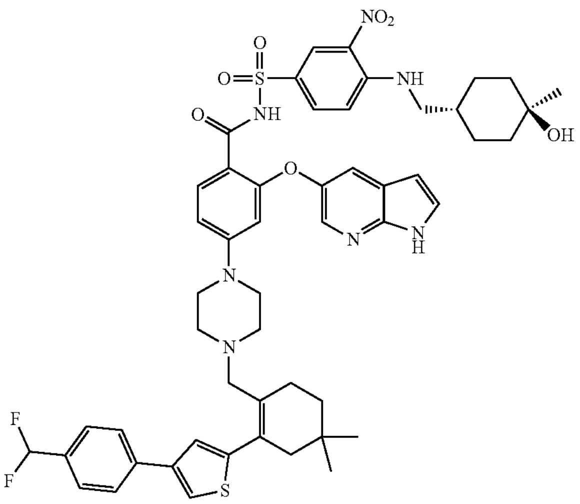 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(F)F)cc3)cs2)C1]

Essentially the same protocol of preparation of Example 42 was used to afford the example (9.3 mg) as a yellow solid. $^1$H NMR (400 MHz, DMSO-$d_6$) δ 11.64 (s, 1H), 8.59-8.49 (m, 2H), 8.03 (d, J=2.4 Hz, 1H), 7.87-7.85 (m, 1H), 7.82-7.76 (m, 3H), 7.58-7.56 (m, 2H), 7.54-7.44 (m, 3H), 7.37-7.35 (m, 1H), 7.16-6.88 (m, 2H), 6.69 (dd, J=8.9, 1.7 Hz, 1H), 6.37 (d, J=1.7 Hz, 1H), 6.23 (d, J=1.5 Hz, 1H), 4.22 (s, 1H), 3.28-3.26 (m, 2H), 3.15-3.07 (m, 4H), 3.04-3.02 (m, 2H), 2.32-2.27 (m, 4H), 2.22-2.18 (m, 2H), 2.12-2.10 (m, 2H), 1.70-1.62 (m, 3H), 1.56-1.53 (m, 2H), 1.40-1.30 (m, 4H), 1.17-1.14 (m, 2H), 1.10 (s, 3H), 0.94 (s, 6H); MS: 994.4 (M+H$^+$).

Example 50: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(3,4-difluorophenyl)thiophen-2-yl)-4,4-dimethylcyclohex-1-en-1-yl)methyl)piperazin-1-yl)benzamide

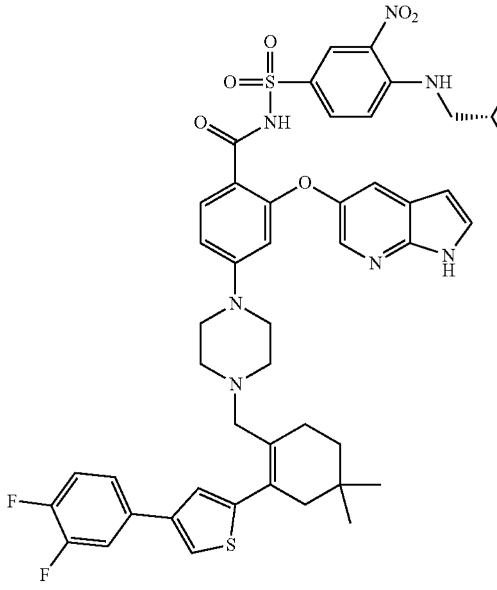

Essentially the same protocol of preparation of Example 42 was used to afford the example (23.6 mg) as a yellow solid. $^1$H NMR (400 MHz, DMSO-$d_6$) δ 11.63 (s, 1H), 8.56-8.54 (m, 2H), 8.02 (d, J=2.5 Hz, 1H), 7.86-7.71 (m, 3H), 7.57-7.38 (m, 5H), 7.32 (d, J=1.0 Hz, 1H), 7.07 (d, J=9.0 Hz, 1H), 6.69 (dd, J=9.0, 1.8 Hz, 1H), 6.37 (dd, J=3.2, 1.8 Hz, 1H), 6.22 (d, J=1.8 Hz, 1H), 3.80-3.75 (m, 3H), 3.67-3.58 (m, 2H), 3.55-3.45 (m, 4H), 3.15-3.07 (m, 4H), 3.04-3.02 (m, 2H), 2.33-2.29 (m, 4H), 2.24-2.17 (m, 2H), 2.11-2.09 (m, 2H), 1.37 (t, J=6.3 Hz, 2H), 0.93 (s, 6H); MS: 954.3 (M+H$^+$).

Example 51: 2-((1H-pyrrolo[2,3-b]pyridin-5-yl)oxy)-4-(4-((2-(4-(3,4-difluorophenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

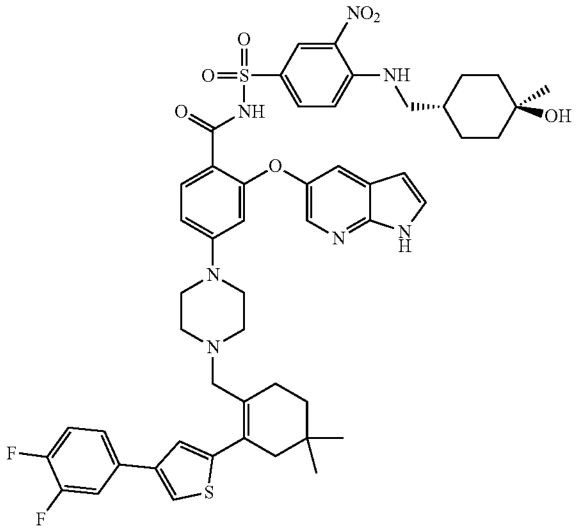 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(F)c(F)c3)cs2)C1]

Essentially the same protocol of preparation of Example 42 was used to afford the example (18 mg) as a yellow solid. $^1$H NMR (400 MHz, DMSO-$d_6$) δ 11.65 (s, 1H), 8.54-8.52 (m, 2H), 8.03-8.02 (m, 1H), 7.83-7.72 (m, 3H), 7.54-7.38 (m, 5H), 7.32-7.31 (m, 1H), 7.05 (d, J=9.4 Hz, 1H), 6.77-6.59 (m, 1H), 6.38-6.32 (m, 1H), 6.22-6.20 (m, 1H), 4.25 (s, 1H), 3.29-3.25 (m, 2H), 3.12-3.08 (m, 4H), 3.05-3.03 (m, 2H), 2.31-2.28 (m, 4H), 2.22-2.19 (m, 2H), 2.11-2.09 (m, 2H), 1.70-1.66 (m, 3H), 1.53-1.49 (m, 2H), 1.41-1.29 (m, 4H), 1.16-1.13 (m, 2H), 1.10 (s, 3H), 0.93 (s, 6H); MS: 980.4 (M+H).

Example 52: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(5-fluoropyridin-2-yl)thiophen-2-yl)-4,4-dimethylcyclohex-1-en-1-yl)methyl)piperazin-1-yl)benzamide

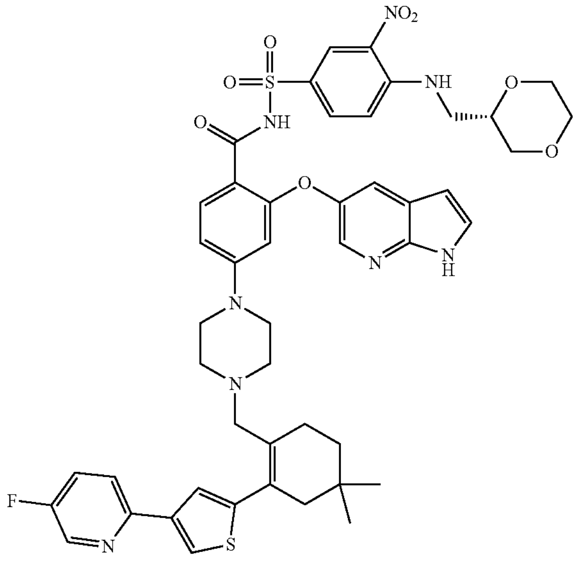 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3ccc(F)cn3)cs2)C1]

Essentially the same protocol of preparation of Example 42 was used to afford the example (1.5 mg) as a yellow solid. MS: 937.3 $(M+H^+)$.

Example 53: 2-((1H-pyrrolo[2,3-b]pyridin-5-yl)oxy)-4-(4-((4,4-dimethyl-2-(4-(2,4,5-trifluorophenyl)thiophen-2-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

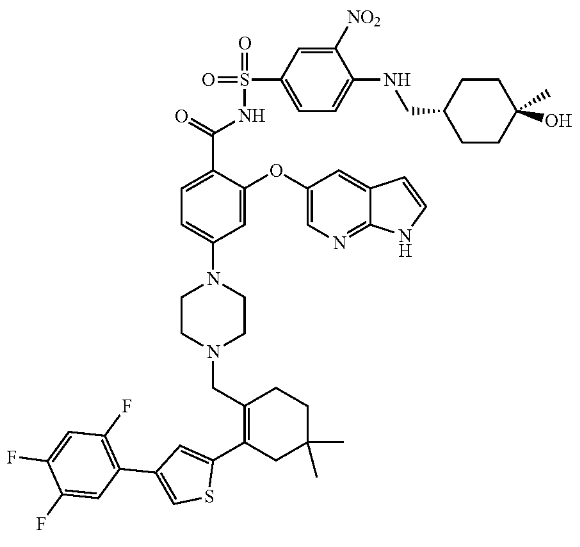 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3cc(F)c(F)cc3F)cs2)C1]

Essentially the same protocol of preparation of Example 42 was used to afford the example (12.6 mg) as a yellow solid. $^1H$ NMR (400 MHz, DMSO-$d_6$) δ 11.65 (s, 1H), 8.54-8.52 (m, 2H), 8.05-8.02 (m, 1H), 7.88-7.81 (m, 1H), 7.81-7.74 (m, 2H), 7.63-7.56 (m, 1H), 7.51-7.47 (m, 3H), 7.28-7.24 (m, 1H), 7.06-7.04 (m, 1H), 6.71-6.68 (m, 1H), 6.39-6.35 (m, 1H), 6.23-6.19 (m, 1H), 4.26 (s, 1H), 3.29-3.26 (m, 2H), 3.10-3.08 (m, 4H), 3.03-3.01 (m, 2H), 2.34-2.26 (m, 4H), 2.24-2.19 (m, 2H), 2.11-2.09 (m, 2H), 1.75-1.63 (m, 3H), 1.56-1.52 (m, 2H), 1.39-1.30 (m, 4H), 1.16-1.13 (m, 2H), 1.10 (s, 3H), 0.93 (s, 6H); MS: 998.4 $(M+H^+)$.

Example 54: 2-((1H-pyrrolo[2,3-b]pyridin-5-yl)oxy)-4-(4-((4,4-dimethyl-2-(4-(2,3,6-trifluorophenyl)thiophen-2-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

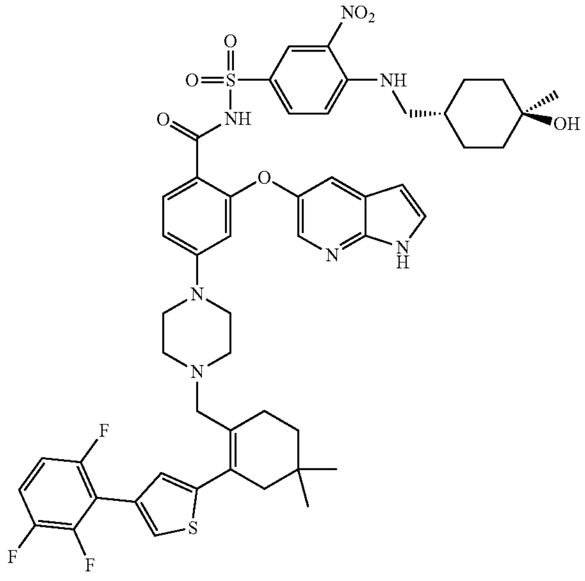 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)ccc(F)c3F)cs2)C1]

Step A: (5-Chlorothiophen-3-yl)boronic acid

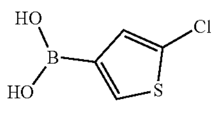

To a solution of thiophen-3-ylboronic acid (500 mg, 3.91 mmol) in $CH_3CN$ (10 mL) was added NCS (522 mg, 3.91 mmol) in one portion; then the reaction mixture was stirred at 60° C. for 12 h. After cooling down to room temperature and removal of volatiles, the residue was loaded onto a silica gel column and eluted with methanol and dichloromethane (with 0.1% AcOH) (1:50) to afford the title compound (270 mg, 43%) as a light yellow oil. $^1H$ NMR (400 MHz, $CD_3OD$) δ 7.65 (s, 1H), 7.15 (s, 1H).

Step B: 2-Chloro-4-(2,3,6-trifluorophenyl)thiophene

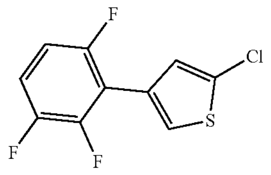 [SMILES: Fc1ccc(F)c(-c2csc(Cl)c2)c1F]

Under Ar, to a solution of (5-chlorothiophen-3-yl)boronic acid (Step A, 270 mg, 1.66 mmol) in a mixed solvent of DME (9 mL) and 2 M $Na_2CO_3$ (3 mL) was added 2-bromo-1,3,4-trifluorobenzene (421 mg, 1.99 mmol) and $PdCl_2$(dppf)·$CH_2Cl_2$ (13.06 mg, 0.166 mmol); then the reaction mixture was stirred at 100° C. for 0.5 h. After cooling down to room temperature, the resulting mixture was diluted with ethyl acetate and then washed with $H_2O$ and brine. The organic layer was dried over $Na_2SO_4$, and concentrated under reduced pressure to give a yellow oil, which was loaded onto a silica gel column and eluted with ethyl acetate and hexane (1:10) to afford the title compound (270 mg, 65%) as a yellow oil. MS: 249.1 (M+H$^+$).

Step C: 2-((1H-pyrrolo[2,3-b]pyridin-5-yl)oxy)-4-(4-((4,4-dimethyl-2-(4-(2,3,6-trifluorophenyl)thiophen-2-yl)cyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 54)

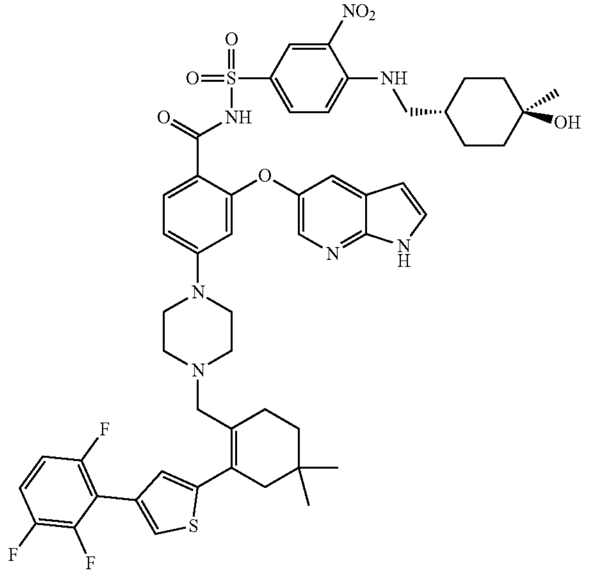 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)ccc(F)c3F)cs2)C1]

Starting from Step B, essentially the same protocol of preparation of Example 42 was used to afford the example (12 mg) as a yellow solid. $^1$H NMR (400 MHz, DMSO-$d_6$) δ 11.64 (s, 1H), 8.54-8.53 (m, 2H), 8.03-8.02 (m, 1H), 7.83-7.71 (m, 2H), 7.51-7.40 (m, 4H), 7.24-7.19 (m, 1H), 7.11-7.09 (m, 1H), 7.06-7.04 (m, 1H), 6.99-6.72 (m, 1H), 6.44-6.32 (m, 1H), 6.24-6.20 (m, 1H), 4.25 (s, 1H), 3.28-3.27 (m, 2H), 3.13-3.06 (m, 4H), 3.04-3.02 (m, 2H), 2.35-2.25 (m, 4H), 2.25-2.18 (m, 2H), 2.13-2.11 (m, 2H), 1.73-1.63 (m, 3H), 1.56-1.53 (m, 2H), 1.41-1.28 (m, 4H), 1.17-1.14 (m, 2H), 1.10 (s, 3H), 0.93 (s, 6H); MS: 998.3 (M+H$^+$).

Example 55: 2-((1H-pyrrolo[2,3-b]pyridin-5-yl)oxy)-4-(4-((2-(4-(3-cyano-5-fluorophenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

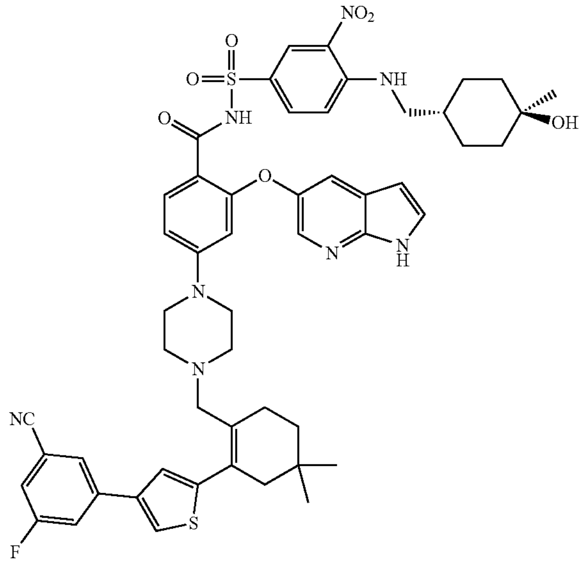 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3cc(F)cc(C#N)c3)cs2)C1]

Step A: 3-(5-chlorothiophen-3-yl)-5-fluorobenzonitrile

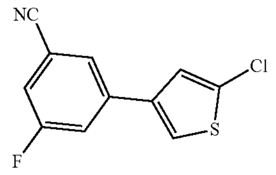 [SMILES: N#Cc1cc(F)cc(-c2csc(Cl)c2)c1]

Under Ar, to a solution of 4-bromo-2-chlorothiophene (300 mg, 1.52 mmol) in a mixed solvent of DME (9 mL) and 2 M $Na_2CO_3$ (3 mL) was added (3-cyano-5-fluorophenyl)boronic acid (376 mg, 2.28 mmol) and $PdCl_2$(dppf)·$CH_2Cl_2$ (124 mg, 0.15 mmol); then the reaction mixture was stirred at 100° C. for 0.5 h. After cooling down to room temperature, the resulting mixture was diluted with ethyl acetate and then washed with $H_2O$ and brine. The organic layer was dried over $Na_2SO_4$, and concentrated under reduced pressure to give a yellow oil, which was loaded onto a silica gel column and eluted with ethyl acetate and hexane (1:10) to afford the title compound (330 mg, 91%) as a white solid. $^1$H NMR (400 MHz, $CD_3OD$) δ 7.84 (t, J=1.3 Hz, 1H), 7.74-7.69 (m, 2H), 7.47-7.42 (m, 2H).

Step B: tert-butyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate

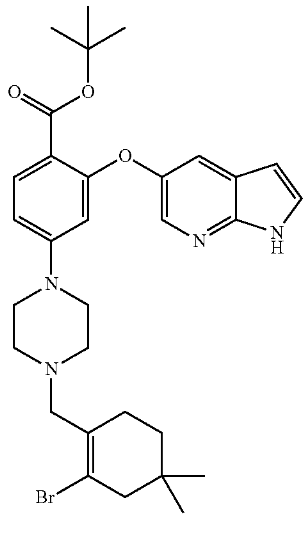 [SMILES: CC1(C)CCC(CN2CCN(c3ccc(C(=O)OC(C)(C)C)c(Oc4cnc5[nH]ccc5c4)c3)CC2)=C(Br)C1]

Under Ar, to a solution of 2-((1H-pyrrolo[2,3-b]pyridin-5-yl)oxy)-4-(4-((2-bromo-4,4-dimethylcyclohex-1-en-1-yl)methyl)piperazin-1-yl)benzoic acid (400 mg, 0.74 mmol) in dry THF (6 mL) was added tert-butyl pivalimidate (0.12 g, 0.74 mmol) and $BF_3 \cdot OEt_2$ (0.85 g, 5.93 mmol); then the reaction mixture was stirred at room temperature for 12 h. The resulting mixture was quenched by sat. $NaHCO_3$, diluted with ethyl acetate and then washed with $H_2O$ and brine. The organic layer was dried over $Na_2SO_4$, and concentrated under reduced pressure to give a yellow oil, which was loaded onto a silica gel column and eluted with ethyl acetate and hexane (1:1) to afford the title compound (310 mg, 70%) as a white solid. MS: 595.2 ($M+H^+$).

Step C: tert-butyl 2-((1H-pyrrolo[2,3-b]pyridin-5-yl)oxy)-4-(4-((4,4-dimethyl-2-(4,4,5,5-tetramethyl-1,3,2-dioxaborolan-2-yl)cyclohex-1-en-1-yl)methyl)piperazin-1-yl)benzoate

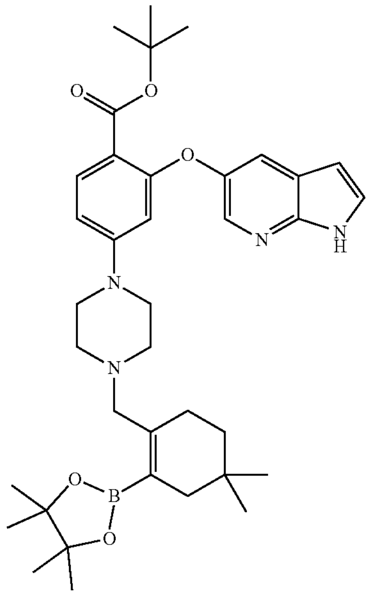 [SMILES: CC1(C)CCC(CN2CCN(c3ccc(C(=O)OC(C)(C)C)c(Oc4cnc5[nH]ccc5c4)c3)CC2)=C(B2OC(C)(C)C(C)(C)O2)C1]

Under Ar, to a solution of tert-butyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Step B, 0.31 g, 0.52 mmol) in 1,4-dioxane (15 mL) was added 4,4,4',4',5,5,5',5'-octamethyl-2,2'-bi(1,3,2-dioxaborolane) (200 mg, 0.78 mmol), potassium acetate (150 mg, 1.56 mmol) and $PdCl_2$(dppf) (38 mg, 0.052 mmol); then the reaction mixture was stirred at 100° C. for 12 h. After cooling down to room temperature, the resulting mixture was diluted with ethyl acetate and then washed with $H_2O$ and brine. The organic layer was dried over $Na_2SO_4$, and concentrated under reduced pressure to give a yellow oil, which was loaded onto a silica gel column and eluted with DCM and MeOH (40:1) to afford the title compound (320 mg, 96%) as a yellow oil. MS: 643.2 ($M+H^+$)

Step D: tert-butyl 2-((1H-pyrrolo[2,3-b]pyridin-5-yl)oxy)-4-(4-((2-(4-(3-cyano-5-fluorophenyl)thiophen-2-yl)-4,4-dimethylcyclohex-1-en-1-yl)methyl)piperazin-1-yl)benzoate

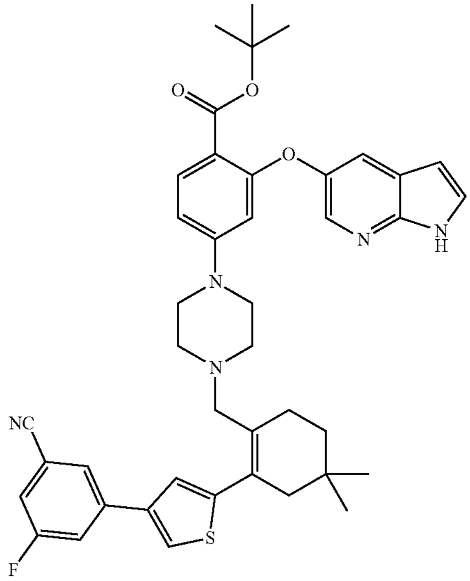 [SMILES: CC1(C)CCC(CN2CCN(c3ccc(C(=O)OC(C)(C)C)c(Oc4cnc5[nH]ccc5c4)c3)CC2)=C(c2cc(-c3cc(F)cc(C#N)c3)cs2)C1]

Under Ar, to a solution of tert-butyl 2-((1H-pyrrolo[2,3-b]pyridin-5-yl)oxy)-4-(4-((4,4-dimethyl-2-(4,4,5,5-tetramethyl-1,3,2-dioxaborolan-2-yl)cyclohex-1-en-1-yl)methyl)piperazin-1-yl)benzoate (Step C, 270 mg, 0.42 mmol) in a mixed solvent of DME (12 mL) and $H_2O$ (3 mL) was added 3-(5-chlorothiophen-3-yl)-5-fluorobenzonitrile (Step A, 100 mg, 0.42 mmol), $Na_2CO_3$ (134 mg, 0.13 mmol) and Pd(dppf)$Cl_2$ (34.3 mg, 0.042 mmol); then the reaction mixture was stirred at 120° C. for 45 min. After cooling down to room temperature, the resulting mixture was diluted with ethyl acetate and then washed with $H_2O$ and brine. The organic layer was dried over $Na_2SO_4$, and concentrated under reduced pressure to give a yellow oil, which was loaded onto a silica gel column and eluted with DCM and MeOH (30:1) to afford the title compound (100 mg, 33%) as a yellow oil. MS: 718.3 (M+$H^+$).

Step E: 2-((1H-pyrrolo[2,3-b]pyridin-5-yl)oxy)-4-(4-((2-(4-(3-cyano-5-fluorophenyl)thiophen-2-yl)-4,4-dimethylcyclohex-1-en-1-yl)methyl)piperazin-1-yl)benzoic acid

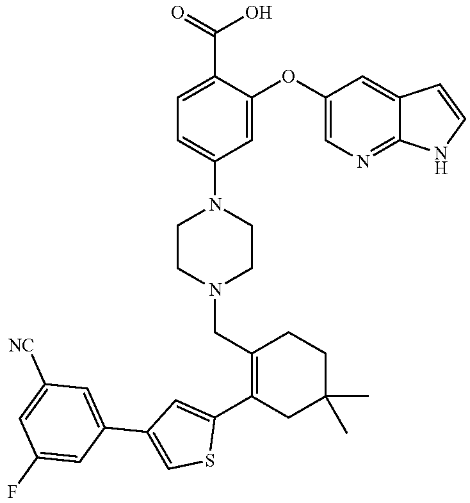 [SMILES: CC1(C)CCC(CN2CCN(c3ccc(C(=O)O)c(Oc4cnc5[nH]ccc5c4)c3)CC2)=C(c2cc(-c3cc(F)cc(C#N)c3)cs2)C1]

Under Ar, to a solution of tert-butyl 2-((1H-pyrrolo[2,3-b]pyridin-5-yl)oxy)-4-(4-((2-(4-(3-cyano-5-fluorophenyl)thiophen-2-yl)-4,4-dimethylcyclohex-1-en-1-yl)methyl)piperazin-1-yl)benzoate (Step D, 100 mg, 0.14 mmol) was dissolved into DCM (5 mL) was added TFA (0.5 mL); then the reaction mixture was stirred at room temperature for 2 h. The resulting mixture was diluted with dichloromethane and then washed with $H_2O$ and brine. The organic layer was dried over $Na_2SO_4$, and concentrated under reduced pressure to give the crude title compound (60 mg) as a yellow oil, which was directly used for the next step without purification. MS: 662.3 (M+$H^+$).

Step F: 2-((1H-pyrrolo[2,3-b]pyridin-5-yl)oxy)-4-(4-((2-(4-(3-cyano-5-fluorophenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 55)

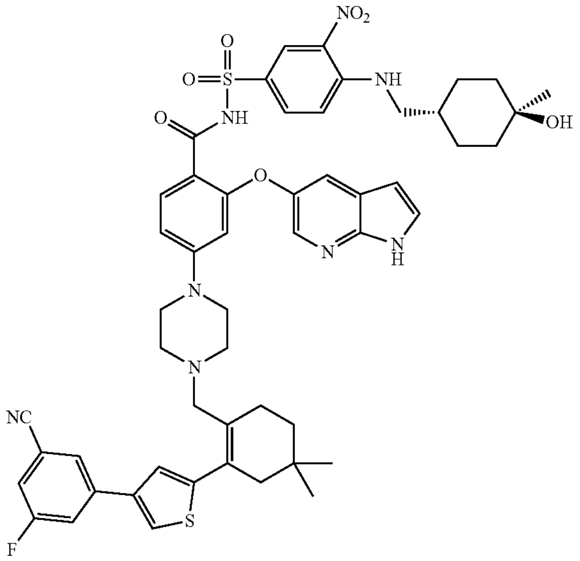 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3cc(F)cc(C#N)c3)cs2)C1]

Under Ar, to a solution of the crude 2-((1H-pyrrolo[2,3-b]pyridin-5-yl)oxy)-4-(4-((2-(4-(3-cyano-5-fluorophenyl)thiophen-2-yl)-4,4-dimethylcyclohex-1-en-1-yl)methyl)piperazin-1-yl)benzoic acid (Step E, 60 mg) in a mixed solvent of DCM (5 mL) and DMF (1 mL) was added 3-(((ethylimino)methylene)amino)-N,N-dimethylpropan-1-amine hydrochloride (26.1 mg, 0.14 mmol), N,N-dimethylpyridin-4-amine (22.5 mg, 0.18 mmol) and 4-((((1r,4r)-4-hydroxy-4-methylcyclohexyl)methyl)amino)-3-nitrobenzenesulfonamide (31.1 mg, 0.091 mmol); then the reaction mixture was stirred at 35° C. for 12 h. After cooling down to room temperature, the resulting mixture was diluted with ethyl acetate and then washed with $H_2O$ and brine. The organic layer was dried over $Na_2SO_4$, and concentrated under reduced pressure to give a yellow oil, which was purified by C18 prep-HPLC column to afford the title compound (19.9 mg, 22% over 2 steps) as a yellow solid. $^1H$ NMR (400 MHz, DMSO-$d_6$) δ 11.64 (s, 1H), 8.53-8.50 (m, 2H), 8.12-8.09 (m, 1H), 8.07-8.05 (m, 1H), 8.03-8.01 (m, 1H), 7.98-7.96 (m, 1H), 7.78-7.68 (m, 2H), 7.52-7.47 (m, 4H), 7.04-7.02 (m, 1H), 6.72-6.66 (m, 1H), 6.39-6.34 (m, 1H), 6.24-6.20 (m, 1H), 4.22 (s, 1H), 3.28-3.25 (m, 2H), 3.17-3.13 (m, 4H), 3.04-3.02 (m, 2H), 2.33-2.26 (m, 4H), 2.25-2.18 (m, 2H), 2.12-2.10 (m, 2H), 1.71-1.67 (m, 3H), 1.56-1.53 (m, 2H), 1.39-1.29 (m, 4H), 1.16-1.13 (m, 2H), 1.10 (s, 3H), 0.94 (s, 6H); MS: 987.4 (M+H$^+$).

Example 56: 2-((1H-pyrrolo[2,3-b]pyridin-5-yl)oxy)-4-(4-((2-(4-(4-(2-cyanopropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

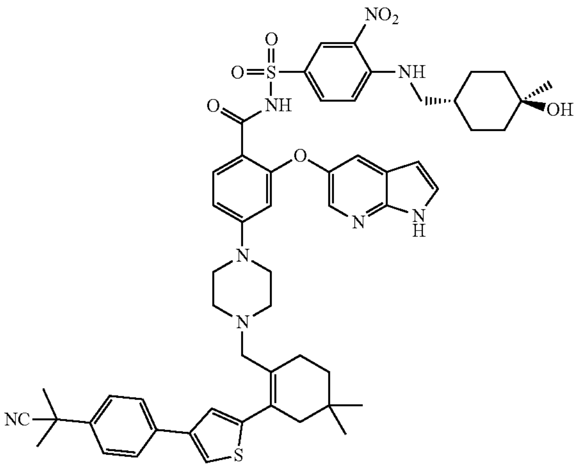 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(C)(C)C#N)cc3)cs2)C1]

Step A: 2-(4-(5-Chlorothiophen-3-yl)phenyl)-2-methylpropanenitrile

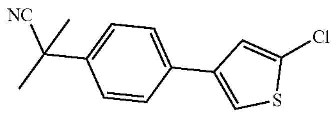 [SMILES: CC(C)(C#N)c1ccc(-c2csc(Cl)c2)cc1]

Under Ar, to a solution of 2-(4-bromophenyl)-2-methylpropanenitrile (500 mg, 2.23 mmol) in a mixed solvent of DCE (9 mL) and 2M $Na_2CO_3$ (3 mL) was added (5-chlorothiophen-3-yl)boronic acid (Step A of Example 54, 540 mg, 3.35 mmol) and $PdCl_2(dppf)\cdot CH_2Cl_2$ (1.82 g, 2.23 mmol); then the reaction mixture was stirred at 100° C. for 0.5 h with microwave assistance. After cooling down to room temperature, the resulting mixture was diluted with ethyl acetate and then washed with $H_2O$ and brine. The organic layer was dried over $Na_2SO_4$, and concentrated under reduced pressure to give a yellow oil, which was loaded onto a silica gel column and eluted with ethyl acetate and hexane (1:10) to afford the title compound (130 mg, 22%) as a yellow solid. MS: 262.1 (M+H$^+$).

Step B: 2-((1H-pyrrolo[2,3-b]pyridin-5-yl)oxy)-4-(4-((2-(4-(4-(2-cyanopropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 56)

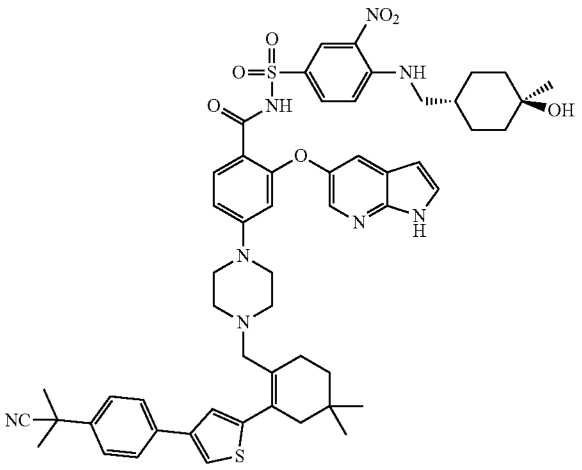 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(C)(C)C#N)cc3)cs2)C1]

Starting from Step A, essentially the same protocol of preparation of Example 55 was used to afford the example (18 mg) as a yellow solid. $^1H$ NMR (400 MHz, DMSO-$d_6$) δ 11.65 (s, 1H), 8.55-8.51 (m, 2H), 8.03 (d, J=2.6 Hz, 1H), 7.79-7.77 (m, 2H), 7.72-7.70 (m, 2H), 7.52-7.48 (m, 5H), 7.30 (d, J=1.3 Hz, 1H), 7.06 (d, J=9.2 Hz, 1H), 6.70 (dd, J=9.0, 2.1 Hz, 1H), 6.38-6.37 (m, 1H), 6.22 (d, J=2.0 Hz, 1H), 4.22 (s, 1H), 3.28-3.27 (m, 2H), 3.13-3.09 (m, 4H), 3.04-3.02 (m, 2H), 2.33-2.31 (m, 4H), 2.21-2.19 (m, 2H), 2.13-2.11 (m, 2H), 1.69 (s, 6H), 1.67-1.63 (m, 3H), 1.56-1.53 (m, 2H), 1.41-1.28 (m, 4H), 1.17-1.14 (m, 2H), 1.10 (s, 3H), 0.94 (s, 6H); MS: 1011.4 (M+H$^+$).

Example 57: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(4,6-difluoro-1H-indol-7-yl)thiophen-2-yl)-4,4-dimethylcyclohex-1-en-1-yl)methyl)piperazin-1-yl)benzamide

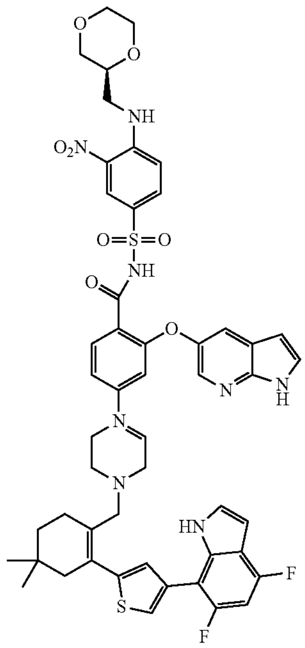

Step A: 4,6-difluoro-7-(thiophen-3-yl)-1H-indole

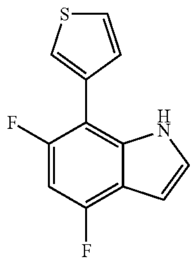 [SMILES: Fc1cc(F)c2cc[nH]c2c1-c1ccsc1]

In a flame-dried over 100 mL round-bottomed flask, 7-bromo-4,6-difluoro-1H-indole (100 mg, 0.431 mmol), thiophen-3-ylboronic acid (83 mg, 0.646 mmol), $Na_2CO_3$ (228 mg, 2.155 mmol) were dissolved into a mixed solvent of 1,4-dioxane (5 mL) and water (1 mL) under argon to give a solution; $PdCl_2(dppf)\cdot CH_2Cl_2$ (35.2 mg, 0.043 mmol) was added to the reaction mixture at room temperature; the reaction mixture was stirred at 100° C. for 12 h. Sat. $NaHCO_3$ (10 mL) was added to the reaction mixture followed by extraction with dichloromethane (10 mL×2). The combined organic layers were dried over $Na_2SO_4$, and concentrated under reduced pressure to give a yellow oil, which was loaded onto a silica gel column and eluted with methanol and dichloromethane (1:30) to afford the title compound (75 mg, 74%) as an off-white solid. $^1H$ NMR (400 MHz, DMSO-$d_6$) δ 11.30 (s, 1H), 7.81-7.77 (m, 1H), 7.77-7.73 (m, 1H), 7.37 (d, J=4.9 Hz, 1H), 7.34 (t, J=2.8 Hz, 1H), 6.94 (t, J=10.7 Hz, 1H), 6.57-6.54 (m, 1H); MS: 236.1 (M+H$^+$).

Step B: 4,6-difluoro-7-(thiophen-3-yl)-1-((2-(trimethylsilyl)ethoxy)methyl)-1H-indole

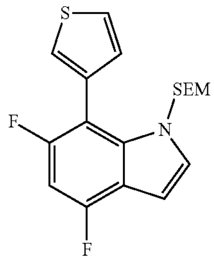 [SMILES: C[Si](C)(C)CCOCn1ccc2c(F)cc(F)c(-c3ccsc3)c21]

In a flame-dried over 100 mL round-bottomed flask, 4,6-difluoro-7-(thiophen-3-yl)-1H-indole (Step A, 500 mg, 2.125 mmol) and DIEA (824 mg, 6.38 mmol) were dissolved into dry $CH_2Cl_2$ (5 mL) under argon to give a solution; (2-(Chlorometho-xy)ethyl)trimethylsilane (709 mg, 4.25 mmol) was added at room temperature and the reaction mixture was stirred at 22° C. for 12 h. Sat. $NaHCO_3$ (10 mL) was added to the reaction mixture followed by extraction with dichloromethane (10 mL×2). The combined organic layers were dried over $Na_2SO_4$, and concentrated under reduced pressure to give a yellow oil, which was loaded onto a silica gel column and eluted with ethyl acetate and hexane (1:5) to afford the title compound (600 mg, 77%) as an off-white solid. $^1$H NMR (400 MHz, $CDCl_3$) δ 7.44 (dd, J=4.9, 3.0 Hz, 1H), 7.37 (dd, J=3.0, 1.2 Hz, 1H), 7.16 (dd, J=4.9, 1.2 Hz, 1H), 7.09 (d, J=3.4 Hz, 1H), 6.71 (t, J=9.8 Hz, 1H), 6.62 (d, J=3.4 Hz, 1H), 4.88 (s, 2H), 3.15-3.06 (m, 2H), 0.79-0.72 (m, 2H), 0.02 (s, 9H).

Step C: (4-(4,6-difluoro-1-((2-(trimethylsilyl)ethoxy)methyl)-1H-indol-7-yl)thiophen-2-yl)boronic acid

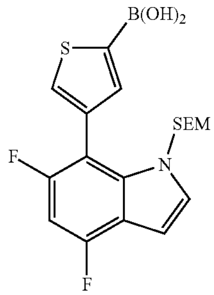 [SMILES: C[Si](C)(C)CCOCn1ccc2c(F)cc(F)c(-c3csc(B(O)O)c3)c21]

In a flame-dried over 100 mL round-bottomed flask, 4,6-difluoro-7-(thiophen-3-yl)-1-((2-(trimethylsilyl)ethoxy)methyl)-1H-indole (Step B, 300 mg, 0.821 mmol) was dissolved into dry THF (10 mL) under argon at −78° C. to give a solution. LDA (820 mL, 2 M in THF, 1.64 mmol) was added to the reaction mixture at −78° C., then the mixture was stirred at −78° C. for 1 h; triisopropyl borate (309 mg, 1.64 mmol) was followed dropwise; the reaction mixture was stirred at −78° C. for 0.5 h, allowed to warm up to room temperature gradually and stirred for 1 h. MeOH (10 mL) was added to quench the reaction, the resulting mixture was partitioned with aq. $NH_4Cl$ and EA, and the aqueous layer was extracted with EA twice. The combined organic layers were dried over $Na_2SO_4$, and concentrated under reduced pressure to give a yellow oil, which was loaded onto a silica gel column and eluted with methanol and dichloromethane (1:30) to afford the title compound (336 mg, quantitatively) as an off-white solid.

Step D: Methyl 2-((1H-pyrrolo[2,3-b]pyridin-5-yl)oxy)-4-(4-((2-(4-(4,6-difluoro-1-((2-(trimethylsilyl)ethoxy)methyl)-1H-indol-7-yl)thiophen-2-yl)-4,4-dimethylcyclohex-1-en-1-yl)methyl)piperazin-1-yl)benzoate

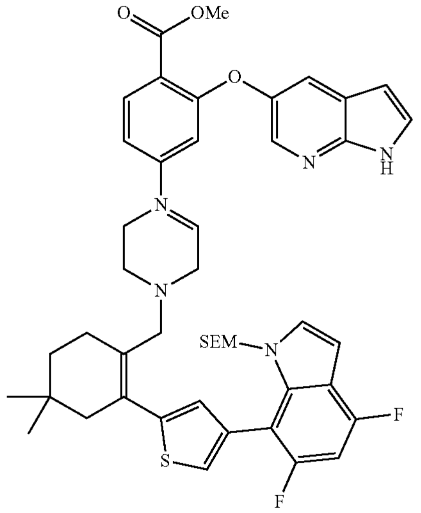

In a flame-dried over 100 mL round-bottomed flask, methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 150 mg, 0.271 mmol), (4-(4,6-difluoro-1-((2-(trimethylsilyl)-ethoxy)methyl)-1H-indol-7-yl)thiophen-2-yl)boronic acid (Step C, 333 mg, 0.813 mmol) and $Na_2CO_3$ (144 mg, 1.355 mmol) were dissolved into a mixed solvent of 1,4-dioxane (7.5 mL) and water (1.5 mL) under argon to give a solution; $PdCl_2(dppf)\cdot CH_2Cl_2$ (44.3 mg, 0.054 mmol) was added at room temperature and the reaction mixture was stirred at 100° C. for 12 h. After cooling down to room temperature, sat. $NaHCO_3$ (10 mL) was added to the reaction mixture followed by extraction with dichloromethane (10 mL×2). The combined organic layers were dried over $Na_2SO_4$, and concentrated under reduced pressure to give a yellow oil, which was loaded onto a silica gel column and eluted with MeOH and DCM (1:50) to afford the title compound (100 mg, 44%) as an off-white solid. MS: 839.1 (M+H$^+$).

Step E: 2-((1H-pyrrolo[2,3-b]pyridin-5-yl)oxy)-4-(4-((2-(4-(4,6-difluoro-1-((2-(trimethylsilyl)ethoxy) methyl)-1H-indol-7-yl)thiophen-2-yl)-4,4-dimethyl-cyclohex-1-en-1-yl)methyl)piperazin-1-yl)benzoic acid

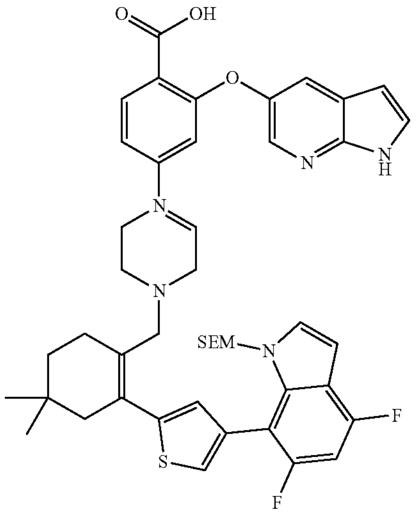

In a flame-dried over 100 mL round-bottomed flask, methyl 2-((1H-pyrrolo[2,3-b]pyridin-5-yl)oxy)-4-(4-((2-(4-(4,6-difluoro-1-((2-(trimethylsilyl)ethoxy)methyl)-1H-indol-7-yl)thiophen-2-yl)-4,4-dimethylcyclohex-1-en-1-yl) methyl)piperazin-1-yl)benzoate (Step D, 55 mg, 0.066 mmol) was dissolved into a mixed solvent of water (2 mL), THF (4 mL) and MeOH (2 mL) under argon to give a solution; sodium hydroxide (26.2 mg, 0.656 mmol) was added at room temperature and the reaction mixture was stirred at 40° C. for 16 h. 1 N HCl (1 mL) was added to adjust pH 4-5 and the resulting mixture was concentrated under reduced pressure. The residue as the crude title compound was directly used for the next step without purification. MS: 825.1 (M+H+).

Step F: (S)—N-((4-(((1,4-dioxan-2-yl)methyl) amino)-3-nitrophenyl)sulfonyl)-2-((1H-pyrrolo[2,3-b]pyridin-5-yl)oxy)-4-(4-((2-(4-(4,6-difluoro-1-((2-(trimethylsilyl)ethoxy)-methyl)-1H-indol-7-yl) thiophen-2-yl)-4,4-dimethylcyclohex-1-en-1-yl) methyl)-piperazin-1-yl)benzamide

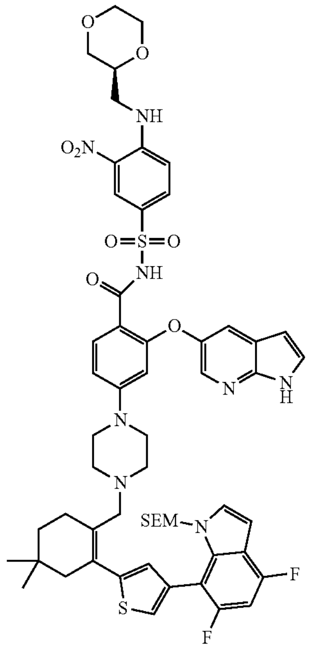 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3c(F)cc(F)c4ccn(COCC[Si](C)(C)C)c34)cs2)C1]

In a flame-dried over 100 mL round-bottomed flask, (S)-4-(((1,4-dioxan-2-yl)methyl)amino)-3-nitrobenzene-sulfonamide (32.3 mg, 0.1 mmol), the crude 2-((1H-pyrrolo [2,3-b]pyridin-5-yl)oxy)-4-(4-((2-(4-(4,6-difluoro-1-((2-(trimethylsilyl)etho-xy)methyl)-1H-indol-7-yl)thiophen-2-yl)-4,4-dimethylcyclohex-1-en-1-yl)methyl)-piperazin-1-yl)benzoic acid (Step E, 42 mg), N,N-dimethylpyridin-4-amine (18.7 mg, 0.15 mmol) were dissolved into dry $CH_2Cl_2$ (5 mL) under argon to give a solution; EDCl (19.5 mg, 0.1 mmol) was added at room temperature and the reaction mixture was stirred at 40° C. for 12 h. Sat. $NaHCO_3$ (10 mL) was added to the reaction mixture followed by extraction with dichloromethane (10 mL×2). The combined organic layers were dried over $Na_2SO_4$, and concentrated under reduced pressure to give a yellow oil, which was loaded onto a silica gel column and eluted with methanol and dichloromethane (1:40) to afford the title compound (12 mg, 21% over 2 steps) as a yellow solid. MS: 1124.0 (M+H+).

Step G: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(4,6-difluoro-1H-indol-7-yl)thiophen-2-yl)-4,4-dimethylcyclohex-1-en-1-yl)methyl)piperazin-1-yl)benzamide (Example 57)

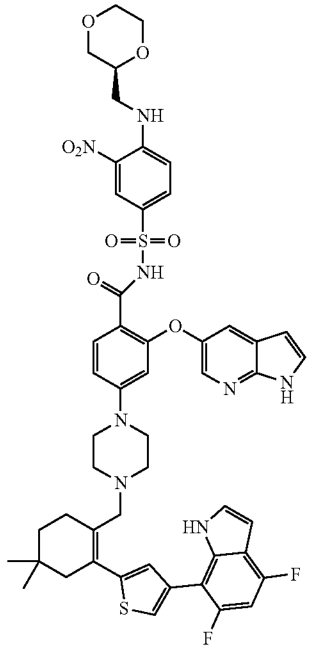 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3c(F)cc(F)c4cc[nH]c34)cs2)C1]

In a flame-dried over 100 mL round-bottomed flask, (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(4,6-difluoro-1-((2-(trimethylsilyl)ethoxy)methyl)-1H-indol-7-yl)thiophen-2-yl)-4,4-dimethylcyclohex-1-en-1-yl)methyl)piperazin-1-yl)benzamide (Step F, 12 mg, 10.68 μmol) was dissolved into dry $CH_2Cl_2$ (1.5 mL) under argon to give a solution; TFA (0.5 mL) was added and the reaction mixture was stirred at 22° C. for 1 h. After removal of volatiles, the residue was purified by C18 prep-HPLC column to afford the title compound (2 mg, 19%) as a yellow solid. $^1H$ NMR (400 MHz, DMSO-$d_6$) δ 11.48 (s, 1H), 11.30 (brs, 1H), 8.34 (d, J=2.0 Hz, 1H), 8.29 (t, J=5.3 Hz, 1H), 7.89 (d, J=2.6 Hz, 1H), 7.67 (s, 1H), 7.63-7.52 (m, 2H), 7.39 (s, 1H), 7.20 (d, J=2.6 Hz, 2H), 7.14 (s, 1H), 6.91 (t, J=10.7 Hz, 1H), 6.74 (d, J=9.1 Hz, 1H), 6.70-6.66 (m, 1H), 6.64 (d, J=8.7 Hz, 1H), 6.54 (d, J=3.2 Hz, 1H), 6.29 (d, J=1.9 Hz, 1H), 6.26 (d, J=3.3 Hz, 1H), 3.82-3.72 (m, 3H), 3.68-3.57 (m, 2H), 3.54-3.46 (m, 2H), 3.08 (s, 2H), 3.07-2.98 (m, 4H), 2.37-2.30 (m, 4H), 2.28-2.20 (m, 2H), 2.16 (s, 2H), 2.05-1.91 (m, 2H), 1.51-1.36 (m, 2H), 0.95 (s, 6H); MS: 994.0 (M+$H^+$).

Example 58: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(2-(dimethylamino)phenyl)thiophen-2-yl)-4,4-dimethylcyclohex-1-en-1-yl)methyl)piperazin-1-yl)benzamide

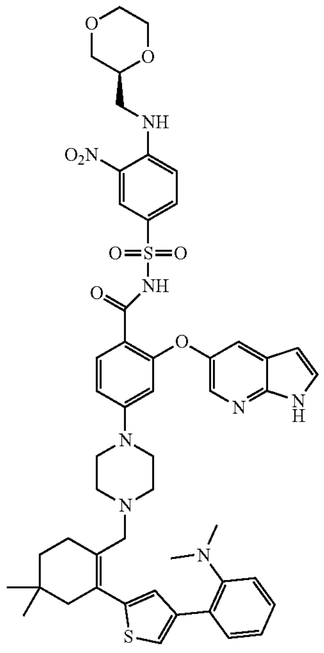 [SMILES: CN(C)c1ccccc1-c1csc(C2=C(CN3CCN(c4ccc(C(=O)NS(=O)(=O)c5ccc(NC[C@H]6COCCO6)c([N+](=O)[O-])c5)c(Oc5cnc6[nH]ccc6c5)c4)CC3)CCC(C)(C)C2)c1]

Step A: N,N-dimethyl-2-(thiophen-3-yl)aniline

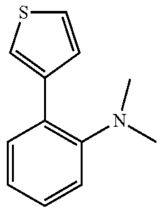

In a flame-dried over 100 mL round-bottomed flask, 2-bromo-N,N-dimethylaniline (0.5 g, 2.5 mmol), thiophen-3-ylboronic acid (0.48 g, 3.75 mmol), $PdCl_2(dppf)\cdot CH_2Cl_2$ (204 mg, 0.25 mmol) were dissolved into a mixed solvent of 1,4-dioxane (15 mL) and water (3 mL) under argon to give a solution; $Na_2CO_3$ (795 mg, 7.50 mmol) was added at room temperature in small portions and the reaction mixture was stirred at 100° C. for 12 h. After cooling down to room temperature, sat. $NaHCO_3$ (20 mL) was added to the reaction mixture followed by extraction with dichloromethane (20 mL×2). The combined organic layers were dried over $Na_2SO_4$, and concentrated under reduced pressure to give a light yellow oil, which was loaded onto a silica gel column and eluted with methanol and dichloromethane (1:50) to afford the title compound (0.4 g, 79%) as an off-white solid. $^1H$ NMR (400 MHz, $CDCl_3$) δ 7.49 (d, J=3.8 Hz, 2H), 7.37-7.31 (m, 2H), 7.29-7.23 (m, 2H), 7.05 (d, J=8.0 Hz, 1H), 7.00 (t, J=7.4 Hz, 1H), 2.59 (s, 6H).

Step B: (4-(2-(Dimethylamino)phenyl)thiophen-2-yl)boronic acid

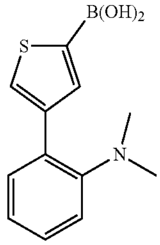 [SMILES: CN(C)c1ccccc1-c1csc(B(O)O)c1]

In a flame-dried over 100 mL round-bottomed flask, N,N-dimethyl-2-(thiophen-3-yl)aniline (Step A, 0.32 g, 1.574 mmol) was dissolved into dry THF (10 mL) under argon at −78° C. to give a solution; LDA (1.2 mL, 2 M in THF, 2.36 mmol) was added at −78° C. and the mixture was stirred at −78° C. for 1 h; Triisopropyl borate (0.474 g, 2.52 mmol, 1.6) was followed dropwise; the reaction mixture was stirred at −78° C. for 0.5 h, allowed to warm up to room temperature gradually and stirred for 1 h. MeOH (10 mL) was added to quench the reaction and the resulting mixture was partitioned with EA and aq. $NH_4Cl$. The aqueous layer was extracted with EA twice, the combined organic layers were dried over $Na_2SO_4$, and concentrated under reduced pressure to give a light yellow oil, which was directly used for the next step without purifications. MS: 248.1 ($M+H^+$).

Step C: Methyl 2-((1H-pyrrolo[2,3-b]pyridin-5-yl)oxy)-4-(4-((2-(4-(2-(dimethylamino)-phenyl)thiophen-2-yl)-4,4-dimethylcyclohex-1-en-1-yl)methyl)piperazin-1-yl)benzoate

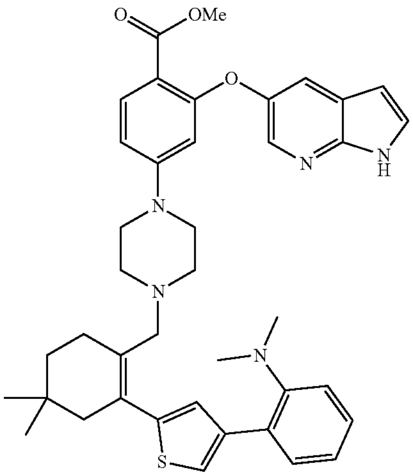 [SMILES: COC(=O)c1ccc(N2CCN(CC3=C(c4cc(-c5ccccc5N(C)C)cs4)CC(C)(C)CC3)CC2)cc1Oc1cnc2[nH]ccc2c1]

In a flame-dried over 100 mL round-bottomed flask, methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (100 mg, 0.181 mmol), the crude (4-(2-(dimethylamino)phenyl)thiophen-2-yl)boronic acid (Step B, 179 mg) and $PdCl_2(dppf)\cdot CH_2Cl_2$ (14.75 mg, 0.018 mmol) were dissolved into a mixed solvent of 1,4-dioxane (7.5 mL) and water (1.5 mL) under argon to give a solution; $Na_2CO_3$ (96 mg, 0.9 mmol) was added and the reaction mixture was stirred at 100° C. for 12 h. After cooling down to room temperature, sat. $NaHCO_3$ (10 mL) was added to the reaction mixture followed by extraction with dichloromethane (10 mL×2). The combined organic layers were dried over $Na_2SO_4$, and concentrated under reduced pressure to give a yellow oil, which was loaded onto a silica gel column and eluted with methanol and dichloromethane (1:50) to afford the title compound (110 mg, 90% over 2 steps) as an off-white solid. $^1H$ NMR (400 MHz, DMSO-$d_6$) δ 11.65 (s, 1H), 7.99 (d, J=2.6 Hz, 1H), 7.75 (d, J=9.0 Hz, 1H), 7.52-7.45 (m, 2H), 7.41 (d, J=2.5 Hz, 1H), 7.31-7.15 (m, 3H), 7.03-6.91 (m, 2H), 6.77 (dd, J=9.0, 2.2 Hz, 1H), 6.41-6.34 (m, 2H), 3.64 (s, 3H), 3.23-3.12 (m, 4H), 3.07 (s, 2H), 2.46 (s, 6H), 2.32 (s, 4H), 2.25-2.18 (m, 2H), 2.09 (s, 2H), 1.38 (t, J=6.0 Hz, 2H), 0.93 (s, 6H); MS: 677.0 ($M+H^+$).

Step D: 2-((1H-pyrrolo[2,3-b]pyridin-5-yl)oxy)-4-(4-((2-(4-(2-(dimethylamino) phen-yl)thiophen-2-yl)-4,4-dimethylcyclohex-1-en-1-yl)methyl)piperazin-1-yl)benzoic acid

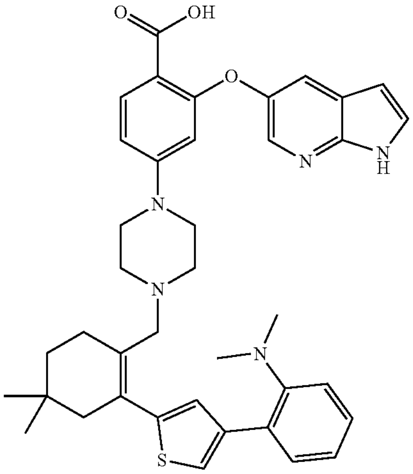 [SMILES: CN(C)c1ccccc1-c1csc(C2=C(CN3CCN(c4ccc(C(=O)O)c(Oc5cnc6[nH]ccc6c5)c4)CC3)CCC(C)(C)C2)c1]

In a flame-dried over 100 mL round-bottomed flask, methyl 2-((1H-pyrrolo[2,3-b]pyridin-5-yl)oxy)-4-(4-((2-(4-(2-(dimethylamino)phenyl)thiophen-2-yl)-4,4-dimethylcyclohex-1-en-1-yl)methyl)piperazin-1-yl)benzoate (Step C, 110 mg, 0.163 mmol) was dissolved into a mixed solvent of water (2 mL), THF (4 mL) and MeOH (2 mL) under argon to give a solution; sodium hydroxide (52.1 mg, 1.302 mmol) was added and the reaction mixture was stirred at 40° C. for 16 h. After cooling down to room temperature and dilution with water, 1 N HCl was added to adjust pH 4-5 and the resulting mixture was extracted with EA twice, the combined organic layers were dried over $Na_2SO_4$, and concentrated under reduced pressure to give a yellow oil, which was directly used without purification. MS: 662.8 ($M+H^+$).

Step E: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(2-(dimethylamino)phenyl)thiophen-2-yl)-4,4-dimethylcyclohex-1-en-1-yl)methyl)piperazin-1-yl)benzamide (Example 58)

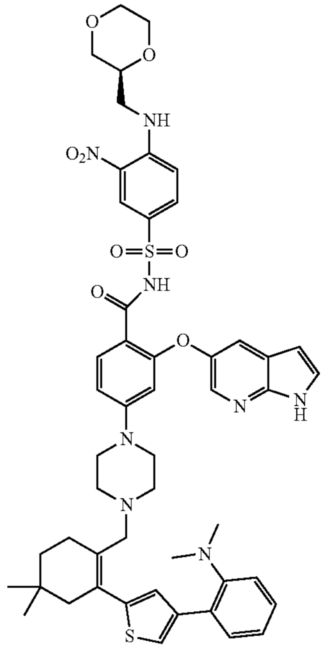 [SMILES: CN(C)c1ccccc1-c1csc(C2=C(CN3CCN(c4ccc(C(=O)NS(=O)(=O)c5ccc(NC[C@H]6COCCO6)c([N+](=O)[O-])c5)c(Oc5cnc6[nH]ccc6c5)c4)CC3)CCC(C)(C)C2)c1]

In a flame-dried over 100 mL round-bottomed flask, the crude 2-((1H-pyrrolo[2,3-b]pyridin-5-yl)oxy)-4-(4-((2-(4-(2-(dimethylamino)phenyl)thiophen-2-yl)-4,4-dimethylcyclohex-1-en-1-yl)methyl)piperazin-1-yl)benzoic acid (Step D, 100 mg), N,N-dimethylpyridin-4-amine (55.4 mg, 0.45 mmol), (S)-4-(((1,4-dioxan-2-yl)methyl)amino)-3-nitrobenzenesulfonamide (96 mg, 0.3 mmol) were dissolved into dry $CH_2Cl_2$ (10 mL) under argon to give a solution; EDCl (57.9 mg, 0.3 mmol) was added and the reaction mixture was stirred at 40° C. for 12 h. After cooling down to room temperature, sat. $NaHCO_3$ (10 mL) was added to the reaction mixture followed by extraction with dichloromethane (10 mL×2). The combined organic layers were dried over $Na_2SO_4$, and concentrated under reduced pressure to give a yellow oil, which was purified by C18 prep-HPLC column to afford the title compound (36 mg, 25% over 2 steps) as a yellow solid. $^1H$ NMR (400 MHz, DMSO-$d_6$) δ 11.66 (s, 1H), 11.52 (brs, 1H), 8.66-8.41 (m, 2H), 8.01 (s, 1H), 7.79 (d, J=9.2 Hz, 1H), 7.54-7.45 (m, 4H), 7.26 (dd, J=7.5, 1.5 Hz, 1H), 7.24-7.19 (m, 1H), 7.17 (d, J=1.0 Hz, 1H), 7.12-7.01 (m, 1H), 7.00-6.89 (m, 2H), 6.69 (dd, J=9.0, 1.7 Hz, 1H), 6.40-6.32 (m, 1H), 6.22 (d, J=1.6 Hz, 1H), 3.84-3.75 (m, 2H), 3.70-3.56 (m, 2H), 3.54-3.44 (m, 2H), 3.42-3.27 (m, 3H), 3.11 (brs, 4H), 3.06 (s, 2H), 2.45 (s, 6H), 2.37-2.25 (m, 4H), 2.25-2.15 (m, 2H), 2.08 (s, 2H), 1.38 (t, J=6.2 Hz, 2H), 0.92 (s, 6H); MS: 961.8 (M+H$^+$).

Example 59: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(4-((2-(4-(4-(2-hydroxypropan-2-yl)phenyl)thiophen-2-yl)-4,4-dimethylcyclohex-1-en-1-yl)methyl)piperazin-1-yl)benzamide

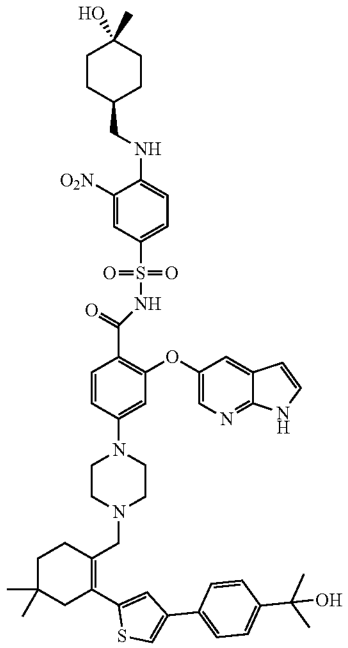 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(C)(C)O)cc3)cs2)C1]

Essentially the same protocol of preparation of Example 58 was used to afford the example (50 mg) as a yellow solid. $^1H$ NMR (400 MHz, DMSO-$d_6$) δ 11.67 (s, 1H), 11.48 (brs, 1H), 8.63-8.47 (m, 2H), 8.03 (d, J=2.5 Hz, 1H), 7.77 (d, J=8.0 Hz, 1H), 7.68 (d, J=1.1 Hz, 1H), 7.57 (d, J=8.3 Hz, 2H), 7.53-7.47 (m, 3H), 7.45 (d, J=8.4 Hz, 2H), 7.27 (d, J=1.0 Hz, 1H), 7.06 (d, J=9.2 Hz, 1H), 6.70 (dd, J=8.9, 1.6 Hz, 1H), 6.37 (dd, J=3.1, 1.8 Hz, 1H), 6.23 (d, J=1.5 Hz, 1H), 5.01 (s, 1H), 4.25 (s, 1H), 3.27 (t, J=6.2 Hz, 2H), 3.16-3.08 (m, 4H), 3.04 (s, 2H), 2.37-2.26 (m, 4H), 2.25-2.15 (m, 2H), 2.11 (s, 2H), 1.75-1.59 (m, 3H), 1.54 (d, J=12.8 Hz, 2H), 1.42 (s, 6H), 1.40-1.28 (m, 4H), 1.17-1.05 (m, 5H), 0.93 (s, 6H); MS: 1003.7 (M+H$^+$).

Example 60: 2-((1H-pyrrolo[2,3-b]pyridin-5-yl)oxy)-4-(4-((2-(4-(4-(1,1,1,3,3,3-hexafluoro-2-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

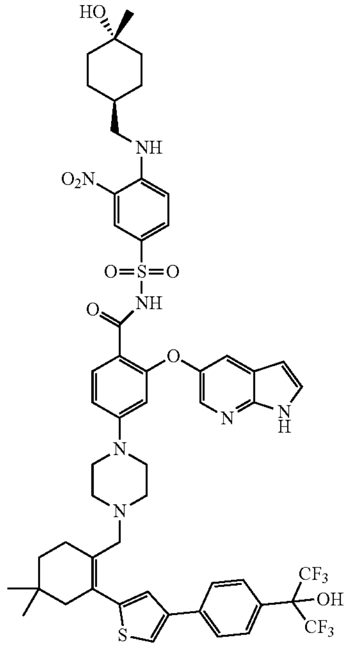 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(O)(C(F)(F)F)C(F)(F)F)cc3)cs2)C1]

Essentially the same protocol of preparation of Example 58 was used to afford the example (70 mg) as a yellow solid. $^1H$ NMR (400 MHz, DMSO-$d_6$) δ 11.62 (s, 1H), 8.69 (s, 1H), 8.56-8.42 (m, 2H), 8.01 (d, J=2.5 Hz, 1H), 7.85 (d, J=1.3 Hz, 1H), 7.81 (d, J=8.6 Hz, 2H), 7.75 (d, J=8.8 Hz, 1H), 7.67 (d, J=8.3 Hz, 2H), 7.51 (d, J=8.9 Hz, 1H), 7.49-7.43 (m, 2H), 7.33 (d, J=1.2 Hz, 1H), 7.01 (d, J=8.2 Hz, 1H), 6.69 (dd, J=8.9, 2.0 Hz, 1H), 6.36 (dd, J=3.2, 1.8 Hz, 1H), 6.23 (d, J=1.8 Hz, 1H), 4.21 (s, 1H), 3.28-3.23 (m, 2H), 3.14-3.07 (m, 4H), 3.04 (s, 2H), 2.33-2.26 (m, 4H), 2.25-2.18 (m, 2H), 2.12 (s, 2H), 1.74-1.59 (m, 3H), 1.58-1.50 (m, 2H), 1.43-1.29 (m, 4H), 1.19-1.05 (m, 5H), 0.94 (s, 6H); MS: 1111.5 ($M+H^+$).

Example 61: 2-((1H-pyrrolo[2,3-b]pyridin-5-yl)oxy)-4-(4-((2-(4-((4-fluorophenyl)ethynyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

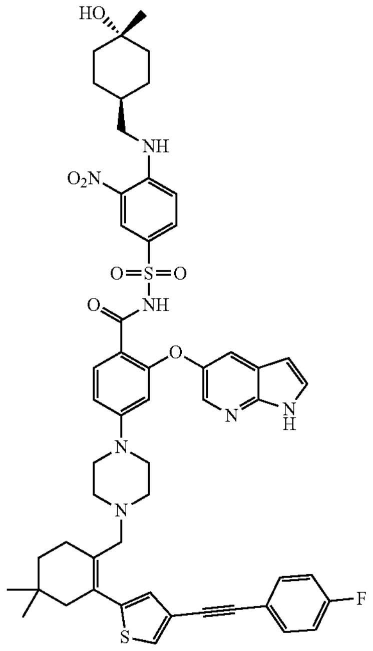 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(C#Cc3ccc(F)cc3)cs2)C1]

Essentially the same protocol of preparation of Example 58 was used to afford the example (2 mg) as a yellow solid. $^1H$ NMR (400 MHz, DMSO-$d_6$) δ 11.63 (s, 1H), 8.59-8.44 (m, 2H), 8.02 (s, 1H), 7.76 (s, 2H), 7.60-7.45 (m, 4H), 7.25 (t, J=8.9 Hz, 2H), 7.18 (s, 1H), 6.95 (s, 1H), 6.69 (d, J=8.5 Hz, 1H), 6.64 (s, 1H), 6.36 (s, 1H), 6.23 (s, 1H), 4.22 (s, 1H), 3.14-3.04 (m, 4H), 3.03-2.94 (m, 2H), 2.31-2.24 (m, 4H), 2.23-2.15 (m, 2H), 2.06 (s, 2H), 2.04-1.94 (m, 2H), 1.73-1.59 (m, 2H), 1.57-1.50 (m, 2H), 1.49-1.41 (m, 1H), 1.40-1.29 (m, 4H), 1.19-1.03 (m, 5H), 0.92 (s, 6H); MS: 987.4 ($M+H^+$).

Example 62: 2-((1H-pyrrolo[2,3-b]pyridin-5-yl)oxy)-4-(4-((2-(4-(2-fluoro-4-(2-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

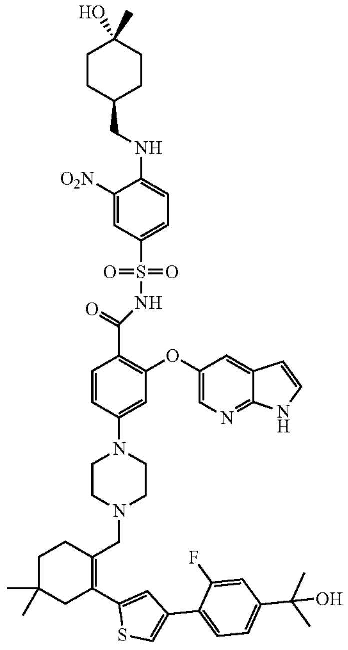 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(C)(C)O)cc3F)cs2)C1]

Step A: Methyl 3-fluoro-4-(thiophen-3-yl)benzoate

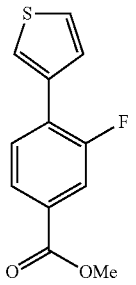 [SMILES: COC(=O)c1ccc(-c2ccsc2)c(F)c1]

In a flame-dried over 100 mL round-bottomed flask, methyl 4-bromo-3-fluorobenzoate (5 g, 21.46 mmol), thiophen-3-ylboronic acid (3.43 g, 26.8 mmol) and $PdCl_2$(dppf)$\cdot CH_2Cl_2$ (1.752 g, 2.146 mmol) were dissolved into a mixed solvent of 1,4-dioxane (120 mL) and water (30 mL) under argon to give a solution; $Na_2CO_3$ (5.69 g, 53.6 mmol) was added at room temperature in small portions and the reaction mixture was stirred at 100° C. for 16 h. Sat. $NaHCO_3$ (100 mL) was added to the reaction mixture followed by extraction with ethyl acetate (100 mL×2). The combined organic layers were dried over $Na_2SO_4$, and concentrated reduced pressure to give a light yellow oil, which was loaded onto a silica gel column and eluted with ethyl acetate and hexane (1:50) to afford the title compound (4 g, 79%) as an off-white solid. $^1$H NMR (400 MHz, DMSO-$d_6$) δ 8.02 (dt, J=2.8, 1.3

Hz, 1H), 7.90 (t, J=7.9 Hz, 1H), 7.82 (dd, J=8.1, 1.7 Hz, 1H), 7.77 (dd, J=11.8, 1.6 Hz, 1 H), 7.72 (dd, J=5.1, 2.9 Hz, 1H), 7.57 (dt, J=5.1, 1.5 Hz, 1H), 3.87 (d, J=3.1 Hz, 3H).

Step B: 2-(3-Fluoro-4-(thiophen-3-yl)phenyl)propan-2-ol

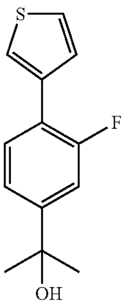 [SMILES: CC(C)(O)c1ccc(-c2ccsc2)c(F)c1]

In a flame-dried over 100 mL round-bottomed flask, methyl 3-fluoro-4-(thiophen-3-yl)benzoate (Step A, 1.1 g, 4.66 mmol) was dissolved into dry THF (30 mL) under argon at 0° C. to give a solution; MeMgBr (4.7 mL, 3M in 2-MeTHF, 14 mmol) was added dropwise at 0° C.; the reaction mixture was stirred at 0° C. for 0.5 h, allowed to warm up to room temperature gradually and stirred for 3 h. MeOH (10 mL) was slowly added to quench the reaction, the resulting mixture was partitioned with EA and aq. $NH_4Cl$. The aqueous layer was extracted with EA twice, the combined organic layers were dried over $Na_2SO_4$, and concentrated under reduced pressure to give a yellow oil, which was loaded onto a silica gel column and eluted with ethyl acetate and hexane (1:20) to afford the title compound (0.8 g, 73%) as an off-white solid. $^1$H NMR (400 MHz, DMSO-$d_6$) δ 7.85-7.81 (m, 1H), 7.70-7.65 (m, 2H), 7.51 (d, J=5.0 Hz, 1H), 7.39-7.32 (m, 2H), 5.18 (s, 1H), 1.47 (s, 6H); MS: 219.4 ($M-H_2O+H^+$).

Step C: (4-(2-Fluoro-4-(2-hydroxypropan-2-yl)phenyl)thiophen-2-yl)boronic acid

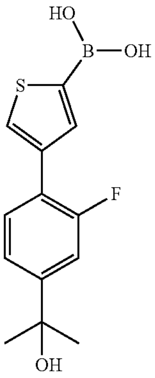 [SMILES: CC(C)(O)c1ccc(-c2csc(B(O)O)c2)c(F)c1]

In a flame-dried over 100 mL round-bottomed flask, 2-(3-fluoro-4-(thiophen-3-yl)phenyl)propan-2-ol (Step B, 0.75 g, 3.17 mmol) was dissolved into dry THF (30 mL) under argon at 0° C. to give a solution; LDA (4.8 mL, 2 M in THF, 9.52 mmol) was added dropwise at 0° C. and the mixture was stirred at 0° C. for 1 h; triisopropyl borate (1.791 g, 9.52 mmol) was followed dropwise over 0.5 h; the reaction mixture was stirred at 0° C. for 0.5 h, allowed to warm up to room temperature and stirred for 12 h. MeOH (10 mL) was added to quench the reaction, and the resulting mixture was concentrated under reduced pressure to give the crude product as a light yellow oil, which was directly used for the next step without purification. MS: 262.9 ($M-H_2O+H^+$).

Step D: 2-((1H-pyrrolo[2,3-b]pyridin-5-yl)oxy)-4-(4-((2-(4-(2-fluoro-4-(2-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 62)

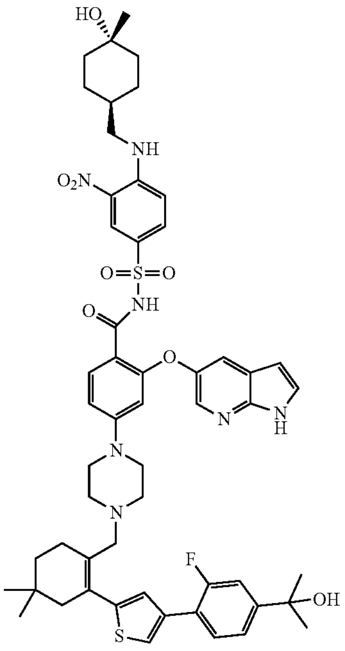 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(C)(C)O)cc3F)cs2)C1]

Starting from Step C, essentially the same protocol of preparation of Example 58 was used to afford the example (100 mg) as a yellow solid. $^1H$ NMR (400 MHz, DMSO-$d_6$) δ 11.65 (s, 1H), 8.59-8.50 (m, 2H), 8.04 (d, J=2.4 Hz, 1H), 7.78 (d, J=9.7 Hz, 1H), 7.67 (s, 1H), 7.59 (t, J=8.4 Hz, 1H), 7.55-7.45 (m, 3H), 7.33-7.26 (m, 2H), 7.23 (s, 1H), 7.06 (d, J=9.4 Hz, 1H), 6.70 (d, J=9.1 Hz, 1H), 6.37 (s, 1H), 6.23 (s, 1H), 5.13 (s, 1H), 4.22 (s, 1H), 3.29-3.24 (m, 2H), 3.16-3.07 (m, 4H), 3.03 (s, 2H), 2.34-2.25 (m, 4H), 2.25-2.17 (m, 2H), 2.11 (s, 2H), 1.75-1.60 (m, 3H), 1.59-1.49 (m, 2H), 1.43 (s, 6H), 1.41-1.28 (m, 4H), 1.19-1.06 (m, 5H), 0.94 (s, 6H); MS: 1021.8 ($M+H^+$).

Example 63: 2-((1H-pyrrolo[2,3-b]pyridin-5-yl)oxy)-4-(4-((2-(4-(2,6-difluoro-4-(2-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

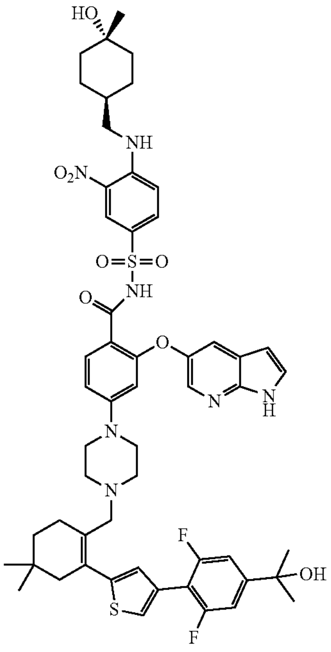 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(C(C)(C)O)cc3F)cs2)C1]

Essentially the same protocol of preparation of Example 62 was used to afford the example (120 mg) as a yellow solid. $^1H$ NMR (400 MHz, DMSO-$d_6$) δ 11.65 (s, 1H), 11.47 (brs, 1H), 8.59-8.49 (m, 2H), 8.03 (d, J=2.4 Hz, 1H), 7.78 (d, J=8.2 Hz, 1H), 7.64 (s, 1H), 7.56-7.45 (m, 3H), 7.21 (d, J=10.1 Hz, 2H), 7.10-7.02 (m, 2H), 6.70 (dd, J=9.0, 1.9 Hz, 1H), 6.37 (s, 1H), 6.23 (d, J=1.9 Hz, 1H), 5.26 (s, 1H), 4.21 (s, 1H), 3.31-3.25 (m, 2H), 3.14-3.07 (m, 4H), 3.03 (s, 2H), 2.35-2.25 (m, 4H), 2.25-2.17 (m, 2H), 2.11 (s, 2H), 1.73-1.59 (m, 3H), 1.58-1.49 (m, 2H), 1.42 (s, 6H), 1.40-1.28 (m, 4H), 1.17-1.04 (m, 5H), 0.93 (s, 6H); MS: 1039.8 ($M+H^+$).

Example 64: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((2-(4-(2,6-difluoro-4-(2-hydroxypropan-2-yl)phenyl)thiophen-2-yl)-4,4-dimethylcyclohex-1-en-1-yl)methyl)piperazin-1-yl)benzamide

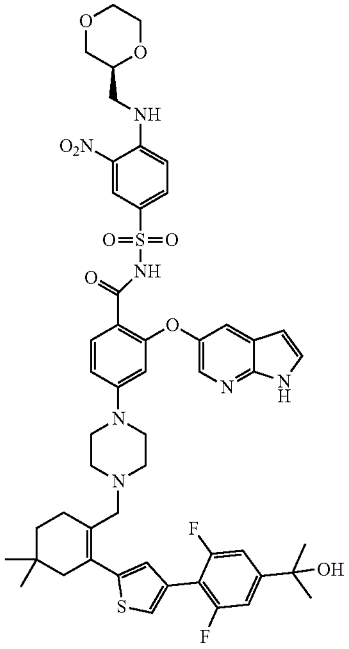 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2cc(-c3c(F)cc(C(C)(C)O)cc3F)cs2)C1]

Essentially the same protocol of preparation of Example 62 was used to afford the example (90 mg) as a yellow solid. $^1$H NMR (400 MHz, DMSO-$d_6$) δ 11.62 (s, 1H), 8.60-8.46 (m, 2H), 8.02 (d, J=2.4 Hz, 1H), 7.78 (d, J=8.7 Hz, 1H), 7.64 (s, 1H), 7.53-7.45 (m, 3H), 7.21 (d, J=6.7 Hz, 2H), 7.10-7.01 (m, 2H), 6.70 (dd, J=8.9, 1.9 Hz, 1H), 6.36 (dd, J=3.1, 1.8 Hz, 1H), 6.24 (d, J=1.9 Hz, 1H), 5.27 (s, 1H), 3.84-3.73 (m, 3H), 3.69-3.56 (m, 2H), 3.53-3.43 (m, 2H), 3.42-3.34 (m, 2H), 3.14-3.07 (m, 4H), 3.05-2.99 (m, 2H), 2.32-2.26 (m, 4H), 2.25-2.16 (m, 2H), 2.11 (s, 2H), 1.42 (s, 6H), 1.38 (t, J=6.5 Hz, 2H), 0.93 (s, 6H); MS: 1013.9 (M+H$^+$).

Example 65: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(4-((2-(4-(4-(2-hydroxypropan-2-yl)-2,6-dimethylphenyl)thiophen-2-yl)-4,4-dimethylcyclohex-1-en-1-yl)methyl)piperazin-1-yl)benzamide

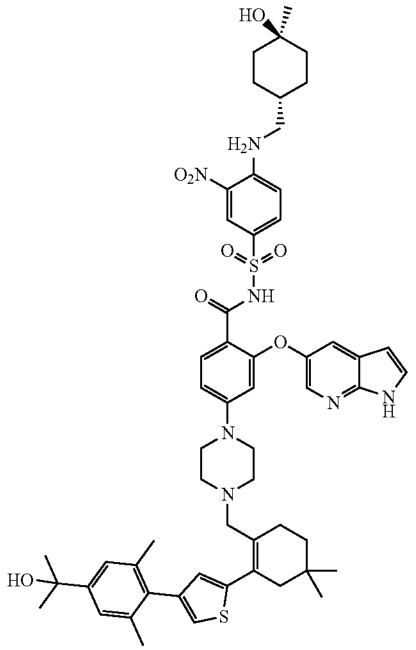 [SMILES: Cc1cc(C(C)(C)O)cc(C)c1-c1csc(C2=C(CN3CCN(c4ccc(C(=O)NS(=O)(=O)c5ccc(NC[C@H]6CC[C@](C)(O)CC6)c([N+](=O)[O-])c5)c(Oc5cnc6[nH]ccc6c5)c4)CC3)CCC(C)(C)C2)c1]

Essentially the same protocol of preparation of Example 62 was used to afford the example (31.2 mg) as a yellow solid. $^1$H NMR (400 MHz, DMSO-$d_6$) δ 11.68 (s, 1H), 11.49 (brs, 1H), 8.64-8.49 (m, 2H), 8.03 (d, J=2.4 Hz, 1H), 7.78 (d, J=8.9 Hz, 1H), 7.54-7.44 (m, 3H), 7.17-7.12 (m, 3H), 7.06 (d, J=9.3 Hz, 1H), 6.69 (d, J=7.5 Hz, 1H), 6.62 (s, 1H), 6.39-6.32 (m, 1H), 6.25-6.18 (m, 1H), 4.92 (s, 1H), 4.26 (s, 1H), 3.28 (t, J=6.0 Hz, 2H), 3.13-3.00 (m, 6H), 2.30-2.15 (m, 6H), 2.13-2.10 (m, 2H), 2.02 (s, 6H), 1.72-1.58 (m, 3H), 1.57-1.50 (m, 2H), 1.40 (s, 6H), 1.37-1.22 (m, 4H), 1.17-1.05 (m, 5H), 0.93 (s, 6H); MS: 1030.5 (M+H$^+$).

Example 66: 2-((1H-pyrrolo[2,3-b]pyridin-5-yl)oxy)-4-(4-((2-(4-(2,6-dichloro-4-(2-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

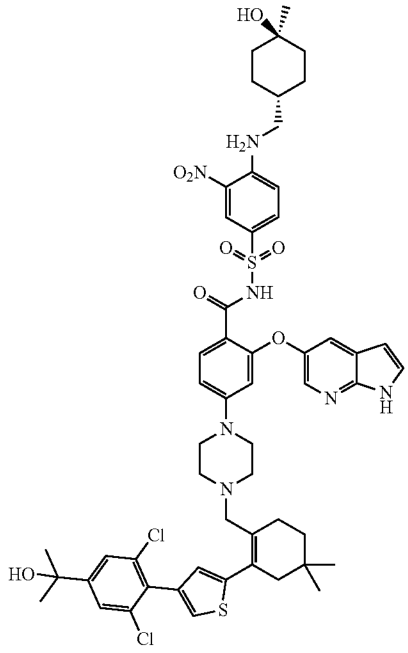 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(Cl)cc(C(C)(C)O)cc3Cl)cs2)C1]

Essentially the same protocol of preparation of Example 62 was used to afford the example (17.7 mg) as a yellow solid. $^{1}H$ NMR (400 MHz, DMSO-$d_6$) δ 11.48 (s, 1H), 8.36-8.32 (m, 1H), 8.28 (t, J=5.3 Hz, 1H), 7.90 (d, J=2.2 Hz, 1H), 7.63-7.51 (m, 4H), 7.43 (s, 1H), 7.38 (d, J=3.1 Hz, 1H), 7.20 (d, J=2.2 Hz, 1H), 6.80 (s, 1H), 6.72 (d, J=9.2 Hz, 1H), 6.63 (d, J=8.4 Hz, 1H), 6.33-6.22 (m, 2H), 5.32 (s, 1H), 4.25 (s, 1H), 3.22-3.18 (m, 2H), 3.08-3.04 (m, 2H), 3.04-2.97 (m, 4H), 2.35-2.26 (m, 4H), 2.24-2.18 (m, 2H), 2.14-2.09 (m, 2H), 1.72-1.57 (m, 3H), 1.57-1.49 (m, 2H), 1.43 (s, 6H), 1.40-1.29 (m, 4H), 1.17-1.04 (m, 5H), 0.94 (s, 6H); MS: 1070.4 (M+H$^+$).

Example 67: 2-((1H-pyrrolo[2,3-b]pyridin-5-yl)oxy)-4-(4-((2-(4-(2,6-difluoro-4-(3-hydroxypentan-3-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

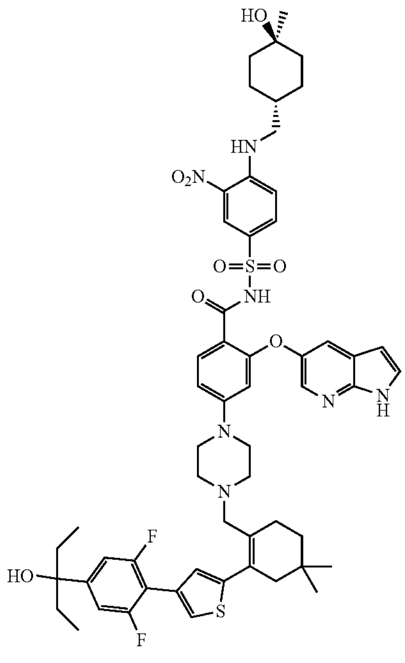 [SMILES: CCC(O)(CC)c1cc(F)c(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Essentially the same protocol of preparation of Example 62 was used to afford the example (51 mg) as a yellow solid. $^{1}H$ NMR (400 MHz, DMSO-$d_6$) δ 11.67 (s, 1H), 11.49 (brs, 1H), 8.57-8.51 (m, 2H), 8.04-8.03 (m, 1H), 7.79 (d, J=9.2 Hz, 1H), 7.59-7.44 (m, 4H), 7.08-7.01 (m, 4H), 6.68 (d, J=9.2 Hz, 1H), 6.39-6.37 (m, 1H), 6.22-6.19 (m, 1H), 4.74 (s, 1H), 4.23 (s, 1H), 3.28-3.27 (m, 2H), 3.09-3.07 (m, 4H), 2.59-2.57 (m, 2H), 2.11-2.09 (m, 4H), 2.01-1.99 (m, 2H), 1.89-1.87 (m, 2H), 1.79-1.60 (m, 7H), 1.56-1.53 (m, 2H), 1.37-1.24 (m, 6H), 1.10 (s, 3H), 0.91 (s, 6H), 0.61 (t, J=7.2 Hz, 6H); MS: 1066.4 (M+H$^+$).

Example 68: 2-((1H-pyrrolo[2,3-b]pyridin-5-yl) oxy)-4-(4-((2-(4-(2,6-difluoro-4-(2-hydroxypropan-2-yl-1,1,1,3,3,3-d6)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl) amino)-3-nitrophenyl)sulfonyl)benzamide

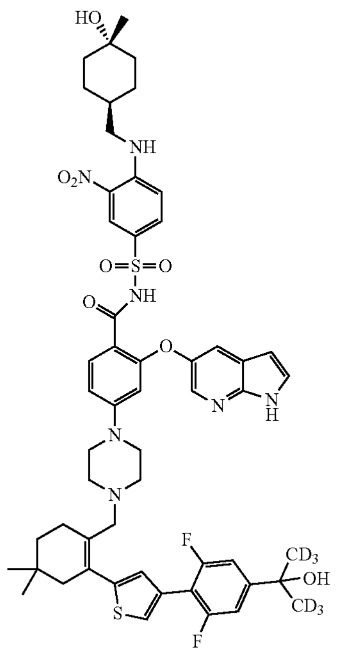 [SMILES: [2H]C([2H])([2H])C(O)(c1cc(F)c(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1)C([2H])([2H])[2H]]

Essentially the same protocol of preparation of Example 62 was used to afford the example (54 mg) as a yellow solid. $^1$H NMR (400 MHz, DMSO-$d_6$) δ 11.64 (s, 1H), 11.49 (brs, 1H), 8.58-8.46 (m, 2H), 8.03 (d, J=2.5 Hz, 1H), 7.77 (d, J=9.1 Hz, 1H), 7.63 (s, 1H), 7.55-7.42 (m, 3H), 7.26-7.16 (m, 2H), 7.10-6.99 (m, 2H), 6.70 (dd, J=9.0, 2.0 Hz, 1H), 6.37 (dd, J=3.2, 1.8 Hz, 1H), 6.23 (d, J=2.0 Hz, 1H), 5.24 (s, 1H), 4.21 (s, 1H), 3.29-3.22 (m, 2H), 3.15-3.07 (m, 4H), 3.03 (s, 2H), 2.35-2.25 (m, 4H), 2.25-2.18 (m, 2H), 2.11 (s, 2H), 1.74-1.59 (m, 3H), 1.59-1.49 (m, 2H), 1.42-1.28 (m, 4H), 1.18-1.10 (m, 2H), 1.10 (s, 3H), 0.93 (s, 6H); MS: 1045.8 (M+$H^+$).

Example 69: 2-((1H-pyrrolo[2,3-b]pyridin-5-yl) oxy)-4-(4-((2-(4-(4-(1-cyclopropyl-1-hydroxyethyl)-2,6-difluorophenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl) amino)-3-nitrophenyl)sulfonyl)benzamide

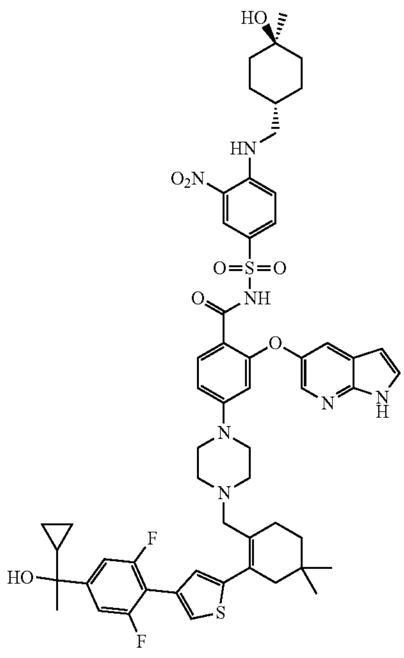 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(C(C)(O)C4CC4)cc3F)cs2)C1]

Step A: 1-(3,5-Difluoro-4-(thiophen-3-yl)phenyl) ethan-1-one

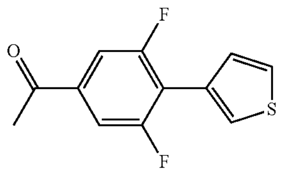 [SMILES: CC(=O)c1cc(F)c(-c2ccsc2)c(F)c1]

Under Ar, to a solution of 1-(4-bromo-3,5-difluorophenyl) ethan-1-one (10 g, 42.5 mmol) in dry DMF (100 mL) was added thiophen-3-ylboronic acid (5.99 g, 46.8 mmol), $PdCl_2$ (dppf) (1.557 g, 2.127 mmol) and $K_2CO_3$ (17.64 g, 128 mmol); then the reaction mixture was stirred at 100° C. for 4 h. After cooling down to room temperature and filtration off through celite, the filtrate was poured onto water and extracted with EA twice. The combined organic layer was washed with water and brine, dried over $Na_2SO_4$ and concentrated under reduced pressure to give a yellow oil, which was purified by silica gel column (hexane:EA, 10:1) to afford the title compound (7 g, 69%) as a yellow oil. $^1$H NMR (400 MHz, $CDCl_3$) δ 7.79-7.75 (m, 1H), 7.60-7.53 (m, 2H), 7.50-7.46 (m, 1H), 7.46-7.43 (m, 1H), 2.61 (s, 3H).

Step B: 1-Cyclopropyl-1-(3,5-difluoro-4-(thiophen-3-yl)phenyl)ethan-1-ol

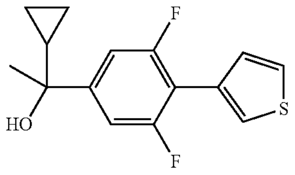 [SMILES: CC(O)(c1cc(F)c(-c2ccsc2)c(F)c1)C1CC1]

Under Ar, to a solution of 1-(3,5-difluoro-4-(thiophen-3-yl)phenyl)ethan-1-one (Step A, 700 mg, 2.94 mmol) in dry THF (15 ml) was added cyclopropylmagnesium bromide (3.5 mL, 1 M in THF, 3.52 mmol) dropwise at 0° C.; the reaction mixture was allowed to warm up to room temperature and stirred for 2 h. Sat. $NH_4Cl$ was added to quench the reaction, the resulting mixture was diluted with ethyl acetate and then washed with $H_2O$ and brine. The organic layer was dried over $Na_2SO_4$, and concentrated under reduce pressure to give a yellow oil, which was loaded onto a silica gel column and eluted with ethyl acetate and hexane (1:10) to afford the title compound (320 mg, 39%) as a colorless oil. $^1H$ NMR (400 MHz, DMSO-$d_6$) δ 7.80-7.76 (m, 1H), 7.70-7.65 (m, 1H), 7.37-7.32 (m, 1H), 7.29-7.22 (m, 2H), 4.96 (s, 1H), 1.43 (s, 3H), 1.25-1.19 (m, 1H), 0.59-0.11 (m, 4H).

Step C: (4-(2,6-Difluoro-4-(3-hydroxypentan-3-yl) phenyl)thiophen-2-yl)boronic acid

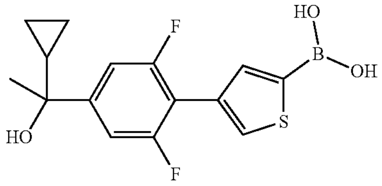 [SMILES: CC(O)(c1cc(F)c(-c2csc(B(O)O)c2)c(F)c1)C1CC1]

Under Ar, to a solution of 1-cyclopropyl-1-(3,5-difluoro-4-(thiophen-3-yl)phenyl)ethan-1-ol (Step B, 320 mg, 1.1 mmol) in dry THF (12 mL) was added LDA (1.7 mL, 2 M in THF, 3.3 mmol) dropwise at 0° C.; then the mixture was stirred at room temperature for 1 h; triisopropyl borate (644 mg, 3.3 mmol) was added slowly and the reaction mixture was stirred at room temperature for 12 h. 2 N HCl was added to quench the reaction, the resulting mixture was diluted with ethyl acetate and then washed with brine. The organic layer was dried over $Na_2SO_4$, and concentrated under reduced pressure to give a yellow oil, which was loaded onto a silica gel column and eluted with ethyl acetate and hexane (1:1) to afford the title compound (101 mg, 27%) as a yellow oil. MS: 325.1 (M+H$^+$).

Step D: 2-((1H-pyrrolo[2,3-b]pyridin-5-yl)oxy)-4-(4-((2-(4-(4-(1-cyclopropyl-1-hydroxyethyl)-2,6-difluorophenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 69)

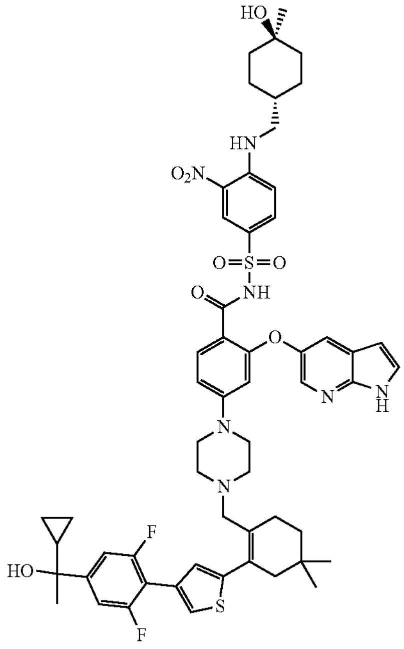 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(C(C)(O)C4CC4)cc3F)cs2)C1]

Starting from Step C, essentially the same protocol of preparation of Example 62 was used to afford the example (20 mg) as a yellow solid. $^1H$ NMR (400 MHz, DMSO-$d_6$) δ 11.65 (s, 1H), 8.55-8.52 (m, 2H), 8.04 (d, J=2.6 Hz, 1H), 7.79 (dd, J=9.2, 2.0 Hz, 1H), 7.64 (s, 1H), 7.55-7.50 (m, 2H), 7.50-7.46 (m, 2H), 7.23 (d, J=10.0 Hz, 3H), 7.11-7.02 (m, 2H), 6.70 (dd, J=9.2, 2.0 Hz, 1H), 6.37 (dd, J=3.2, 1.9 Hz, 1H), 6.23 (d, J=1.7 Hz, 1H), 4.94 (s, 1H), 4.22 (s, 1H), 3.28-3.27 (m, 2H), 3.13-3.07 (m, 4H), 3.05-3.03 (m, 2H), 2.33-2.27 (m, 4H), 2.23-2.17 (m, 2H), 2.11-2.09 (m, 2H), 1.70-1.61 (m, 3H), 1.56-1.52 (m, 2H), 1.41 (s, 3H), 1.41-1.14 (m, 5H), 1.10 (s, 3H), 0.93 (s, 6H), 0.55-0.16 (m, 4H); MS: 1064.4 (M+H$^+$).

Example 70: 2-((1H-pyrrolo[2,3-b]pyridin-5-yl)oxy)-N-((4-((((1r,4r)-4-hydroxy-4-methylcyclohexyl)methyl)amino)-3-nitrophenyl)sulfonyl)-4-(4-((2-(4-(3-(2-hydroxypropan-2-yl)phenyl)thiophen-2-yl)-4,4-dimethylcyclohex-1-en-1-yl)methyl)piperazin-1-yl)benzamide

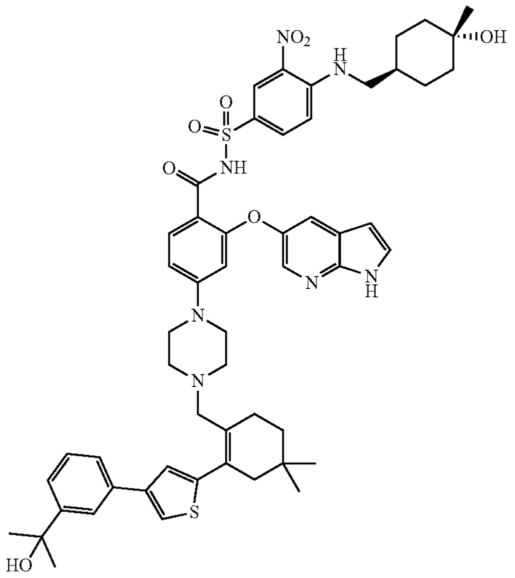 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3cccc(C(C)(C)O)c3)cs2)C1]

Essentially the same protocol of preparation of Example 58 was used to afford the example (60 mg) as a yellow solid. $^1$H NMR (400 MHz, DMSO-$d_6$) δ 11.69 (s, 1H), 8.62-8.53 (m, 2H), 8.07 (d, J=2.6 Hz, 1H), 7.82 (dd, J=9.3, 2.0 Hz, 1H), 7.74 (s, 1H), 7.72 (d, J=1.3 Hz, 1H), 7.58-7.45 (m, 4H), 7.39 (d, J=7.9 Hz, 1H), 7.35-7.29 (m, 2H), 7.10 (d, J=9.4 Hz, 1H), 6.73 (dd, J=9.0, 2.1 Hz, 1H), 6.41 (dd, J=3.3, 1.8 Hz, 1H), 6.25 (d, J=1.9 Hz, 1H), 5.01 (s, 1H), 4.24 (s, 1H), 3.32-3.01 (m, 8H), 2.42-2.20 (m, 6H), 2.17-2.09 (m, 2H), 1.76-1.53 (m, 5H), 1.46 (s, 6H), 1.44-1.32 (m, 4H), 1.22-1.09 (m, 5H), 0.97 (s, 6H); MS: 1003.2 (M+H$^+$).

Example 71: 2-((1H-pyrrolo[2,3-b]pyridin-5-yl)oxy)-4-(4-((2-(4-(3-fluoro-4-(2-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

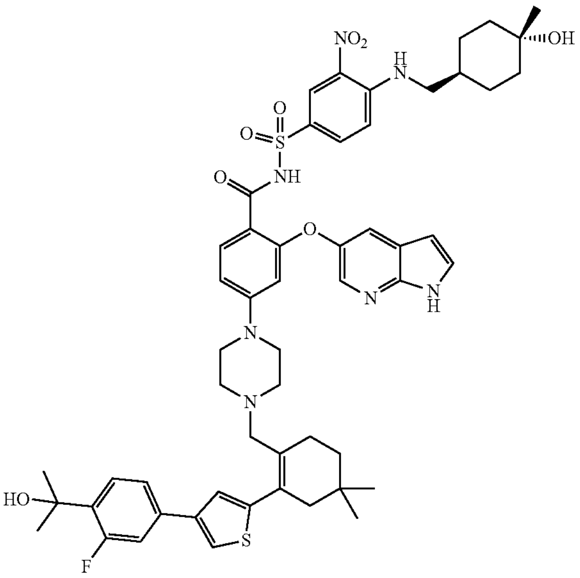 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(C)(C)O)c(F)c3)cs2)C1]

Essentially the same protocol of preparation of Example 62 was used to afford the example (12 mg) as a yellow solid. $^1$H NMR (400 MHz, DMSO-$d_6$) δ 11.67 (s, 1H), 8.59-8.51 (m, 2H), 8.06 (d, J=2.6 Hz, 1H), 7.85-7.77 (m, 2H), 7.63 (t, J=8.5 Hz, 1H), 7.57-7.42 (m, 5H), 7.35 (d, J=1.2 Hz, 1H), 7.07 (d, J=9.3 Hz, 1H), 6.72 (dd, J=9.0, 2.0 Hz, 1H), 6.40 (dd, J=3.3, 1.9 Hz, 1H), 6.25 (d, J=1.9 Hz, 1H), 5.27 (s, 1H), 4.25 (s, 1H), 3.32-3.24 (m, 2H), 3.19-3.01 (m, 6H), 2.39-2.20 (m, 6H), 2.17-2.08 (m, 2H), 1.75-1.55 (m, 5H), 1.51 (s, 6H), 1.45-1.23 (m, 6H), 1.13 (s, 3H), 0.96 (s, 6H); MS: 1021.5 (M+H$^+$).

Example 72: 2-((1H-pyrrolo[2,3-b]pyridin-5-yl)oxy)-4-(4-((2-(4-(2-fluoro-4-(1-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

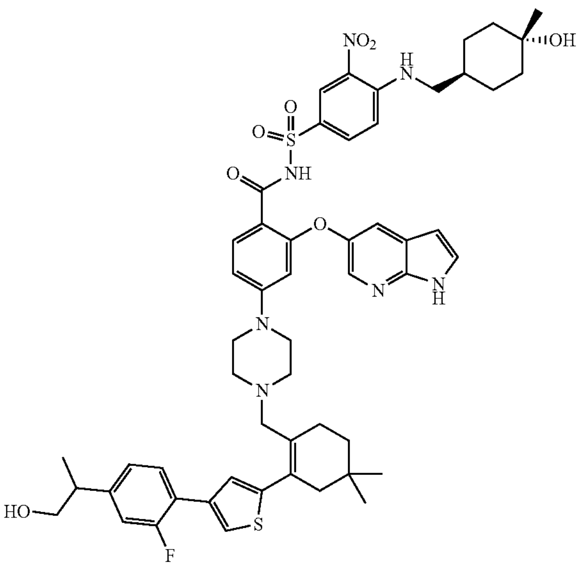 [SMILES: CC(CO)c1ccc(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Step A: Methyl 2-(4-bromo-3-fluorophenyl)propanoate

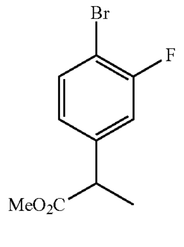

Under Ar, to a solution of methyl 2-(4-bromo-3-fluorophenyl)acetate (1 g, 4.05 mmol) in dry THF (10 mL) was added LDA (6.1 mL, 2 M in THF, 12.14 mmol) at 0° C., and the mixture was stirred at 0° C. for 0.5 h; MeI (3.45 g, 24.29 mmol) was added and the reaction mixture was stirred for 1 h. Aq. $NH_4Cl$ was added to quench the reaction and the resulting mixture was extracted with EA twice. The combined organic layer was washed with brine, dried over $Na_2SO_4$ and concentrated under reduced pressure to give a yellow oil, which was purified by a silica gel column (hexane:EA, 30:1) to afford the title compound (500 mg, 47%) as a yellow oil. MS: 284.5 (M+Na$^+$).

Step B: Methyl 2-(3-fluoro-4-(thiophen-3-yl)phenyl)propanoate

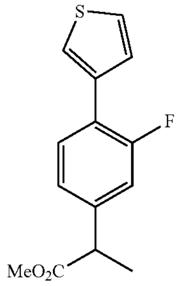 [SMILES: COC(=O)C(C)c1ccc(-c2ccsc2)c(F)c1]

Under Ar, to a solution of methyl 2-(4-bromo-3-fluorophenyl)propanoate (Step A, 500 mg, 1.92 mmol) in a mixed solvent of dioxane (10 mL) and water (2 mL) was added thiophen-3-ylboronic acid (245 mg, 1.915 mmol), $Na_2CO_3$ (609 mg, 5.75 mmol) and $PdCl_2$(dppf) (140 mg, 0.192 mmol); the reaction mixture was stirred at 100° C. for 6 h. After cooling down to room temperature and removal of volatiles, the residue was purified by silica gel column (hexane:EA, 20:1) to afford the title compound (450 mg, 89%) as a yellow oil. MS: 265.2 (M+H$^+$).

Step C: 2-(3-Fluoro-4-(thiophen-3-yl)phenyl)propan-1-ol

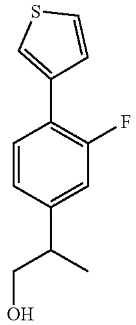 [SMILES: CC(CO)c1ccc(-c2ccsc2)c(F)c1]

Under Ar, to a solution of methyl 2-(3-fluoro-4-(thiophen-3-yl)phenyl)propanoate (Step B, 450 mg, 1.703 mmol) in dry THF (15 mL) was added LAH (64.6 mg, 1.7 mmol) at 0° C., then the reaction mixture was stirred for 1 h. $Na_2SO_4O \cdot 10H_2O$ was added to quench the reaction, the resulting mixture was diluted with EA and filtered off through celite. The filtrate was concentrated under reduced pressure to give a yellow oil, which was purified by silica gel column (hexane:EA, 5:1) to afford the title compound (300 mg, 75%) as a yellow oil. MS: 237.2 (M+H$^+$).

Step D: (4-(2-Fluoro-4-(1-hydroxypropan-2-yl)phenyl)thiophen-2-yl)boronic acid

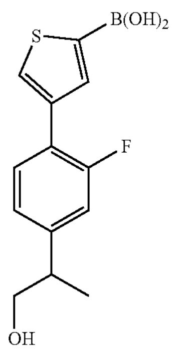 [SMILES: CC(CO)c1ccc(-c2csc(B(O)O)c2)c(F)c1]

Under Ar, to a solution of 2-(3-fluoro-4-(thiophen-3-yl)phenyl)propan-1-ol (Step C, 300 mg, 1.270 mmol) in dry THF (10 mL) was added LDA (3.2 mL, 2 M in THF, 6.35 mmol) at 0° C., and the mixture was stirred for 0.5 h; Triisopropyl borate (716 mg, 3.81 mmol) was added, and the reaction mixture was stirred at room temperature for 2 h. Aq. $NH_4Cl$ was added to quench the reaction and the resulting mixture was extracted with EA twice. The combined organic layer was washed with brine, dried over $Na_2SO_4$ and concentrated under reduced pressure to give the crude title compound as a yellow oil, which was directly used for the next step without purification. MS: 281.2 (M+H$^+$).

Step E: 2-((1H-pyrrolo[2,3-b]pyridin-5-yl)oxy)-4-(4-((2-(4-(2-fluoro-4-(1-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 72)

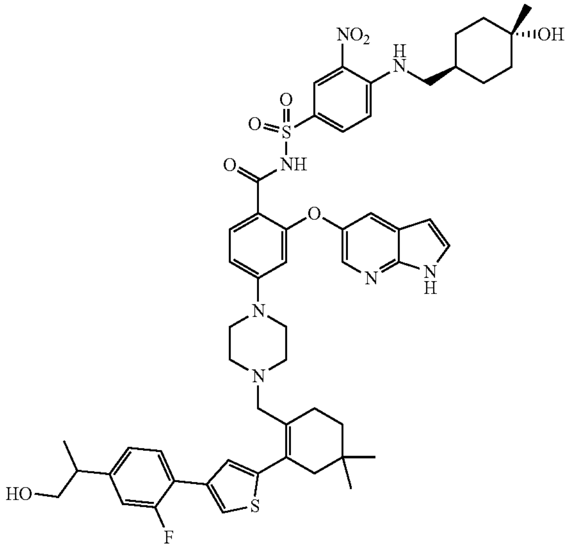 [SMILES: CC(CO)c1ccc(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Starting from Step D, essentially the same protocol of preparation of Example 62 was used to afford the example (10 mg) as a yellow solid. $^1$H NMR (400 MHz, DMSO-d$_6$) δ 11.67 (s, 1H), 8.60-8.51 (m, 2H), 8.06 (d, J=2.5 Hz, 1H), 7.80 (dd, J=9.2, 1.8 Hz, 1H), 7.68 (s, 1H), 7.62-7.47 (m, 4H), 7.24 (s, 1H), 7.18-7.03 (m, 3H), 6.72 (dd, J=9.0, 1.8 Hz, 1H), 6.40 (dd, J=3.2, 1.8 Hz, 1H), 6.26 (d, J=1.7 Hz, 1H), 4.70 (t, J=5.2 Hz, 1H), 4.27 (s, 1H), 3.58-3.46 (m, 2H), 3.31-3.25 (m, 2H), 3.17-3.02 (m, 6H), 2.91-2.80 (m, 1H), 2.39-2.19 (m, 6H), 2.18-2.10 (m, 2H), 1.77-1.52 (m, 5H), 1.45-1.29 (m, 4H), 1.28-1.14 (m, 5H), 1.13 (s, 3H), 0.96 (s, 6H). MS: 1021.2 (M+H$^+$).

Example 73: 2-((1H-pyrrolo[2,3-b]pyridin-5-yl)oxy)-4-(4-((2-(4-(2-fluoro-4-(2-hydroxy-2-methylpropyl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

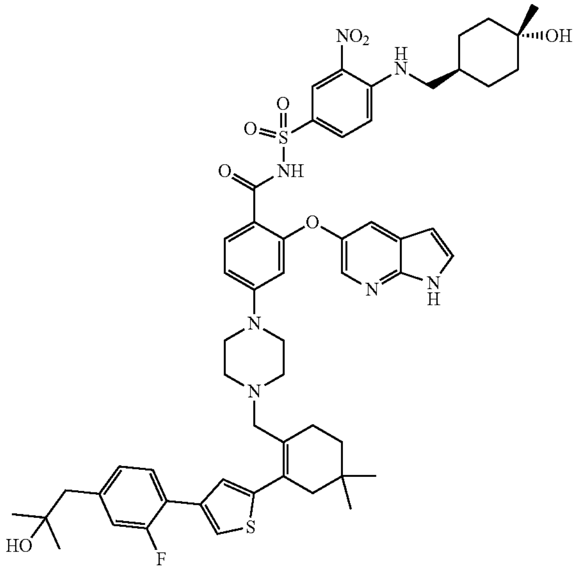 [SMILES: CC(C)(O)Cc1ccc(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Step A: Methyl 2-(3-fluoro-4-(thiophen-3-yl)phenyl)acetate

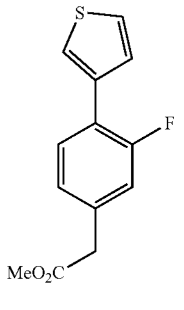 [SMILES: COC(=O)Cc1ccc(-c2ccsc2)c(F)c1]

Under Ar, to a solution of thiophen-3-ylboronic acid (311 mg, 2.43 mmol) in a mixed solvent of dioxane (10 mL) and water (2 mL) was added methyl 2-(4-bromo-3-fluorophenyl)acetate (500 mg, 2.03 mmol), $Na_2CO_3$ (643 mg, 6.07 mmol) and $PdCl_2$(dppf) (148 mg, 0.202 mmol); then the reaction mixture was stirred at 100° C. for 6 h. After cooling down to room temperature and removal of volatiles, the residue was purified by silica gel column (hexane:EA, 30:1) to afford the title compound (490 mg, 97%) as a yellow oil. $^1$H NMR (400 MHz, $CDCl_3$) δ 7.65-7.61 (m, 1H), 7.56 (t, J=8.0 Hz, 1H), 7.47-7.40 (m, 2H), 7.15 (s, 1H), 7.12 (s, 1H), 3.76 (s, 3H), 3.68 (s, 2H).

Step B: 1-(3-Fluoro-4-(thiophen-3-yl)phenyl)-2-methylpropan-2-ol

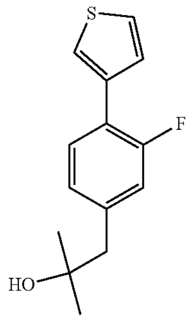 [SMILES: CC(C)(O)Cc1ccc(-c2ccsc2)c(F)c1]

Under Ar, to a solution of methyl 2-(3-fluoro-4-(thiophen-3-yl)phenyl)acetate (Step A, 400 mg, 1.598 mmol) in dry THF (10 mL) was added MeMgBr (2.66 mL, 3 M in 2-MeTHF, 7.99 mmol) at 0° C., then the reaction mixture was stirred for 2 h. Aq. $NH_4Cl$ was added to quench the reaction, and the resulting mixture was extracted with EA twice. The combined organic layers were washed with brine, dried over $Na_2SO_4$ and concentrated under reduced pressure to give a yellow oil, which was purified by silica gel column (hexane:EA, 5:1) to afford the title compound (240 mg, 60%) as a colorless oil. $^1$H NMR (400 MHz, $CDCl_3$) δ 7.65-7.62 (m, 1H), 7.54 (t, J=8.1 Hz, 1H), 7.48-7.45 (m, 1H), 7.43 (dd, J=5.0, 2.9 Hz, 1H), 7.09 (s, 1H), 7.07-7.04 (m, 1H), 2.82 (s, 2H), 1.30 (s, 6H).

Step C: (4-(2-Fluoro-4-(2-hydroxy-2-methylpropyl)phenyl)thiophen-2-yl)boronic acid

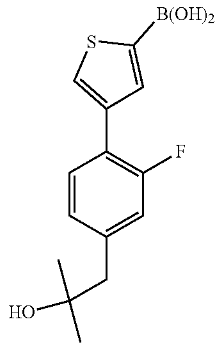 [SMILES: CC(C)(O)Cc1ccc(-c2csc(B(O)O)c2)c(F)c1]

Under Ar, to a solution of 1-(3-fluoro-4-(thiophen-3-yl)phenyl)-2-methylpropan-2-ol (Step B, 100 mg, 0.399 mmol) in dry THF (10 mL) was added LDA (1 mL, 2 M in THF, 2 mmol) at 0° C., and the mixture was stirred for 0.5 h; triisopropyl borate (225 mg, 1.2 mmol) was added, and the reaction mixture was stirred at room temperature for 2 h. Aq. $NH_4Cl$ was added to quench the reaction, and the resulting mixture was extracted with EA twice. The combined organic layers were washed with brine, dried over $Na_2SO_4$ and concentrated under reduced pressure to give the crude title compound as a yellow oil, which was directly used for the next step without purification. MS: 295.2 (M+H[+]).

Step D: 2-((1H-pyrrolo[2,3-b]pyridin-5-yl)oxy)-4-(4-((2-(4-(2-fluoro-4-(2-hydroxy-2-methylpropyl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 73)

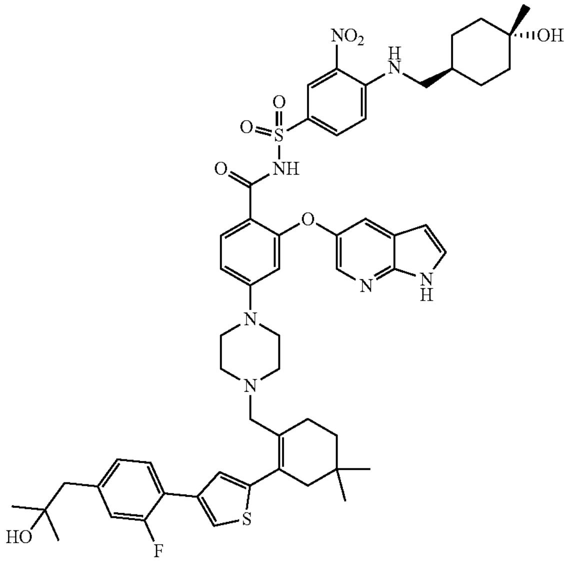 [SMILES: CC(C)(O)Cc1ccc(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Starting from Step C, essentially the same protocol of preparation of Example 62 was used to afford the example (20 mg) as a yellow solid. $^1$H NMR (400 MHz, DMSO-$d_6$) δ 11.64 (s, 1H), 8.58-8.46 (m, 2H), 8.04 (d, J=2.4 Hz, 1H), 7.77 (d, J=8.7 Hz, 1H), 7.70 (s, 1H), 7.61-7.52 (m, 2H), 7.48 (d, J=2.5 Hz, 2H), 7.26 (s, 1H), 7.12 (d, J=12.8 Hz, 1H), 7.08 (d, J=8.0 Hz, 1H), 7.02 (d, J=9.4 Hz, 1H), 6.72 (d, J=7.2 Hz, 1H), 6.38 (s, 1H), 6.27 (s, 1H), 4.41 (s, 1H), 4.27 (s, 1H), 3.30-3.25 (m, 2H), 3.16-3.01 (m, 6H), 2.69 (s, 2H), 2.39-2.19 (m, 6H), 2.18-2.08 (m, 2H), 1.77-1.52 (m, 6H), 1.45-1.31 (m, 5H), 1.13 (s, 3H), 1.10 (s, 6H), 0.96 (s, 6H); MS: 1035.2 (M+H[+]).

Example 74: 2-((1H-pyrrolo[2,3-b]pyridin-5-yl)oxy)-4-(4-((2-(4-(2,6-difluoro-4-(1-hydroxy-2-methylpropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

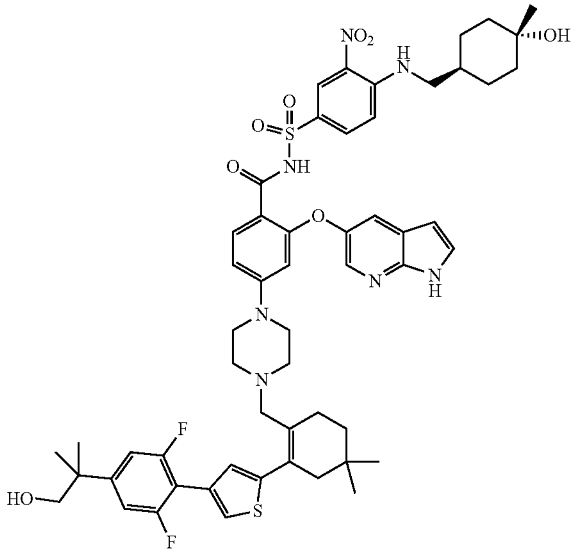 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(C(C)(C)CO)cc3F)cs2)C1]

Step A: 2-(3,5-Difluorophenyl)-2-methylpropanenitrile

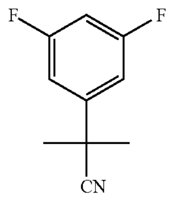

Under Ar, to a solution of 2-(3,5-difluorophenyl)acetonitrile (1 g, 6.53 mmol) in dry THF (20 mL) was added LDA (9.8 mL, 2 M in THF, 19.59 mmol) at −50° C., then the mixture was stirred for 0.5 h. MeI (3.71 g, 26.1 mmol) was added slowly, and the reaction mixture was stirred at room temperature for 2 h. Aq. $NH_4Cl$ was added to quench the reaction, and the resulting mixture was extracted with EA twice. The combined organic layers were washed with brine, dried over $Na_2SO_4$ and concentrated under reduced pressure to give a yellow oil, which was purified by silica gel column (hexane:EA, 20:1) to afford the title compound (1 g, 85%) as a yellow oil. $^1H$ NMR (400 MHz, $CDCl_3$) δ 7.09-7.02 (m, 2H), 6.86-6.77 (m, 1H), 1.76 (s, 6H).

Step B: 2-(3,5-Difluoro-4-iodophenyl)-2-methylpropanenitrile

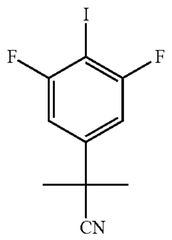

Under Ar, to a solution of 2-(3,5-difluorophenyl)-2-methylpropanenitrile (Step A, 200 mg, 1.11 mmol) in dry THF (5 mL) was added nBuLi (0.54 mL, 2.5 M in n-hexane, 1.33 mmol) dropwise at −60° C., then the mixture was stirred for 0.5 h. A solution of iodine (420 mg, 1.66 mmol) in dry THF was added at −60° C. dropwise, and the reaction mixture was allowed to warm up to room temperature and stirred for 2 h. Aq. $NH_4Cl$ was added to quench the reaction, and the resulting mixture was extracted with EA twice. The combined organic layers were washed with aq. $Na_2S_2O_3$ and brine, dried over $Na_2SO_4$ and concentrated under reduced pressure to afford the title compound (230 mg, 68%) as a yellow solid. $^1H$ NMR (400 MHz, $CDCl_3$) δ 7.10-7.04 (m, 2H), 1.76 (s, 6H).

Step C: 2-(3,5-Difluoro-4-(thiophen-3-yl)phenyl)-2-methylpropanenitrile

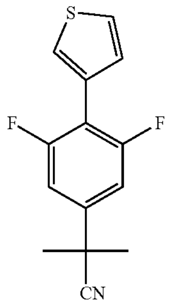 [SMILES: CC(C)(C#N)c1cc(F)c(-c2ccsc2)c(F)c1]

Under Ar, to a solution of 2-(3,5-difluoro-4-iodophenyl)-2-methylpropanenitrile (Step B, 230 mg, 0.75 mmol) in a mixed solvent of dioxane (10 mL) and water (2 mL) was added thiophen-3-ylboronic acid (96 mg, 0.749 mmol), $Na_2CO_3$ (238 mg, 2.25 mmol) and $PdCl_2(dppf)$ (54.8 mg, 0.075 mmol), the reaction mixture was stirred at 100° C. for 6 h. After cooling down to room temperature and removal of volatiles, the residue was purified by silica gel column (hexane:EA, 20:1) to afford the title compound (190 mg, 96%) as a white solid. $^1H$ NMR (400 MHz, $CDCl_3$) δ 7.69 (s, 1H), 7.45 (s, 2H), 7.19-7.11 (m, 2H), 1.78 (s, 6H).

Step D: 2-(3,5-Difluoro-4-(thiophen-3-yl)phenyl)-2-methylpropanoic acid

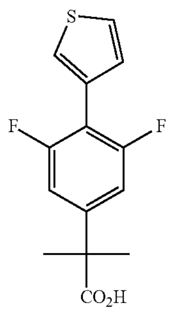 [SMILES: CC(C)(C(=O)O)c1cc(F)c(-c2ccsc2)c(F)c1]

To a solution of 2-(3,5-difluoro-4-(thiophen-3-yl)phenyl)-2-methylpropanenitrile (Step C, 500 mg, 1.90 mmol) in a mixed solvent of EtOH (3 mL) and water (3 mL) was added NaOH (1.14 g, 28.5 mmol), the reaction mixture was refluxed for 24 h. After cooling down to room temperature, the mixture was treated with 2 N HCl to adjust to pH 2-3 and extracted with EA twice. The combined organic layer was washed with brine, dried over $Na_2SO_4$ and concentrated under reduced pressure to give the crude title compound (500 mg) as a yellow solid, which was directly used for the next step without purification. MS: 283.2 ($M+H^+$).

Step E: 2-(3,5-Difluoro-4-(thiophen-3-yl)phenyl)-2-methylpropan-1-ol

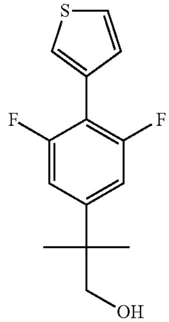

Under Ar, to a solution of 2-(3,5-difluoro-4-(thiophen-3-yl)phenyl)-2-methylpropanoic acid (Step D, 500 mg, 1.77 mmol) in dry THF (20 mL) was added $BH_3$·THF (3.54 mL, 1 M in THF, 3.54 mmol) at 0° C., the reaction mixture was stirred at room temperature for 16 h. Aq. $NH_4Cl$ was added to quench the reaction, and the resulting mixture was extracted with EA twice. The combined organic layers were washed with brine, dried over $Na_2SO_4$ and concentrated under reduced pressure to give a yellow oil, which was purified by silica gel column (hexane:EA, 5:1) to afford the title compound (220 mg, 46%) as a colorless oil. MS: 269.3 ($M+H^+$).

Step F: (4-(2,6-Difluoro-4-(1-hydroxy-2-methylpropan-2-yl)phenyl)thiophen-2-yl)boronic acid

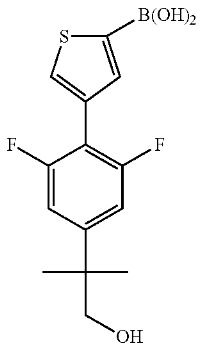 [SMILES: CC(C)(CO)c1cc(F)c(-c2csc(B(O)O)c2)c(F)c1]

Under Ar, to a solution of 2-(3,5-difluoro-4-(thiophen-3-yl)phenyl)-2-methylpropan-1-ol (Step E, 100 mg, 0.37 mmol) in THF (10 mL) was added LDA (0.93 mL, 2 M in THF, 1.863 mmol) at 0° C., the mixture was stirred for 0.5 h; triisopropyl borate (210 mg, 1.12 mmol) was added, and the reaction mixture was stirred at room temperature for 2 h. Aq. $NH_4Cl$ was added to quench the reaction, and the resulting mixture was extracted with EA twice. The combined organic layers were washed with brine, dried over $Na_2SO_4$ and concentrated under reduced pressure to give the crude title compound as a yellow oil, which was directly used for the next step without purification. MS: 313.2 ($M+H^+$).

Step G: 2-((1H-pyrrolo[2,3-b]pyridin-5-yl)oxy)-4-(4-((2-(4-(2,6-difluoro-4-(1-hydroxy-2-methylpropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 74)

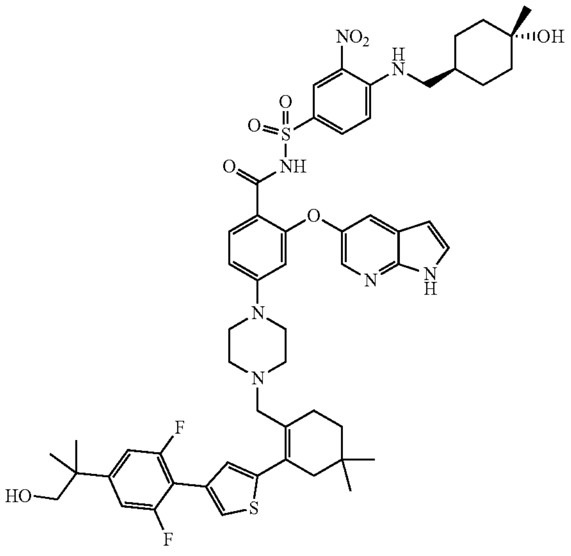 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(C(C)(C)CO)cc3F)cs2)C1]

Starting from Step F, essentially the same protocol of preparation of Example 62 was used to afford the example (8 mg) as a yellow solid. $^1$H NMR (400 MHz, DMSO-$d_6$) δ 11.68 (s, 1H), 8.57 (s, 2H), 8.06 (d, J=2.4 Hz, 1H), 7.81 (d, J=8.9 Hz, 1H), 7.66 (s, 1H), 7.56-7.49 (m, 3H), 7.18 (s, 1H), 7.15 (s, 1H), 7.11-7.06 (m, 2H), 6.73 (d, J=8.6 Hz, 1H), 6.40 (s, 1H), 6.26 (s, 1H), 4.79 (t, J=5.4 Hz, 1H), 4.26 (s, 1H), 3.45 (d, J=5.3 Hz, 2H), 3.32-3.27 (m, 2H), 3.18-3.00 (m, 6H), 2.39-2.21 (m, 6H), 2.17-2.10 (m, 2H), 1.76-1.52 (m, 6H), 1.45-1.30 (m, 5H), 1.24 (s, 6H), 1.13 (s, 3H), 0.96 (s, 6H); MS: 1053.2 (M+H$^+$).

Example 75: 2-((1H-pyrrolo[2,3-b]pyridin-5-yl)oxy)-4-(4-((2-(4-(2-fluoro-5-(2-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

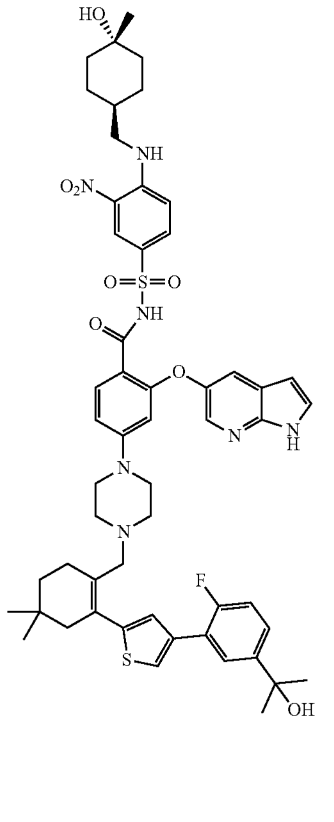 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3cc(C(C)(C)O)ccc3F)cs2)C1]

Essentially the same protocol of preparation of Example 62 was used to afford the example (35 mg) as a yellow solid. $^1$H NMR (400 MHz, DMSO-$d_6$) δ 11.65 (s, 1H), 11.44 (brs, 1H), 8.59-8.47 (m, 2H), 8.04 (d, J=2.6 Hz, 1H), 7.79 (d, J=7.5 Hz, 1H), 7.71-7.65 (m, 2H), 7.52 (d, J=1.6 Hz, 1H), 7.51-7.46 (m, 2H), 7.42-7.34 (m, 1H), 7.25 (s, 1H), 7.18-7.11 (m, 1H), 7.07 (d, J=9.3 Hz, 1H), 6.70 (dd, J=9.0, 2.0 Hz, 1H), 6.38 (dd, J=3.3, 1.8 Hz, 1H), 6.22 (d, J=1.9 Hz, 1H), 5.04 (s, 1H), 4.21 (s, 1H), 3.28-3.23 (m, 2H), 3.16-3.07 (m, 4H), 3.03 (s, 2H), 2.39-2.26 (m, 4H), 2.26-2.18 (m, 2H), 2.12 (s, 2H), 1.74-1.59 (m, 3H), 1.59-1.50 (m, 2H), 1.42 (s, 6H), 1.41-1.37 (m, 2H), 1.37-1.29 (m, 2H), 1.19-1.06 (m, 5H), 0.94 (s, 6H); MS: 1021.7 (M+H$^+$).

Example 76: 2-((1H-pyrrolo[2,3-b]pyridin-5-yl)oxy)-4-(4-((2-(4-(2-fluoro-4-(2-methoxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

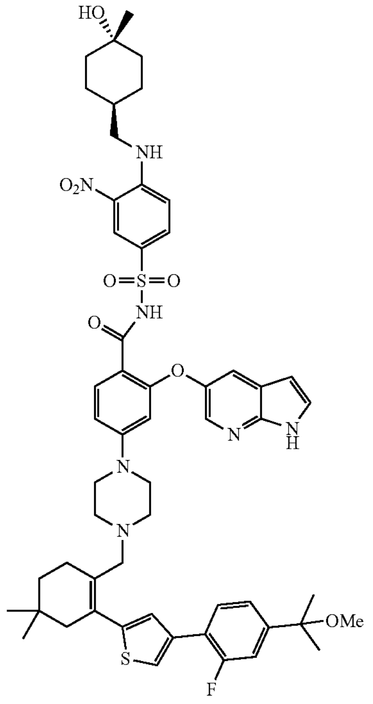 [SMILES: COC(C)(C)c1ccc(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Step A: 3-(2-Fluoro-4-(2-methoxypropan-2-yl)phenyl)thiophene

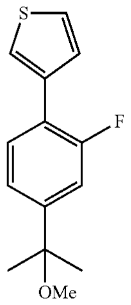 [SMILES: COC(C)(C)c1ccc(-c2ccsc2)c(F)c1]

In a flame-dried over 100 mL round-bottomed flask, 2-(3-fluoro-4-(thiophen-3-yl)phenyl)propan-2-ol (Step B of Example 62, 250 mg, 1.06 mmol) was dissolved into a mixed solvent of dry $CH_2Cl_2$ (4 mL) and MeOH (4 mL) under argon at 25° C. to give a solution; 4-methylbenzenesulfonic acid (36 mg, 0.212 mmol) was added and the reaction mixture was stirred at 25° C. for 3 h. Sat. $NaHCO_3$ (10 mL) was added to the reaction mixture followed by extraction with dichloromethane (10 mL×2). The combined organic layers were dried over $Na_2SO_4$, and concentrated under reduced pressure to give a yellow oil, which was loaded onto a silica gel column and eluted with ethyl acetate and hexane (1:50) to afford the title compound (200 mg, 76%) as a light yellow oil. $^1$H NMR (400 MHz, DMSO-$d_6$) δ 7.83 (dt, J=2.6, 1.2 Hz, 1H), 7.69 (t, J=7.4 Hz, 1H), 7.67-7.65 (m, 1H), 7.50 (dt, J=5.1, 1.4 Hz, 1H), 7.27 (t, J=2.0 Hz, 1H), 7.24 (dd, J=7.1, 1.7 Hz, 1H), 3.02 (s, 3H), 1.47 (s, 6H); MS: 219.6 (M−MeOH+H$^+$).

Step B: (4-(2-Fluoro-4-(2-methoxypropan-2-yl)phenyl)thiophen-2-yl)boronic acid

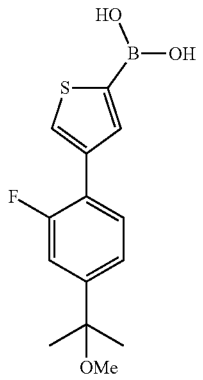 [SMILES: COC(C)(C)c1ccc(-c2csc(B(O)O)c2)c(F)c1]

In a flame-dried over 100 mL round-bottomed flask, 3-(2-fluoro-4-(2-methoxypropan-2-yl)phenyl)thiophene (Step A, 200 mg, 0.8 mmol) was dissolved into dry THF (10 mL) under argon at 0° C. to give a solution; LDA (1.6 mL, 2 M in THF, 3.19 mmol) was added at 0° C., and the mixture was stirred at 0° C. for 1 h; triisopropyl borate (450 mg, 2.4 mmol) was added dropwise, the reaction mixture was stirred at 0° C. for 0.5 h, allowed to gradually warm up to room temperature and stirred for 12 h. MeOH (10 mL) was added to quench the reaction, and the resulting mixture was partitioned with aq. $NH_4Cl$ and EA. The aqueous layer was extracted with EA twice, the combined organic layers were dried over $Na_2SO_4$, and concentrated under reduced pressure to give the crude title compound as a yellow oil, which was directly used for the next step without purification.

Step C: 2-((1H-pyrrolo[2,3-b]pyridin-5-yl)oxy)-4-(4-((2-(4-(2-fluoro-4-(2-methoxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 76)

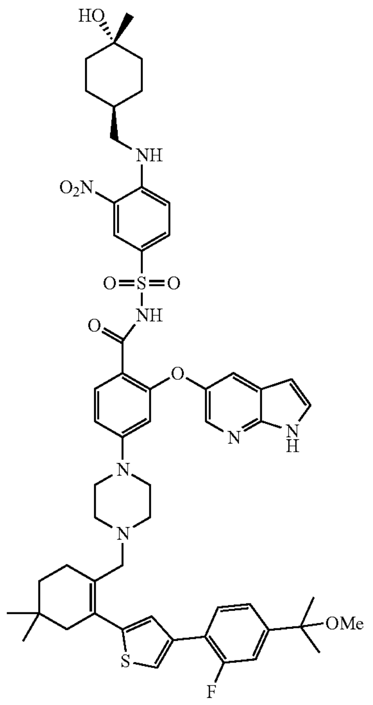 [SMILES: COC(C)(C)c1ccc(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Starting from Step B, essentially the same protocol of preparation of Example 62 was used to afford the example (3 mg) as a yellow solid. $^1$H NMR (400 MHz, DMSO-$d_6$) δ 11.58 (s, 1H), 8.55-8.39 (m, 2H), 7.99 (s, 1H), 7.75-7.69 (m, 2H), 7.65 (t, J=8.3 Hz, 1H), 7.53 (d, J=8.7 Hz, 1H), 7.49-7.34 (m, 2H), 7.26-7.23 (m, 2H), 7.21 (dd, J=6.3, 1.6 Hz, 1H), 7.18 (s, 1H), 6.68 (dd, J=8.7, 1.7 Hz, 1H), 6.34 (s, 1H), 6.25 (s, 1H), 4.21 (s, 1H), 3.27-3.22 (m, 2H), 3.12-3.06 (m, 4H), 3.03 (s, 2H), 3.01 (s, 3H), 2.35-2.27 (m, 4H), 2.25-2.19 (m, 2H), 2.12 (s, 2H), 1.74-1.60 (m, 3H), 1.59-1.51 (m, 2H), 1.45 (s, 6H), 1.41-1.36 (m, 2H), 1.35-1.29 (m, 2H), 1.19-1.12 (m, 2H), 1.10 (s, 3H), 0.94 (s, 6H); MS: 1033.9 (M+H$^+$).

Example 77: 2-((1H-pyrrolo[2,3-b]pyridin-5-yl)oxy)-4-(4-((2-(4-(2,6-difluoro-4-(1-hydroxycyclobutyl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

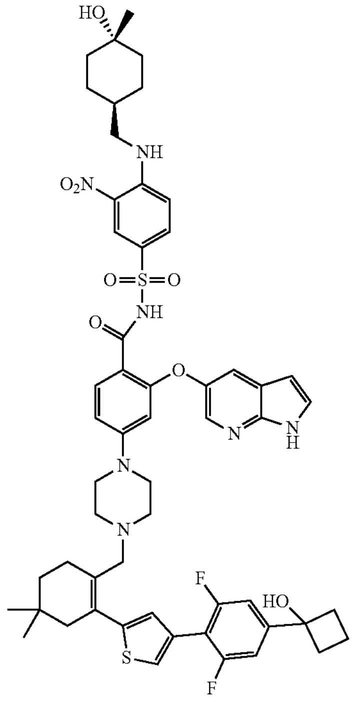 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(C4(O)CCC4)cc3F)cs2)C1]

Step A: 1-(4-Bromo-3,5-difluorophenyl)cyclobutan-1-ol

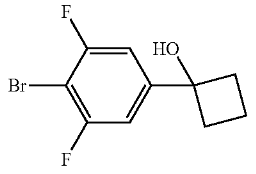 [SMILES: OC1(c2cc(F)c(Br)c(F)c2)CCC1]

In a flame-dried over 100 mL round-bottomed flask, 2-bromo-1,3-difluoro-5-iodobenzene (1.5 g, 4.70 mmol) was dissolved into dry THF (30 mL) under argon at 0° C. to give a solution, i-PrMgCl–LiCl (683 mg, 4.70 mmol) was added at 0° C. and the mixture was stirred at 0° C. for 1 h; cyclobutanone (330 mg, 4.70 mmol) was then followed in one portion at 0° C., the reaction mixture was allowed to gradually warm up to room temperature and stirred for 16 h. MeOH (10 mL) was added to quench the reaction and the resulting mixture was partitioned with aq. $NH_4Cl$ and EA. The aqueous layer was extracted with EA twice, the combined organic layers were dried over $Na_2SO_4$, and concentrated under reduced pressure to give a yellow oil, which was loaded onto a silica gel column and eluted with ethyl acetate and hexane (1:5) to afford the title compound (450 mg, 36%) as an off-white solid. $^1H$ NMR (400 MHz, DMSO-$d_6$) δ 7.38 (d, J=8.0 Hz, 1H), 5.74 (s, 1H), 2.66-2.55 (m, 2H), 2.36-2.19 (m, 3H), 1.87-1.73 (m, 1H); MS: 247.1 (M−$H_2O$+$H^+$).

Step B: 1-(3,5-Difluoro-4-(thiophen-3-yl)phenyl)cyclobutan-1-ol

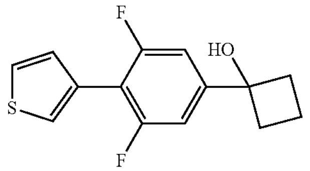 [SMILES: OC1(c2cc(F)c(-c3ccsc3)c(F)c2)CCC1]

In a flame-dried over 100 mL round-bottomed flask, 1-(4-bromo-3,5-difluorophenyl)cyclobutan-1-ol (Step A, 450 mg, 1.71 mmol), thiophen-3-ylboronic acid (274 mg, 2.14 mmol), and $PdCl_2$(dppf)·$CH_2Cl_2$ (140 mg, 0.171 mmol) were dissolved into a mixed solvent of 1,4-dioxane (10 mL) and water (2.5 mL) under argon to give a solution. $Na_2CO_3$ (544 mg, 5.13 mmol) was added and the reaction mixture was stirred at 100° C. for 16 h. After cooling down to room temperature, sat. $NaHCO_3$ (80 mL) was added to the reaction mixture followed by extraction with ethyl acetate (80 mL×2). The combined organic layers were dried over $Na_2SO_4$, and concentrated under reduced pressure to give a yellow oil, which was loaded onto a silica gel column and eluted with ethyl acetate and hexane (1:50) to afford the title compound (410 mg, 90%) as an off-white solid. $^1H$ NMR (400 MHz, DMSO-$d_6$) δ 8.05 (dd, J=2.9, 1.4 Hz, 1H), 7.68-7.61 (m, 2H), 7.41 (d, J=10.3 Hz, 2H), 5.64 (s, 1H), 2.68-2.54 (m, 2H), 2.36-2.16 (m, 3H), 1.86-1.75 (m, 1H); MS: 249.5 (M−$H_2O$+$H^+$).

Step C: (4-(2,6-Difluoro-4-(1-hydroxycyclobutyl)phenyl)thiophen-2-yl)boronic acid

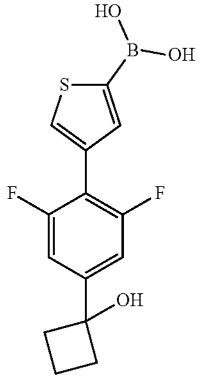 [SMILES: OB(O)c1cc(-c2c(F)cc(C3(O)CCC3)cc2F)cs1]

In a flame-dried over 100 mL round-bottomed flask, 1-(3,5-difluoro-4-(thiophen-3-yl)phenyl)cyclobutan-1-ol (Step B, 400 mg, 1.5 mmol) was dissolved into dry THF (30 mL) under argon at 0° C. to give a solution; LDA (2.4 mL, 2 M in THF, 4.72 mmol) was added at 0° C. and the mixture was stirred for 1 h; Triisopropyl borate (4.85 g, 4.51 mmol) was added dropwise; the reaction mixture was stirred at 0° C. for 0.5 h, allowed to gradually warm up to room temperature and stirred for 12 h. MeOH (10 mL) was added to quench the reaction, and the resulting mixture was partitioned with aq. $NH_4Cl$ and EA. The aqueous layer was extracted with EA twice, the combined organic layers were dried over $Na_2SO_4$, and concentrated under reduced pressure to give the crude title compound as a yellow oil, which was directly used for the next step without purification. MS: 292.9 ($M-H_2O+H^+$).

Step D: 2-((1H-pyrrolo[2,3-b]pyridin-5-yl)oxy)-4-(4-((2-(4-(2,6-difluoro-4-(1-hydroxycyclobutyl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 77)

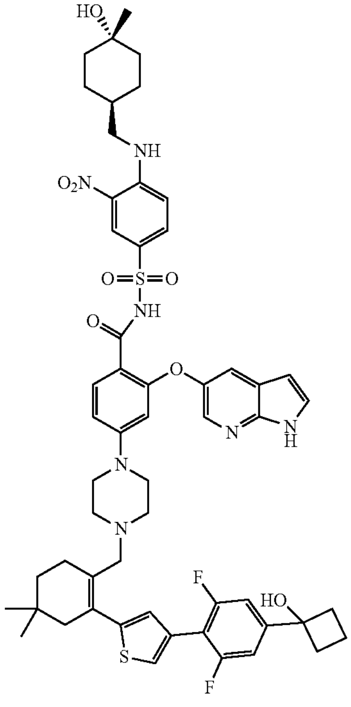 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(C4(O)CCC4)cc3F)cs2)C1]

Starting from Step C, essentially the same protocol of preparation of Example 62 was used to afford the example (2.4 mg) as a yellow solid. $^1H$ NMR (400 MHz, DMSO-$d_6$) δ 11.62 (s, 1H), 8.55-8.43 (m, 2H), 8.03 (d, J=2.1 Hz, 1H), 7.94 (d, J=1.3 Hz, 1H), 7.76 (d, J=7.9 Hz, 1H), 7.56 (d, J=8.8 Hz, 1H), 7.50-7.43 (m, 2H), 7.41 (d, J=1.2 Hz, 1H), 7.40 (s, 1H), 7.38 (s, 1H), 7.00 (d, J=5.6 Hz, 1H), 6.71 (d, J=8.9 Hz, 1H), 6.38 (s, 1H), 6.27 (s, 1H), 5.64 (s, 1H), 4.24 (s, 1H), 3.29-3.25 (m, 2H), 3.15-3.08 (m, 4H), 3.05 (s, 2H), 2.67-2.57 (m, 2H), 2.35-2.30 (m, 4H), 2.28-2.20 (m, 3H), 2.14 (s, 2H), 2.08-1.98 (m, 1H), 1.86-1.77 (m, 1H), 1.77-1.62 (m, 3H), 1.62-1.53 (m, 2H), 1.45-1.38 (m, 2H), 1.38-1.32 (m, 2H), 1.21-1.10 (m, 6H), 0.97 (s, 6H); MS: 1051.5 ($M+H^+$).

Example 78: 2-((1H-pyrrolo[2,3-b]pyridin-5-yl)oxy)-4-(4-((2-(4-(2-fluoro-4-(1,1,1-trifluoro-2-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

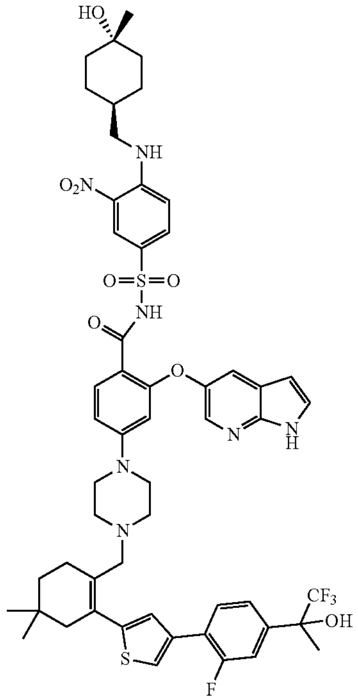 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(C)(O)C(F)(F)F)cc3F)cs2)C1]

Step A: 1-(3-Fluoro-4-(thiophen-3-yl)phenyl)ethan-1-one

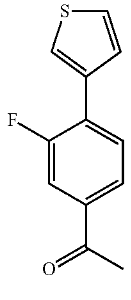

In an oven-dried over 250 mL round-bottomed flask, 1-(4-bromo-3-fluorophenyl)ethan-1-one (3 g, 13.82 mmol), thiophen-3-ylboronic acid (2.30 g, 17.97 mmol), and $Na_2CO_3$ (4.40 g, 41.5 mmol) were dissolved into 1,4-dioxane (100 mL) and water (20 mL) under argon to give a solution; $PdCl_2(dppf)\cdot CH_2Cl_2$ (1.13 g, 1.382 mmol) was added and the reaction mixture was heated to 100° C. for 12 h. After cooling down to room temperature, sat. $NaHCO_3$ (50 mL) was added to the reaction mixture followed by extraction with ethyl acetate (50 mL×3). The combined organic layers were dried over $Na_2SO_4$, and concentrated under reduced pressure to give a yellow oil, which was loaded onto a silica gel column and eluted with ethyl acetate and hexane (1:10) to afford the title compound (2.5 g, 82%) as an off-white solid. $^1H$ NMR (400 MHz, DMSO-$d_6$) δ 8.06-8.00 (m, 1H), 7.90 (t, J=8.0 Hz, 1H), 7.85-7.78 (m, 2H), 7.72 (dd, J=5.0, 3.0 Hz, 1H), 7.59 (d, J=5.1 Hz, 1H), 2.60 (s, 3H); MS: 221.4 (M+H$^+$).

Step B: 1,1,1-trifluoro-2-(3-fluoro-4-(thiophen-3-yl)phenyl)propan-2-ol

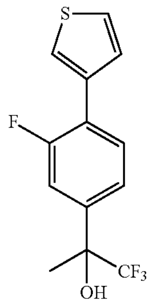 [SMILES: CC(O)(c1ccc(-c2ccsc2)c(F)c1)C(F)(F)F]

In an oven-dried over 250 mL round-bottomed flask, 1-(3-fluoro-4-(thiophen-3-yl)phenyl)ethan-1-one (Step A, 500 mg, 2.27 mmol) and trimethyl(trifluoromethyl)silane (646 mg, 4.54 mmol) were dissolved into dry THF (20 mL) under argon to give a solution; TBAF (1.19 g, 4.54 mmol) was added and the reaction mixture was stirred at room temperature for 12 h. After removal of volatiles, the residue was loaded onto a silica gel column and eluted with ethyl acetate and hexane (1:10) to afford the title compound (560 mg, 85%) as an off-white solid. $^1H$ NMR (400 MHz, DMSO-$d_6$) δ 7.91-7.86 (m, 1H), 7.75 (t, J=8.4 Hz, 1H), 7.68 (dd, J=5.0, 3.0 Hz, 1H), 7.52 (dt, J=5.0, 1.4 Hz, 1H), 7.50-7.42 (m, 2H), 6.77 (s, 1H), 1.71 (s, 3H); MS: 291.2 (M+H$^+$).

Step C: (4-(2-fluoro-4-(1,1,1-trifluoro-2-hydroxypropan-2-yl)phenyl)thiophen-2-yl)boronic acid

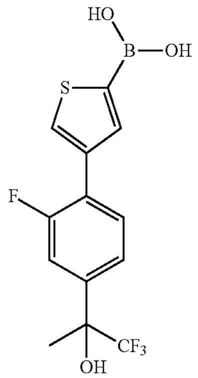 [SMILES: CC(O)(c1ccc(-c2csc(B(O)O)c2)c(F)c1)C(F)(F)F]

In a flame-dried over 100 mL round-bottomed flask, 1,1,1-trifluoro-2-(3-fluoro-4-(thiophen-3-yl)phenyl)propan-2-ol (Step B, 290 mg, 1 mmol) was dissolved into dry THF (10 mL) under argon at 0° C. to give a solution; LDA (1.5 mL, 2 M in THF, 3 mmol) was added at 0° C. and the mixture was stirred for 1 h; Triisopropyl borate (564 mg, 3 mmol) was added dropwise; the reaction mixture was stirred at 0° C. for 0.5 h, allowed to gradually warm up to room temperature and stirred for 16 h. MeOH (10 mL) was added to quench the reaction, and the resulting mixture was partitioned with aq. $NH_4Cl$ and EA. The aqueous layer was extracted with EA twice, the combined organic layers were dried over $Na_2SO_4$, and concentrated under reduced pressure to give the crude title compound as a yellow oil, which was directly used for the next step without purification. MS: 335.1 (M+H$^+$).

Step D: 2-((1H-pyrrolo[2,3-b]pyridin-5-yl)oxy)-4-(4-((2-(4-(2-fluoro-4-(1,1,1-trifluoro-2-hydroxypropan-2-yl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 78)

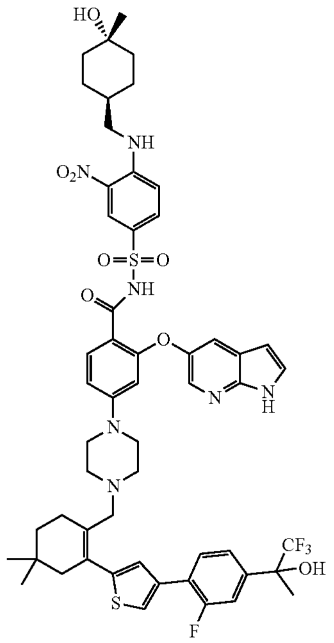 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3ccc(C(C)(O)C(F)(F)F)cc3F)cs2)C1]

Starting from Step C, essentially the same protocol of preparation of Example 62 was used to afford the example (50 mg) as a yellow solid. $^1H$ NMR (400 MHz, DMSO-$d_6$) δ 11.68 (s, 1H), 8.60-8.50 (m, 2H), 8.08-8.03 (m, 1H), 7.82-7.77 (m, 2H), 7.74 (t, J=8.4 Hz, 1H), 7.57-7.42 (m, 5H), 7.29 (s, 1H), 7.06 (d, J=9.3 Hz, 1H), 6.79 (s, 1H), 6.73 (d, J=9.1 Hz, 1H), 6.39 (s, 1H), 6.26 (s, 1H), 4.26 (s, 1H), 3.33-3.28 (m, 2H), 3.17-3.10 (m, 4H), 3.06 (s, 2H), 2.39-2.30 (m, 4H), 2.29-2.20 (m, 2H), 2.14 (s, 2H), 1.79-1.64 (m, 6H), 1.61-1.51 (m, 2H), 1.46-1.31 (m, 4H), 1.21-1.07 (m, 5H), 0.97 (s, 6H); MS: 1075.8 (M+H$^+$).

Example 79: 2-((1H-pyrrolo[2,3-b]pyridin-5-yl)oxy)-4-(4-((2-(4-(1-hydroxy-1-methyl-2,3-dihydro-1H-inden-5-yl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

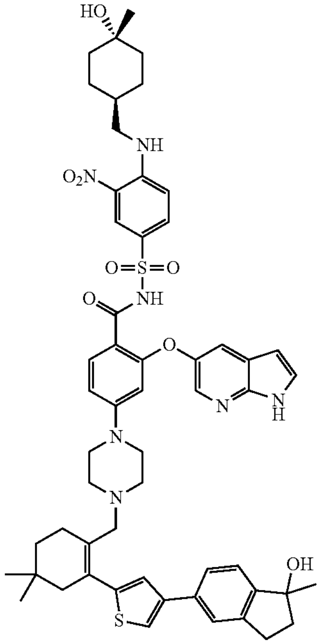

Essentially the same protocol of preparation of Example 69 was used to afford the example (48 mg) as a yellow solid. $^1$H NMR (400 MHz, DMSO-$d_6$) δ 11.61 (s, 1H), 8.56-8.43 (m, 2H), 8.00 (d, J=2.3 Hz, 1H), 7.74 (d, J=8.9 Hz, 1H), 7.65 (s, 1H), 7.52 (d, J=8.9 Hz, 1H), 7.50-7.41 (m, 4H), 7.32-7.25 (m, 2H), 6.99 (d, J=7.5 Hz, 1H), 6.69 (d, J=9.0 Hz, 1H), 6.35 (s, 1H), 6.24 (s, 1H), 4.95 (s, 1H), 4.22 (s, 1H), 3.29-3.23 (m, 2H), 3.14-3.07 (m, 4H), 3.03 (s, 2H), 2.96-2.85 (m, 1H), 2.80-2.68 (m, 1H), 2.35-2.26 (m, 4H), 2.25-2.17 (m, 2H), 2.12 (s, 2H), 2.05 (t, J=7.3 Hz, 2H), 1.74-1.60 (m, 3H), 1.58-1.49 (m, 2H), 1.41-1.36 (m, 5H), 1.36-1.28 (m, 2H), 1.18-1.10 (m, 2H), 1.10 (s, 3H), 0.94 (s, 6H); MS: 1015.6 (M+H$^+$).

Example 80: 2-((1H-pyrrolo[2,3-b]pyridin-5-yl)oxy)-4-(4-((2-(4-(4-(2-acetamidopropan-2-yl)-2,6-difluorophenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

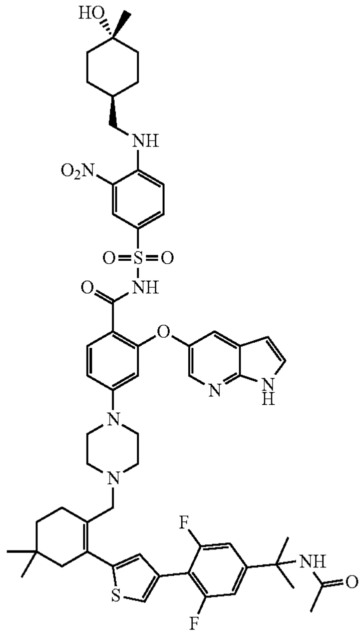 [SMILES: CC(=O)NC(C)(C)c1cc(F)c(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Step A: N-(2-(3,5-difluoro-4-(thiophen-3-yl)phenyl)propan-2-yl)acetamide

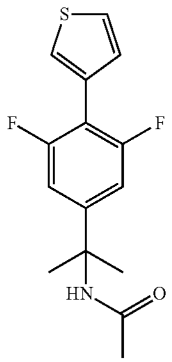 [SMILES: CC(=O)NC(C)(C)c1cc(F)c(-c2ccsc2)c(F)c1]

In a flame-dried over 100 mL round-bottomed flask, 2-(3,5-difluoro-4-(thiophen-3-yl)phenyl)propan-2-ol (prepared by using the same protocol of Step B of Example 62, 100 mg, 0.393 mmol) was dissolved into dry acetonitrile (5 mL) under argon at 25° C. to give a solution, Sulfuric acid (386 mg, 3.93 mmol) was added and the reaction mixture was stirred at 25° C. for 2 h, aq. $NaHCO_3$ (10 mL) was added slowly to the reaction mixture followed by extraction with ethyl acetate (20 mL×2). The combined organic layers were dried over $Na_2SO_4$, and concentrated under reduced pressure to give a yellow oil, which was loaded onto a silica gel column and eluted with ethyl acetate and hexane (1:2) to afford the title compound (100 mg, 86%) as an off-white solid. $^1$H NMR (400 MHz, DMSO-$d_6$) δ 8.15 (s, 1H), 7.80-7.73 (m, 1H), 7.72-7.64 (m, 1H), 7.37-7.27 (m, 1H), 7.07 (d, J=10.2 Hz, 2H), 1.85 (s, 3H), 1.53 (s, 6H); MS: 296.3 (M+H$^+$).

Step B: (4-(4-(2-Acetamidopropan-2-yl)-2,6-difluorophenyl)thiophen-2-yl)boronic acid

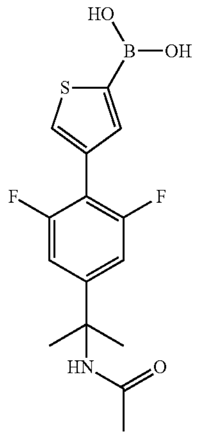 [SMILES: CC(=O)NC(C)(C)c1cc(F)c(-c2csc(B(O)O)c2)c(F)c1]

In a flame-dried over 100 mL round-bottomed flask, N-(2-(3,5-difluoro-4-(thiophen-3-yl)phenyl)propan-2-yl)acetamide (Step A, 200 mg, 0.68 mmol) was dissolved into dry THF (10 mL) under argon at 0° C. to give a solution; LDA (1 mL, 2 M in THF, 2 mmol) was added at 0° C. and the mixture was stirred for 1 h; triisopropyl borate (382 mg, 2.03 mmol) was added dropwise; the reaction mixture was stirred at 0° C. for 0.5 h, allowed to gradually warm up to room temperature and stirred for 16 h. MeOH (10 mL) was added to quench the reaction, and the resulting mixture was partitioned with aq. $NH_4Cl$ and EA. The aqueous layer was extracted with EA twice, the combined organic layers were dried over $Na_2SO_4$, and concentrated under reduced pressure to give the crude title compound as a yellow oil, which was directly used for the next step without purification. MS: 340.1 (M+H$^+$).

Step C: 2-((1H-pyrrolo[2,3-b]pyridin-5-yl)oxy)-4-(4-((2-(4-(4-(2-acetamidopropan-2-yl)-2,6-difluorophenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 80)

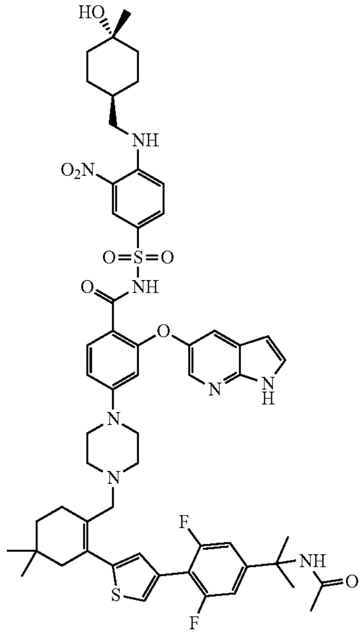 [SMILES: CC(=O)NC(C)(C)c1cc(F)c(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Starting from Step B, essentially the same protocol of preparation of Example 62 was used to afford the example (30 mg) as a yellow solid. $^1$H NMR (400 MHz, DMSO-$d_6$) δ 11.64 (s, 1H), 8.59-8.47 (m, 2H), 8.13 (s, 1H), 8.03 (d, J=2.2 Hz, 1H), 7.78 (d, J=9.5 Hz, 1H), 7.63 (s, 1H), 7.55-7.44 (m, 3H), 7.10-6.99 (m, 4H), 6.70 (d, J=9.8 Hz, 1H), 6.37 (s, 1H), 6.23 (s, 1H), 4.21 (s, 1H), 3.30-3.23 (m, 2H), 3.14-3.07 (m, 4H), 3.05-2.98 (m, 2H), 2.36-2.25 (m, 4H), 2.24-2.17 (m, 2H), 2.11 (s, 2H), 1.84 (s, 3H), 1.74-1.59 (m, 3H), 1.58-1.47 (m, 8H), 1.42-1.28 (m, 4H), 1.19-1.04 (m, 5H), 0.93 (s, 6H); MS: 1078.2 (M+H$^+$).

Example 81: 2-((1H-pyrrolo[2,3-b]pyridin-5-yl)oxy)-4-(4-((2-(4-(2,6-difluoro-4-(2-hydroxypropan-2-yl)phenyl)-5-methylthiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide

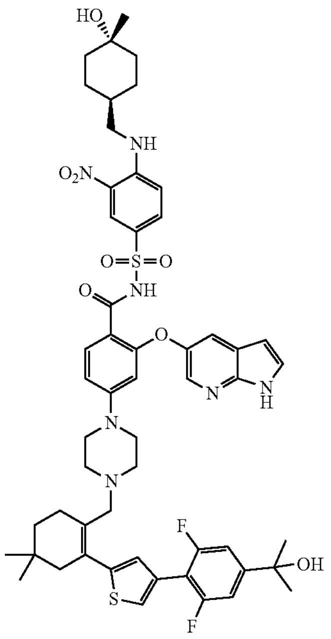 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(C(C)(C)O)cc3F)cs2)C1]

Essentially the same protocol of preparation of Example 63 was used to afford the example (30 mg) as a yellow solid. $^1$H NMR (400 MHz, DMSO-$d_6$) δ 11.63 (s, 1H), 8.60-8.41 (m, 2H), 8.01 (d, J=2.5 Hz, 1H), 7.74 (d, J=9.7 Hz, 1H), 7.52 (d, J=8.8 Hz, 1H), 7.49-7.38 (m, 2H), 7.22 (d, J=9.3 Hz, 2H), 7.00 (d, J=9.2 Hz, 1H), 6.72 (s, 1H), 6.69 (dd, J=9.0, 2.0 Hz, 1H), 6.35 (dd, J=3.2, 1.8 Hz, 1H), 6.24 (d, J=1.9 Hz, 1H), 5.28 (s, 1H), 4.23 (s, 1H), 3.26 (t, J=6.4 Hz, 2H), 3.12-3.03 (m, 6H), 2.34-2.25 (m, 4H), 2.22 (s, 3H), 2.21-2.15 (m, 2H), 2.11-2.04 (m, 2H), 1.74-1.62 (m, 3H), 1.58-1.49 (m, 2H), 1.43 (s, 6H), 1.40-1.28 (m, 4H), 1.18-1.10 (m, 2H), 1.10 (s, 3H), 0.91 (s, 6H); MS: 1053.5 (M+H$^+$).

Example 82: 2-(4-(5-(2-((4-(3-((1H-pyrrolo[2,3-b]pyridin-5-yl)oxy)-4-(((4-((((1r,4r)-4-hydroxy-4-methylcyclohexyl)methyl)amino)-3-nitrophenyl)sulfonyl)carbamoyl)phenyl)piperazin-1-yl)methyl)-5,5-dimethylcyclohex-1-en-1-yl)thiophen-3-yl)-3,5-difluorophenyl)-2-methylpropanoic acid

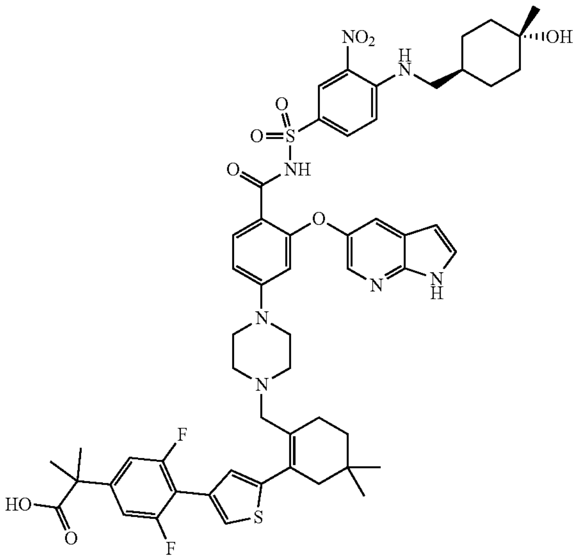 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(C(C)(C)C(=O)O)cc3F)cs2)C1]

Step A: Methyl 2-(3,5-difluoro-4-(thiophen-3-yl)phenyl)-2-methylpropanoate

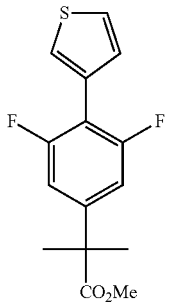 [SMILES: COC(=O)C(C)(C)c1cc(F)c(-c2ccsc2)c(F)c1]

To a solution of 2-(3,5-difluoro-4-(thiophen-3-yl)phenyl)-2-methylpropanoic acid (Step D of Example 74, 500 mg, 1.77 mmol) in a mixed solvent of MeOH (15 mL) and DMF (1 mL) was added $SOCl_2$ (1.05 g, 8.86 mmol) dropwise at 15-20° C., then the reaction mixture was stirred at room temperature for 6 h. After removal of volatiles, the resulting mixture was treated with EA, washed with aq. $NaHCO_3$ and brine, dried over $Na_2SO_4$ and concentrated under reduced pressure to give a yellow oil, which was purified by silica gel column (hexane:EA, 10:1) to afford the title compound (300 mg, 57%) as a yellow oil. MS: 297.2 (M+H$^+$).

Step B: (4-(2,6-Difluoro-4-(1-methoxy-2-methyl-1-oxopropan-2-yl)phenyl)thiophen-2-yl)boronic acid

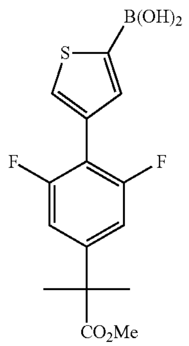 [SMILES: COC(=O)C(C)(C)c1cc(F)c(-c2csc(B(O)O)c2)c(F)c1]

Under Ar, to a solution of methyl 2-(3,5-difluoro-4-(thiophen-3-yl)phenyl)-2-methylpropanoate (Step A, 120 mg, 0.41 mmol) and triisopropyl borate (152 mg, 0.81 mmol) in dry THF (10 mL) was added LDA (410 μL, 0.81 mmol) at 0° C., then the reaction mixture was stirred at room temperature for 1 h. Aq. $NH_4Cl$ was added to quench the reaction and the resulting mixture was extracted with EA twice. The combined organic layer was washed with brine, dried over $Na_2SO_4$ and concentrated under reduced pressure to give the crude title compound as a yellow oil, which was directly used for the next step without purification. MS: 341.1 (M+H$^+$).

Step C: Methyl 2-(4-(5-(2-((4-(3-((1H-pyrrolo[2,3-b]pyridin-5-yl)oxy)-4-(((4-((((1r,4r)-4-hydroxy-4-methylcyclohexyl)methyl)amino)-3-nitrophenyl)sulfonyl)carbamoyl)phenyl)piperazin-1-yl)methyl)-5,5-dimethylcyclohex-1-en-1-yl)thiophen-3-yl)-3,5-difluorophenyl)-2-methylpropanoate

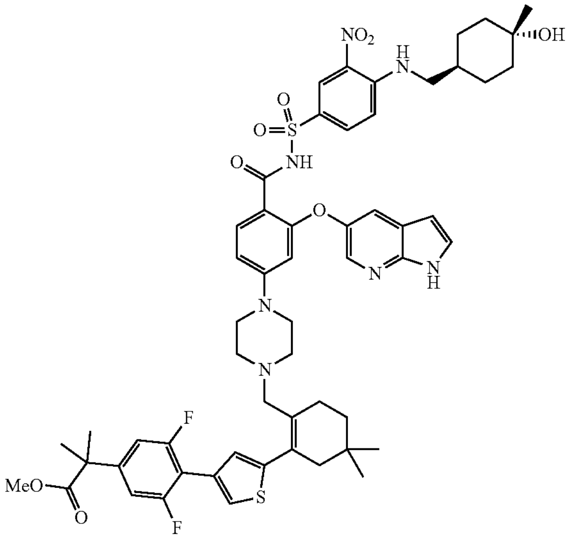 [SMILES: COC(=O)C(C)(C)c1cc(F)c(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Under Ar, to a solution of the crude (4-(2,6-difluoro-4-(1-methoxy-2-methyl-1-oxopropan-2-yl)phenyl)thiophen-2-yl)boronic acid (Step B, 79 mg) in a mixed solvent of dioxane (15 mL) and water (3 mL) was added 2-((1H-pyrrolo[2,3-b]pyridin-5-yl)oxy)-4-(4-((2-bromo-4,4-dimethylcyclohex-1-en-1-yl)methyl)piperazin-1-yl)-N-((4-((((1s,4s)-4-hydroxy-4-methylcyclohexyl)methyl)amino)-3-nitrophenyl)sulfonyl)benzamide (prepared by using the same protocol of Step B of Example 21, 100 mg, 0.116 mmol), $PdCl_2(dppf)$ (8.46 mg, 0.012 mmol) and $Na_2CO_3$ (36.8 mg, 0.347 mmol), then the reaction mixture was stirred at 100° C. for 16 h. After cooling down to room temperature and removal of volatiles, the residue was purified by silica gel column (hexane:EA, 1:4) to afford the title compound (50 mg, 40% over 2 steps) as a yellow oil. MS: 1081.3 (M+H$^+$).

Step D: 2-(4-(5-(2-((4-(3-((1H-pyrrolo[2,3-b]pyridin-5-yl)oxy)-4-(((4-((((1r,4r)-4-hydroxy-4-methylcyclohexyl)methyl)amino)-3-nitrophenyl)sulfonyl)carbamoyl)phenyl)piperazin-1-yl)methyl)-5,5-dimethylcyclohex-1-en-1-yl)thiophen-3-yl)-3,5-difluorophenyl)-2-methylpropanoic acid (Example 82)

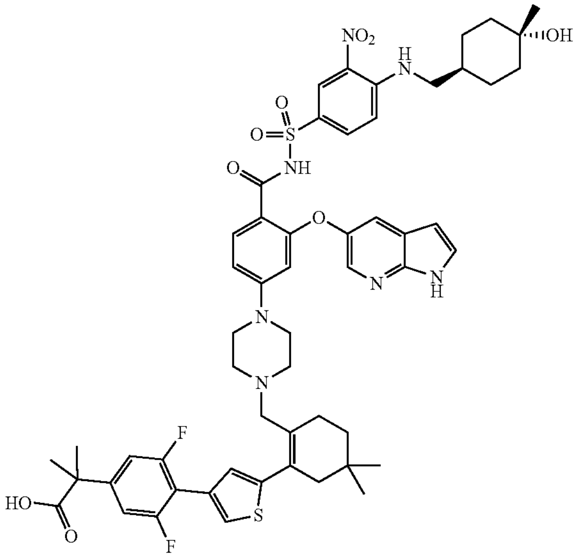 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2cc(-c3c(F)cc(C(C)(C)C(=O)O)cc3F)cs2)C1]

Under Ar, to a solution of methyl 2-(4-(5-(2-((4-(3-((1H-pyrrolo[2,3-b]pyridin-5-yl)oxy)-4-(((4-((((1s,4s)-4-hydroxy-4-methylcyclohexyl)methyl)amino)-3-nitrophenyl)sulfonyl)carbamoyl)phenyl)piperazin-1-yl)methyl)-5,5-dimethylcyclohex-1-en-1-yl)thiophen-3-yl)-3,5-difluorophenyl)-2-methylpropanoate (Step C, 50 mg, 0.046 mmol) in a mixed solvent of MeOH (4 mL) and THF (4 mL) was added 3N NaOH (4 mL), then the reaction mixture was stirred at 25° C. for 16 h. The resulting mixture was diluted with water, adjusted to pH 4-5 with 1 N HCl, and extracted with DCM twice. The organic layer was washed with brine, dried over $Na_2SO_4$ and concentrated under reduced pressure to give a yellow oil, which was purified by C18 prep-HPLC column to afford the title compound (8 mg, 16%) as a yellow solid. $^1$H NMR (400 MHz, DMSO-$d_6$) δ 11.68 (s, 1H), 8.62-8.50 (m, 2H), 8.06 (d, J=2.3 Hz, 1H), 7.81 (d, J=8.4 Hz, 1H), 7.69 (s, 1H), 7.57-7.46 (m, 3H), 7.21-7.01 (m, 4H), 6.73 (d, J=7.9 Hz, 1H), 6.40 (s, 1H), 6.26 (s, 1H), 4.28 (s, 1H), 3.30-3.26 (m, 2H), 3.18-3.01 (m, 6H), 2.40-2.19 (m, 6H), 2.17-2.07 (m, 2H), 1.64 (dd, J=55.5, 12.8 Hz, 6H), 1.51 (s, 6H), 1.46-1.28 (m, 5H), 1.13 (s, 3H), 0.95 (s, 6H); MS: 1067.2 (M+H$^+$).

Examples 83 and 84: 2-((1H-pyrrolo[2,3-b]pyridin-5-yl)oxy)-4-(4-((2-(4-(2,6-difluoro-4-((R)-1-hydroxyethyl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 83) and 2-((1H-pyrrolo[2,3-b]pyridin-5-yl)oxy)-4-(4-((2-(4-(2,6-difluoro-4-((S)-1-hydroxyethyl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 84)

Example 83

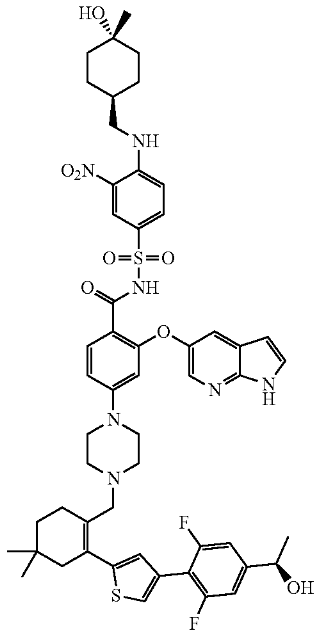

and

Example 84

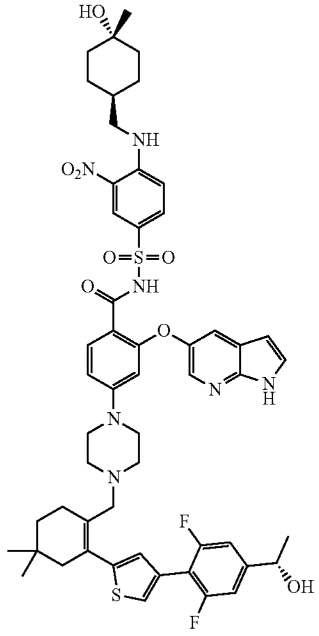

Step A: 1-(3,5-Difluoro-4-(thiophen-3-yl)phenyl)ethan-1-ol

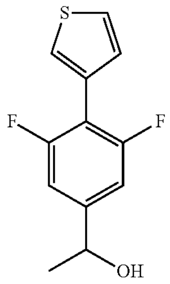 [SMILES: CC(O)c1cc(F)c(-c2ccsc2)c(F)c1]

To a solution of 1-(3,5-difluoro-4-(thiophen-3-yl)phenyl)ethan-1-one (Step A of Example 69, 22 g, 92 mmol) in THF (200 mL) was added $NaBH_4$ (3.49 g, 92 mmol) in small portions at 0° C., then the reaction mixture was stirred at room temperature for 16 h. The reaction was quenched with 0.5 N HCl and the resulting mixture was separated with brine and EA, the aqueous layer was extracted with EA twice. The combined organic layer was washed with brine, dried over $Na_2SO_4$ and concentrated under reduced pressure to give the crude title compound (20.5 g) as a yellow oil, which was directly used for the next step without purification. MS: 223.1 ($M-H_2O+H^+$).

Step B: (4-(2,6-Difluoro-4-(1-hydroxyethyl)phenyl)thiophen-2-yl)boronic acid

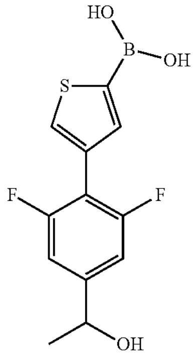 [SMILES: CC(O)c1cc(F)c(-c2csc(B(O)O)c2)c(F)c1]

Under Ar, to a solution of the crude 1-(3,5-difluoro-4-(thiophen-3-yl)phenyl)ethan-1-ol (Step A, 2 g) and triisopropyl borate (4.7 g, 24.97 mmol) in dry THF (50 mL) was slowly added LDA (12.5 mL, 2 M in THF, 24.97 mmol) at 0° C., the reaction mixture was stirred at 0-10° C. for 2 h. Aq. $NH_4Cl$ was added to quench the reaction, and the resulting mixture was extracted with EA twice. The combined organic layers were washed with brine, dried over $Na_2SO_4$ and concentrated under reduced pressure to give the crude title compound as a yellow oil, which was directly used for the next step without purification. MS: 267.1 ($M-H_2O+H^+$).

Step C: Methyl 2-((1H-pyrrolo[2,3-b]pyridin-5-yl)oxy)-4-(4-((2-(4-(2,6-difluoro-4-(1-hydroxyethyl)phenyl)thiophen-2-yl)-4,4-dimethylcyclohex-1-en-1-yl)methyl)piperazin-1-yl)benzoate

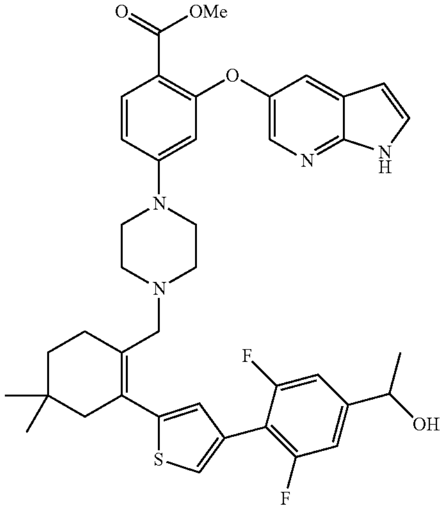 [SMILES: COC(=O)c1ccc(N2CCN(CC3=C(c4cc(-c5c(F)cc(C(C)O)cc5F)cs4)CC(C)(C)CC3)CC2)cc1Oc1cnc2[nH]ccc2c1]

Under Ar, to a solution of methyl 2-((1H-pyrrolo[2,3-b]pyridin-5-yl)oxy)-4-(4-((2-bromo-4,4-dimethylcyclohex-1-en-1-yl)methyl)piperazin-1-yl)benzoate (Intermediate 1, 2.5 g, 4.52 mmol) in a mixed solvent of dioxane (50 mL) and water (10 mL) was added the crude (4-(2,6-difluoro-4-(1-hydroxyethyl)phenyl)thiophen-2-yl)boronic acid (Step B, 2 g), $K_2CO_3$ (2.92 g, 21.1 mmol) and $PdCl_2(dppf)$ (515 mg, 0.704 mmol); then the reaction mixture was stirred at 100° C. for 4 h. After cooling down to room temperature, the resulting mixture was poured onto water and extracted with EA twice. The combined organic layer was washed with brine, dried over $Na_2SO_4$ and concentrated under reduced pressure to give a yellow oil, which was purified by silica gel column (EA:hexane; 3:1) to afford the title compound (2.6 g, 52% over 3 steps) as a yellow solid. MS: 713.9 (M+H$^+$).

Step D: Methyl (R)-2-((1H-pyrrolo[2,3-b]pyridin-5-yl)oxy)-4-(4-((2-(4-(2,6-difluoro-4-(1-hydroxyethyl)phenyl)thiophen-2-yl)-4,4-dimethylcyclohex-1-en-1-yl)methyl)piperazin-1-yl)benzoate (P1) and methyl (S)-2-((1H-pyrrolo[2,3-b]pyridin-5-yl)oxy)-4-(4-((2-(4-(2,6-difluoro-4-(1-hydroxyethyl)phenyl)thiophen-2-yl)-4,4-dimethylcyclohex-1-en-1-yl)methyl)piperazin-1-yl)benzoate (P2)

P1

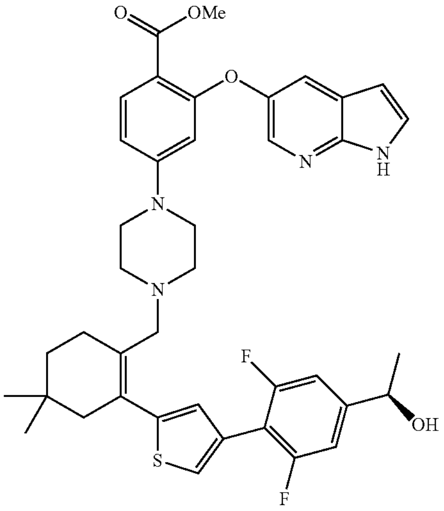

and

P2

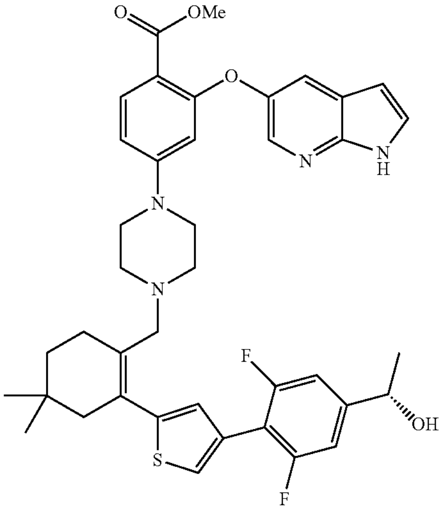

Methyl 2-((1H-pyrrolo[2,3-b]pyridin-5-yl)oxy)-4-(4-((2-(4-(2,6-difluoro-4-(1-hydroxyethyl)phenyl)thiophen-2-yl)-4,4-dimethylcyclohex-1-en-1-yl)methyl)piperazin-1-yl)benzoate (Step C, 26.75 g) was subjected to chiral SFC resolution with Lux Cellulose-4 column to provide the title compounds (P1: 8.72 g, 99.8% ee; P2: 9.91 g, 98.1% ee) as yellow solid.

Step E: (R)-2-((1H-pyrrolo[2,3-b]pyridin-5-yl)oxy)-4-(4-((2-(4-(2,6-difluoro-4-(1-hydroxyethyl)phenyl)thiophen-2-yl)-4,4-dimethylcyclohex-1-en-1-yl)methyl)piperazin-1-yl)benzoic acid

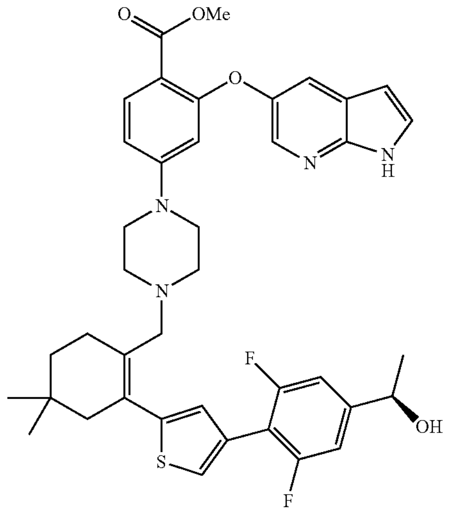 [SMILES: COC(=O)c1ccc(N2CCN(CC3=C(c4cc(-c5c(F)cc([C@@H](C)O)cc5F)cs4)CC(C)(C)CC3)CC2)cc1Oc1cnc2[nH]ccc2c1]

To a solution of methyl (R)-2-((1H-pyrrolo[2,3-b]pyridin-5-yl)oxy)-4-(4-((2-(4-(2,6-difluoro-4-(1-hydroxyethyl)phenyl)thiophen-2-yl)-4,4-dimethylcyclohex-1-en-1-yl)methyl)piperazin-1-yl)benzoate (P1 of Step D, 4.5 g, 6.31 mmol) in a mixed solvent of MeOH (30 mL) and THF (30 mL) was slowly added 3N NaOH (30 mL) at room temperature, the reaction mixture was stirred at 40° C. for 6 h. After cooling down to room temperature, the resulting mixture was adjusted to pH 3-4 with 1 N HCl and extracted with DCM twice. The combined organic layer was washed with brine, dried over $Na_2SO_4$ and concentrated under reduced pressure to give the crude title compound (4.4 g) as a yellow solid, which was directly used for the next step without purification. MS: 699.5 (M+H$^+$).

Step F: 2-((1H-pyrrolo[2,3-b]pyridin-5-yl)oxy)-4-(4-((2-(4-(2,6-difluoro-4-((R)-1-hydroxyethyl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 83)

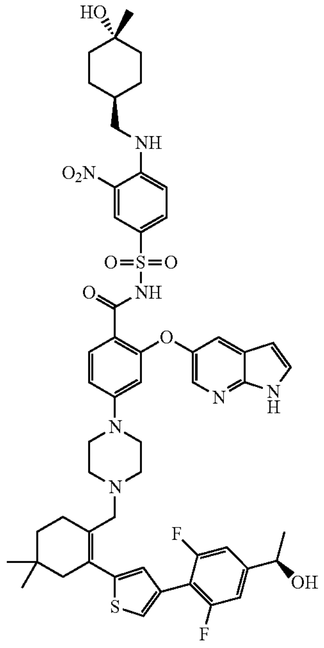 [SMILES: C[C@@H](O)c1cc(F)c(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Under Ar, to a solution of the crude (R)-2-((1H-pyrrolo[2,3-b]pyridin-5-yl)oxy)-4-(4-((2-(4-(2,6-difluoro-4-(1-hydroxyethyl)phenyl)thiophen-2-yl)-4,4-dimethylcyclohex-1-en-1-yl)methyl)piperazin-1-yl)benzoic acid (Step E, 4 g) in dry DCM (60 mL) was added DMAP (1.75 g, 14.31 mmol), 4-((((1r,4r)-4-hydroxy-4-methylcyclohexyl)methyl)amino)-3-nitrobenzenesulfonamide (1.97 g, 5.72 mmol), EDC (1.65 g, 8.59 mmol) in small portions; then the reaction mixture was stirred at 20-25° C. for 16 h. The resulting mixture was diluted with DCM (50 mL), washed with 1 N HCl (30 mL) and brine (20 mL), dried over $Na_2SO_4$ and concentrated under reduced pressure to give a yellow oil, which was purified by C18 prep-HPLC column to afford the title compound (2.5 g, 43% over 2 steps) as a yellow solid. $^1$H NMR (400 MHz, DMSO-$d_6$) δ 11.72 (s, 1H), 8.63-8.55 (m, 2H), 8.07 (d, J=2.6 Hz, 1H), 7.83-7.78 (m, 1H), 7.67 (s, 1H), 7.57-7.49 (m, 3H), 7.18-7.07 (m, 4H), 6.73 (dd, J=9.0, 1.6 Hz, 1H), 6.40 (dd, J=3.2, 1.8 Hz, 1H), 6.26 (d, J=1.6 Hz, 1H), 5.46 (d, J=4.5 Hz, 1H), 4.81-4.71 (m, 1H), 4.29 (s, 1H), 3.31 (t, J=6.1 Hz, 2H), 3.18-3.09 (m, 4H), 3.09-2.99 (m, 2H), 2.38-2.27 (m, 4H), 2.27-2.19 (m, 2H), 2.16-2.11 (m, 2H), 1.76-1.53 (m, 5H), 1.44-1.31 (m, 7H), 1.20-1.08 (m, 5H), 0.95 (s, 6H). MS: 1025.1 (M+H$^+$).

Step G: 2-((1H-pyrrolo[2,3-b]pyridin-5-yl)oxy)-4-(4-((2-(4-(2,6-difluoro-4-((S)-1-hydroxyethyl)phenyl)thiophen-2-yl)-4,4-dimethylcyclohex-1-en-1-yl)methyl)piperazin-1-yl)-N-((4-((((1r,4r)-4-hydroxy-4-methylcyclohexyl)methyl)amino)-3-nitrophenyl)sulfonyl)benzamide (Example 84)

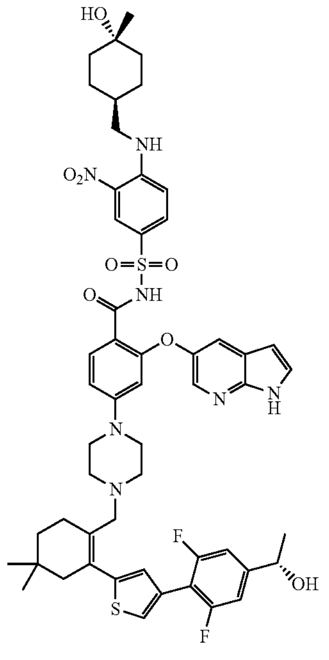 [SMILES: C[C@H](O)c1cc(F)c(-c2csc(C3=C(CN4CCN(c5ccc(C(=O)NS(=O)(=O)c6ccc(NC[C@H]7CC[C@](C)(O)CC7)c([N+](=O)[O-])c6)c(Oc6cnc7[nH]ccc7c6)c5)CC4)CCC(C)(C)C3)c2)c(F)c1]

Starting from P2 in Step D, essentially the same protocol of preparation of Example 83 was used to afford the example (185 mg, in salt form with AcOH, 25% over 2 steps) as a yellow solid. $^1$H NMR (400 MHz, DMSO-$d_6$) δ 12.00 (s, 1H), 11.71 (s, 1H), 8.64-8.51 (m, 2H), 8.07 (s, 1H), 7.81 (d, J=9.0 Hz, 1H), 7.67 (s, 1H), 7.59-7.46 (m, 3H), 7.20-7.02 (m, 4H), 6.73 (d, J=8.4 Hz, 1H), 6.40 (s, 1H), 6.26 (s, 1H), 5.46 (d, J=4.0 Hz, 1H), 4.84-4.66 (m, 1H), 4.28 (s, 1H), 3.32-3.26 (m, 2H), 3.19-3.01 (m, 6H), 2.39-2.18 (m, 6H), 2.16-2.07 (m, 2H), 1.94 (s, 3H), 1.79-1.51 (m, 5H), 1.44-1.30 (m, 7H), 1.22-1.05 (m, 5H), 0.95 (s, 6H); MS: 1025.1 (M+H$^+$).

BIOLOGICAL EXAMPLES

Bcl-2 WT and Bcl-2 G101V Inhibition:

Assay Conditions:

Assay plate: Greiner Bio-One 655209, Black, flat bottom 96 well Plate

Assay buffer: 100 mM potassium phosphate, pH 7.5; 100 μg/ml bovine gamma globulin; 0.02% sodium azide, plus 0.01% Triton X (added right before assay) Assay volume: 100 μL Final [DMSO]=2.5% (2.5 μL compound solution in DMSO plus 97.5 μL of protein/tracer mixture or tracer only solution in assay buffer)

Incubation time: 1 hours

Final Concentrations: [Bcl2]=20 nM, [Flu-BIM]=5 nM

Procedures:

Assay solution preparations: (a) Prepare the complex solution (Protein plus Flu-BIM) in following concentrations: 20.5 nM of Bcl2 protein and 5.1 nM Flu-BIM in the assay buffer; (b) Prepare the positive control which is the free Flu-BIM (5.1 nM) in the assay buffer. Note: concentrations here are adjusted to achieve final 20 and 5 nM for protein and tracer respectively after these solutions are mixed with compound solution later.

Prepare the stock solutions of the tested compounds in DMSO which is 10 mM. From these solutions prepare working solutions in DMSO for each compound in the highest concentration that will be tested in the binding assay (usually if it is the first screening we are using 100 μM (final) as the highest concentrations and after determination of the IC50 value, the tested concentration range needs to be adjusted).

Compounds were 3× diluted for 11 dose points.

Add 2.5 μl compounds in assay plates

Add 2.5 μl DMSO in all control wells and blank wells

In the blank well, add 97.5 μl of assay buffer only (these well are blank controls and will be used during measuring the plate)

In the positive control wells add 97.5 μl tracer only solution, that is equal to 100% inhibition.

In the negative control wells add 97.5 μl of the complex solution, that is equal to 0% inhibition.

In the rest of the plate add 97.5 μl of the complex solution.

Cover the plate with aluminium foil, and put it on the shaker for incubation around 1 h and measure the polarization values on plate reader: excitation wavelength at 485 nm and emission wavelength at 530 nm.

$IC_{50}$ values were determined by nonlinear regression fitting of the log(inhibitor) vs. response variable slope (four parameters) by Graphpad Prism 8.2.1 (mP values vs compound concentrations).

RS4; 11Bcl-2-G101V, RS4; 11Bcl-2-D103E, RS4; 11Bcl-2-V156D and RS4; 11Bcl-2-G101V-D103E cells were obtained from Cobioer Biosciences. Cells were maintained in the RPMI-1640 medium with 10% FBS, 1% P/S and puromycin (1 μg/mL) at 37° C. and an atmosphere of 5% $CO_2$.

CTG Assay:

The effect of representative Compounds of the Disclosure on cell viability was determined using CellTiter-Glo® (CTG) luminescent cell viability assay (Promega, USA) according to the manufacturer's instructions. 95 μL of cell suspension (10000 cells/well) in culture medium were seeded into 96-well plates and cultured 4 hours. Each tested compound was serially diluted in blank culture medium, and 5 μL of the compound dilution was added to the corresponding well of the cell plate. After the addition of the tested compound, the cells were incubated at 37° C. in an atmosphere of 5% $CO_2$ for 3 days. At the end of 3 days, 30 μL of CTG solution was added to each well of the plate and mix contents for 2 minutes on an orbital shaker. Allow the plate to incubate at room temperature for 15 mins to stabilize signal and record RLU on the Biotek plate reader. The readings were normalized to the vehicle cells, and the $IC_{50}$ was calculated using GraphPad Prism 8 software.

MV-4-11 cells were obtained from University of Michigan. Cells were maintained in the RPMI-1640 medium with 10% FBS and 1% P/S at 37° C. and an atmosphere of 5% $CO_2$.

CCK-8 Assay:

The effect of representative Compounds of the Disclosure on cell viability was determined using Cell Counting Kit-8 (CCK-8) assay (Shanghai Life iLab Biotech) according to the manufacturer's instructions. Each tested compound was serially diluted in culture medium, and 100 μL of the compound dilution was added to the corresponding well of the cell plate. 100 μL of MV-4-11 cell suspension (20000 cells/well) in culture medium were seeded into 96-well plates. The cells were incubated at 37° C. in an atmosphere of 5% $CO_2$ for 3 days. At the end of 3 days, 20 μL of CCK-8 solution was added to each well of the plate and incubated for 1-4 hours. The plates were read at 450 nm on the Biotek plate reader. The readings were normalized to the vehicle cells, and the $IC_{50}$ was calculated using GraphPad Prism 8 software.

TABLE A

| Example # | Bcl-2 w.t. (FP, nM) | Bcl-2 G101V (FP, nM) | MV-4-11 (10% FBS, nM) | RS4; 11-Bcl-2-G101V (10% FBS, nM) |
|---|---|---|---|---|
| 1 | 15.74 | 32.74 | 27 | 1170 |
| 2 | 15.88 | 32.62 | 28 | 1300 |
| 3 | 27.66 | 45.65 | 214 | 3800 |
| 4 | — | — | 54 | 3250 |
| 5 | — | — | 79 | 3820 |
| 6 | 16.18 | 33.93 | 66 | 3940 |
| 7 | — | — | 209 | 4270 |
| 8 | 17.71 | 30.92 | 21 | 1440 |
| 9 | — | — | 167 | 5420 |
| 10 | 20.25 | 27.72 | 16 | 1040 |
| 11 | 20.87 | 37.58 | 54 | 2360 |
| 12 | — | — | 164 | 4030 |
| 13 | — | — | 25 | 1790 |
| 14 | — | — | 98 | 2660 |
| 15 | 27.55 | 65.11 | 466 | 8810 |
| 16 | 42.04 | 94.72 | 445 | 5630 |
| 17 | 30.92 | 49.48 | 262 | 4250 |
| 18 | 37.49 | 66.29 | 323 | 2040 |
| 19 | 24.58 | 40.91 | 138 | 980 |
| 20 | — | — | >1000 | >10000 |
| 21 | 27.07 | 64.24 | 323 | 3790 |
| 22 | 25.4 | 42.76 | 83 | 440 |
| 23 | 15.73 | 28.2 | 180 | 930 |
| 24 | 15.89 | 30.06 | 40 | 340 |
| 25 | 25.41 | 39.09 | 225 | 1810 |
| 26 | 26.37 | 57.79 | 246 | 2590 |
| 27 | — | — | 126 | 1040 |
| 28 | 20.66 | 47.03 | 276 | 1210 |
| 29 | 26.74 | 71.28 | 422 | 750 |
| 30 | 23.63 | 65.95 | 564 | 1440 |
| 31 | 25.98 | 59.24 | 147 | 880 |
| 32 | 15.85 | 25.67 | 80 | 560 |
| 33 | 23.88 | 33.12 | 6 | 630 |
| 34 | 41.14 | 47.93 | 18 | 1460 |
| 35 | 40.42 | 47.59 | 799 | 6160 |
| 36 | 36.28 | 46.21 | 36 | 570 |
| 37 | 20.47 | 34.89 | 11 | 290 |
| 38 | 20.15 | 35.4 | 28 | 1640 |
| 39 | 31.58 | 36 | 260 | 2310 |
| 40 | 40.24 | 43.41 | 45 | 3550 |
| 41 | 44.05 | 34.39 | 50 | 3230 |
| 42 | 38.66 | 50.67 | 26 | 480 |
| 43 | 21.15 | 33.67 | 8 | 280 |
| 44 | 31 | 46.26 | 31 | 830 |
| 45 | 33.81 | 48.98 | 57 | 1680 |
| 46 | 22.52 | 43.55 | 9 | 230 |
| 47 | — | — | 5 | 190 |
| 48 | 20.23 | 36.74 | 9 | 810 |
| 49 | 38.44 | 43.64 | 9 | 420 |
| 50 | 30.35 | 42.74 | 65 | 1950 |
| 51 | 35.5 | 45.51 | 52 | 1140 |
| 52 | — | — | 296 | 4990 |
| 53 | 27.76 | 36.62 | 9 | 430 |
| 54 | 22.76 | 33.24 | 7 | 270 |
| 55 | 31.15 | 47.53 | 72 | 1140 |
| 56 | 16.11 | 27.55 | 68 | 1910 |
| 57 | — | — | 1213 | 5810 |
| 58 | 20.11 | 34.13 | 178 | 3050 |
| 59 | 29.29 | 38.54 | 2 | 290 |
| 60 | 20.37 | 34.06 | 303 | 3410 |

TABLE A-continued

| Example # | Bcl-2 w.t. (FP, nM) | Bcl-2 G101V (FP, nM) | MV-4-11 (10% FBS, nM) | RS4; 11-Bcl-2-G101V (10% FBS, nM) |
|---|---|---|---|---|
| 61 | — | — | 107 | 3180 |
| 62 | 15.67 | 23.67 | 4 | 140 |
| 63 | 16.26 | 32.31 | 9 | 14 |
| 64 | 16.45 | 37.05 | 7 | 30 |
| 65 | — | — | 192 | 598 |
| 66 | — | — | 132 | 361 |
| 67 | 27.23 | 33.69 | 251 | 840 |
| 68 | 23.21 | 27.76 | 9 | 21 |
| 69 | 24.78 | 29.03 | 473 | 300 |
| 70 | 19.79 | 36.86 | 95 | 1460 |
| 71 | 15.43 | 20.3 | 12 | 330 |
| 72 | 20.54 | 26.98 | 12 | 440 |
| 73 | 23.7 | 25.19 | 8 | 490 |
| 74 | 38.47 | 30.21 | 52 | 230 |
| 75 | 19.2 | 34.34 | 118 | 1580 |
| 76 | — | — | 95 | 1700 |
| 77 | — | — | 25 | 490 |
| 78 | 16.76 | 33.24 | 59 | 580 |
| 79 | 15.8 | 22.14 | 11 | 170 |
| 80 | 15.64 | 23.4 | 111 | 420 |
| 81 | 34.58 | 102.7 | 270 | 1710 |
| 82 | 18.11 | 22.31 | 114 | 1270 |
| 83 | — | — | 2 | 20 |
| 84 | — | — | 7 | 70 |
| ABT-199 | 15.15 | 25.64 | 38 | 2686 |
| APG-2575 | 15.83 | 34.36 | 34 | 2428 |

TABLE B

| Example # | RS4; 11-BCL2-V156D (10% FBS, nM) | RS4; 11-BCL2-D103E (10% FBS, nM) |
|---|---|---|
| 63 | 19 | 183 |
| 83 | 8 | 48 |
| 84 | 8 | 98 |
| ABT-199 | 671 | 1514 |
| APG-2575 | 324 | 516 |

Having now fully described this invention, it will be understood by those of ordinary skill in the art that the same can be performed within a wide and equivalent range of conditions, formulations, and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound of Formula (I):

(I)

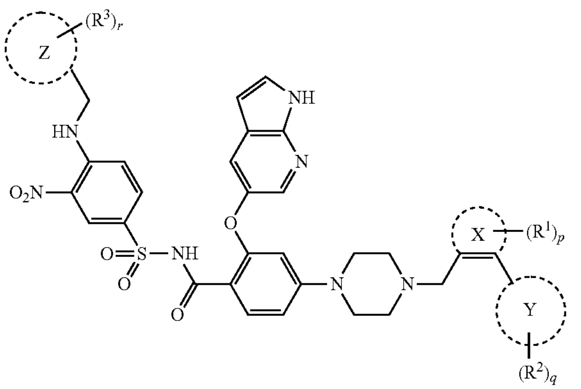

or a pharmaceutically acceptable salt or solvate thereof, wherein:

Ring X is a 5- or 6-membered ring, containing one or more additional degrees of unsaturation;

each $R^1$ independently is selected from the group consisting of $C_{1-6}$ alkyl, $C_{2-6}$ alkenyl, $C_{2-6}$ alkynyl, $C_{1-6}$ haloalkyl, and halogen;

p is 0, 1, or 2;

Ring Y is a 5- to 9-membered mono- or fused-ring system, including at least one S, and optionally containing one or more additional heteroatom selected from the group consisting of O, N, or S, and containing one or more degrees of unsaturation;

each $R^2$ independently is selected from the group consisting of $(CH_2)_t$—$R_4$, CONH—$R_4$, NHC(O)—$R_4$, $NHR_4$, and (C≡C)—$R_4$;

each $R^4$ independently is $C_{1-6}$ alkyl, $C_{2-6}$ alkenyl, $C_{2-6}$ alkynyl, $C_{1-6}$ haloalkyl, $C_{3-10}$ cycloalkyl, aryl, $C_{3-10}$ heterocyclyl, heteroaryl;

each $R^4$ may be substituted with one or more of the group consisting of $C_{1-6}$ alkyl, $C_{2-6}$ alkenyl, $C_{2-6}$ alkynyl, $C_{1-6}$ haloalkyl, halogen, $C_{3-6}$ cycloalkyl, $C_{3-6}$ heterocyclyl, $OSO_2CH_3$, $NH_2$, $NHC_{1-6}$ alkyl, N($C_{1-6}$ alkyl), $C_{1-6}$ alkoxy, OH, $C_{1-6}$ alkyl-OH, $C_{2-6}$ alkyl (OH) ($C_{3-46}$cycloalkyl), $C_{1-6}$ haloalkyl-OH, $C_{3-6}$ cycloalkyl-OH, $C_{1-6}$ alkyl-COOH, $C_{1-6}$ alkyl-O—$C_{1-6}$ alkyl, CN, $C_{1-6}$ alkyl-CN, $C_{1-6}$ alkyl-NHC(O)—$C_{1-6}$ alkyl, and $C_{1-6}$ alkyl-C (O) NH—$C_{1-6}$ alkyl;

q is 1 or 2;

each t is 0, 1, 2, 3, 4, 5, or 6;

Ring Z is a saturated 6-membered ring, optionally containing one or more O;

each $R^3$ is selected from the group consisting of one or more of $C_{1-6}$ alkyl, $C_{1-6}$ alkoxy, and OH; and r is 0, 1, or 2.

2. The compound of Formula (I) according to claim 1, which is the compound of Formula (Ix):

(Ix)

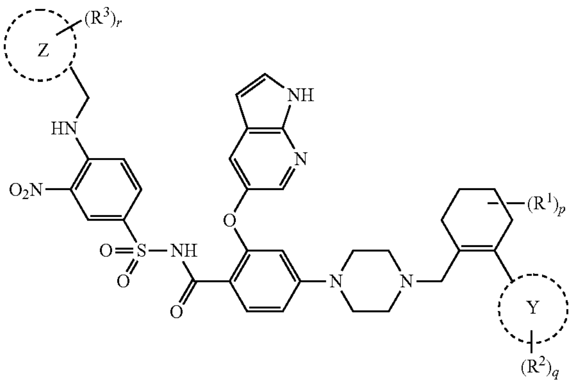

or a pharmaceutically acceptable salt or solvate thereof.

3. The compound of Formula (Ix) according to claim 2, wherein p is 2 and each $R^1$ is $C_{1-6}$ alkyl.

4. The compound of Formula (Ix) according to claim 2, which is the compound of Formula (Ixi):

(Ixi)

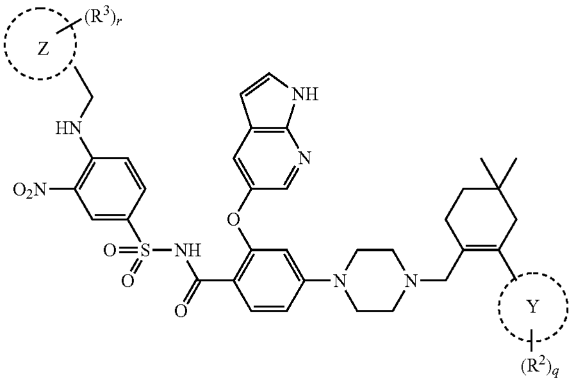

or a pharmaceutically acceptable salt or solvate thereof.

5. The compound of Formula (I) according to claim 1, wherein Ring Y is a thiophene.

6. The compound of Formula (I) according to claim 5, which is the compound of Formula (Iy):

(Iy)

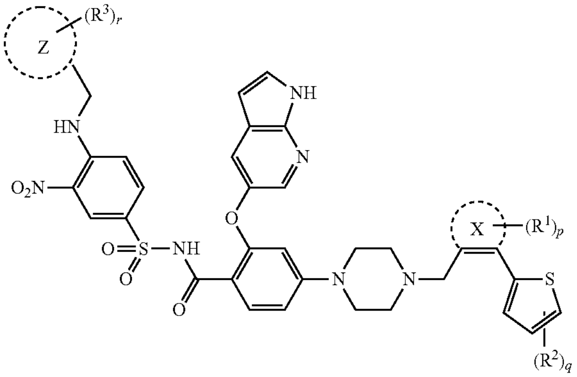

or a pharmaceutically acceptable salt or solvate thereof.

7. The compound of Formula (Iy) according to claim 6, wherein q is 1; $R^2$ is $R^4$, wherein $R^4$ is aryl.

8. The compound of Formula (Iy) according to claim 7, which is the compound of Formula (Iyi):

(Iyi)

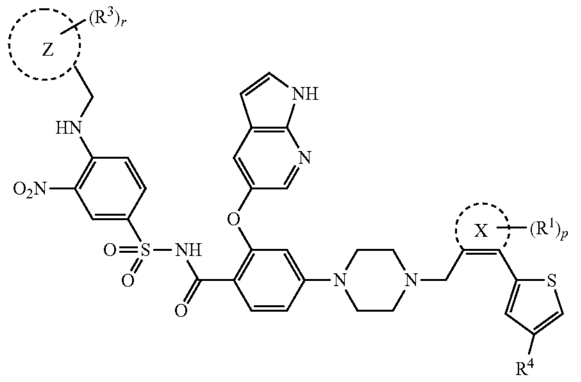

or a pharmaceutically acceptable salt or solvate thereof.

9. The compound of Formula (Iyi) according to claim 8, wherein $R^4$ is phenyl.

10. The compound of claim 9, wherein $R^4$ is substituted with one or more of the group consisting of $C_{1-6}$ alkyl, $C_{1-6}$ haloalkyl, halogen, OH, $C_{1-6}$ alkyl-OH, and $C_{1-6}$ haloalkyl-OH.

11. The compound of claim 10, wherein $R^4$ is substituted with one or more of the group consisting of halogen, $C_{1-6}$ alkyl-OH, and $C_{1-6}$ haloalkyl-OH.

12. The compound of Formula (I) according to claim 1, wherein Ring Z is selected from a substituted cyclohexyl and a 1,4-dixoane.

13. The compound of Formula (I) according to claim 12, wherein the cyclohexyl is substituted with a methyl and an OH group, from the same atom, and located para to the point of attachment from the depicted amine:

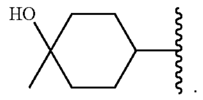

14. The compound of Formula (I) according to claim 13, having the depicted stereochemistry:

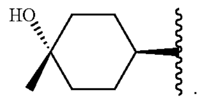

15. The compound of Formula (I) according to claim 13, having the depicted stereochemistry:

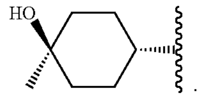

16. The compound of Formula (Ixi) or a pharmaceutically acceptable salt or solvate thereof according to claim 4, wherein Ring Y is a thiophene; and Ring Z is a substituted cyclohexyl or 1,4-dixoane.

17. A compound, or a pharmaceutically acceptable salt thereof, selected from the group consisting of:

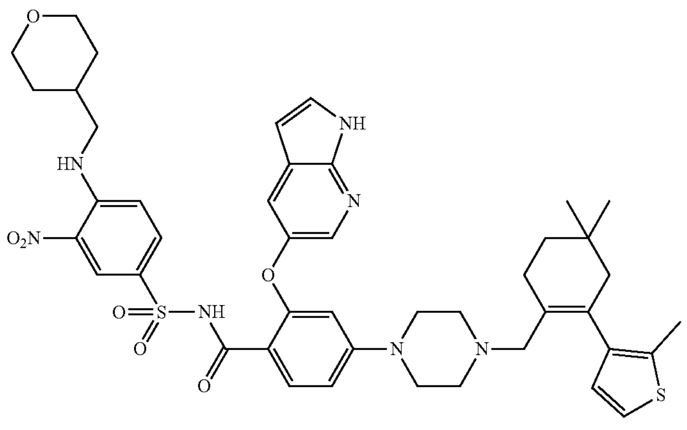

-continued
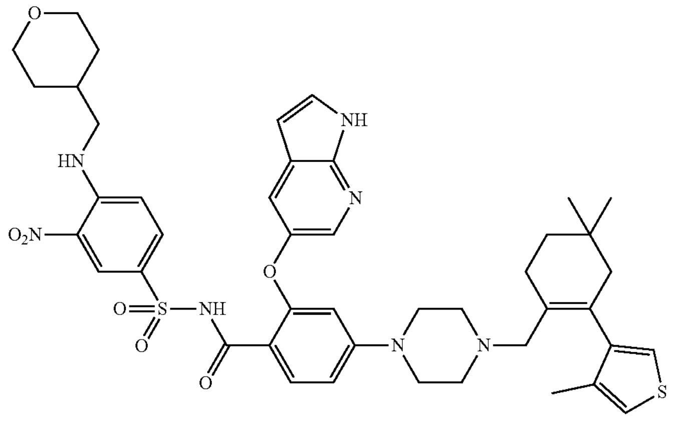
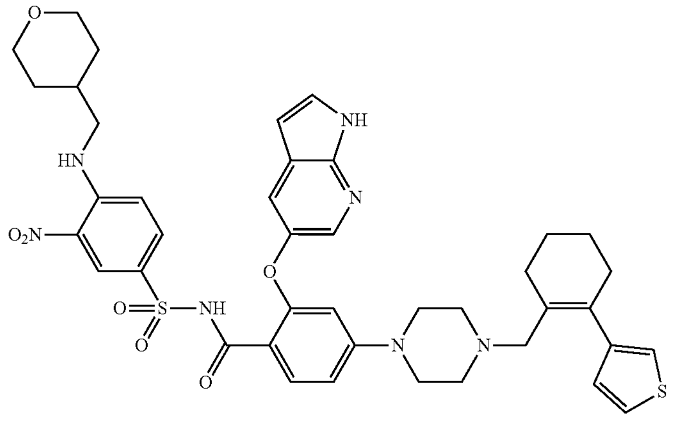
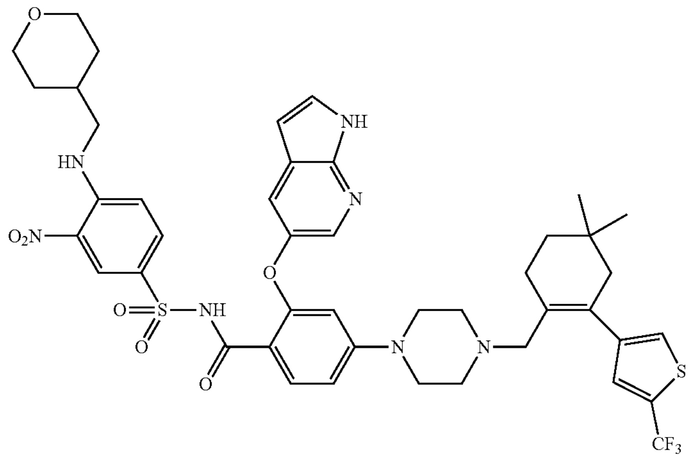
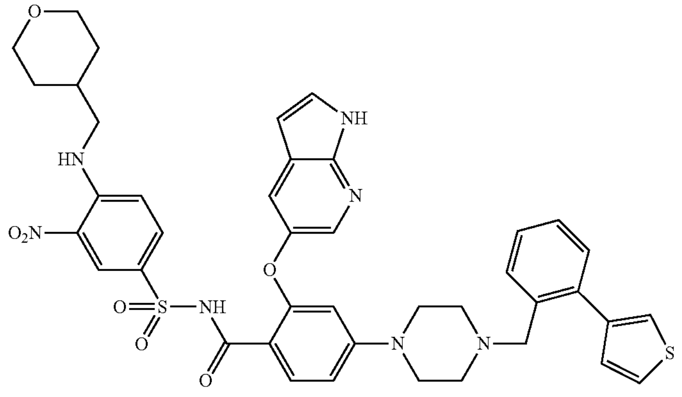

-continued
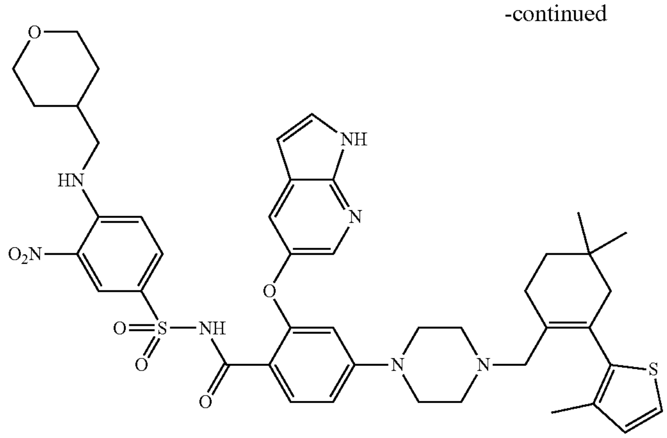
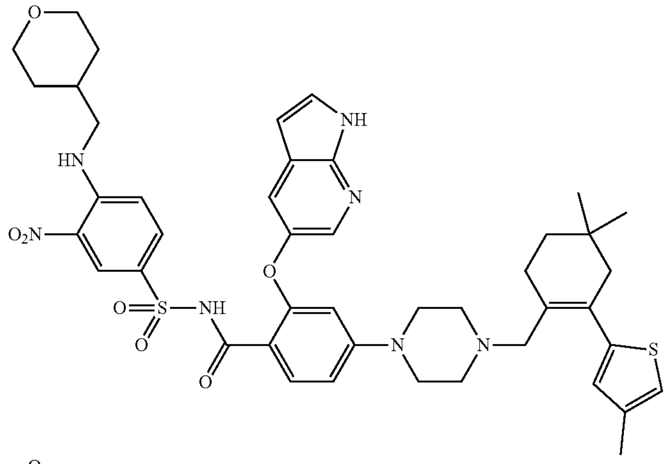
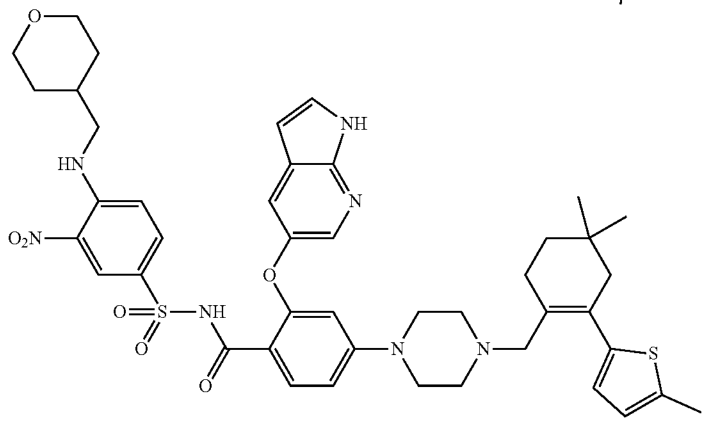
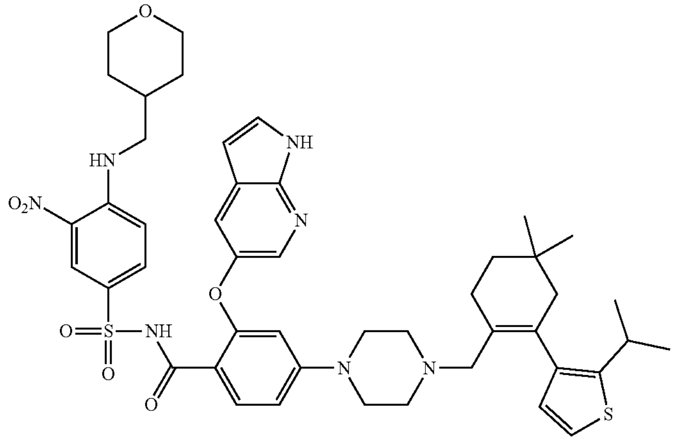

-continued
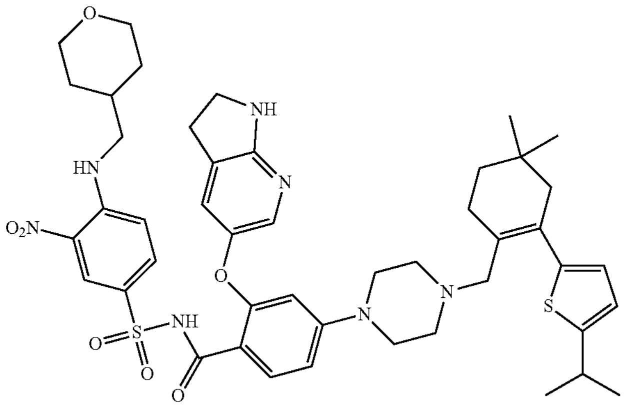
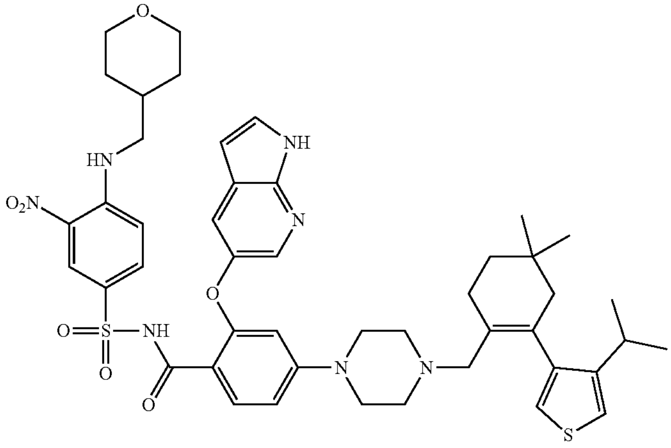
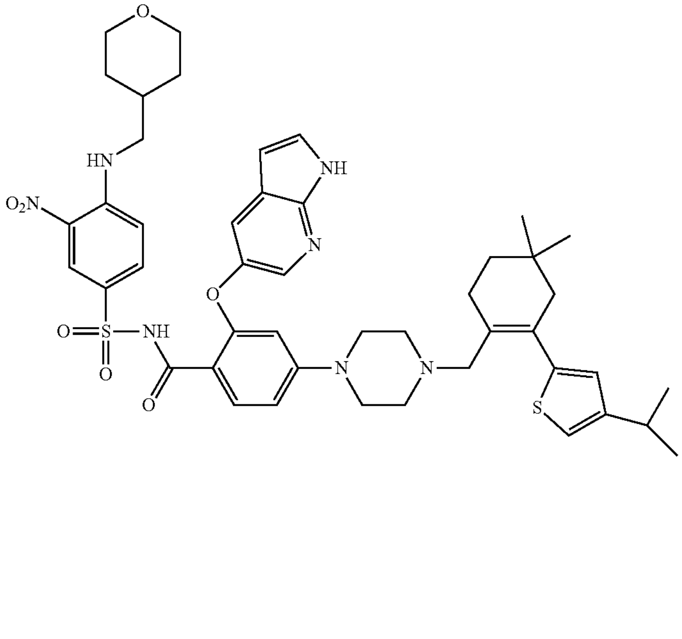

-continued
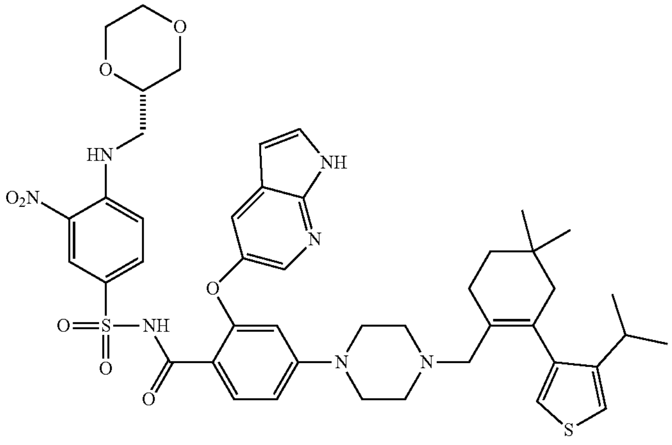
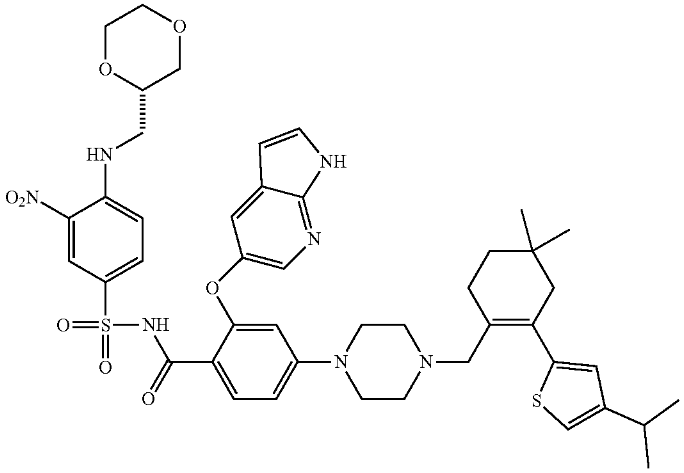
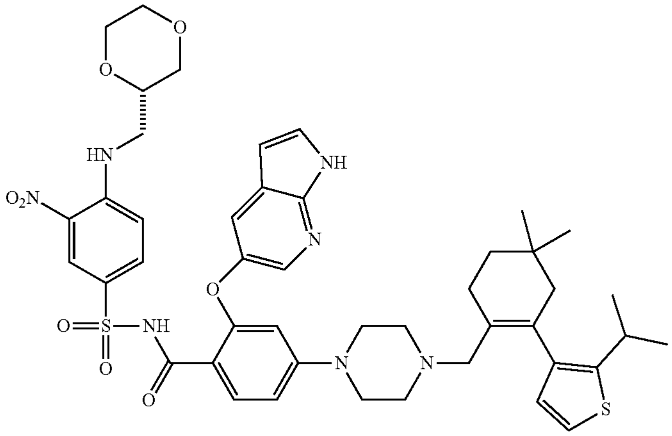

-continued
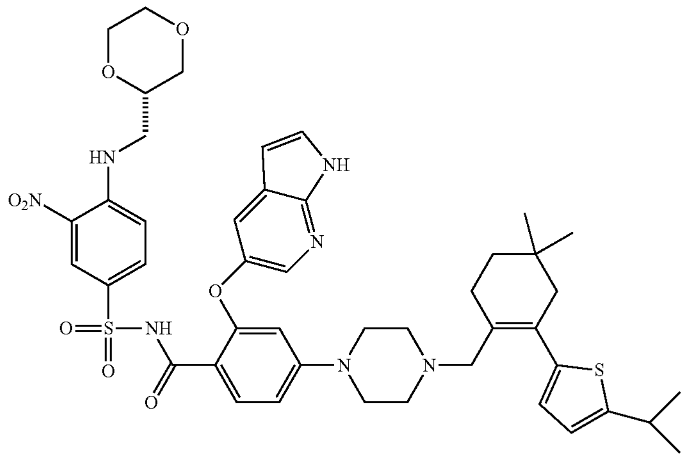
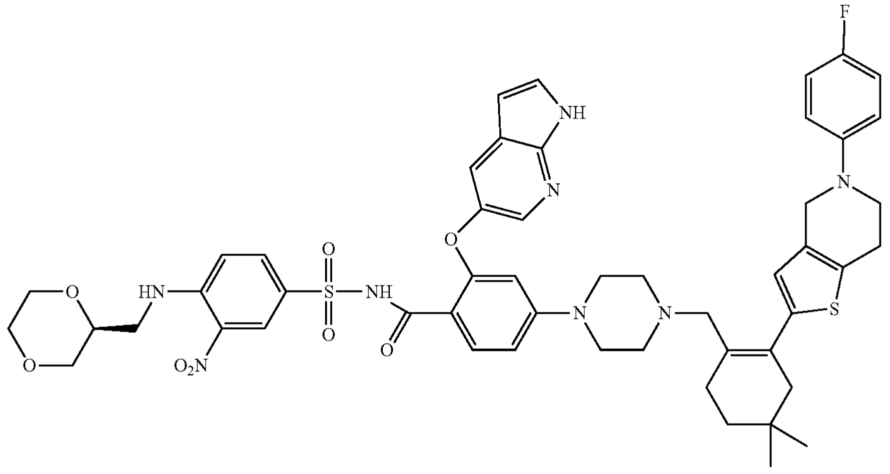
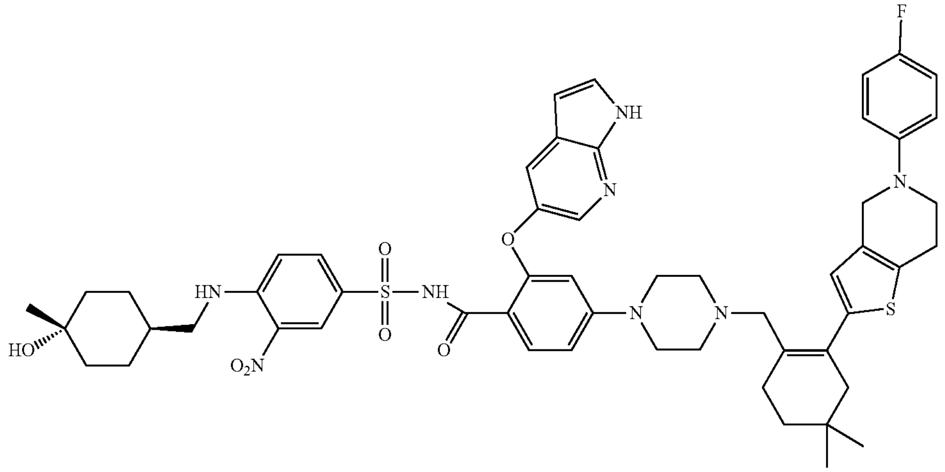

-continued
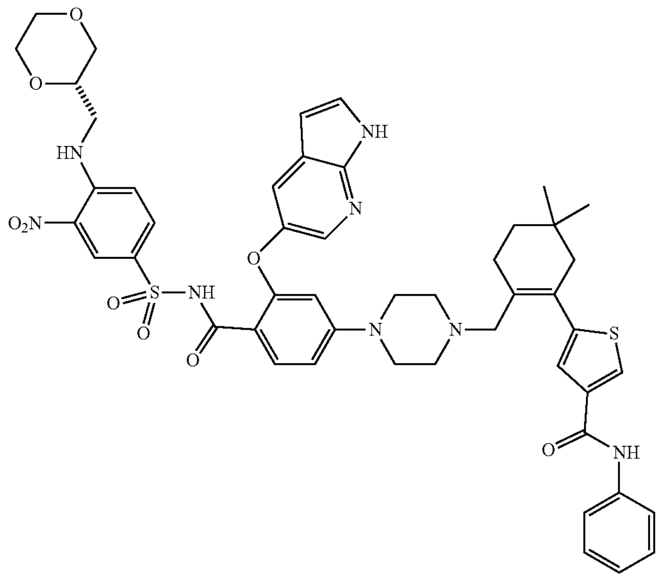
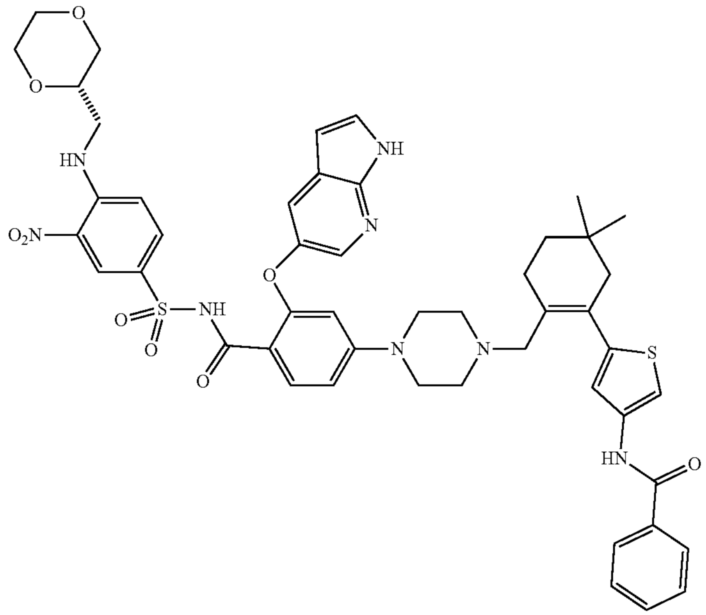

-continued
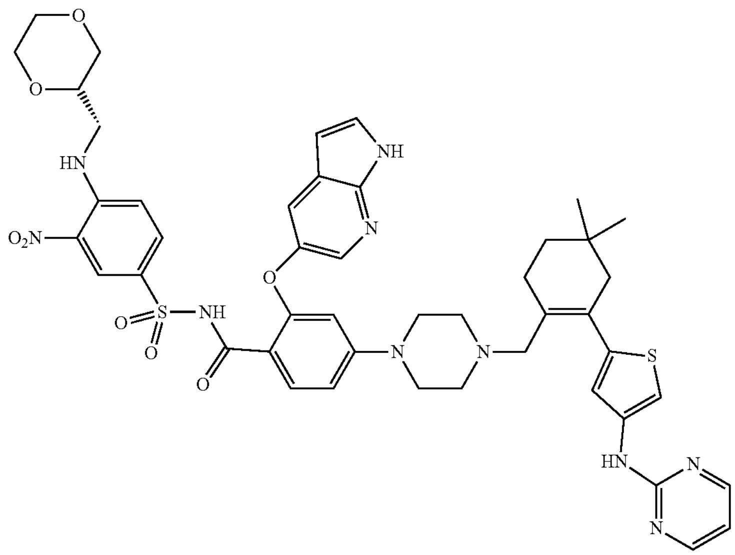
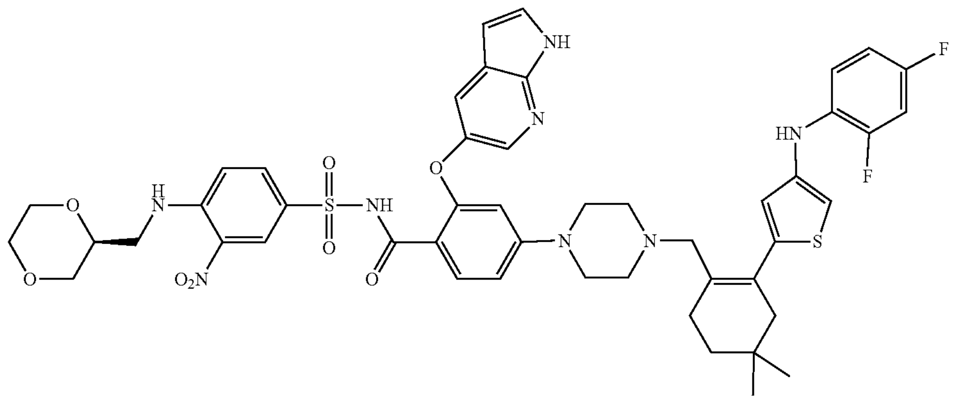
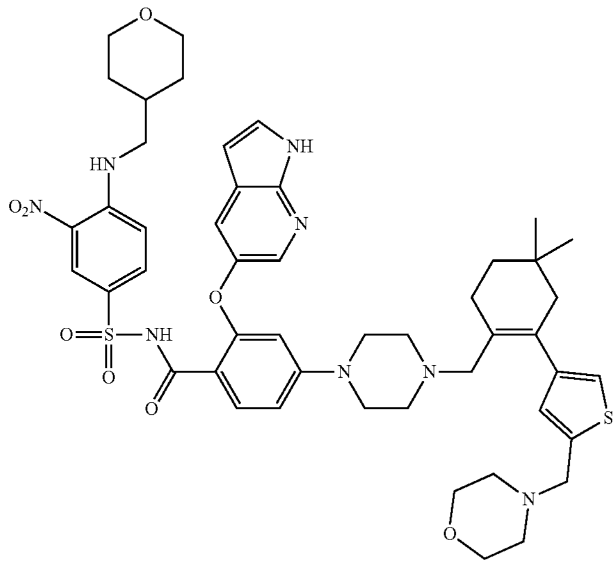

-continued
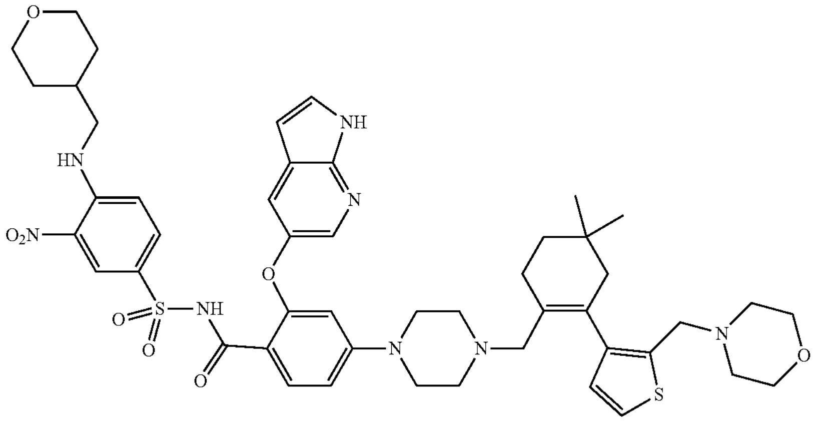
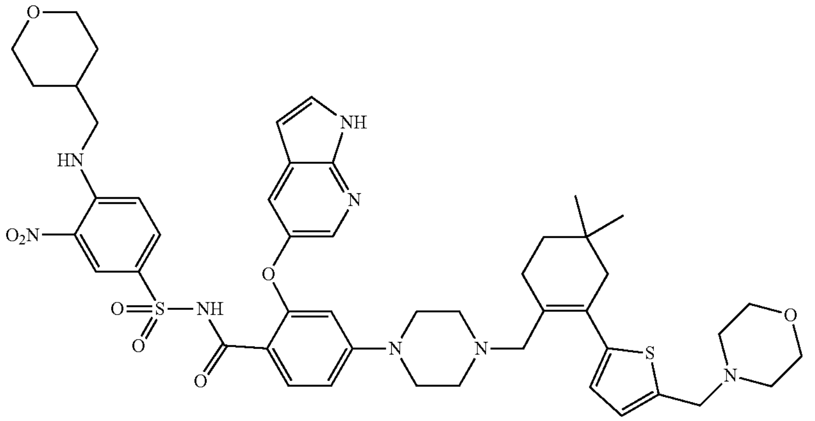
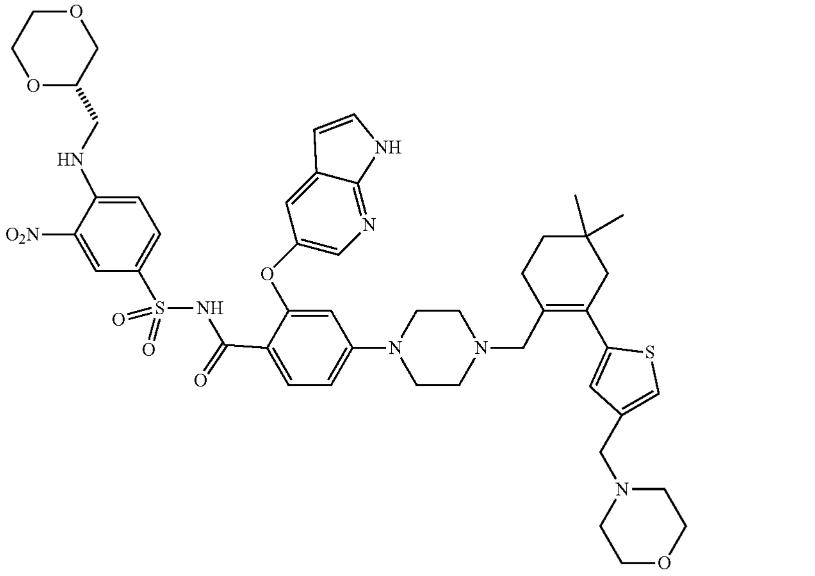

-continued
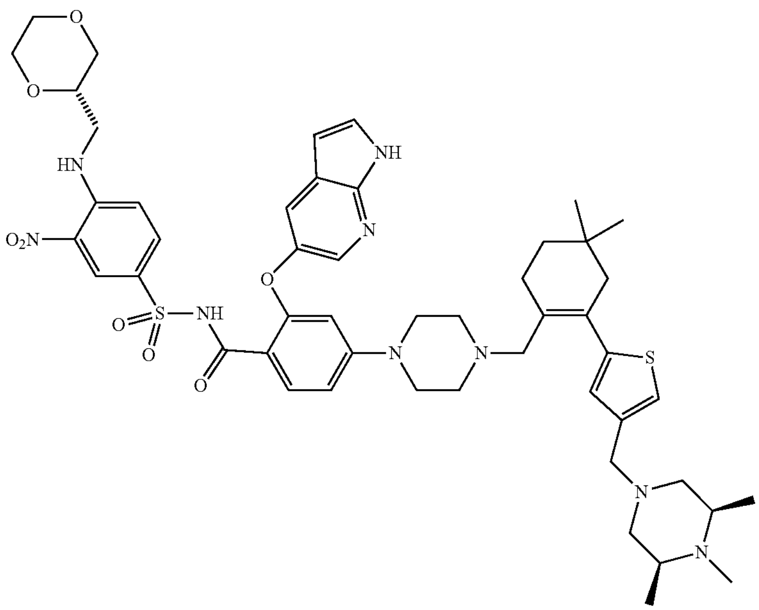
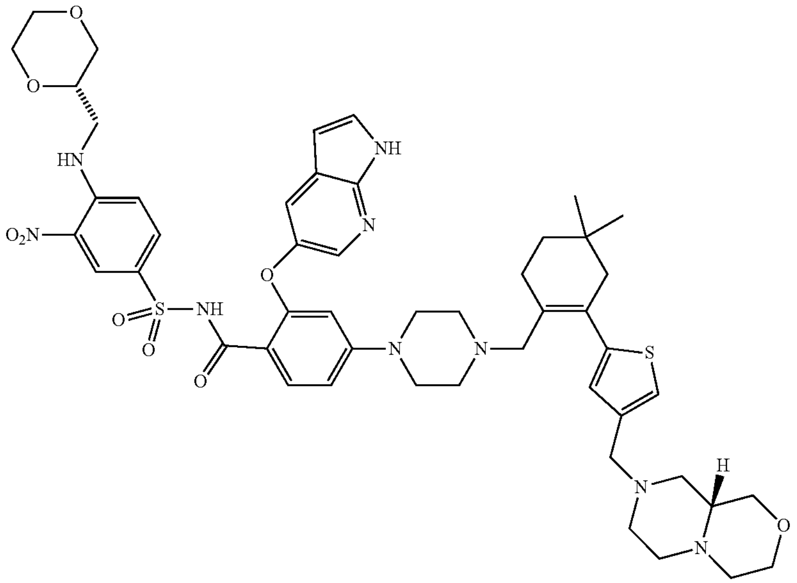

-continued
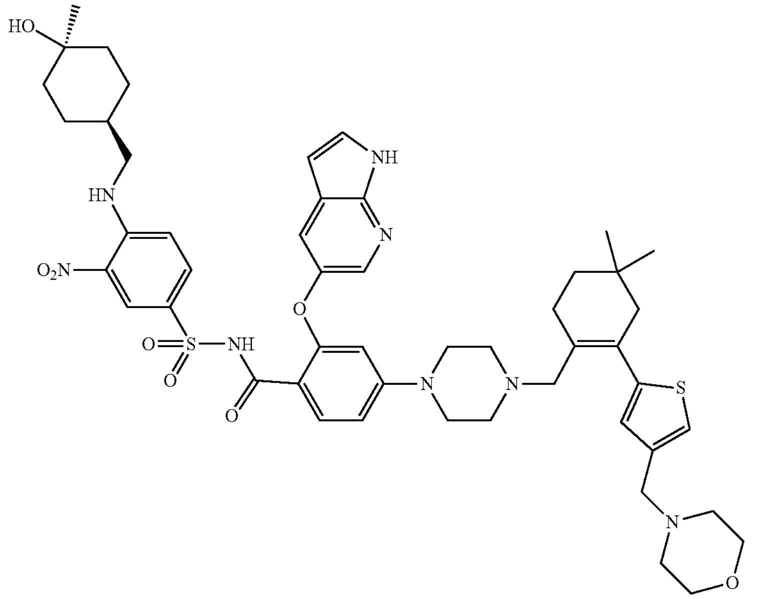
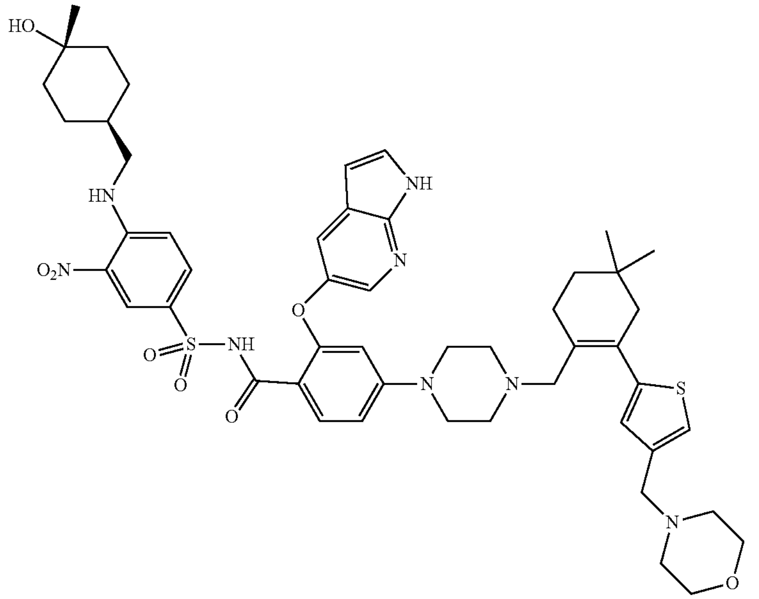

-continued
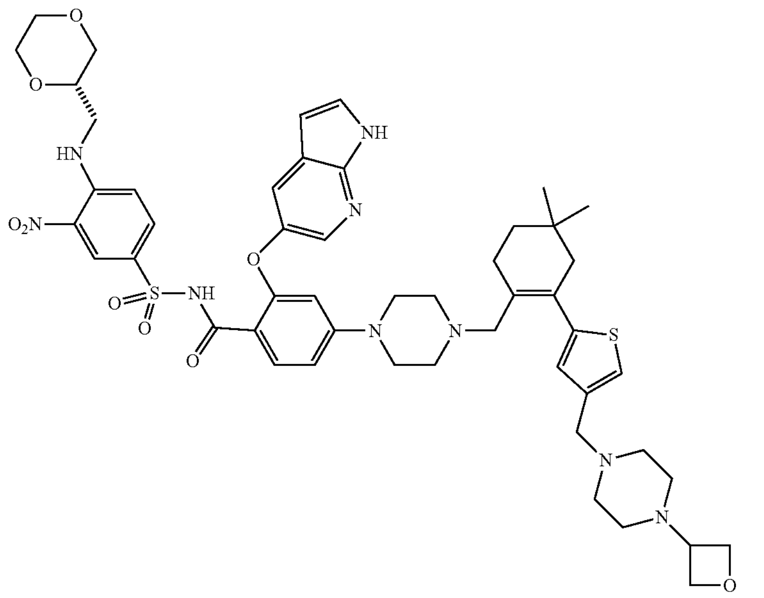
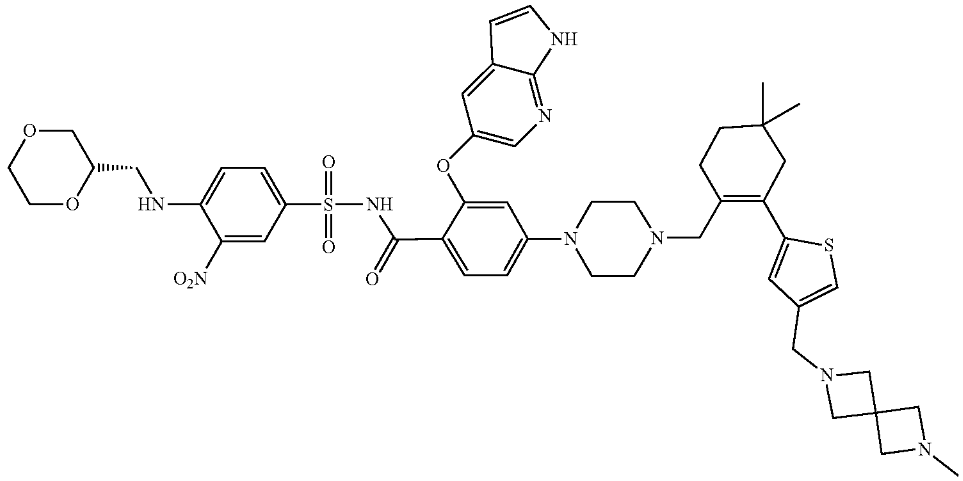
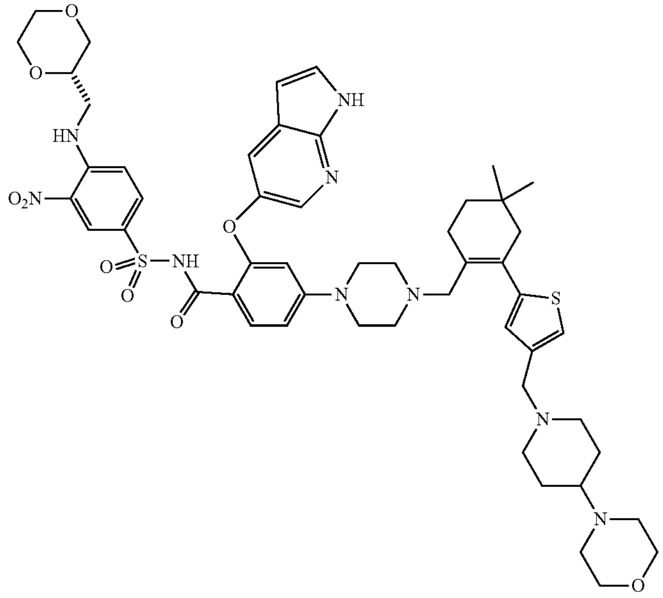

-continued
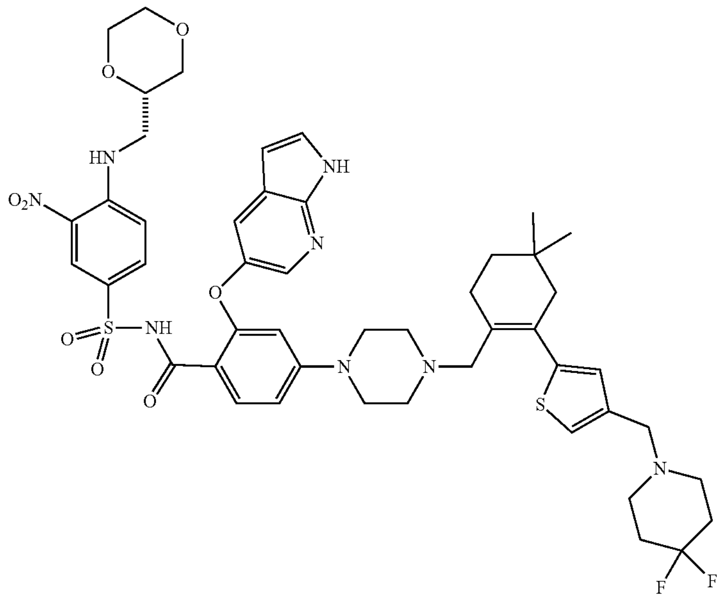
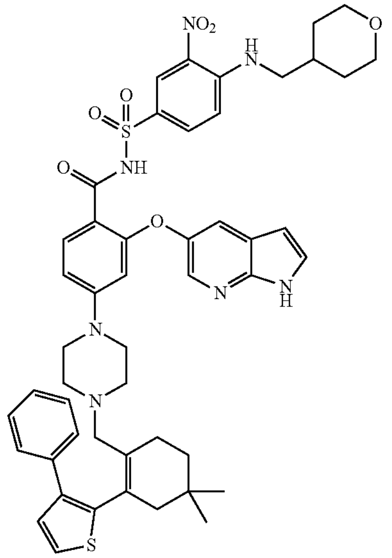
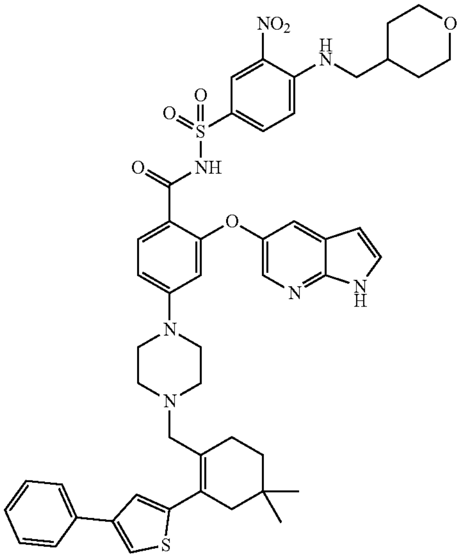

-continued
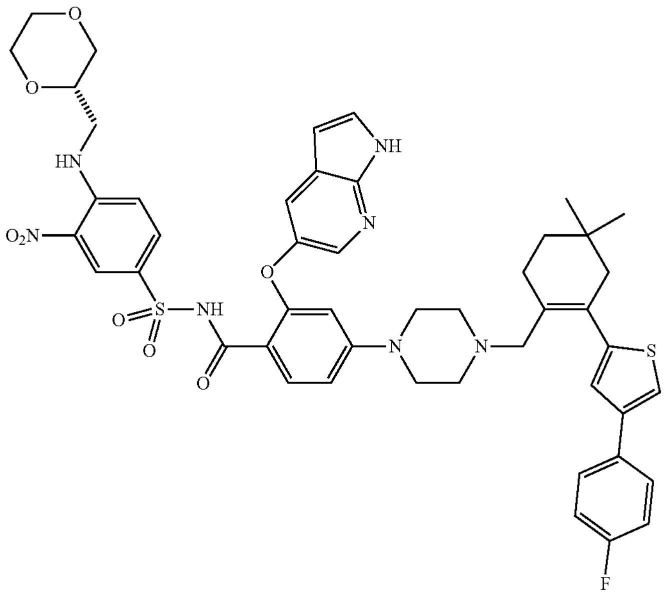
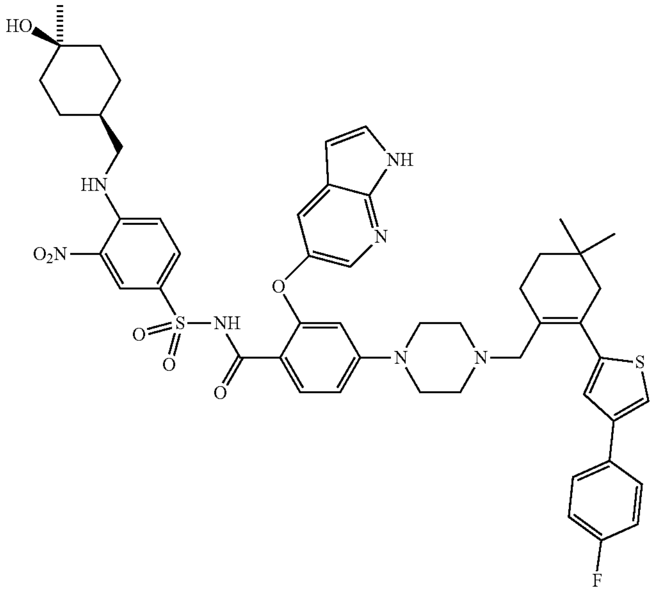

-continued
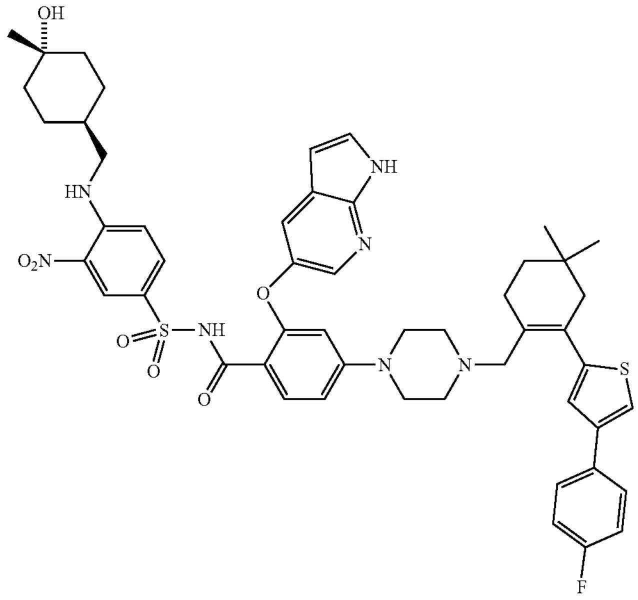
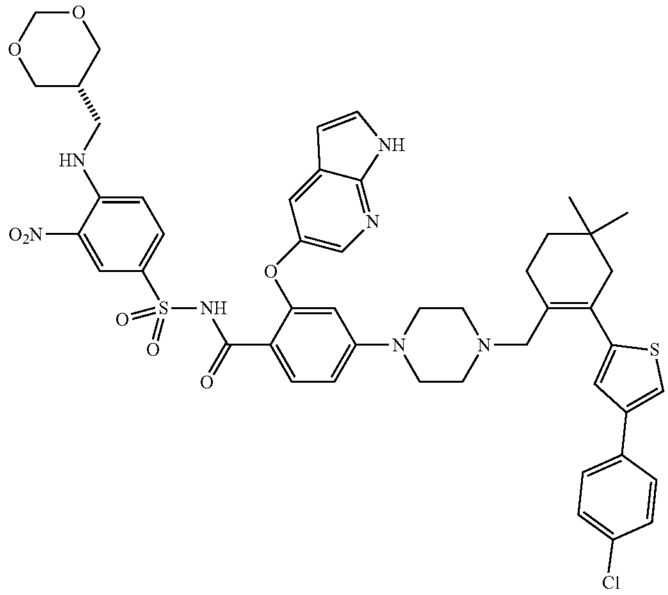

-continued
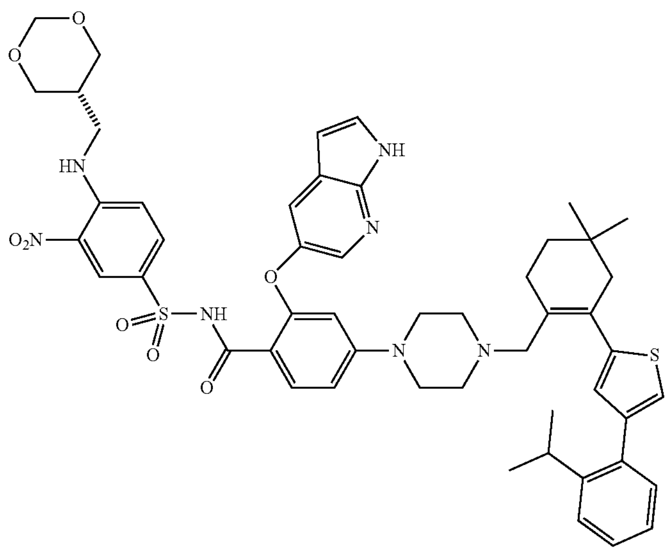
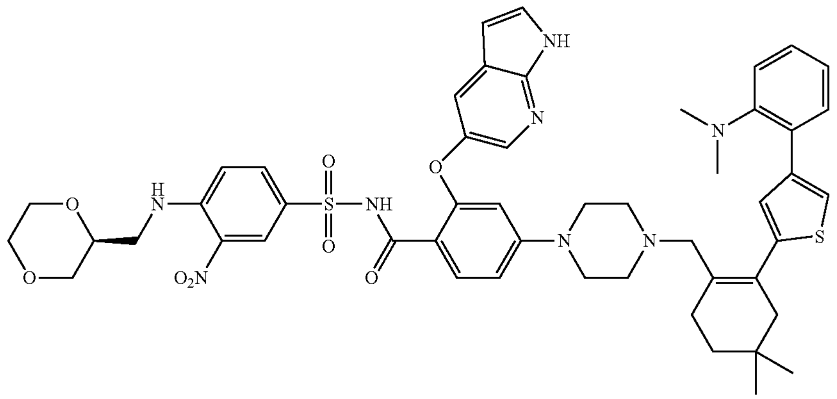
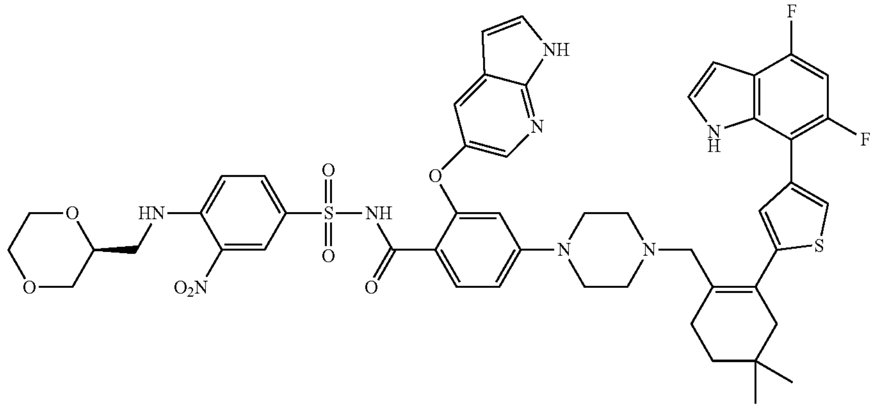

-continued
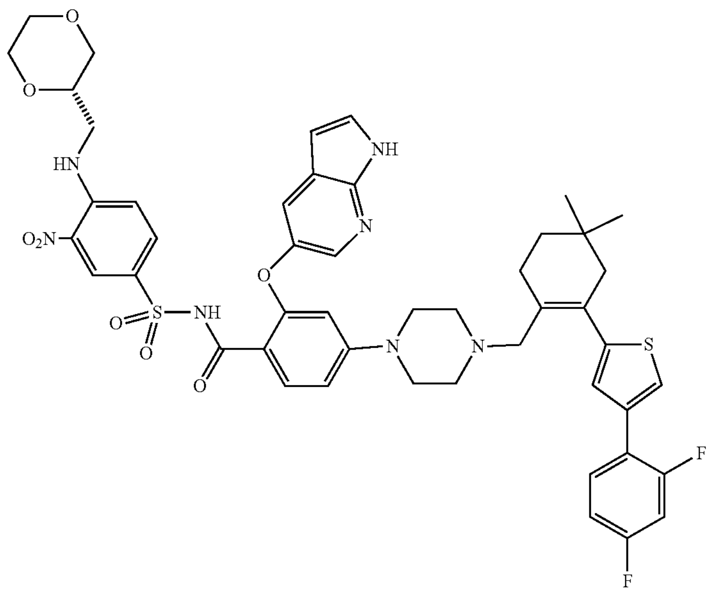
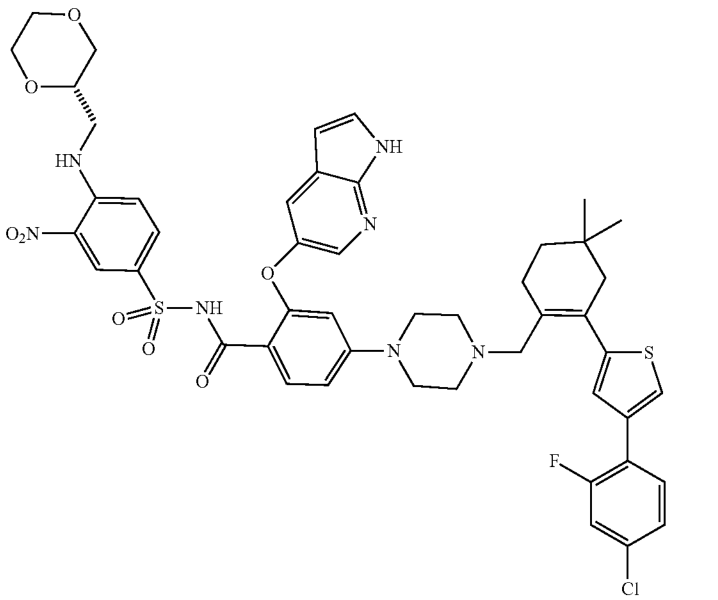

-continued
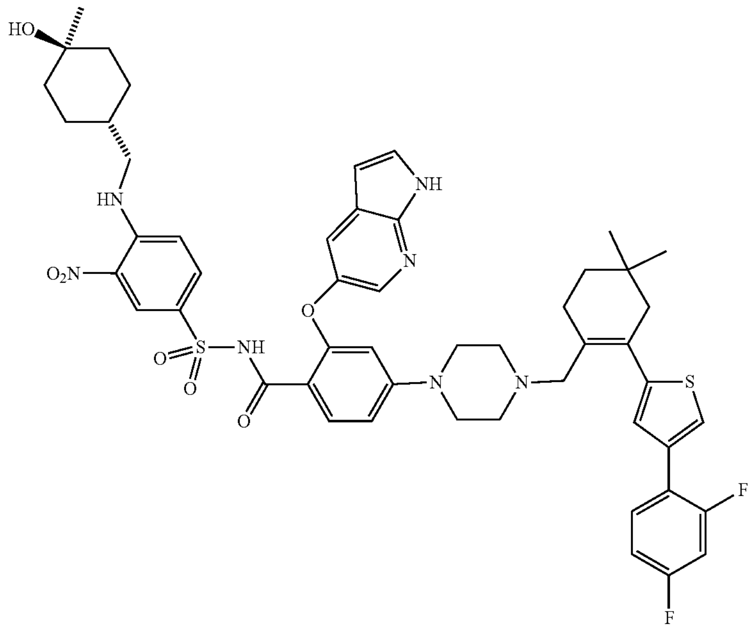
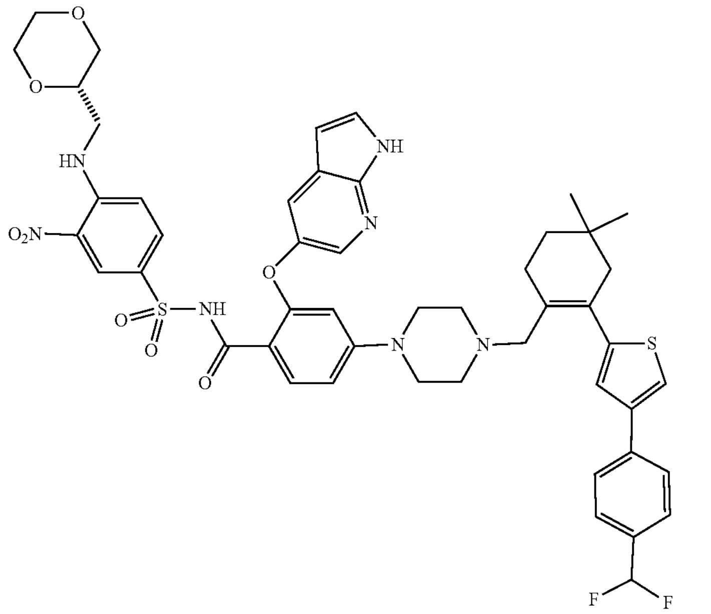
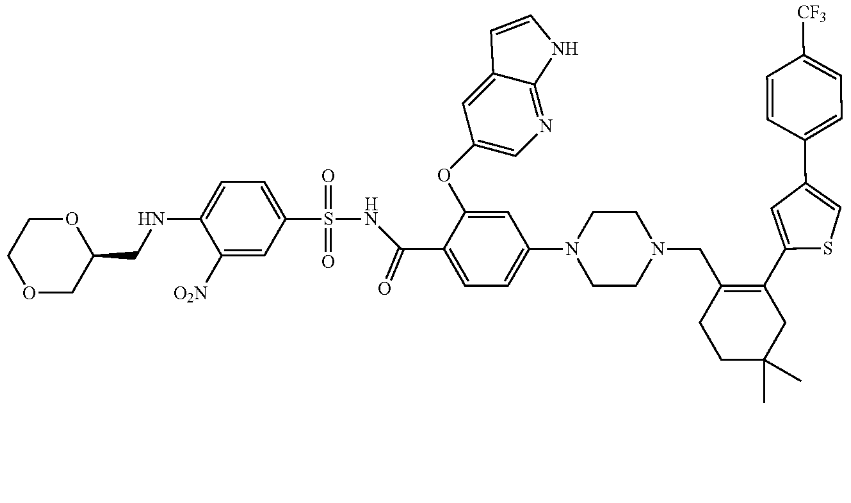

-continued
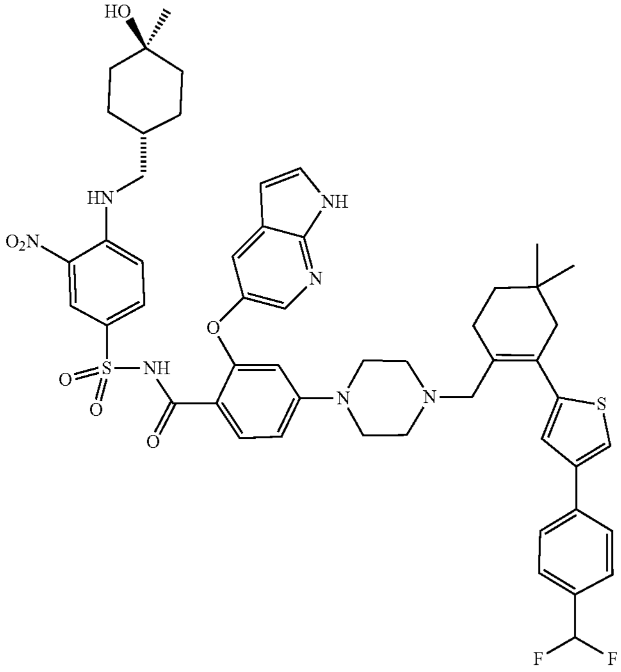
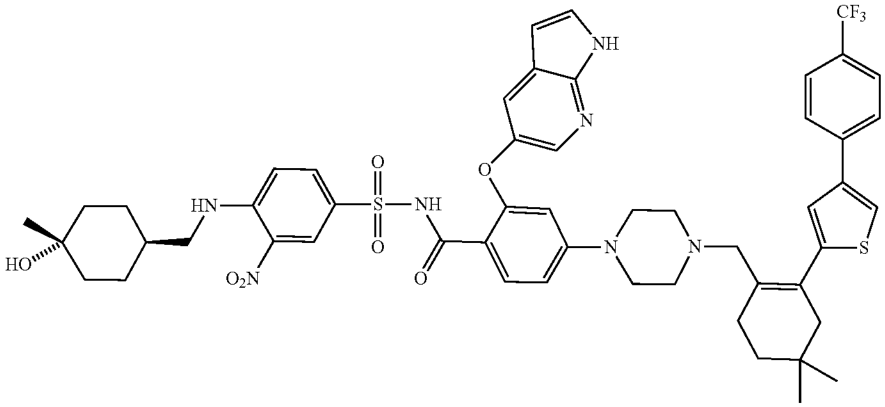
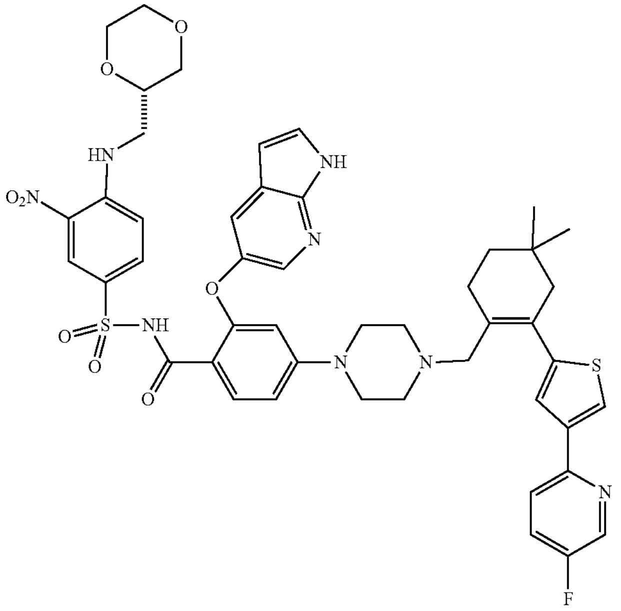

-continued
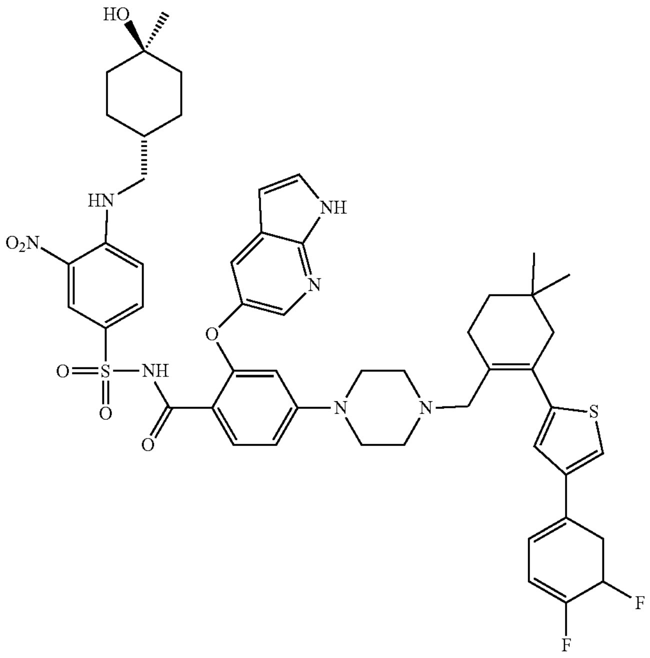
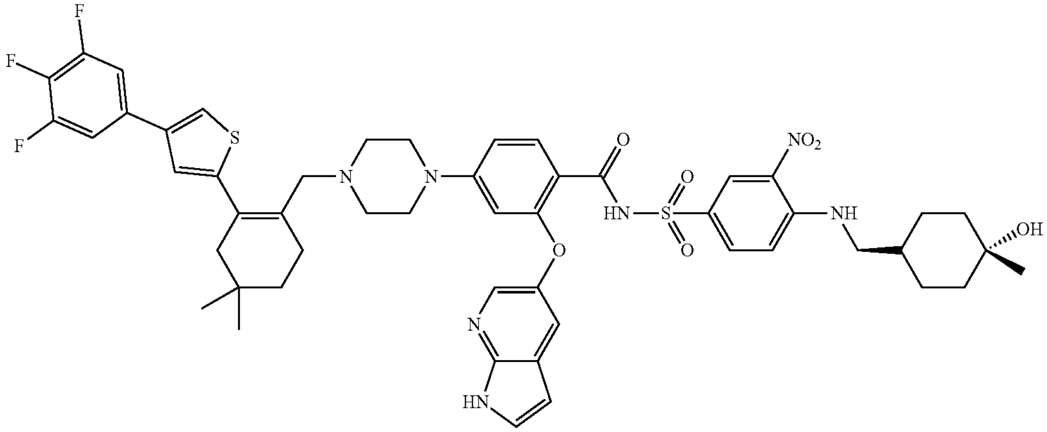
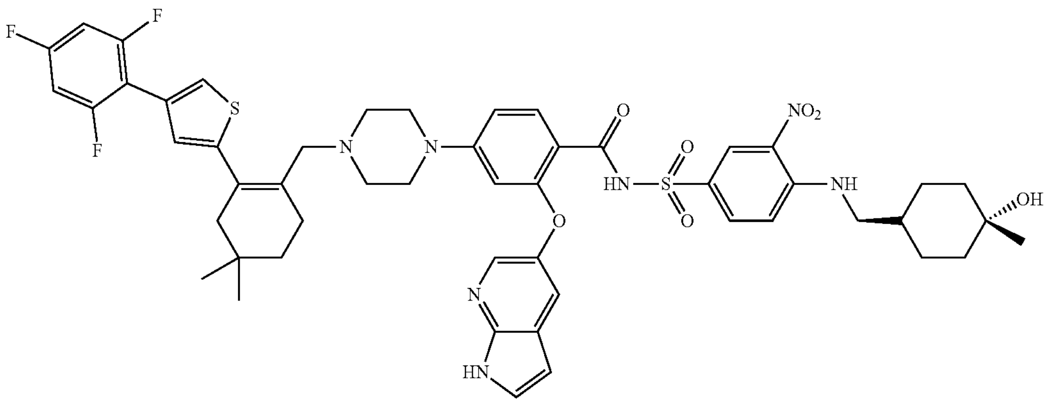

-continued
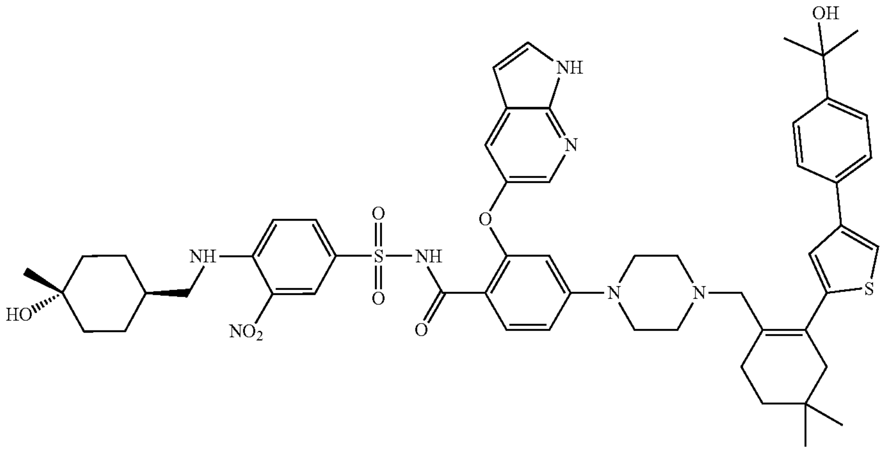
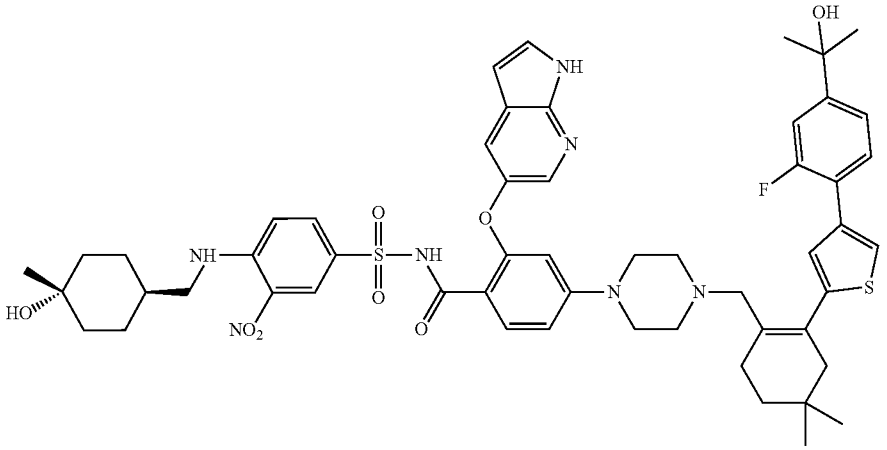
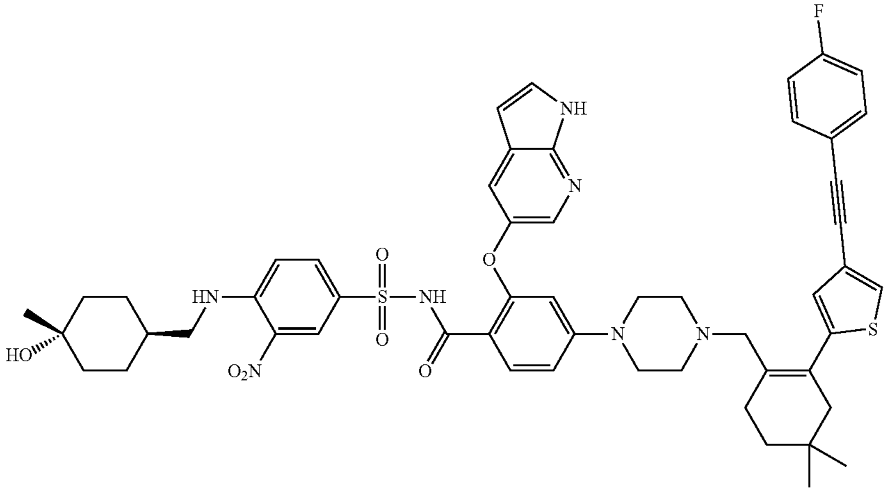

-continued
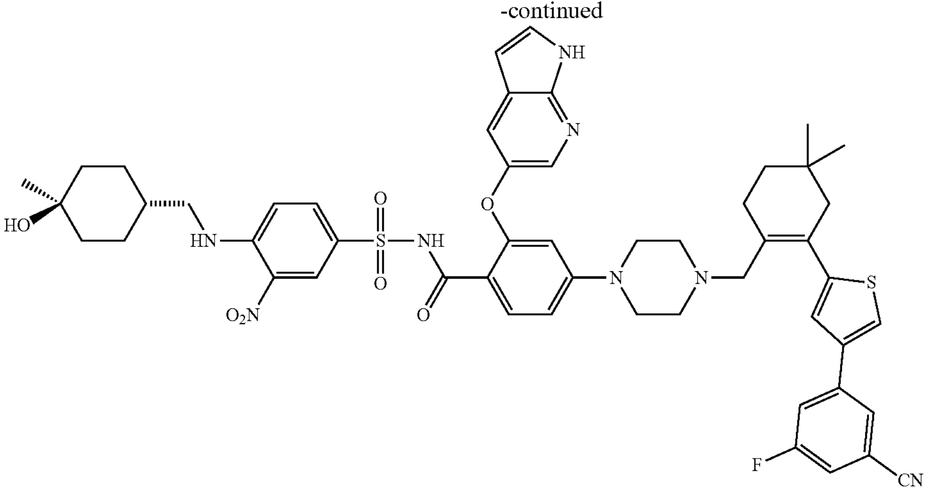
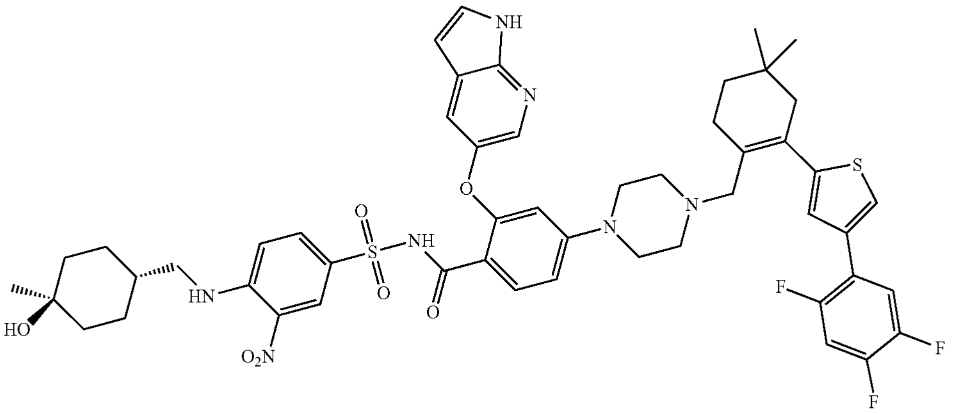
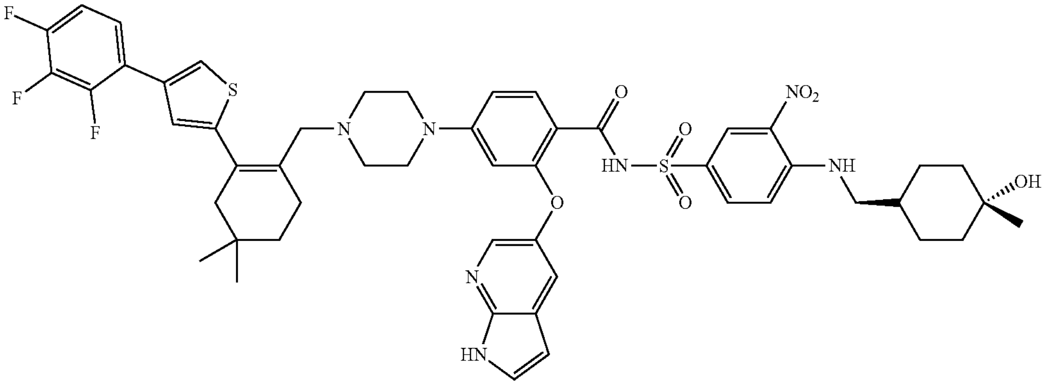
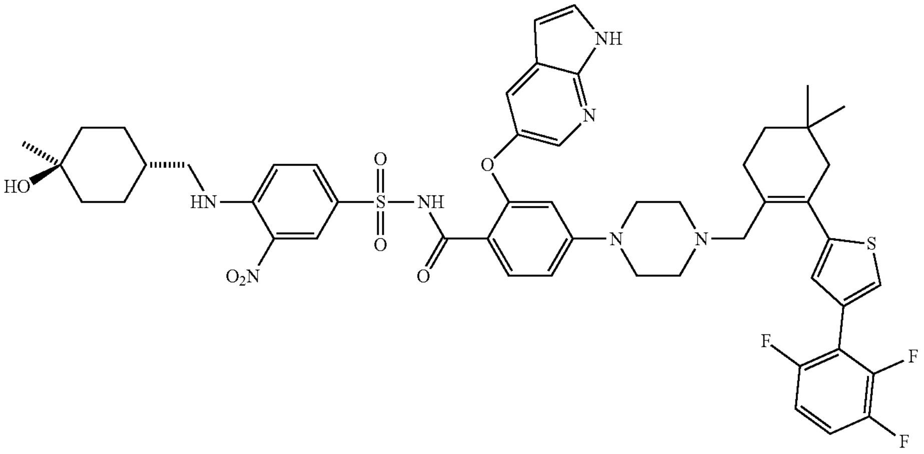

-continued
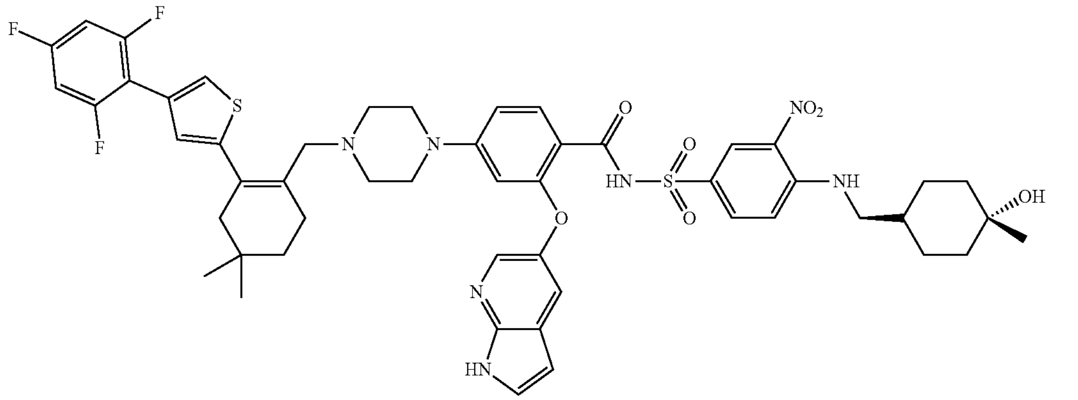
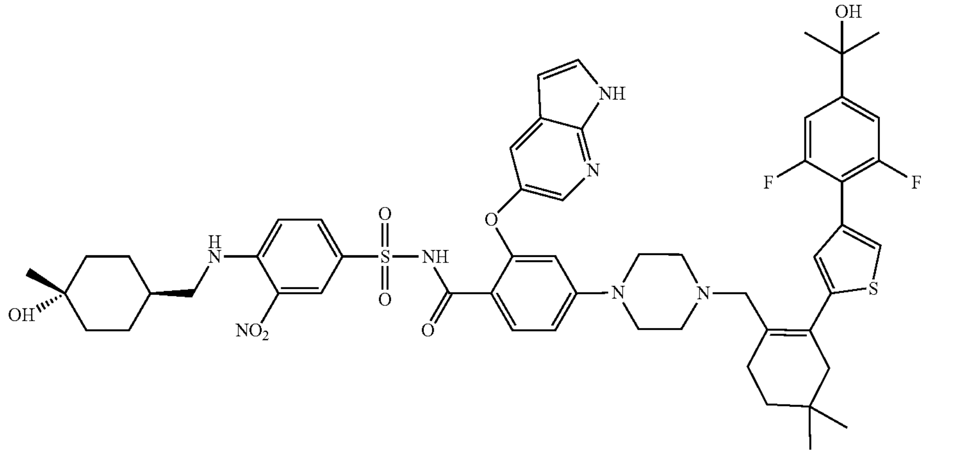
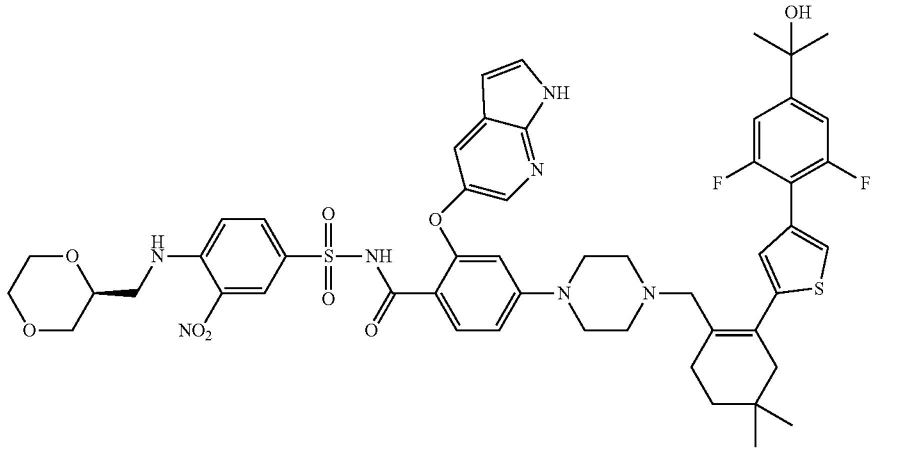
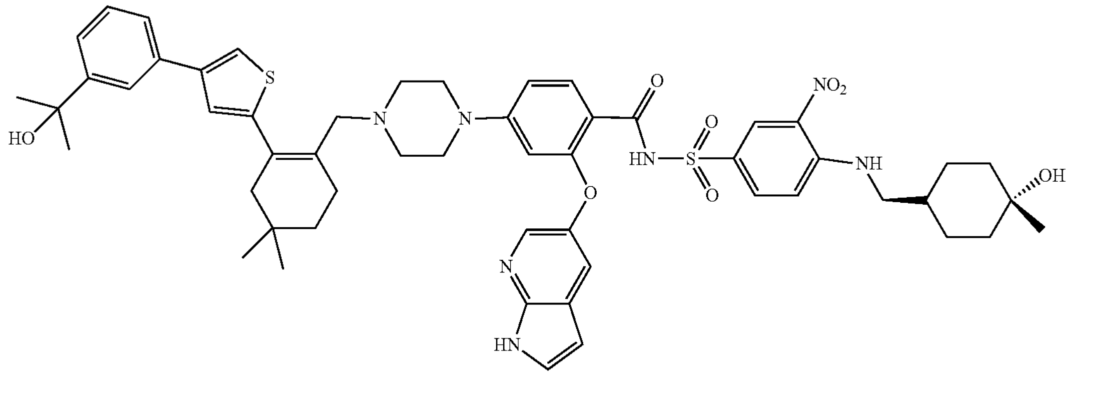

-continued
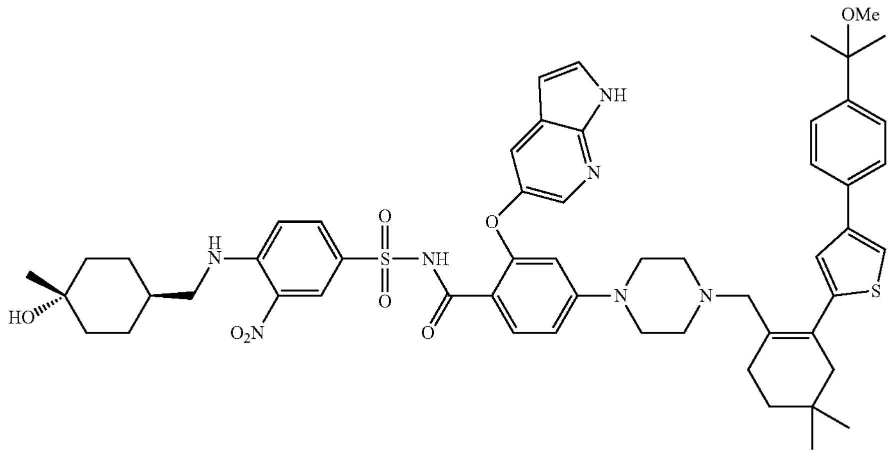
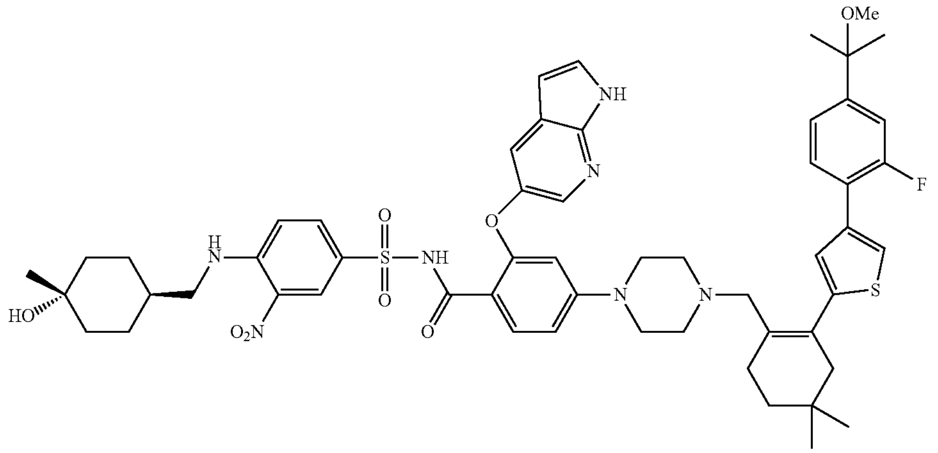
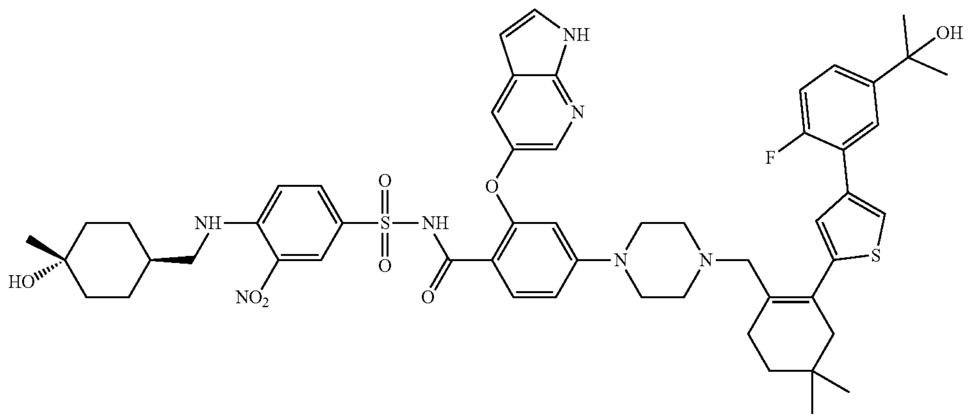

-continued
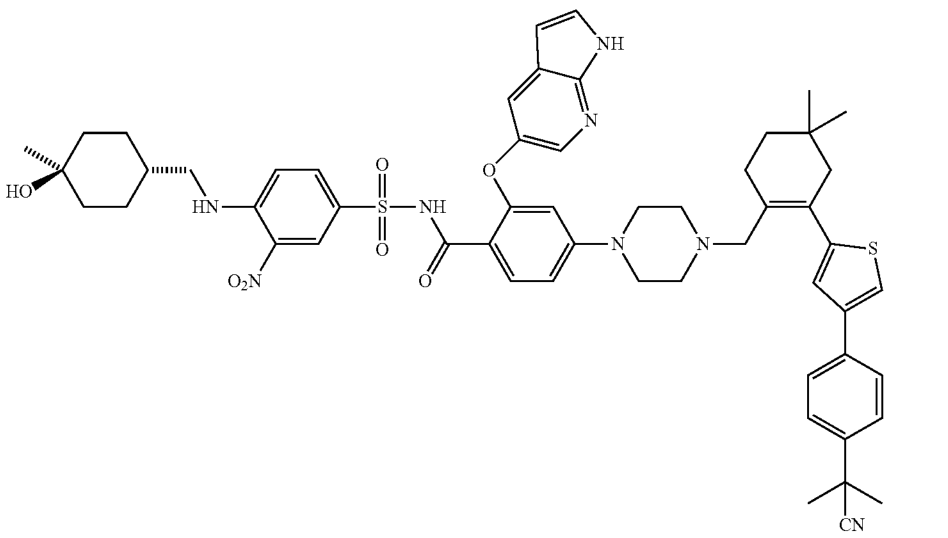
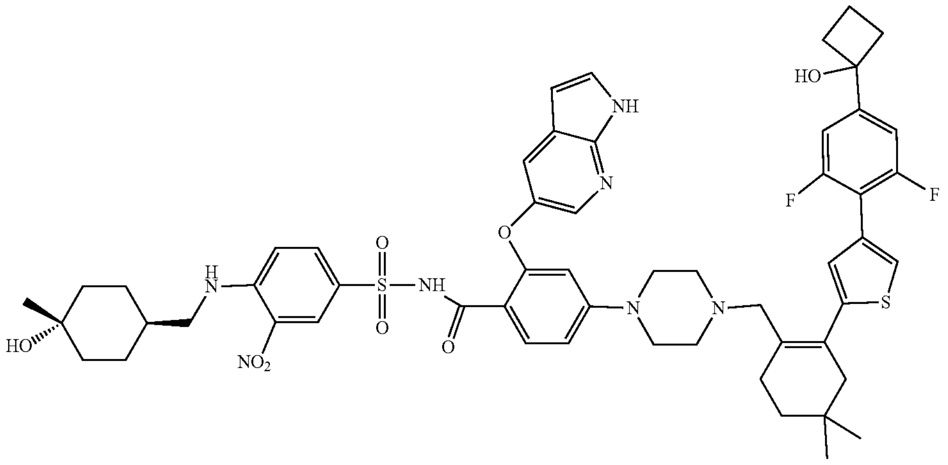
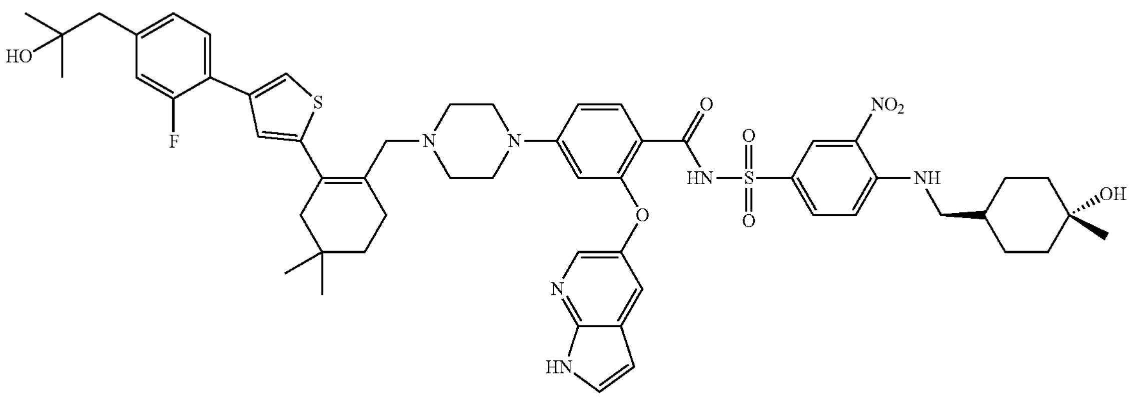

-continued
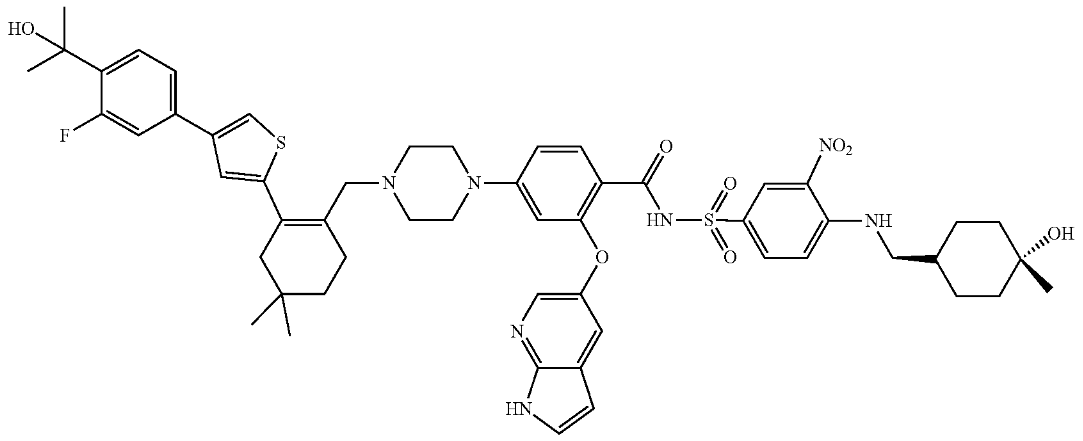
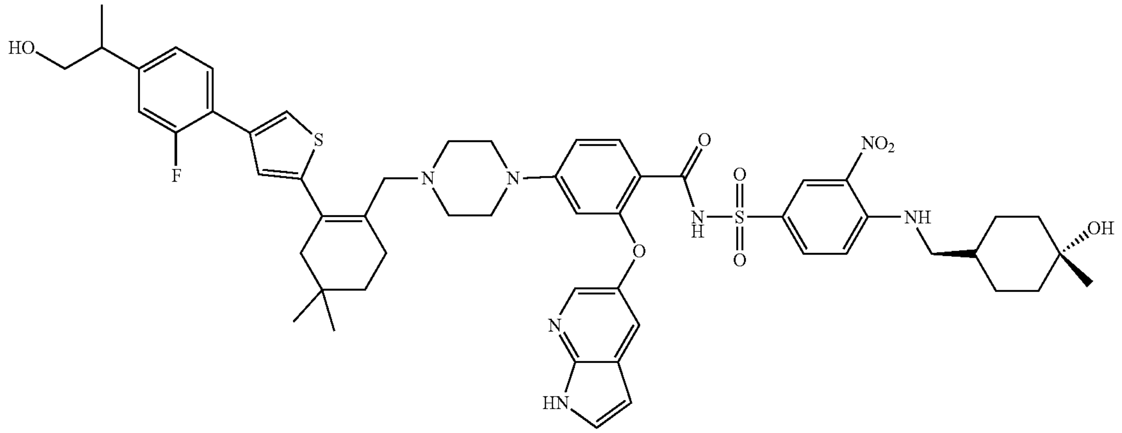
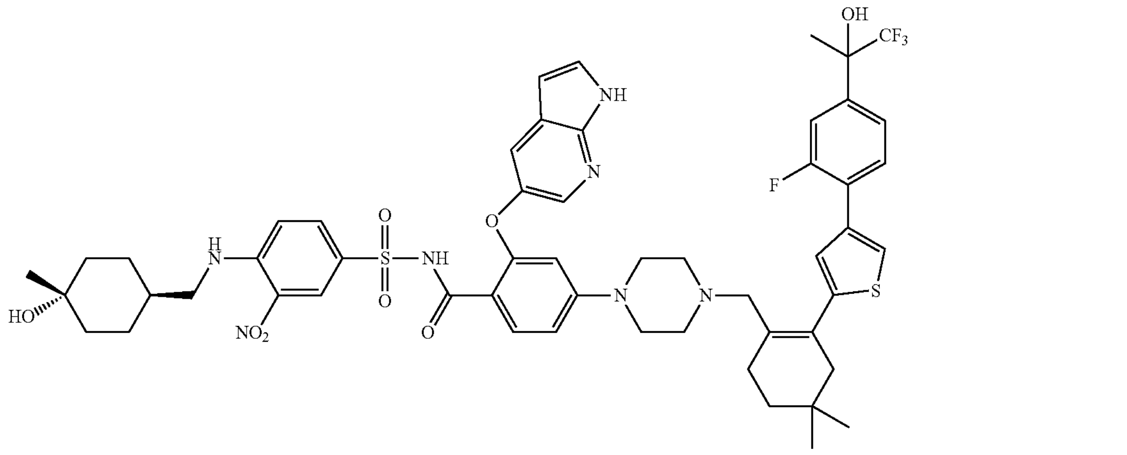

-continued
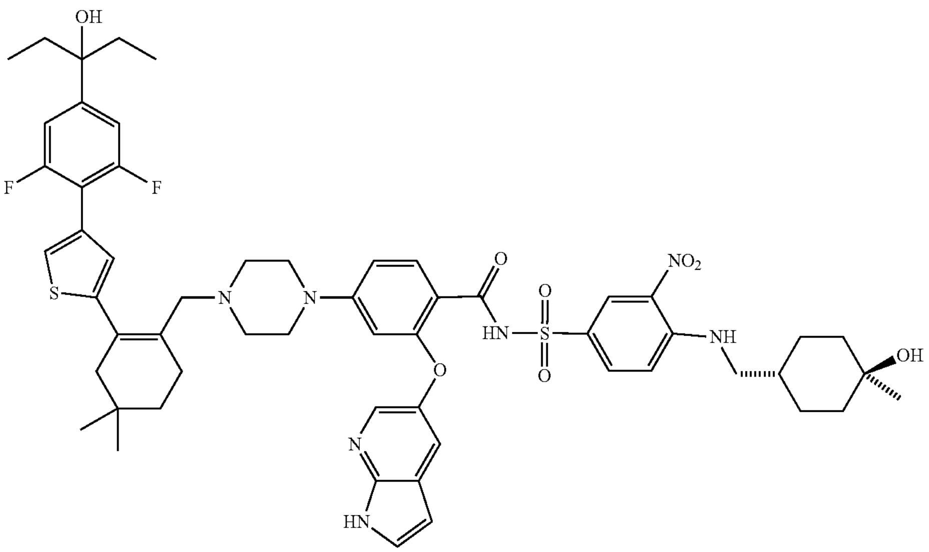
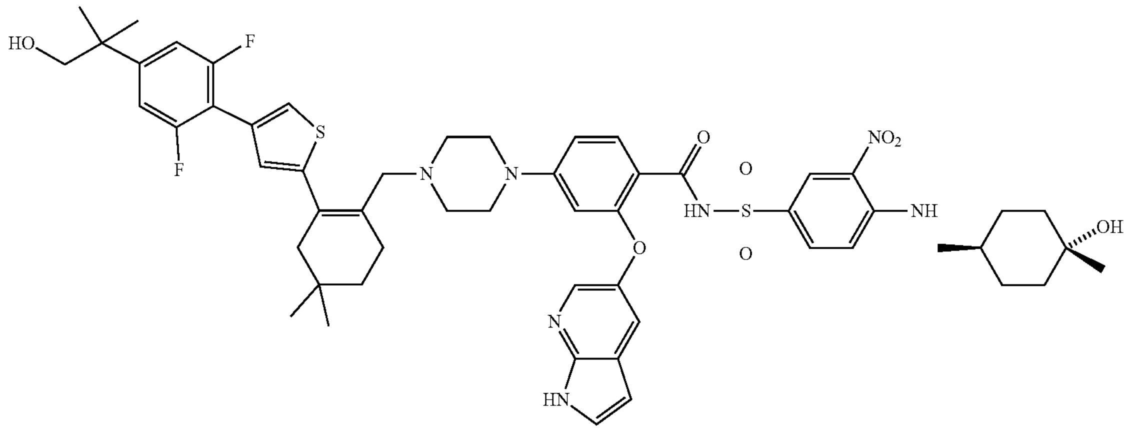
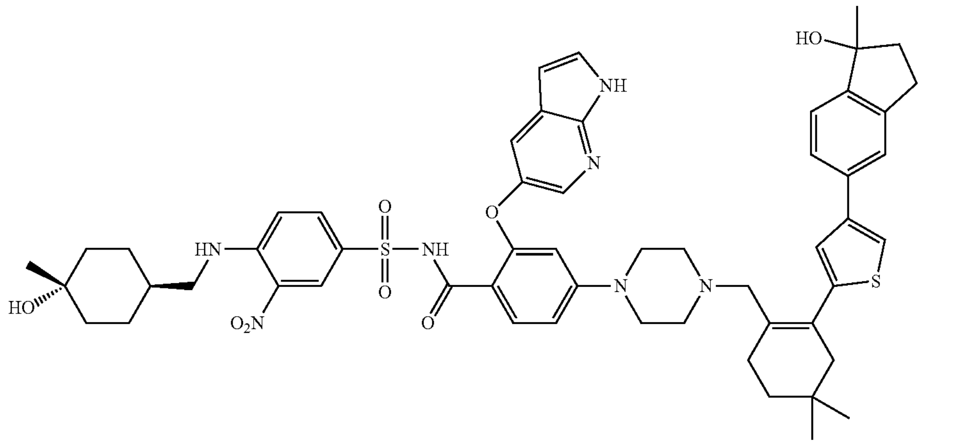

-continued
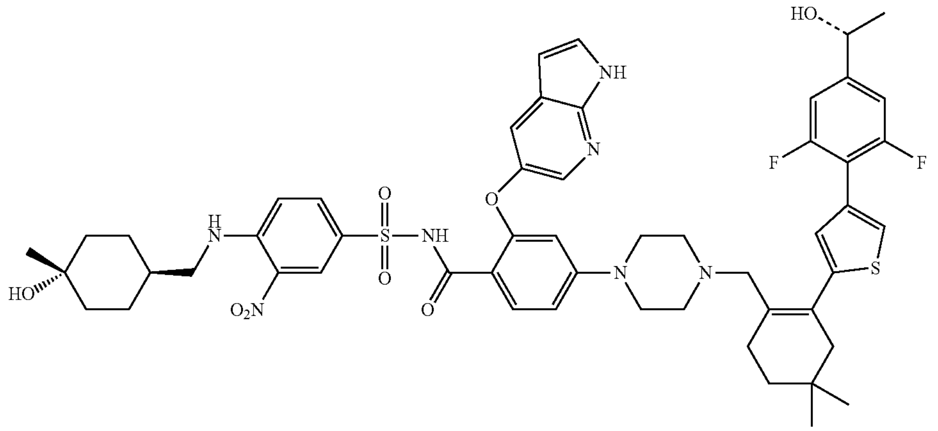
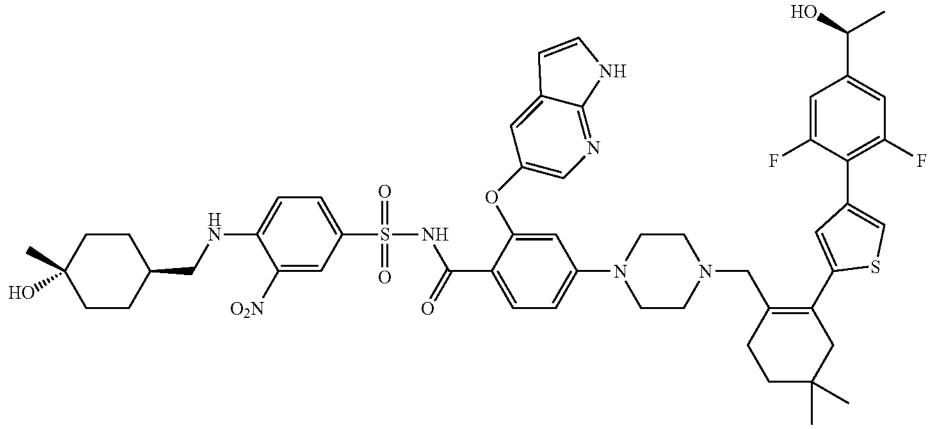
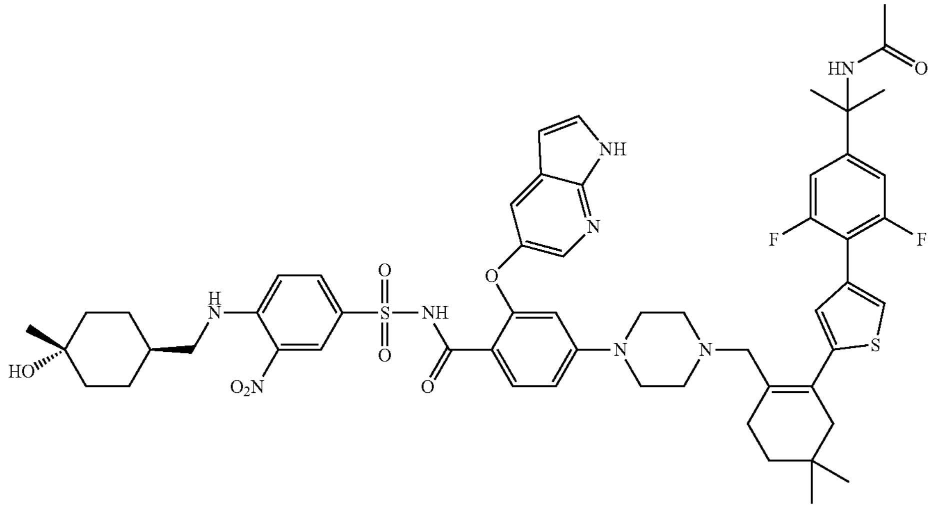

-continued
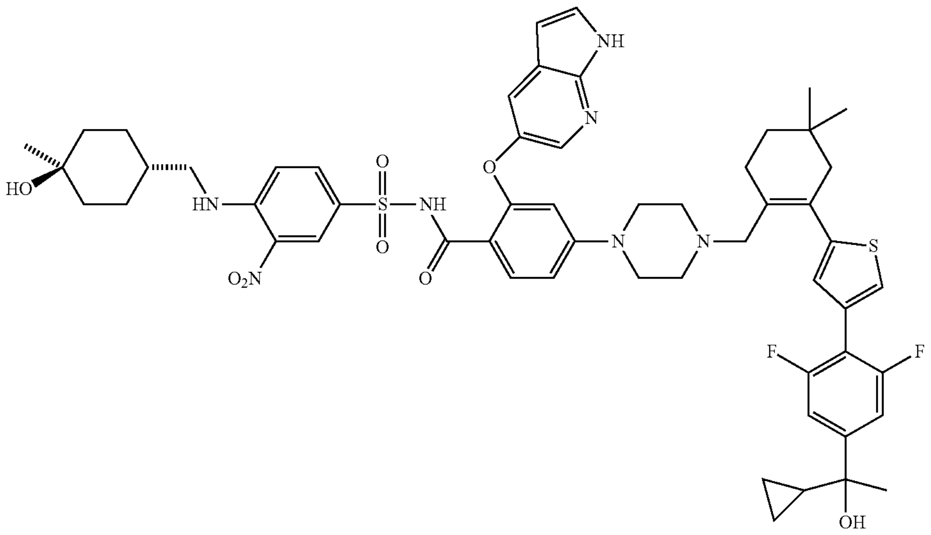
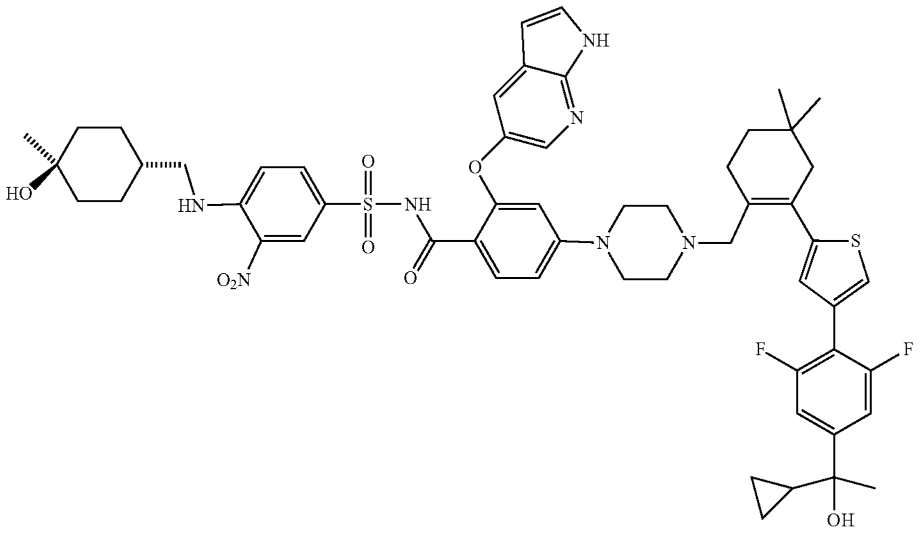
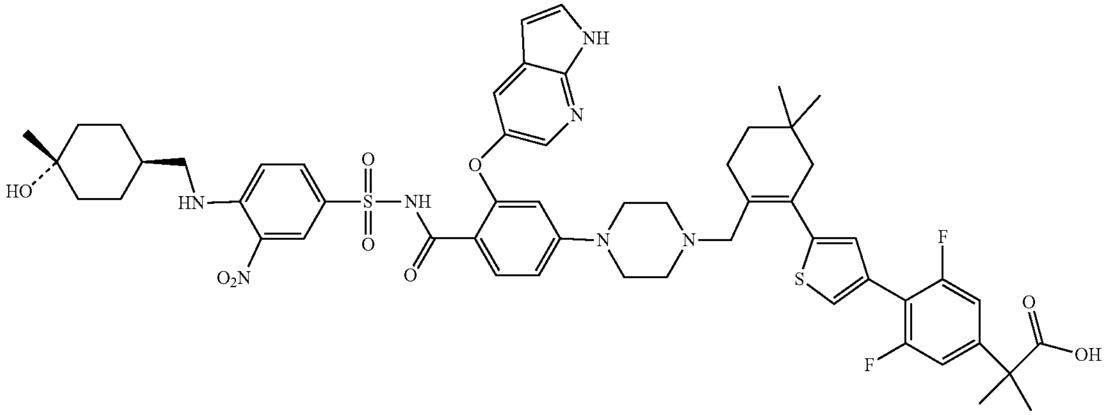

-continued

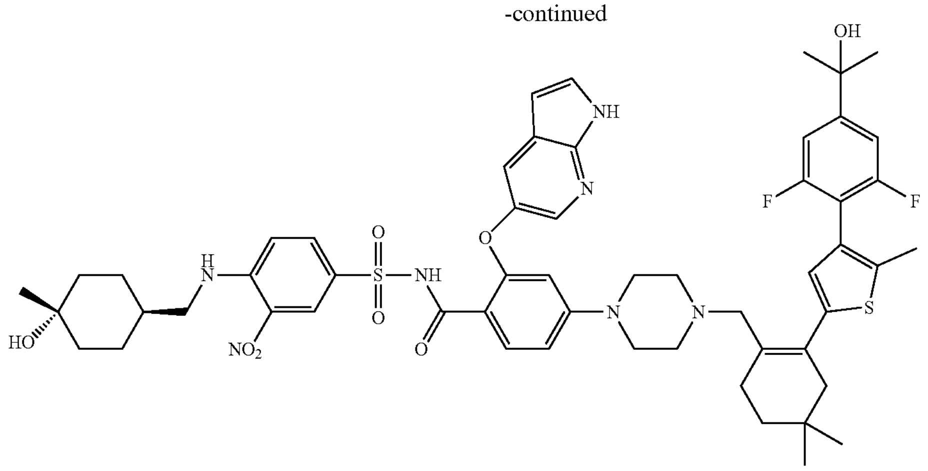

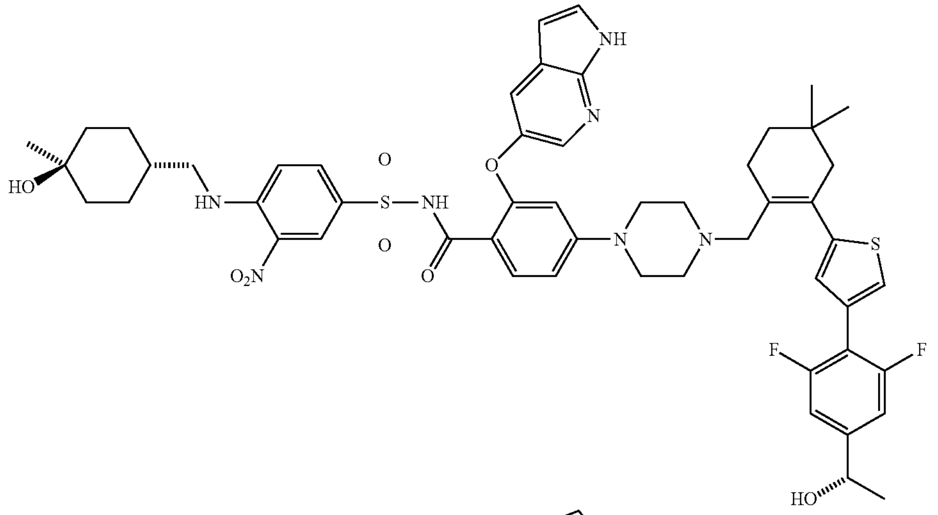

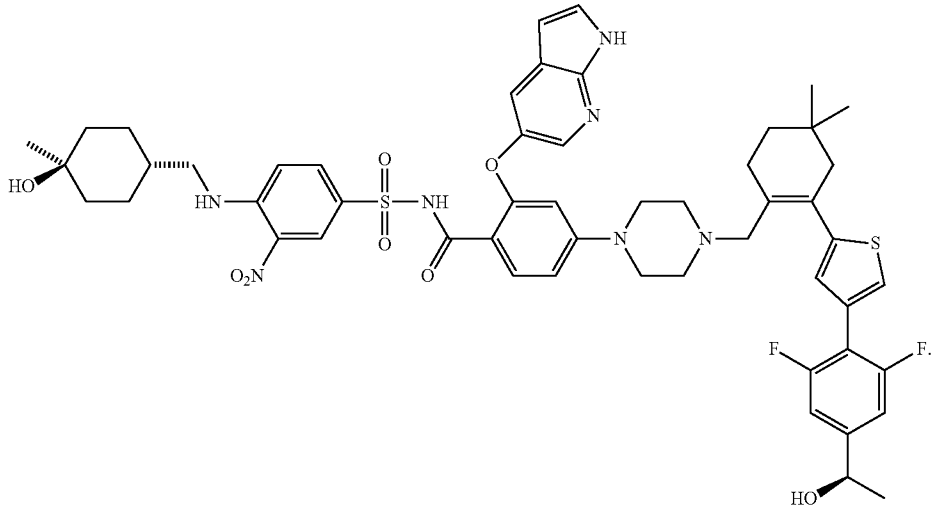

18. The compound of Formula (I) according to claim 1 wherein the pharmaceutically acceptable salt form is trifluoroacetate or formate.

19. The compound of claim 1, wherein at least one hydrogen atom is replaced with a deuterium atom.

20. A pharmaceutical composition comprising the compound of Formula (I) according to claim 1, or a pharmaceutically acceptable salt or solvate thereof, and a pharmaceutically acceptable carrier.

21. A method of treating cancer in a patient in need thereof, the method comprising administering to the patient a therapeutically effective amount of the compound of Formula (I) according to claim 1, or a pharmaceutically acceptable salt or solvate thereof, wherein the cancer is selected from the group consisting of acute monocytic leukemia, acute myelogenous leukemia, chronic myelogenous leukemia, chronic lymphocytic leukemia, mixed lineage leukaemia, NUT-midline carcinoma, multiple myeloma, small cell lung cancer, neuroblastoma, Burkitt's lymphoma, cervical cancer, esophageal cancer, ovarian cancer, colorectal cancer, prostate cancer, and breast cancer.

* * * * *